United States Patent
Haydar et al.

(10) Patent No.: US 11,560,370 B1
(45) Date of Patent: Jan. 24, 2023

(54) 5-MEMBERED HETEROARYL CARBOXAMIDE COMPOUNDS FOR TREATMENT OF HBV

(71) Applicant: Assembly Biosciences, Inc., Carmel, IN (US)

(72) Inventors: Simon Nicolas Haydar, Carmel, IN (US); Leping Li, Carmel, IN (US); Mark G. Bures, Carmel, IN (US); Roopa Rai, Carmel, IN (US); Lynne Bannen, Carmel, IN (US); Michael Walker, Carmel, IN (US)

(73) Assignee: Assembly Biosciences, Inc., South San Francisco, CA (US)

( * ) Notice: Subject to any disclaimer, the term of this patent is extended or adjusted under 35 U.S.C. 154(b) by 0 days.

(21) Appl. No.: 17/287,681

(22) PCT Filed: Oct. 22, 2019

(86) PCT No.: PCT/US2019/057362
§ 371 (c)(1),
(2) Date: Apr. 22, 2021

(87) PCT Pub. No.: WO2020/086533
PCT Pub. Date: Apr. 30, 2020

Related U.S. Application Data

(60) Provisional application No. 62/748,906, filed on Oct. 22, 2018, provisional application No. 62/858,790, filed on Jun. 7, 2019.

(51) Int. Cl.
| | | |
|---|---|---|
| *A61P 31/20* | (2006.01) |
| *A61K 31/40* | (2006.01) |
| *A61K 31/4025* | (2006.01) |
| *A61K 31/415* | (2006.01) |
| *A61K 31/4155* | (2006.01) |
| *A61K 31/42* | (2006.01) |
| *A61K 31/422* | (2006.01) |
| *A61K 31/425* | (2006.01) |
| *A61K 31/427* | (2006.01) |
| *C07D 231/38* | (2006.01) |
| *C07D 261/14* | (2006.01) |
| *C07D 401/08* | (2006.01) |
| *C07D 403/04* | (2006.01) |
| *C07D 403/08* | (2006.01) |
| *C07D 403/10* | (2006.01) |
| *C07D 403/12* | (2006.01) |
| *C07D 405/04* | (2006.01) |
| *C07D 407/04* | (2006.01) |
| *C07D 409/04* | (2006.01) |
| *C07D 409/08* | (2006.01) |
| *C07D 413/04* | (2006.01) |
| *C07D 413/08* | (2006.01) |
| *C07D 417/08* | (2006.01) |

(52) U.S. Cl.
CPC ............ *C07D 403/08* (2013.01); *A61P 31/20* (2018.01); *C07D 231/38* (2013.01); *C07D 401/08* (2013.01); *C07D 403/04* (2013.01); *C07D 403/10* (2013.01); *C07D 403/12* (2013.01); *C07D 405/04* (2013.01); *C07D 413/04* (2013.01); *C07D 413/08* (2013.01); *C07D 417/08* (2013.01)

(58) Field of Classification Search
CPC ..... A61P 31/20; A61K 31/40; A61K 31/4025; A61K 31/415; A61K 31/4155; A61K 31/42; A61K 31/422; A61K 31/425; A61K 31/427; C07D 231/38; C07D 261/14; C07D 401/08; C07D 403/04; C07D 403/08; C07D 403/10; C07D 403/12; C07D 405/04; C07D 407/04; C07D 409/04; C07D 409/08; C07D 413/04; C07D 413/08; C07D 417/08
See application file for complete search history.

(56) References Cited

FOREIGN PATENT DOCUMENTS

| WO | 2013006394 A1 | 1/2013 |
|---|---|---|
| WO | 2013010069 A1 | 1/2013 |
| WO | 2013102655 A1 | 7/2013 |
| WO | 2014033167 A1 | 3/2014 |
| WO | 2014033170 A1 | 3/2014 |
| WO | 2014033176 A1 | 3/2014 |
| WO | 2014037480 A1 | 3/2014 |
| WO | 2014074906 A1 | 5/2014 |
| WO | 2014089296 A2 | 6/2014 |
| WO | 2014106019 A2 | 7/2014 |
| WO | 2014131847 A1 | 9/2014 |
| WO | 2014161888 A1 | 10/2014 |
| WO | 2014184328 A1 | 11/2014 |
| WO | 2014184350 A1 | 11/2014 |
| WO | 2014184365 A1 | 11/2014 |
| WO | 2015011281 A1 | 1/2015 |

(Continued)

OTHER PUBLICATIONS

Zhou et al., Enolate-Mediated 1,3-Dipolar Cycloaddition Reaction of β-Functionalized Ketones With Nitrile Oxides: Direct Access to 3,4,5-Trisubstituted Isoxazoles, Organic & Biomolecular Chemistry, vol. 14, No. 23 pp. 5246-5250, 2016.*

(Continued)

*Primary Examiner* — Brenda L Coleman
(74) *Attorney, Agent, or Firm* — Barnes & Thornburg LLP

(57) ABSTRACT

The present disclosure provides, in part, 5-membered heteroaryl carboxamide compounds, and pharmaceutical compositions thereof, useful for disruption of HBV core protein assembly, and methods of treating Hepatitis B (HBV) infection.

30 Claims, 2 Drawing Sheets

(56) References Cited

FOREIGN PATENT DOCUMENTS

WO 2015118057 A1 8/2015

OTHER PUBLICATIONS

CAS printout for Registry No. 1494073-16-3, 2-amino-4-cyclopentyl-N-cyclopropyl-3-thiophenecarboxamide, Dec. 13, 2013.*

CAS printout for Registry No. 1952255-05-8, 3-cyclohexyl-N-[4-[(cyclopenylamino)carbonyl]phenyl]-1-methyl-1H-pyrazole-4-carboxamide, Jul. 14, 2016.*

Bertz et al., "Reaction of Dimethyl Sodio-3-ketoglutarate with Glyoxal and Substituted Glyoxals: First Expeditious Preparation of Bicyclo[3.3.0]octane-3,7-dione; Synthesis and Crystal Structure of 5,7-dihydroxy-4-methoxycarbonyl-3-phenyl-1-indanone," Tetrahedron, vol. 38, (1982), pp. 63-70.

International Preliminary Report on Patentability, issued in PCT/US2019/057362, dated Apr. 27, 2021.

International Search Report, issued in PCT/US2019/057362, dated Feb. 18, 2020.

Jin et al., "Design of N-Cinnamyl Sulfinamides as New Sulfur-Containing Olefin Ligands for Asymmetric Catalysis Achieving Structural Simplicity with a Categorial Linear Framework," Org. Biomol. Chem., vol. 10, (2012), pp. 1764-1768.

Lahlali et al., "Novel Potent Capsid Assembly Modulators Regulate Multiple Steps of the Hepatitis B Virus Life Cycle," Antimicrobial Agents and Chemotherapy, vol. 62, No. 10, (2018), pp. 1-15 XP055584508.

Mani et al., "Preclinical Profile of AB-423, an Inhibitor of Hepatitis B Virus Pregenomic RNA Encapsidation," Antimicrobial Agents and Chemotherapy, vol. 62, No. 6, (2018), pp. 1-22 XP055665526.

Rautio et al., "Prodrugs: Design and Clinical Applications," Nature Reviews Drug Discovery, vol. 7, (2008), pp. 255-270.

Schlicksup et al., "Hepatitis B Virus Core Protein Allosteric Modulators can Distort and Disrupt Intact Capsids," eLife, (2018), pp. 1-23.

Wang et al., "Transbody Against Hepatitis B Virus Core Protein Inhibits Hepatitis B Virus Replication in vitro," Int. Immunopharmacol, vol. 25, Issue 2, (2014), pp. 363-369. //dx.doi.org/10.1016/j.intimp.2015.01.028.

* cited by examiner

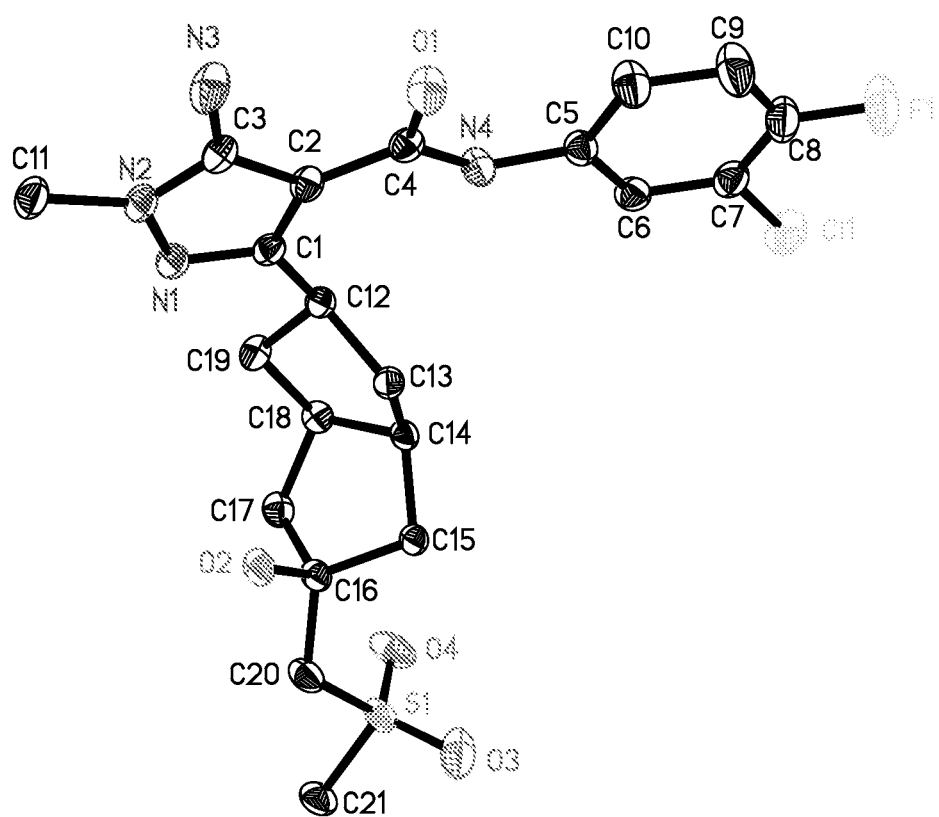
Fig. 1 The ORTEP plot for compound AIA-227-2

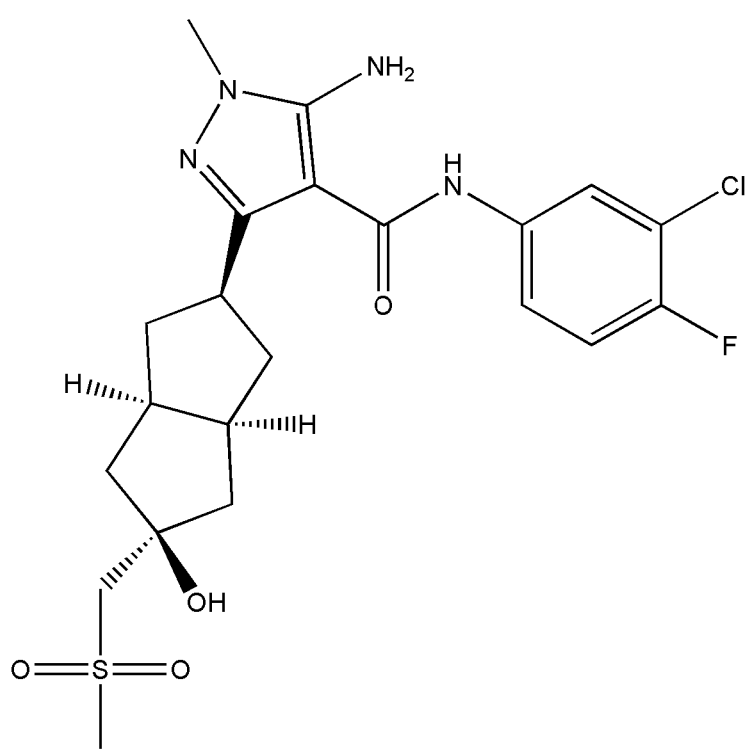
Fig. 2 The relative stereochemistry scheme of compound AIA-227-2.

5-MEMBERED HETEROARYL CARBOXAMIDE COMPOUNDS FOR TREATMENT OF HBV

CROSS-REFERENCE TO RELATED APPLICATIONS

This application is a National Stage application of International Application No. PCT/US2019/057362, filed Oct. 22, 2019, which claims the benefit of U.S. Provisional Patent Application No. 62/748,906, filed Oct. 22, 2018, and U.S. Provisional Patent Application No. 62/858,790, filed Jun. 7, 2019, the entire contents of all of which are incorporated by reference herein.

BACKGROUND

Hepatitis B (HBV) causes viral hepatitis that can further lead to chronic liver disease and increase the risk of liver cirrhosis and liver cancer (hepatocellular carcinoma). Worldwide, about 2 billion people have been infected with HBV, around 360 million people are chronically infected, and every year HBV infection causes more than one half million deaths. HBV can be spread by body fluids: from mother to child, by sex, and via blood products. Children born to HBV-positive mothers may also be infected, unless vaccinated at birth.

The hepatitis virus particle is composed of a lipid envelope studded with surface protein (HBsAg) that surrounds the viral core. The core is composed of a protein shell, or capsid, built of 120 core protein (Cp) dimers, which in turn contains the relaxed circular DNA (rcDNA) viral genome as well as viral and host proteins. In an infected cell, the genome is found as a covalently closed circular DNA (cccDNA) in the host cell nucleus. The cccDNA is the template for viral RNAs and thus viral proteins. In the cytoplasm, Cp assembles around a complex of full-length viral RNA (the so-called pregenomic RNA or pgRNA and viral polymerase (P). After assembly, P reverse transcribes the pgRNA to rcDNA within the confines of the capsid to generate the DNA-filled viral core.

At present, chronic HBV is primarily treated with nucleos(t)ide analogs (e.g., entecavir) that suppress the virus while the patient remains on treatment, but do not eliminate the infection, even after many years of treatment. Once a patient starts taking nucleos(t)ide analogs, most must continue taking them or risk the possibility of a life-threatening immune response due to viral rebound. Further, nucleotide therapy may lead to the emergence of antiviral drug resistance.

The only FDA approved alternative to nucleos(t)ide analogs is treatment with interferon α or pegylated interferon α. Unfortunately, the adverse event incidence and profile of interferon α can result in poor tolerability, and many patients are unable to complete therapy. Moreover, only a small percentage of patients are considered appropriate for interferon therapy, as only a small subset of patients is likely to have a sustained clinical response to a course of interferon therapy. As a result, interferon-based therapies are used in only a small percentage of all diagnosed patients who elect treatment.

Thus, current HBV treatments can range from palliative to watchful waiting. Nucleotide analogs suppress virus production, treating the symptom, but leave the infection intact. Interferon α has severe side effects and less tolerability among patients and is successful as a finite treatment strategy in only a small minority of patients. There is a clear on-going need for more effective treatments for HBV infections.

SUMMARY

The present disclosure provides, in part, 5-membered heteroaryl carboxamide compounds and pharmaceutical compositions thereof, useful for disruption of HBV core protein assembly, and methods of treating HBV infections.

In one aspect, the disclosure provides a compound of Formula I:

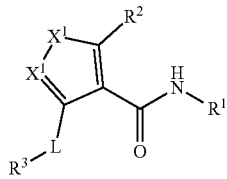

Formula I or a pharmaceutically acceptable salt thereof, where the variables are described in the detailed description.

In another aspect, the disclosure provides pharmaceutical compositions comprising a compound of Formula I, or a pharmaceutically acceptable salt thereof, and a pharmaceutically acceptable excipient.

In another aspect, the disclosure provides a method of treating an HBV infection in a subject in need thereof, comprising: administering to the subject a therapeutically effective amount of compound of Formula I, or a pharmaceutically acceptable salt thereof.

In another aspect, the disclosure provides a method of treating an HBV infection in a subject in need thereof, comprising: administering to the subject a pharmaceutical composition comprising a therapeutically effective amount of a compound of Formula I, or a pharmaceutically acceptable salt thereof, and a pharmaceutically acceptable excipient.

BRIEF DESCRIPTION OF DRAWINGS

FIG. 1 shows the ORTEP plot for compound CP-AIA-227-2.

FIG. 2 shows the relative stereochemistry scheme of compound CP-AIA-227-2.

DETAILED DESCRIPTION

The features and other details of the disclosure will now be more particularly described. Before further description of the present disclosure, certain terms employed in the specification, examples and appended claims are collected here. These definitions should be read in light of the remainder of the disclosure and as understood by a person of skill in the art. Unless defined otherwise, all technical and scientific terms used herein have the same meaning as commonly understood by a person of ordinary skill in the art.

I. Definitions

The term "alkenyl" as used herein refers to an unsaturated straight or branched hydrocarbon having at least one carbon-carbon double bond. Exemplary alkenyl groups include, but are not limited to, a straight or branched group of 2-6 carbon atoms, referred to herein as $C_{2-6}$alkenyl. Exemplary alkenyl groups include, but are not limited to, vinyl, allyl, butenyl, pentenyl, etc. . . .

The term "alkoxy" as used herein refers to a straight or branched alkyl group attached to oxygen (i.e., alkyl-O—). Exemplary alkoxy groups include, but are not limited to, alkoxy groups of 1-6 or 1-4 carbon atoms, referred to herein as $C_{1-6}$alkoxy and $C_{1-4}$alkoxy, respectively. Exemplary alkoxy groups include, but are not limited to methoxy, ethoxy, isopropoxy, etc. . . .

The term "alkoxyalkyl" as used herein refers to an alkyl group substituted with an alkoxy group. Examples include, but are not limited to, $CH_3CH_2OCH_2$—, $CH_3OCH_2CH_2$— and $CH_3OCH_2$—.

The term "alkyl" as used herein refers to a saturated straight or branched hydrocarbon. Exemplary alkyl groups include, but are not limited to, straight or branched hydrocarbons of 1-6 or 1-4 carbon atoms, referred to herein as $C_{1-6}$ alkyl and $C_{1-4}$ alkyl, respectively. Exemplary alkyl groups include, but are not limited to, methyl, ethyl, n-propyl, isopropyl, 2-methyl-1-butyl, 3-methyl-2-butyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, t-butyl, n-pentyl, isopentyl, neopentyl, n-hexyl, etc . . . . The term "alkylene" as used herein refers to a biradical alkyl group.

The term "alkynyl" as used herein refers to an unsaturated straight or branched hydrocarbon having at least one carbon-carbon triple bond. Exemplary alkynyl groups include, but are not limited to, straight or branched groups of 2-6 carbon atoms, referred to herein as $C_{2-6}$alkynyl. Exemplary alkynyl groups include, but are not limited to, ethynyl, propynyl, butynyl, pentynyl, hexynyl, methylpropynyl, etc. . . .

The term "carbonyl" as used herein refers to the biradical —C(O)—.

The term "cyano" as used herein refers to the radical —CN.

The term "cycloalkyl" as used herein refers to a saturated monocyclic hydrocarbon group of, for example, 3-6 carbons, referred to herein as $C_{3-6}$ monocycloalkyl, or bicyclic hydrocarbon ring structure of, for example, 8-12 carbons, referred to herein as $C_{8-12}$bicycloalkyl. For bicyclic cycloalkyl groups, the two rings may be attached through the same or different carbons. Exemplary monocyclic cycloalkyl groups include, but are not limited to, cyclohexyl, cyclopentyl, cyclopentenyl, cyclobutyl and cyclopropyl. Exemplary bicyclic cycloalkyl groups include, but are not limited to, spiro[2.5]octanyl, spiro[3.5]nonanyl, bicyclo[2.2.2]octanyl, bicyclo[4.1.0]heptanyl, octahydropentalenyl, bicyclo[4.2.0]octanyl, bicyclo[1.1.1]pentanyl, bicyclo[2.2.1]heptanyl, and bicyclo[2.2.2]octanyl.

The term "cycloalkenyl" as used herein refers to a partially unsaturated monocyclic hydrocarbon group of, for example, 4-6 carbons, referred to herein as $C_{4-6}$monocycloalkenyl, or bicyclic hydrocarbon ring structure of, for example, 8-12 carbons, referred to herein as $C_{8-12}$bicycloalkenyl. For bicyclic cycloalkenyl groups: 1) either one or both rings may contain one or more double bonds and 2) the two rings may be attached through the same or different ring carbons. Exemplary monocyclic cycloalkenyl groups include, but are not limited to, cyclopropenyl, cyclobutenyl, cyclopentenyl, cyclohexenyl and cycloheptenyl. Exemplary bicyclic cycloalkenyl groups include, but are not limited to, spiro[2.5]oct-5-enyl, spiro[2.5]oct-4-enyl, spiro[3.5]non-5-enyl, spiro[3.5]non-6-enyl, bicyclo[4.1.0]hept-3-enyl, bicyclo[4.1.0]hept-2-enyl, and bicyclo[2.2.2]oct-2-enyl.

The term "carbocyclyl" as used herein refers to a bicyclic ring system formed by fusing a phenyl ring to a $C_{3-6}$monocycloalkyl or $C_{4-6}$monocycloalkenyl ring. Examples of carbocyclyls include, but are not limited to, 2,3-dihydro-1H-indenyl, 1,2,3,4-tetrahydronaphthalenyl and 1H-indenyl.

The terms "halo" or "halogen" as used herein refer to F, Cl, Br or I.

The term "haloalkyl" as used herein refers to an alkyl group substituted with one or more halogen atoms. For example, halo$C_{1-6}$alkyl refers to a straight or branched alkyl group of 1-6 carbon atoms substituted with one or more halogen atoms. Examples include, but are not limited to, $CH_2F$—, $CHCl_2$—, —$CHF_2$, $CF_3$—, $CF_3CH_2$—, $CH_3CF_2$, $CF_3CCl_2$— and $CF_3CF_2$—.

The term "haloalkoxy" as used herein refers to an alkoxy group substituted with one or more halogen atoms. Examples include, but are not limited to, $CCl_3O$—, $CF_3O$—, $CHF_2O$—$CF_3CH_2O$—, and $CF_3CF_2O$—.

The terms "heteroaryl" as used herein refers to a 5-6 membered monocyclic or 8-12 membered bicyclic aromatic ring system containing one to four independently selected heteroatoms, such as nitrogen, oxygen and sulfur. Where possible, the heteroaryl ring may be linked to the adjacent radical though carbon or nitrogen. Examples of 5-6 membered monocyclic heteroaryl groups include, but are not limited to, furanyl, thiophenyl (also referred to as thienyl), pyrrolyl, thiazolyl, oxazolyl, isothiazolyl, isoxazolyl, imidazolyl, pyrazolyl, 1H-1,2,3-triazolyl, 2H-1,2,3-triazolyl, 1,2,4-triazolyl, pyridinyl (also referred to as pyridyl), pyridazinyl, pyrimidinyl, pyrazinyl, 1,3,5-triazinyl, 1,2,4-triazinyl, 1,2,3-triazinyl, 1,2,4-oxadiazolyl, 1,3,4-oxadiazolyl, 1,2,5-oxadiazolyl, 1,2,4-thiadiazolyl, 1,3,4-thiadiazolyl, 1,2,5-thiadiazolyl and tetrazolyl. Examples of 8-12 membered bicyclic heteroaryl groups include, but are not limited to, benzofuranyl, isobenzofuranyl, benzo[b]thiophenyl, benzo[c]thiophenyl, indolyl, isoindolyl, benzo[d]isoxazolyl, benzo[c]isoxazolyl, benzo[d]oxazolyl, benzo[d]isothiazolyl, benzo[c]isothiazolyl, benzo[d]thiazolyl, indazolyl, benzo[d]imidazolyl, benzo[d]imidazolyl, and benzo[d][1,2,3]triazolyl.

The term "heterocycloalkyl" refers to a saturated 3-6 membered monocyclic or 8-12 membered bicyclic ring system, referred to herein as $C_{3-6}$monoheterocycloalkyl and $C_{8-12}$biheterocycloalkyl, containing one to four independently selected heteroatoms, such as nitrogen, oxygen, and sulfur (including its oxidation states: S, S(O) and $SO_2$). Where possible, heterocycloalkyl rings may be linked to the adjacent radical through carbon or nitrogen. Examples of $C_{3-6}$monoheterocycloalkyl groups include, but are not limited to, aziridinyl, oxiranyl, thiiranyl 1,1-dioxide, oxetanyl, azetidinyl, thietanyl 1,1-dioxide, pyrrolidinyl, tetrahydrofuranyl, piperidinyl, tetrahydro-2H-pyranyl, morpholinyl, thiomorpholinyl, and piperazinyl. Examples of $C_{8-12}$biheterocycloalkyl groups include, but are not limited to, 1,4-dioxaspiro[4.5]decanyl and 1,5-dioxaspiro[5.5]undecanyl.

The term "heterocycloalkenyl" refers to a partially unsaturated 3-6 membered monocyclic or 8-12 membered bicyclic ring system, referred to herein as $C_{3-6}$monoheterocycloalkenyl and $C_{8-12}$biheterocycloalkenyl, containing one to four independently selected heteroatoms, such as nitrogen, oxygen, and sulfur (including its oxidation states: S, S(O) or $S(O)_2$. Where possible, heterocycloalkenyl rings may be linked to the adjacent radical through carbon or nitrogen. For bicyclic heterocycloalkenyl groups: 1) either one or both rings may contain one or more double bonds and 2) the two rings may be attached through the same or different ring atoms. Examples of $C_{3-6}$monoheterocycloalkenyl groups include, but are not limited to, 2,3-dihydro-1H-pyrrolyl, 2,5-dihydro-1H-pyrrolyl, 4,5-dihydro-1H-pyrazolyl, 2,3-dihydro-1H-pyrazolyl, 4,5-dihydro-1H-imidazolyl, 2,3-dihydro-1H-imidazolyl, 2,3-dihydrothiophenyl, 2,5-dihydrothiophenyl, 4,5-dihydrothiazolyl, 2,3-dihydrothiazolyl, 4,5-dihydroisothiazolyl, 2,3-dihydroisothiazolyl, 2,3-dihydrofuranyl, 2,5-dihydrofuranyl, 4,5-dihydrooxazolyl, 2,3-dihydrooxazolyl, 4,5-dihydroisoxazolyl, 2,3-dihydroisoxazolyl, 3,4-dihydropyridinyl, 2,3-dihydropyridinyl, 2,3,4,5-tetrahydropyridinyl, 1,6-dihydropyridazinyl, 4,5-dihydropyridazinyl, 3,4,5,6-tetrahydropyridazinyl, 4,5-dihydropyrimidinyl, 1,2,5,6-tetrahydropyrimidinyl, 1,2-dihydropyrimidinyl, 1,2-dihydropyrazinyl, 2,3-dihydropyrazinyl, 1,2,3,6-tetrahydropyrazinyl, 4H-1,4-oxazinyl, 3,4-dihydro-2H-1,4-oxazinyl, 4H-1,4-thiazinyl, and 3,4-dihydro-2H-1,4-thiazinyl. Examples of $C_{8-12}$biheterocycloalkenyl groups include, but are not limited to, 6,7-dihydroindolyl, 4,5-dihydroindolyl, 7,8-dihydroimidazo[1,2-a]pyridinyl, 5,6-dihydroimidazo[1,2-a]pyridinyl, 4,5-dihydrobenzo[d]imidazolyl, 6,7-dihydro-1H-indazolyl, 4,5-dihydro-1H-indazolyl, 4,5-dihydropyrazolo[1,5-a]pyridinyl, and 6,7-dihydropyrazolo[1,5-a]pyridinyl.

The term "heterocyclyl" as used herein refers to a bicyclic ring system formed by either (1) fusing a phenyl ring to a 3-6 membered monocyclic heterocycloalkyl or 4-7 membered monocyclic heterocycloalkenyl ring, or (2) fusing a 5-6 membered monocyclic heteroaryl ring to a $C_{3-6}$ cycloalkyl, $C_{4-7}$ cycloalkenyl, 3-6 membered monocyclic heterocycloalkyl or 4-6 membered monocyclic heterocycloalkenyl ring. Where possible, the rings may be linked to the adjacent radical though carbon or nitrogen. Examples of heterocyclyls include, but are not limited to isochromanyl, 2H-quinolinyl, 6,7,8,9-tetrahydro-5H-[1,2,4]triazolo[4,3-a]azepine, 5,6,8,9-tetrahydro-[1,2,4]triazolo[4,3-d][1,4]oxazepane, 6,7-dihydro-5H,9H-[1,2,4]triazolo[3,4-c][1,4]oxazepane, 5,6,8,9-tetrahydro-712-[1,2,4]triazolo[4,3-d][1,4]diazepine, 8,9-dihydro-5H-[1,2,4]triazolo[4,3-a]azepine, 6,9-dihydro-5H-[1,2,4]triazolo[4,3-a]azepine, 5,6,7,8-tetrahydro-[1,2,4]triazolo[4,3-a]pyridine, 5,6-dihydro-8H-[1,2,4]triazolo[3,4-c][1,4]oxazine, 5,6,7,8-tetrahydroimidazo[1,2-a]pyridine, and 5H,9H-[1,2,4]triazolo[3,4-c][1,4]oxazepine.

The terms "hydroxy" and "hydroxyl" as used herein refers to the radical —OH.

The term "hydroxyalkyl" as used herein refers to an alkyl group substituted with one or more hydroxy groups. Examples include, but are not limited to, $HOCH_2$—, $HOCH_2CH_2$—, $CH_3CH(OH)CH_2$— and $HOCH_2CH(OH)CH_2$—.

The term "hydroxyalkoxy" as used herein refers to an alkoxy group substituted with one or more hydroxy groups. Examples include but are not limited to $HOCH_2O$—, $HOCH_2CH_2O$—, $CH_3CH(OH)CH_2O$— and $HOCH_2CH(OH)CH_2O$—.

The term "$R^aR^bNC_{1-6}$ alkyl-," as used herein refers to an alkyl group substituted with a $R^aR^bN$— group, as defined herein. Examples include but are not limited to $NH_2CH_2$—, $NH(CH_3)CH_2$—, $N(CH_3)_2CH_2CH_2$— and $CH_3CH(NH_2)CH_2$—.

The term "$R^aR^bNC_{1-6}$alkoxy," as used herein refers to an alkoxy group substituted with a $R^aR^bN$— groups, as defined herein. Examples include but are not limited to $NH_2CH_2$—, $NH(CH_3)CH_2O$—, $N(CH_3)_2CH_2CH_2O$— and $CH_3CH(NH_2)CH_2O$—.

The term "oxo" as used herein refers to the radical =O.

As used herein, when a bicyclic ring is shown with a floating point of attachment and/or floating substituents, for example as in

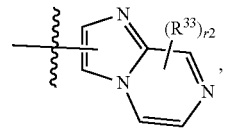

it signifies that the bicyclic ring can be attached via a carbon atom on either ring, and that the substituents (e.g., the $R^{33}$ group(s)) can be independently attached to either or both rings.

The terms "Individual," "patient," or "subject" are used interchangeably and include any animal, including mammals, preferably mice, rats, other rodents, rabbits, dogs, cats, swine, cattle, sheep, horses, or primates, and most preferably humans. The compounds or pharmaceutical compositions of the disclosure can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, dogs, primates, and the like). The mammal treated in the methods of the disclosure is desirably a mammal in which treatment of HBV infection is desired.

The term "modulation" includes antagonism (e.g., inhibition), agonism, partial antagonism and/or partial agonism.

The term "Pharmaceutically acceptable" include molecular entities and compositions that do not produce an adverse, allergic or other untoward reaction when administered to an animal, or a human, as appropriate. For human administration, preparations should meet sterility, pyrogenicity, and general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, fillers, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable excipients.

The term "pharmaceutically acceptable salt(s)" as used herein refers to salts of acidic or basic groups that may be present in compounds used in the compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts, particularly calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

The term "therapeutically effective amount" or "effective amount" as used herein refers to the amount of the subject compound that will elicit the biological or medical response of a tissue, system or animal, (e.g. mammal or human) that is being sought by the researcher, veterinarian, medical doctor or other clinician. The compounds or pharmaceutical compositions of the disclosure are administered in therapeutically effective amounts to treat a disease. Alternatively, a therapeutically effective amount of a compound is the quantity required to achieve a desired therapeutic and/or prophylactic effect.

The term "treating" includes any effect, e.g., lessening, reducing, modulating, or eliminating, via disruption of HBV core protein assembly, that results in the improvement of the disease. "Disruption" includes inhibition of HBV viral assembly and infection.

The compounds of the disclosure may contain one or more chiral centers and, therefore, exist as stereoisomers. The term "stereoisomers" when used herein consist of all enantiomers or diastereomers. These compounds may be designated by the symbols "(+)," "(−)," "R" or "S," depending on the configuration of substituents around the stereogenic carbon atom, but the skilled artisan will recognize that a structure may denote a chiral center implicitly. The present disclosure encompasses various stereoisomers of these compounds and mixtures thereof. Mixtures of enantiomers or diastereomers may be designated "(±)" in nomenclature, but the skilled artisan will recognize that a structure may denote a chiral center implicitly.

The compounds of the disclosure may contain one or more double bonds and, therefore, exist as geometric isomers resulting from the arrangement of substituents around a carbon-carbon double bond. The symbol ═══ denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond.

Compounds of the disclosure may contain a carbocyclic or heterocyclic ring and therefore, exist as geometric isomers resulting from the arrangement of substituents around the ring. The arrangement of substituents around a carbocyclic or heterocyclic ring are designated as being in the "Z" or "E" configuration wherein the terms "Z" and "E" are used in accordance with IUPAC standards. Unless otherwise specified, structures depicting carbocyclic or heterocyclic rings encompass both "Z" and "E" isomers. Substituents around a carbocyclic or heterocyclic ring may also be referred to as "cis" or "trans", where the term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

Individual enantiomers and diastereomers of compounds of the present disclosure can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well-known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantiomeric and diastereoselective transformations and may involve the use of chiral auxiliaries. For examples, see Carreira and Kvaerno, *Classics in Stereoselective Synthesis*, Wiley-VCH: Weinheim, 2009.

The compounds disclosed herein can exist in solvated as well as unsolvated forms with pharmaceutically acceptable solvents such as water, ethanol, and the like, and it is intended that the disclosure embrace both solvated and unsolvated forms. In one embodiment, the compound is amorphous. In one embodiment, the compound is a single polymorph. In another embodiment, the compound is a mixture of polymorphs. In another embodiment, the compound is in a crystalline form.

The disclosure also embraces isotopically labeled compounds of the disclosure which are identical to those recited herein, except that one or more atoms are replaced by an atom having an atomic mass or mass number different from the atomic mass or mass number usually found in nature. Examples of isotopes that can be incorporated into compounds of the disclosure include isotopes of hydrogen, carbon, nitrogen, oxygen, phosphorus, sulfur, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. For example, a compound of the disclosure may have one or more H atom replaced with deuterium.

Certain isotopically-labeled disclosed compounds (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labeled compounds of the disclosure can generally be prepared by following procedures analogous to those disclosed in the examples herein by substituting an isotopically labeled reagent for a non-isotopically labeled reagent.

The term "prodrug" refers to compounds that are transformed in vivo to yield a disclosed compound or a pharmaceutically acceptable salt, hydrate or solvate of the compound. The transformation may occur by various mechanisms (such as by esterase, amidase, phosphatase, oxidative and or reductive metabolism) in various locations (such as in the intestinal lumen or upon transit of the intestine, blood or liver). Prodrugs are well known in the art (for example, see Rautio, Kumpulainen, et al., Nature Reviews Drug Discovery 2008, 7, 255).

II. 5-Membered Heteroaryl Carboxamide Compounds

In one aspect, the present disclosure provides a compound of Formula I

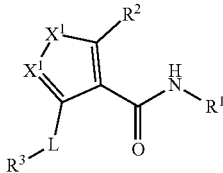

Formula I or a pharmaceutically acceptable salt thereof, wherein:
$X^1$ is $NR^{x1}$, O or S;
$X^2$ is N or $CR^{x2}$;
$X^3$ is O, $NR^7$, $CR^4R^8$, C(O), $S(O)_t$, $C=CR^4R^0$ or $C=NR^4$;
$X^4$ and $X^6$ are independently O or S;
$X^5$ is O, S or $NR^0$;
L is a bond or $C_{1-6}$ alkylene;
$L^1$ is a bond, $C_{1-6}$alkylene, O, $NR^c$, C(O), $C(O)NR^c$, $S(O)_t$ or $S(O)_tNR^c$;
$R^{x1}$ and $R^{x2}$ are independently selected from the group consisting of hydrogen, $C_{1-6}$ alkyl, halo$C_{1-6}$ alkyl and $C_{3-6}$ monocycloalkyl;
$R^a$, $R^b$ and $R^c$ are independently selected for each occurrence from the group consisting of hydrogen, $C_{1-6}$ alkyl, halo$C_{1-6}$ alkyl and $C_{3-6}$ monocycloalkyl;
$R^d$ is hydrogen, OH, $C_{1-6}$ alkyl or $C_{1-6}$ alkoxy;
$R^0$, $R^6$, $R^8$ and $R^{11}$ are independently selected for each occurrence from the group consisting of hydrogen, halogen, OH, CN, $NO_2$, oxo, $R^aN=$, hydrazino, formyl, azido, silyl, siloxy, HOC(O)—, $R^aR^bN$—, $R^aR^bNS(O)_t$—, $C_{1-6}$alkyl, $C_{2-6}$alkenyl, $C_{2-6}$alkynyl, $C_{3-6}$monocycloalkyl, halo$C_{1-6}$alkyl, hydroxy$C_{1-6}$alkyl-, $R^aR^bNC_{1-6}$alkyl-, HOC(O)$C_{1-6}$alkyl-, $R^aR^bNC_{1-6}$alkylNR$^c$—, $C_{1-6}$alkylNR$^a$C$_{1-6}$alkylNR$^c$—, $C_{1-6}$alkoxy, halo$C_{1-6}$alkoxy, hydroxy$C_{1-6}$alkoxy-, $R^aR^bNC_{1-6}$alkoxy-, halo$C_{1-6}$alkoxy$C_{1-6}$alkyl-, $R^aR^bNC(O)$—, $C_{1-6}$alkylC(O)—, $C_{1-6}$alkoxyC(O)—, $C_{1-6}$alkylC(O)O—, $C_{1-6}$alkylS(O)$_q$—, $C_{1-6}$alkylS(O)NR$^c$—, $C_{1-6}$alkylS(O)$_t$C$_{1-6}$alkyl-, $C_{1-6}$alkylS(O)NR$^a$C$_{1-6}$alkyl-, $C_{3-6}$cycloalkylS(O)$_t$C$_{1-6}$alkyl-, $C_{1-6}$alkylC(O)C$_{1-6}$alkyl-, and $C_{1-6}$alkylC(O)OC$_{1-6}$alkyl-;
$R^{0a}$ is independently selected for each occurrence from the group consisting of hydrogen, halogen, OH, CN, $NO_2$, $R^aR^bN$—, $C_{1-6}$alkyl and halo$C_{1-6}$alkyl;

$R^1$ is a phenyl, naphthyl, $C_{3-6}$ monocycloalkyl, $C_{3-6}$ monoheterocycloalkyl, or 5-6 membered monocyclic heteroaryl, wherein: the phenyl, $C_{3-6}$ monocycloalkyl, $C_{3-6}$ monoheterocycloalkyl, or 5-6 membered monocyclic heteroaryl is optionally substituted with one, two, or three independently selected groups;
$R^2$ is hydrogen, halogen, $R^aR^bN$, $C_{1-6}$ alkyl, halo$C_{1-6}$ alkyl, $C_{3-6}$ monocycloalkyl or $C_{1-6}$ alkoxy;
$R^3$ is selected from the group consisting of:

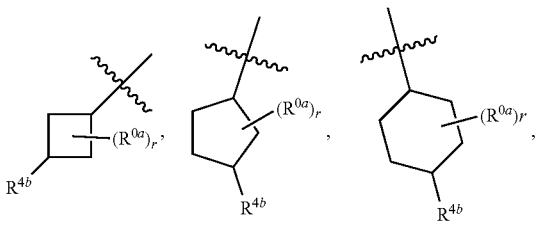

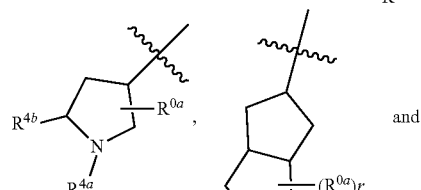

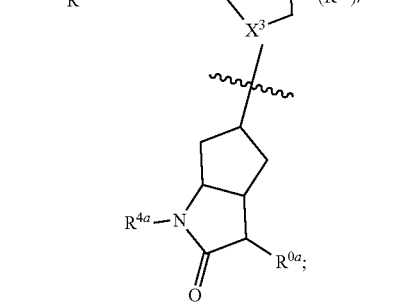

$R^4$ is $R^5$, $R^6$ or $R^5$-$L^1$-;
or $R^4$ and $R^8$ together with the carbon atom to which they are attached form a

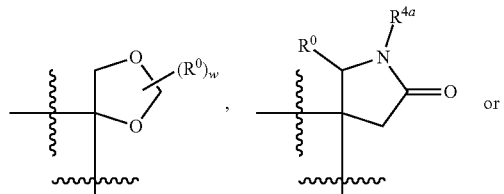

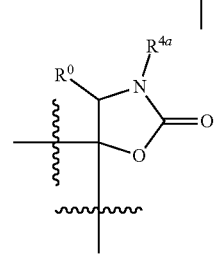

group;
$R^{4a}$ is hydrogen or $C_{1-6}$ alkyl;
$R^{4b}$ is $R^5$, $R^{5a}$, $R^6$ or $R^5$-$L^1$-;

R⁵ is selected from the group consisting of:

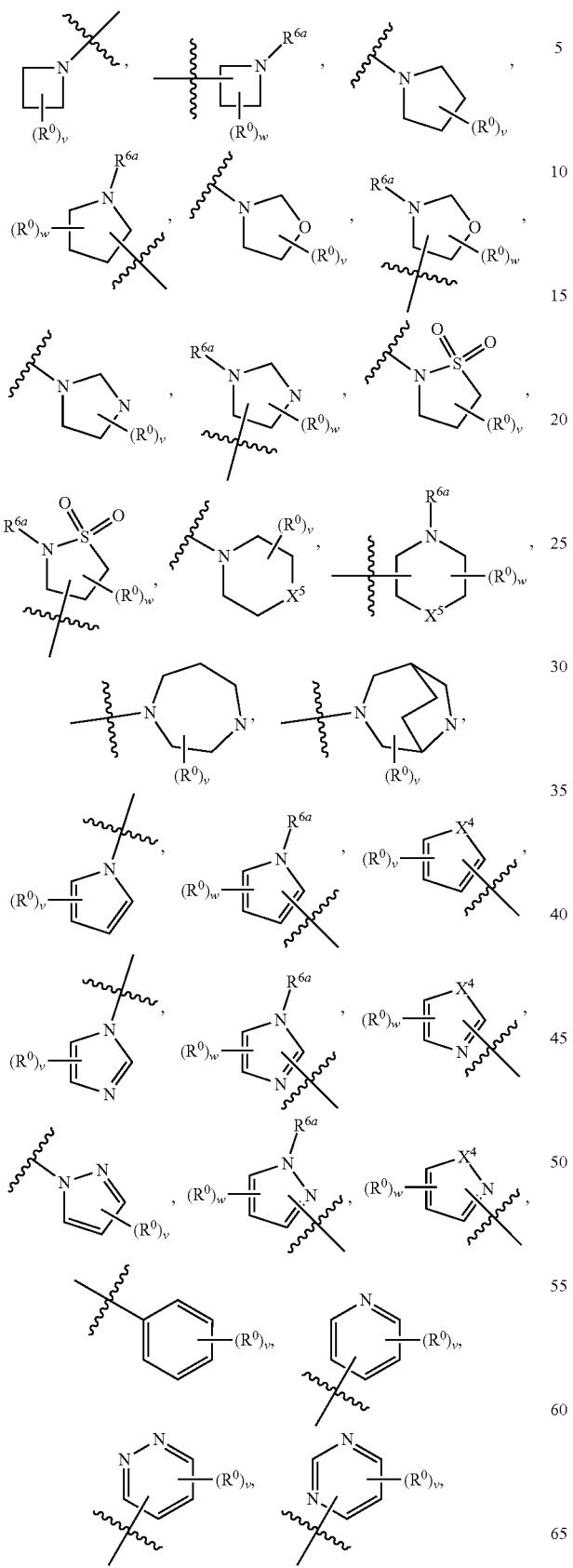

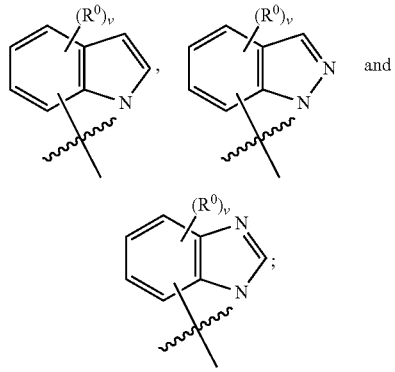

R⁵ᵃ is

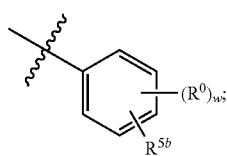

R⁵ᵇ is

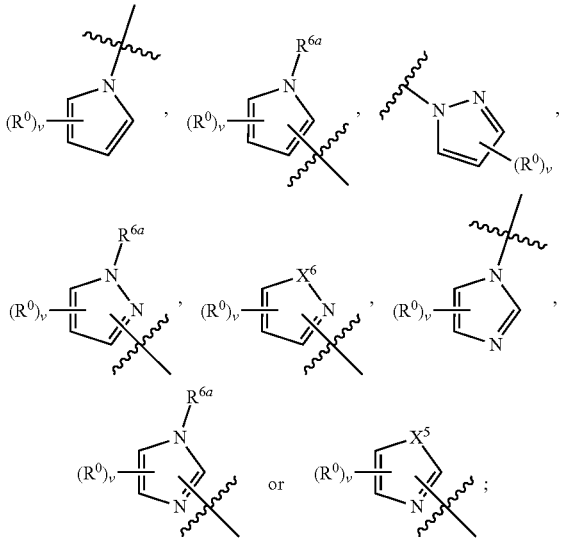

R⁶ᵃ is hydrogen or C₁₋₆ alkyl;

R⁷ is hydrogen, C₁₋₆ alkyl, C₁₋₆ haloalkyl, C₁₋₆ alkoxyC₁₋₆alkyl-, NRᵃRᵇC(O)—, R⁷ᵃC(O)—, C₁₋₆ alkyloxyC(O)—, C₁₋₆ alkylS(O)_q— or C₁₋₆ haloalkylS(O)_q—;

R⁷ᵃ is C₁₋₆ alkyl or C₃₋₆ monocycloalkyl;

q, r, t, and w are independently selected for each occurrence from 0, 1 and 2; and v is independently selected for each occurrence from 0, 1, 2 and 3.

In one aspect, the present disclosure provides a compound of Formula I

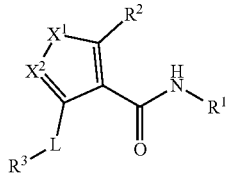

Formula I or a pharmaceutically acceptable salt thereof, wherein:

$X^1$ is $NR^{x1}$, O or S;

$X^2$ is N or $CR^{x2}$;

$X^3$ is O, $NR^7$, $CR^4R^8$, C(O), $S(O)_t$, $C=CR^4R^0$ or $C=NR^4$;

$X^4$ is O or S;

$X^5$ is O, S or $NR^0$;

L is a bond or $C_{1-6}$alkylene;

$L^1$ is a bond, $C_{1-6}$ alkylene, O, $NR^c$, C(O), $C(O)NR^c$, $S(O)_t$ or $S(O)_tNR^c$;

$R^{x1}$ and $R^{x2}$ are independently selected from the group consisting of hydrogen, $C_{1-6}$ alkyl, halo$C_{1-6}$ alkyl and $C_{3-6}$ monocycloalkyl;

$R^a$, $R^b$ and $R^c$ are independently selected for each occurrence from the group consisting of hydrogen, $C_{1-6}$ alkyl, halo$C_{1-6}$ alkyl and $C_{3-6}$ monocycloalkyl;

$R^d$ is hydrogen, OH, $C_{1-6}$alkyl or $C_{1-6}$alkoxy;

$R^0$, $R^6$, $R^8$ and $R^{11}$ are independently selected for each occurrence from the group consisting of hydrogen, halogen, OH, CN, $NO_2$, oxo, $R^dN=$, hydrazino, formyl, azido, silyl, siloxy, HOC(O)—, $R^aR^bN$—, $R^aR^bNS(O)_t$—, $C_{1-6}$alkyl, $C_{2-6}$alkenyl, $C_{2-6}$alkynyl, $C_{3-6}$monocycloalkyl, halo$C_{1-6}$alkyl, hydroxy$C_{1-6}$alkyl-, $R^aR^bNC_{1-6}$alkyl-, HOC(O)$C_{1-6}$alkyl-, $R^aR^bNC_{1-6}$alkylNR$^c$—, $C_{1-6}$alkylNR$^a$C$_{1-6}$alkylNR$^c$—, $C_{1-6}$alkoxy, halo$C_{1-6}$alkoxy, hydroxy$C_{1-6}$alkoxy-, $R^aR^bNC_{1-6}$alkoxy-, $C_{1-6}$alkoxy$C_{1-6}$alkyl-, halo$C_{1-6}$alkoxy$C_{1-6}$alkyl-, $R^aR^bNC(O)$—, $C_{1-6}$alkylC(O)—, $C_{1-6}$alkoxyC(O)—, $C_{1-6}$alkylC(O)O—, $C_{1-6}$alkylS(O)$_q$—, $C_{1-6}$alkylS(O)$_t$NR$^c$—, $C_{1-6}$alkylS(O)$_t$C$_{1-6}$alkyl-, $C_{1-6}$alkylS(O)$_t$NR$^a$C$_{1-6}$alkyl-, $C_{3-6}$cycloalkylS(O)$_t$C$_{1-6}$alkyl-, $C_{1-6}$alkylC(O)C$_{1-6}$alkyl-, and $C_{1-6}$alkylC(O)OC$_{1-6}$alkyl-;

$R^1$ is a phenyl, naphthyl, $C_{3-6}$monocycloalkyl, $C_{3-6}$monoheterocycloalkyl, or 5-6 membered monocyclic heteroaryl, wherein: the phenyl, $C_{3-6}$monocycloalkyl, $C_{3-6}$monoheterocycloalkyl, or 5-6 membered monocyclic heteroaryl is optionally substituted with one, two, or three independently selected $R^{11}$ groups;

$R^2$ is hydrogen, halogen, $R^aR^bN$, $C_{1-6}$alkyl, halo$C_{1-6}$alkyl, $C_{3-6}$monocycloalkyl or $C_{1-6}$alkoxy;

$R^3$ is selected from the group consisting of:

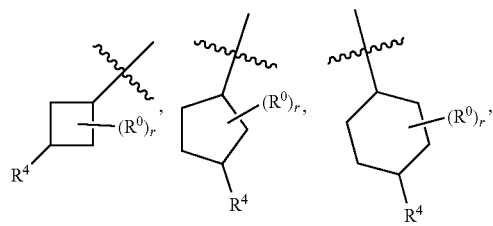

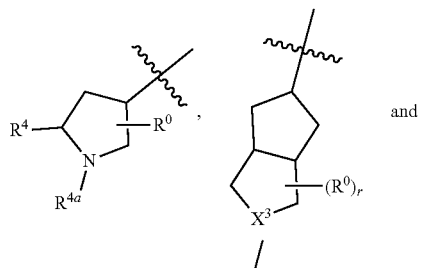

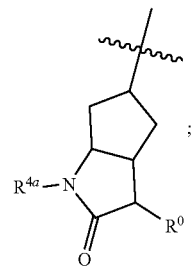

$R^4$ is $R^5$, $R^6$ or $R^5$-$L^1$-.

$R^{4a}$ is hydrogen or $C_{1-6}$alkyl;

$R^5$ is selected from the group consisting of:

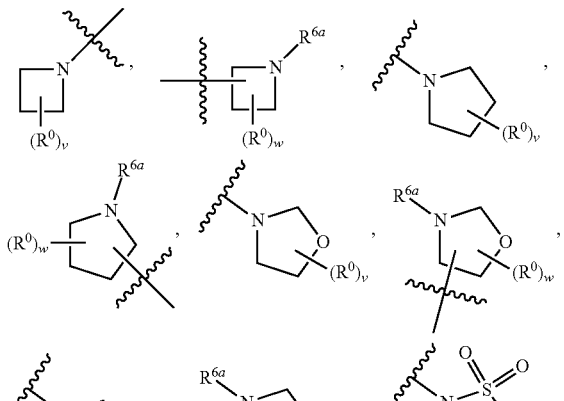

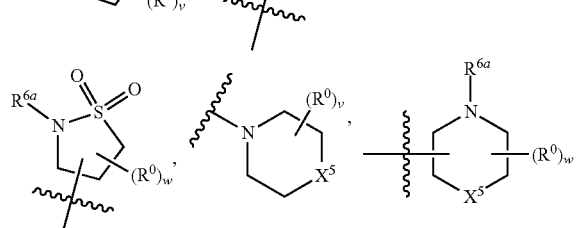

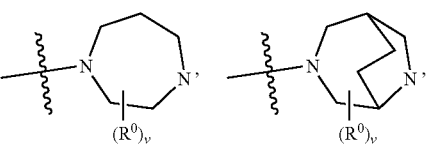

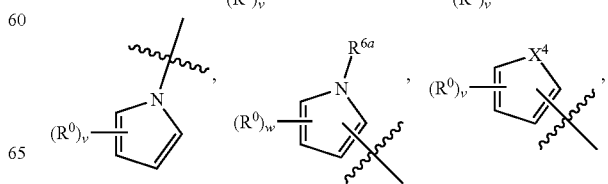

-continued

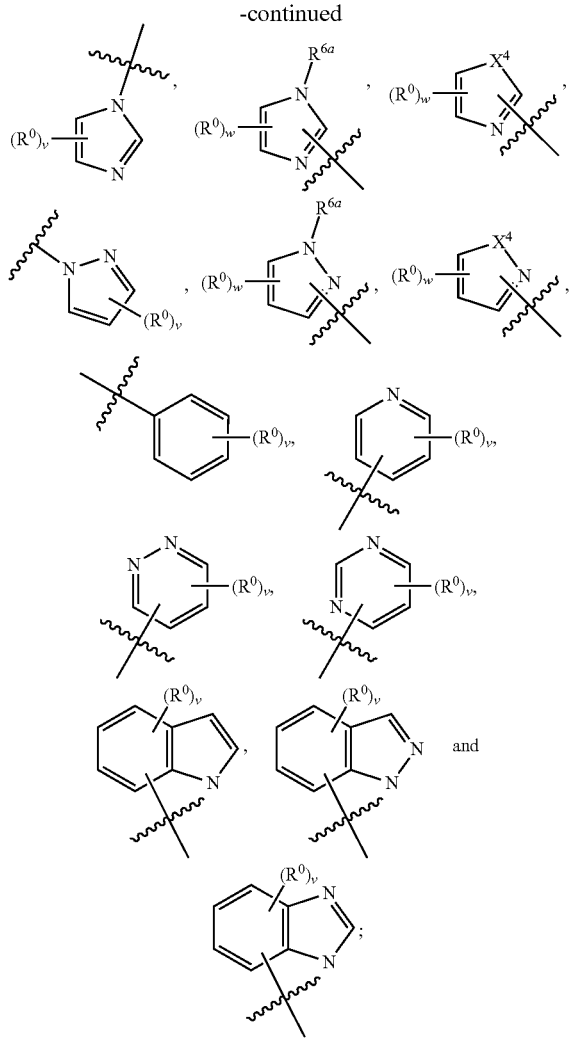

$R^{6a}$ is hydrogen or $C_{1-6}$alkyl;

$R^7$ is hydrogen, $C_{1-6}$alkyl, $C_{1-6}$haloalkyl, $C_{1-6}$alkoxyC$_{1-6}$alkyl-, $NR^aR^bC(O)$—, $R^{7a}C(O)$—, $C_{1-6}$alkyloxyC(O)—, $C_{1-6}$alkylS(O)$_q$— or $C_{1-6}$haloalkylS(O)$_q$—;

$R^{7a}$ is $C_{1-6}$alkyl or $C_{3-6}$monocycloalkyl;

q, r, t, and w are independently selected for each occurrence from 0, 1 and 2; and v is independently selected for each occurrence from 0, 1, 2 and 3.

The following embodiments further describe a compound of Formula I, or a pharmaceutically acceptable salt thereof. It will be appreciated that all chemically allowable combinations of the embodiments described herein are envisioned as further embodiments of the invention.

In certain embodiments, $X^1$ is $NR^{x1}$ and $X^2$ is N.

In certain embodiments, $X^1$ is $NR^{x1}$, $X^2$ is N, and $R^{x1}$ is hydrogen of methyl.

In certain embodiments, $X^1$ is $NR^{x1}$, $X^2$ is N, and $R^{x1}$ is methyl.

In certain embodiments, $X^1$ is O and $X^2$ is N.

In certain embodiments, $X^3$ is $CR^4R^8$.

In certain embodiments, L is a bond.

In certain embodiments, $X^1$ is $NR^{x1}$, $X^2$ is N, $R^{x1}$ is methyl, and L is a bond.

In certain embodiments, L is a $C_{1-6}$alkylene.

In certain embodiments, L1 is a bond.

In certain embodiments, L1 is a $C_{1-6}$alkylene.

In certain embodiments, $R^{0a}$ is hydrogen.

In certain embodiments, $R^1$ is

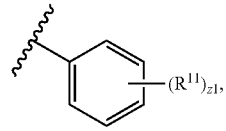

wherein:

$R^{11}$ is independently selected for each occurrence from the group consisting of halogen, CN, $C_{1-6}$alkyl and haloC$_{1-6}$alkyl; and z1 is 0, 1, 2 or 3.

In certain embodiments, $R^{11}$ is independently selected for each occurrence from the group consisting of halogen and CN.

In certain embodiments, $R^{11}$ is independently selected for each occurrence from the group consisting of F, Cl, Br and I.

In certain embodiments, $R^1$ is selected from the group consisting of:

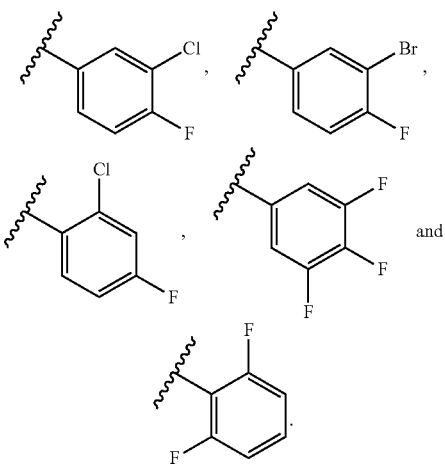

In certain embodiments, $R^1$ is

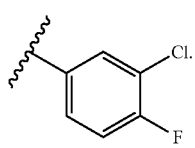

In certain embodiments, $X^1$ is $NR^{x1}$, $X^2$ is N, $R^{x1}$ is methyl, L is a bond, and $R^1$ is

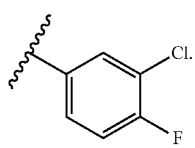 [SMILES: *c1ccc(F)c(Cl)c1]

In certain embodiments, $R^1$ is a $C_{3-6}$monocycloalkyl optionally substituted with one, two, or three substituents independently selected from the group consisting of halogen, CN, $C_{1-6}$alkyl, and halo$C_{1-6}$alkyl.

In certain embodiments, $R^1$ is

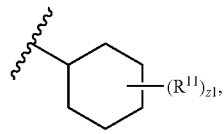

wherein:

$R^{11}$ is independently selected for each occurrence from the group consisting of halogen, CN, $C_{1-6}$alkyl, and halo$C_{1-6}$alkyl; and z1 is 0, 1, 2 or 3.

In certain embodiments, $R^1$ is a $C_{3-6}$monoheterocycloalkyl optionally substituted with one, two, or three substituents independently selected from the group consisting of halogen, CN, $C_{1-6}$alkyl, and halo$C_{1-6}$alkyl.

In certain embodiments, $R^1$ is

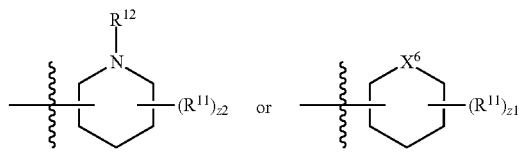

wherein:

$R^{11}$ is independently selected for each occurrence from the group consisting of hydrogen, halogen, CN, $C_{1-6}$alkyl, and halo$C_{1-6}$alkyl;

$R^{12}$ is hydrogen or $C_{1-6}$alkyl;

$X^6$ is O or S;

z1 is 0, 1, 2 or 3; and z2 is 0, 1 or 2.

In certain embodiments, $R^1$ is a 5-6 membered monocyclic heteroaryl optionally substituted with one, two, or three substituents independently selected from the group consisting of halogen, CN, $C_{1-6}$alkyl, and halo$C_{1-6}$alkyl.

In certain embodiments, $R^1$ is

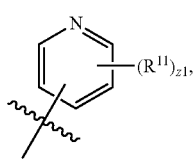

wherein:

$R^{11}$ is independently selected for each occurrence from the group consisting of halogen, CN, $C_{1-6}$alkyl and halo$C_{1-6}$alkyl; and z1 is 0, 1, 2 or 3.

In certain embodiments, $R^2$ is $R^aR^bN$;

In certain embodiments, $R^2$ is $R^aR^bN$, and $R^a$ and $R^b$ are independently selected the group consisting of hydrogen and $C_{1-6}$alkyl.

In certain embodiments, $R^2$ is $NH_2$.

In certain embodiments, $X^1$ is $NR^{x1}$, $X^2$ is N, $R^{x1}$ is methyl, L is a bond, $R^1$ is

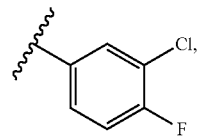 [SMILES: *c1ccc(F)c(Cl)c1]

and $R^2$ is $NH_2$.

In certain embodiments, $R^3$ is

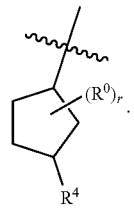

In certain embodiments, $R^3$ is

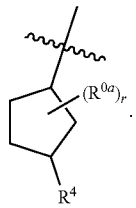

In certain embodiments, $R^3$ is

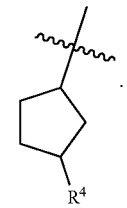

In certain embodiments, $R^3$ is

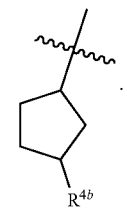

In certain embodiments, R³ is

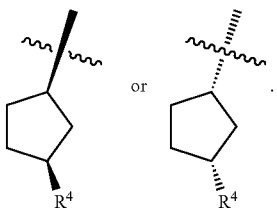 or .

In certain embodiments, R³ is

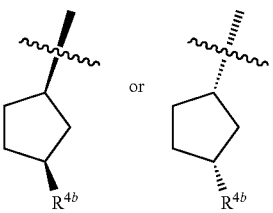 or .

In certain embodiments, R³ is

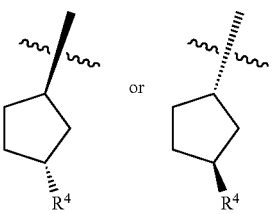 or .

In certain embodiments, R³ is

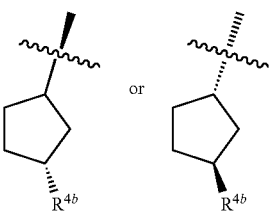 or .

In certain embodiments, R³ is

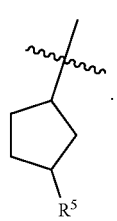.

In certain embodiments, R³ is

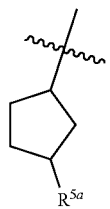.

In certain embodiments, R³ is

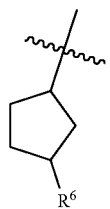.

In certain embodiments, $X^1$ is $NR^{x1}$, $X^2$ is N, $R^{x1}$ is methyl, L is a bond, $R^1$ is

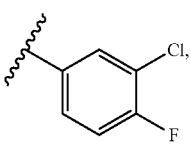 [SMILES: *c1ccc(F)c(Cl)c1]

$R^2$ is $NH_2$, and $R^3$ is

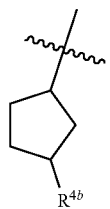.

In certain embodiments, $X^1$ is $NR^{x1}$, $X^2$ is N, $R^{x1}$ is methyl, L is a bond, $R^1$ is

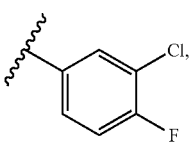 [SMILES: *c1ccc(F)c(Cl)c1]

$R^2$ is $NH_2$, and $R^3$ is
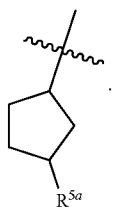
In certain embodiments, $R^3$ is
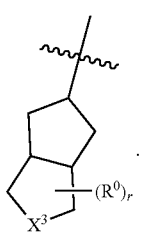
In certain embodiments, $R^3$ is
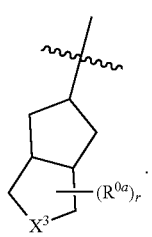
In certain embodiments, $R^3$ is
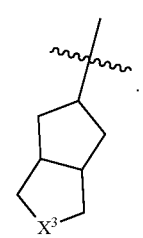
In certain embodiments, $X^1$ is $NR^{x1}$, $X^2$ is N, $R^{x1}$ is methyl, L is a bond, $R^1$ is
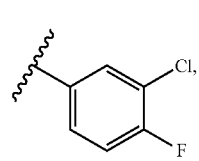 [SMILES: *c1ccc(F)c(Cl)c1]
$R^2$ is $NH_2$, and $R^3$ is
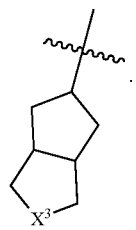
In certain embodiments, $R^3$ is
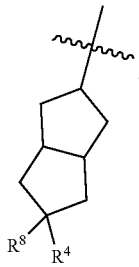
In certain embodiments, $R^3$ is
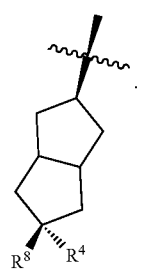
In certain embodiments, $R^3$ is
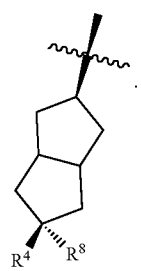

In certain embodiments, $R^3$ is

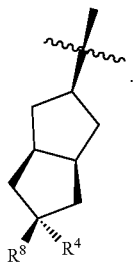

In certain embodiments, $R^3$ is

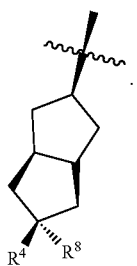

In certain embodiments, $R^4$ is $R^5$.
In certain embodiments, $R^4$ is $R^6$.
In certain embodiments, $R^4$ is $R^5$-$L^1$-.
In certain embodiments, $R^3$ is

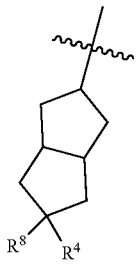

and $R^4$ and $R^8$ together with the carbon atom to which they are attached form a

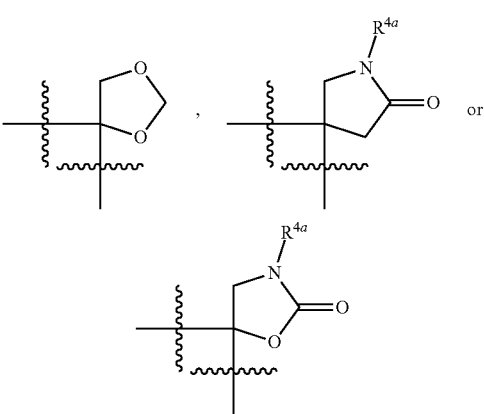

group.

In certain embodiments, $R^3$ is

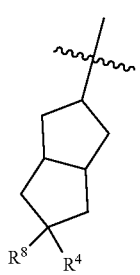

and $R^4$ and $R^8$ together with the carbon atom to which they are attached form a group, wherein $R^{4a}$ is hydrogen or methyl.

In certain embodiments, $R^3$ is

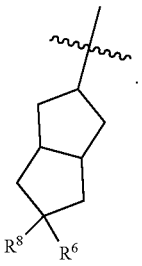

In certain embodiments, $R^3$ is

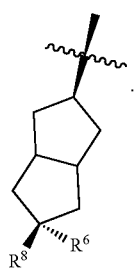

In certain embodiments, $R^3$ is
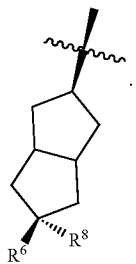
In certain embodiments, $R^3$ is
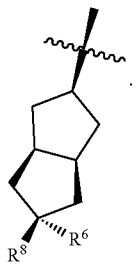
In certain embodiments, $R^3$ is
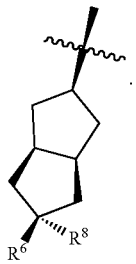
In certain embodiments, $R^5$ is selected from the group consisting of:
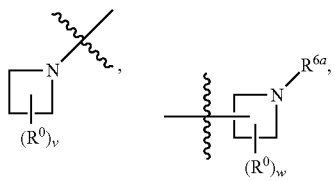 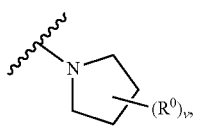
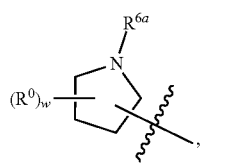 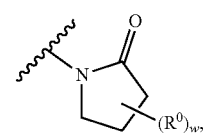
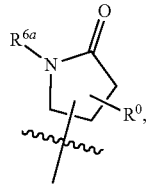 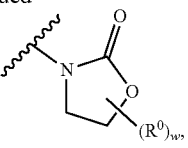
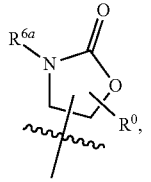 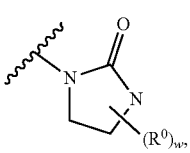
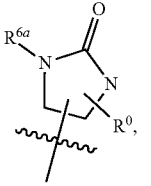 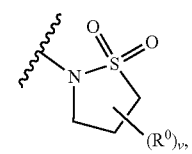
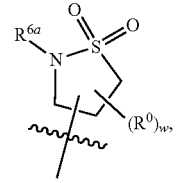 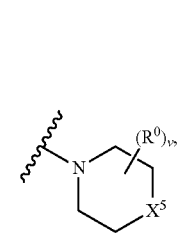
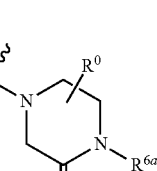
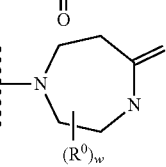 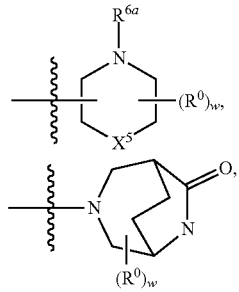
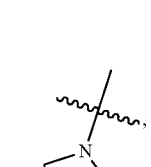
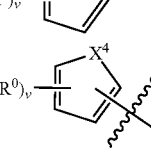 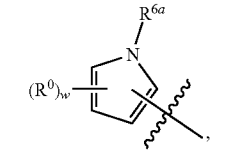
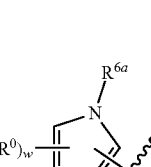 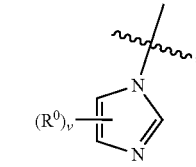
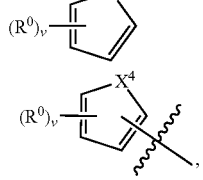 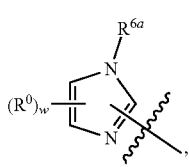 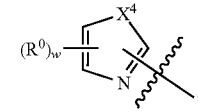

-continued

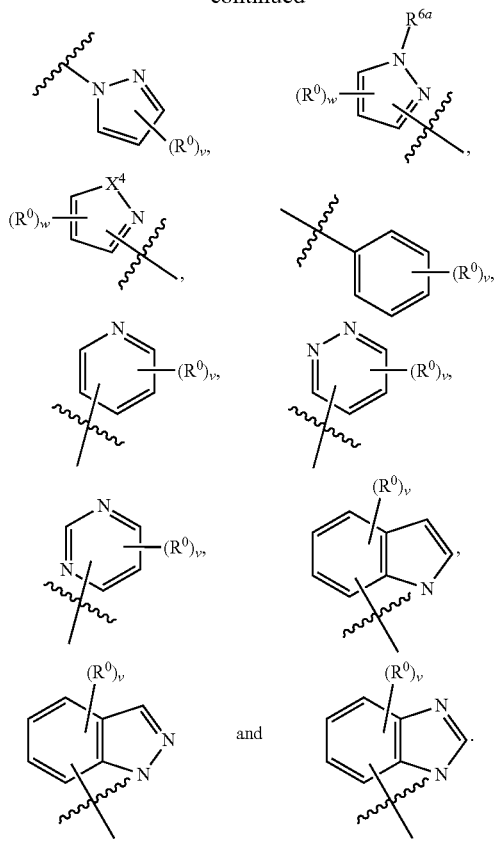

In certain embodiments, $R^5$ is selected from the group consisting of:

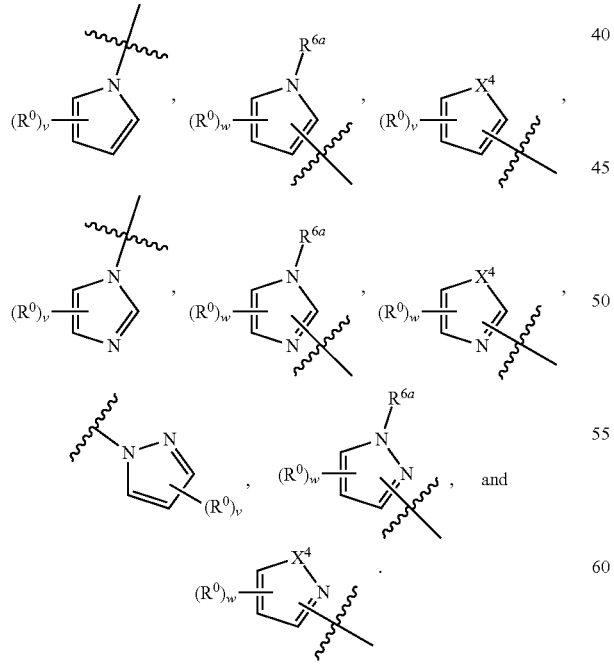

In certain embodiments, $R^6$ is $C_{1-6}alkylS(O)_tC_{1-6}alkyl$- or $C_{1-6}alkylS(O)NR^aC_{1-6}alkyl$-.

In certain embodiments, $R^6$ is $C_{1-6}alkylS(O)_tC_{1-6}alkyl$-.

In certain embodiments, $R^6$ is $C_{1-6}alkylS(O)_tC_{1-6}alkyl$-, and t is 1 or 2.

In certain embodiments, $R^6$ is $C_{1-6}alkylS(O)_tC_{1-6}alkyl$-, and t is 2.

In certain embodiments, $R^8$ is hydrogen, OH or $C_{1-6}alkoxy$.

In certain embodiments, $R^8$ is OH.

In certain embodiments, $R^3$ is

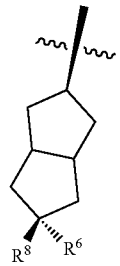

and $R^8$ is hydrogen, OH or $C_{1-6}alkoxy$.

In certain embodiments, $R^3$ is

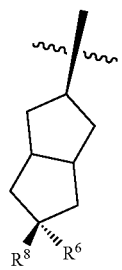

and $R^8$ is OH.

In certain embodiments, $R^3$ is

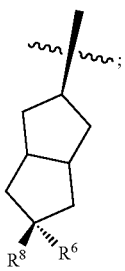

$R^6$ is $C_{1-6}alkylS(O)_tC_{1-6}alkyl$- or $C_{1-6}alkylS(O)NR^aC_{1-6}alkyl$-; and
$R^8$ is hydrogen, OH or $C_{1-6}alkoxy$.

In certain embodiments, $R^3$ is

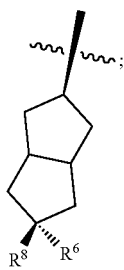

$R^6$ is $C_{1-6}alkylS(O)_tC_{1-6}alkyl$-; and
$R^8$ is hydrogen, OH or $C_{1-6}alkoxy$.

In certain embodiments, $R^3$ is

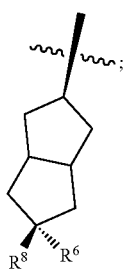

$R^6$ is $C_{1-6}alkylS(O)_tC_{1-6}alkyl$-; and
$R^8$ is OH.

In certain embodiments, $X^1$ is $NR^{x1}$, $X^2$ is N, $R^{x1}$ is methyl, L is a bond, $R^1$ is

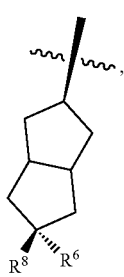

$R^2$ is $NH_2$, $R^3$ is

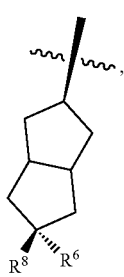

$R^8$ is hydrogen, OH or $C_{1-6}alkoxy$.

In certain embodiments, $X^1$ is $NR^{x1}$, $X^2$ is N, $R^{x1}$ is methyl, L is a bond, $R^1$ is

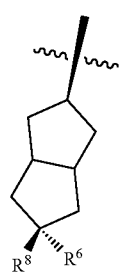

$R^2$ is $NH_2$, $R^3$ is

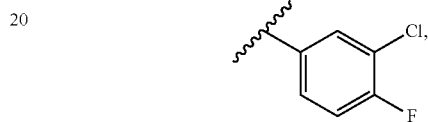

and $R^8$ is OH.

In certain embodiments, $X^1$ is $NR^{x1}$, $X^2$ is N, $R^{x1}$ is methyl, L is a bond, $R^1$ is

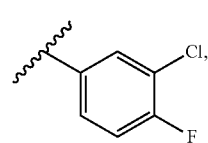 [SMILES: *c1ccc(F)c(Cl)c1]

$R^2$ is $NH_2$, $R^3$ is

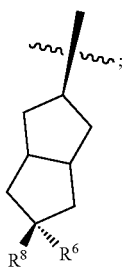

$R^6$ is $C_{1-6}alkylS(O)_tC_{1-6}alkyl$- or $C_{1-6}alkylS(O)_tNR^aC_{1-6}alkyl$-; and
$R^8$ is hydrogen, OH or $C_{1-6}alkoxy$.

In certain embodiments, $X^1$ is $NR^{x1}$, $X^2$ is N, $R^{x1}$ is methyl, L is a bond, $R^1$ is

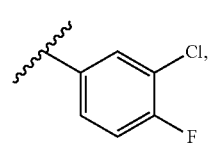

$R^2$ is $NH_2$, $R^3$ is

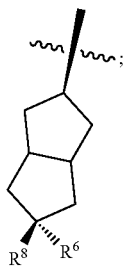

$R^6$ is $C_{1-6}alkylS(O)_tC_{1-6}alkyl$-; and
$R^8$ is hydrogen, OH or $C_{1-6}alkoxy$.

In certain embodiments, $X^1$ is $NR^{x1}$, $X^2$ is N, $R^{x1}$ is methyl, L is a bond, $R^1$ is

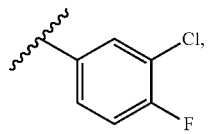 [SMILES: *c1ccc(F)c(Cl)c1]

$R^2$ is $NH_2$, $R^3$ is

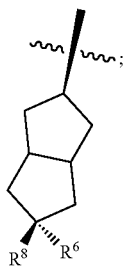

$R^6$ is $C_{1-6}alkylS(O)_tC_{1-6}alkyl$-; and
$R^8$ is OH.

III. Pharmaceutical Compositions and Kits

In another aspect, the disclosure provides pharmaceutical compositions comprising a compound of Formula I, or a pharmaceutically acceptable salt thereof, and a pharmaceutically acceptable excipient. In particular, the present disclosure provides pharmaceutical compositions comprising compounds as disclosed herein formulated together with one or more pharmaceutically acceptable carriers. These formulations include those suitable for oral, rectal, topical, buccal, parenteral (e.g., subcutaneous, intramuscular, intradermal, or intravenous), rectal, vaginal, or aerosol administration, although the most suitable form of administration in any given case will depend on the degree and severity of the condition being treated and on the nature of the particular compound being used. For example, disclosed compositions may be formulated as a unit dose, and/or may be formulated for oral or subcutaneous administration.

In another aspect, the disclosure provides a pharmaceutical composition comprises a compound of Table 17, or a pharmaceutically acceptable salt and/or stereoisomer thereof.

Exemplary pharmaceutical compositions of this disclosure may be used in the form of a pharmaceutical preparation, for example, in solid, semisolid or liquid form, which contains one or more compounds of the disclosure, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

For preparing solid compositions such as tablets, the principal active ingredient may be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the disclosure, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds of the present disclosure may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of this disclosure suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants.

In another aspect, the disclosure provides enteral pharmaceutical formulations including a disclosed compound and an enteric material; and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e. g., Eudragit L30D55, Eudragit FS30D, Eudragit L100, Eudragit 5100, Kollicoat EMM30D, Estacryl 30D, Coateric, and Aquateric). The solubility of each of the above materials is either known or is readily determinable in vitro. The foregoing is a list of possible materials, but one of skill in the art with the benefit of the disclosure would recognize that it is not comprehensive and that there are other enteric materials that would meet the objectives of the present disclosure.

Advantageously, the disclosure also provides kits for use by a e.g. a consumer in need of HBV infection treatment. Such kits include a suitable dosage form such as those described above and instructions describing the method of using such dosage form tomediate, reduce or prevent HBV infection. The instructions would direct the consumer or medical personnel to administer the dosage form according to administration modes known to those skilled in the art. Such kits could advantageously be packaged and sold in single or multiple kit units. An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of a first compound can consist of one tablet or capsule while a daily dose of the second compound can consist of several tablets or capsules and vice versa. The memory aid should reflect this.

IV. Methods

In a further aspect, a method for treating a hepatitis B infection in a patient in need thereof is provided, comprising administering to a subject or patient an effective amount of a disclosed compound, and/or administering a first disclosed compound and optionally, an additional, different disclosed compound(s). In another embodiment, a method for treating a hepatitis B infection in a patient in need thereof is provided, comprising administering to a subject or patient a therapeutically effective amount of a disclosed pharmaceutical composition or a pharmaceutical composition comprising a disclosed compound, or two or more disclosed compounds, and a pharmaceutically acceptable excipient.

For use in accordance with this aspect, the appropriate dosage is expected to vary depending on, for example, the particular compound employed, the mode of administration, and the nature and severity of the infection to be treated as well as the specific infection to be treated and is within the purview of the treating physician. Usually, an indicated administration dose may be in the range between about 0.1 to about 1000 µg/kg body weight. In some cases, the administration dose of the compound may be less than 400 µg/kg body weight. In other cases, the administration dose may be less than 200 µg/kg body weight. In yet other cases, the administration dose may be in the range between about 0.1 to about 100 µg/kg body weight. The dose may be conveniently administered once daily, or in divided doses up to, for example, four times a day or in sustained release form.

A compound of the present disclosure may be administered by any conventional route, in particular: enterally, topically, orally, nasally, e.g. in the form of tablets or capsules, via suppositories, or parenterally, e.g. in the form of injectable solutions or suspensions, for intravenous, intramuscular, sub-cutaneous, or intra-peritoneal injection. Suitable formulations and pharmaceutical compositions will include those formulated in a conventional manner using one or more physiologically acceptable carriers or excipients, and any of those known and commercially available and currently employed in the clinical setting. Thus, the compounds may be formulated for oral, buccal, topical, parenteral, rectal or transdermal administration or in a form suitable for administration by inhalation or insufflation (either orally or nasally).

For oral administration, pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). Tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). Preparations may also contain buffer salts, flavoring, coloring and sweetening agents as appropriate.

Preparations for oral administration may also be suitably formulated to give controlled-release or sustained release of the active compound(s) over an extended period. For buccal administration the compositions may take the form of tablets or lozenges formulated in a conventional manner known to the skilled artisan.

A disclosed compound may also be formulated for parenteral administration by injection e.g. by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain additives such as suspending, stabilizing and/or dispersing agents. Alternatively, the compound may be in powder form for constitution with a suitable vehicle, e.g. sterile pyrogen-free water, before use. Compounds may also be formulated for rectal administration as suppositories or retention enemas, e.g. containing conventional suppository bases such as cocoa butter or other glycerides.

Also contemplated herein are methods and compositions that include a second active agent, or administering a second active agent. For example, in addition to being infected with HBV, a subject or patient can further have HBV infection-related co-morbidities, i.e., diseases and other adverse health conditions associated with, exacerbated by, or precipitated by being infected with HBV. Contemplated herein are disclosed compounds in combination with at least one other agent that has previously been shown to treat these HBV-infection-related conditions.

In some cases, a disclosed compound may be administered as part of a combination therapy in conjunction with one or more antivirals. Example antivirals include nucleoside analogs, interferon α, and other assembly effectors, for instance heteroaryldihydropyrimidines (HAPs) such as methyl 4-(2-chloro-4-fluorophenyl)-6-methyl-2-(pyridin-2-yl)-1,4-dihydropyrimidine-5-carboxylate (HAP-1). For example, provided herein is a method of treating a patient suffering from hepatitis B infection comprising administering to the patient a first amount of a disclosed compound and a second amount of an antiviral, or other anti HBV agent, for example a second amount of a second compound selected from the group consisting of: a HBV capsid assembly promoter (for example, GLS4, BAY 41-4109, AT-130, DVR-23 (e.g., as depicted below),

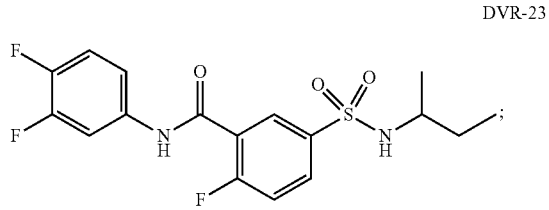 [SMILES: CCC(C)NS(=O)(=O)c1ccc(F)c(C(=O)Nc2ccc(F)c(F)c2)c1]

DVR-23

NVR 3-778, NVR1221 (by code); and N890 (as depicted below):

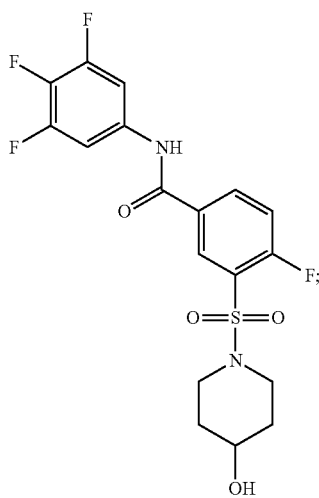 [SMILES: O=C(Nc1cc(F)c(F)c(F)c1)c1ccc(F)c(S(=O)(=O)N2CCC(O)CC2)c1]

other capsid inhibitors such as those disclosed in the following patent applications hereby incorporated by reference: WO2014037480, WO2014184328, WO2013006394, WO2014089296, WO2014106019, WO2013102655, WO2014184350, WO2014184365, WO2014161888, WO2014131847, WO2014033176, WO2014033167, and WO2014033170; Nucleos(t)ide analogs interfering with viral polymerase, such as entecavir (Baraclude), Lamivudine, (Epivir-HBV), Telbivudine (Tyzeka, Sebivo), Adefovir dipivoxil (Hepsera), Tenofovir (Viread), Tenofovir alafenamide fumarate (TAF), prodrugs of tenofovir (e.g. AGX-1009), L-FMAU (Clevudine), LB80380 (Besifovir) and:

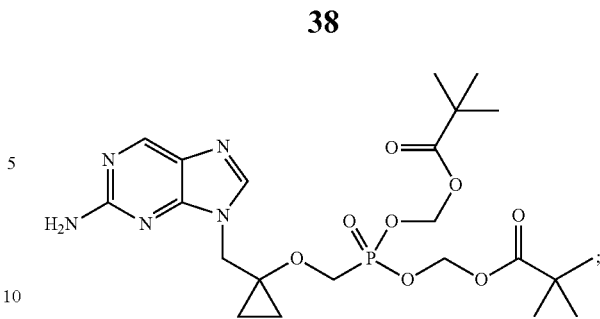

viral entry inhibitors such as Myrcludex B and related lipopeptide derivatives; HBsAg secretion inhibitors such as REP 9AC' and related nucleic acid-based amphipathic polymers, HBF-0529 (PBHBV-001), PBHBV-2-15 as depicted below:

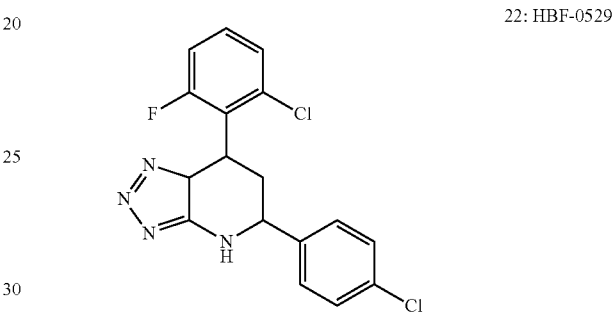

22: HBF-0529

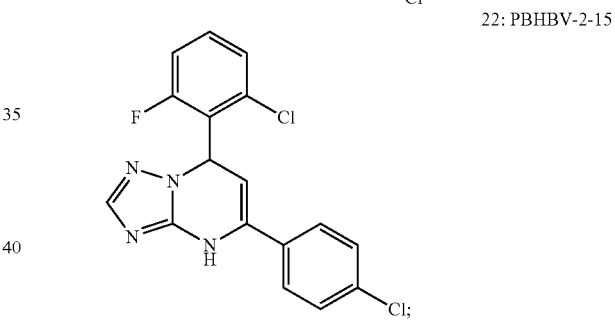

22: PBHBV-2-15 and BM601 as depicted below:

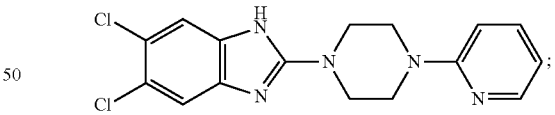

disruptors of nucleocapsid formation or integrity such as NZ-4/W28F:

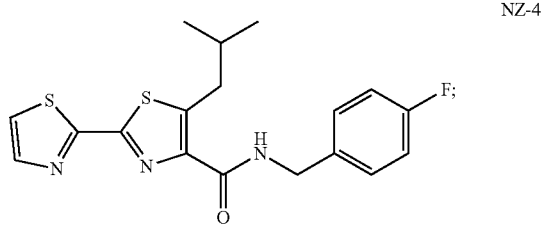 [SMILES: CC(C)Cc1sc(-c2nccs2)nc1C(=O)NCc1ccc(F)cc1]

NZ-4 cccDNA formation inhibitors such as BSBI-25, CCC-0346, CCC-0975 (as depicted below):

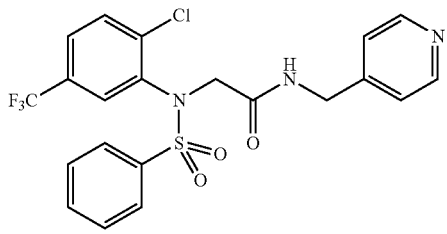

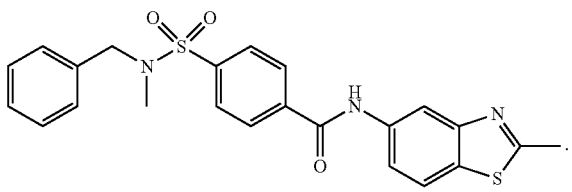

HBc directed transbodies such as those described in Wang Y, et al, Transbody against hepatitis B virus core protein inhibits hepatitis B virus replication in vitro, Int. Immunopharmacol (2014), located at //dx.doi.org/10.1016/j.intimp.2015.01.028; antiviral core protein mutant (such as Cp183-V124W and related mutations as described in WO/2013/010069, WO2014/074906, each incorporated by reference); inhibitors of HBx-interactions such as RNAi, antisense and nucleic acid based polymers targeting HBV RNA; e.g., RNAi (for example ALN-HBV, ARC-520, TKM-HBV, ddRNAi), antisense (ISIS-HBV), or nucleic acid based polymer: (REP 2139-Ca); immunostimulants such as Interferon alpha 2a (Roferon), Intron A (interferon alpha 2b), Pegasys (peginterferon alpha 2a), Pegylated IFN 2b, IFN lambda 1a and PEG IFN lambda 1a, Wellferon, Roferon, Infergen, lymphotoxin beta agonists such as CBE11 and BS1); Non-Interferon Immune enhancers such as Thymosin alpha-1 (Zadaxin) and Interleukin-7 (CYT107); TLR-7/9 agonists such as GS-9620, CYT003, Resiquimod; Cyclophilin inhibitors such as NVP018; OCB-030; SCY-635; Alisporivir; NIM811 and related cyclosporine analogs; vaccines such as GS-4774, TG1050, Core antigen vaccine; SMAC mimetics such as birinapant and other IAP-antagonists; Epigenetic modulators such as KMT inhibitors (EZH1/2, G9a, SETD7, Suv39 inhibitors), PRMT inhibitors, HDAC inhibitors, SIRT agonists, HAT inhibitors, WD antagonists (e.g. OICR-9429), PARP inhibitors, APE inhibitors, DNMT inhibitors, LSD1 inhibitors, JMJD HDM inhibitors, and Bromodomain antagonists; kinase inhibitors such as TKB1 antagonists, PLK1 inhibitors, SRPK inhibitors, CDK2 inhibitors, ATM & ATR kinase inhibitors; STING Agonists; Ribavirin; N-acetyl cysteine; NOV-205 (BAM205); Nitazoxanide (Alinia), Tizoxanide; SB 9200 Small Molecule Nucleic Acid Hybrid (SMNH); DV-601; Arbidol; FXR agonists (such as GW 4064 and Fexaramin); antibodies, therapeutic proteins, gene therapy, and biologics directed against viral components or interacting host proteins.

In some embodiments, the disclosure provides a method of treating a hepatitis B infection in a patient in need thereof, comprising administering a first compound selected from any one of the disclosed compounds, and one or more other HBV agents each selected from the group consisting of HBV capsid assembly promoters, HBF viral polymerase interfering nucleosides, viral entry inhibitors, HBsAg secretion inhibitors, disruptors of nucleocapsid formation, cccDNA formation inhibitors, antiviral core protein mutant, HBc directed transbodies, RNAi targeting HBV RNA, immunostimulants, TLR-7/9 agonists, cyclophilin inhibitors, HBV vaccines, SMAC mimetics, epigenetic modulators, kinase inhibitors, and STING agonists. In some embodiments, the disclosure provides a method of treating a hepatitis B infection in a patient in need thereof, comprising administering an amount of a disclosed compound, and administering another HBV capsid assembly promoter.

In some embodiments, the first and second amounts together comprise a pharmaceutically effective amount. The first amount, the second amount, or both may be the same, more, or less than effective amounts of each compound administered as monotherapies. Therapeutically effective amounts of a disclosed compound and antiviral may be co-administered to the subject, i.e., administered to the subject simultaneously or separately, in any given order and by the same or different routes of administration. In some instances, it may be advantageous to initiate administration of a disclosed compound first, for example one or more days or weeks prior to initiation of administration of the antiviral. Moreover, additional drugs may be given in conjunction with the above combination therapy.

In another embodiment, a disclosed compound may be conjugated (e.g., covalently bound directly or through molecular linker to a free carbon, nitrogen (e.g. an amino group), or oxygen (e.g. an active ester) of a disclosed compound), with a detection moiety, for e.g., a fluorophore moiety (such a moiety may for example re-emit a certain light frequency upon binding to a virus and/or upon photon excitation). Contemplated fluorophores include AlexaFluor® 488 (Invitrogen) and BODIPY FL (Invitrogen), as well as fluorescein, rhodamine, cyanine, indocarbocyanine, anthraquinones, fluorescent proteins, aminocoumarin, methoxycoumarin, hydroxycoumarin, Cy2, Cy3, and the like. Such disclosed compounds conjugated to a detection moiety may be used in e.g. a method for detecting HBV or biological pathways of HBV infection, e.g., in vitro or in vivo; and/or methods of assessing new compounds for biological activity.

V. Examples

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

At least some of the compounds identified as "intermediates" herein are contemplated as compounds of the disclosure.

ABBREVIATIONS

DCM Dichloromethane
EtOAc Ethyl acetate
MeOH Methanol
DMSO Dimethyl sulfoxide
ACN Acetonitrile
DIAD Diisopropyl azodicarboxylate
DIEA Diisopropyl ethylamine
nBuLi n-Butyllithium
iPrOH Isopropanol
AcOH Acetic acid
$BOC_2O$ Di-tert-butyl dicarbonate
$Et_3N$ Triethylamine
DMF N,N-Dimethylformamide
THF Tetrahydrofuran
TEA Triethylamine
TFA Trifluoroacetic acid
TLC Thin-layer chromatography
LCMS Liquid chromatography—mass spectrometry
HPLC High performance liquid chromatography
XPhos 2-Dicyclohexylphosphino-2',4',6'-triisopropylbiphenyl
DPPF 1,1'-Bis(diphenylphosphino)ferrocene
NMO N-Methylmorpholine-N-Oxide
HATU Hexafluorophosphate Azabenzotriazole Tetramethyl Uronium)
SFC Supercritical Fluid Chromatography
NBS N-Bromosuccinimide Methods useful for the synthesis of the compounds of this invention are shown in the schemes below. In Scheme I, a carboxylic acid ester or chloride, I-1, can be condensed with I-2 to provide intermediate I-3 which is subsequently treated with a suitable alkylhalide (I-4). The resulting compound (I-5) can be treated with an appropriately substituted hydrazide (I-6) to form the 5-amino pyrazole template. Saponification and amide bond formation yield the final compound I-10.

In Scheme II, 5-amino-pyrazole ester II-1 is brominated and treated with $Ar_2NH_2$ under appropriate conditions to effect the ester/amide exchange reaction. The resulting intermediate II-3 can be coupled with II-9 under catalytic (Pd(0) or Pd(II)) conditions to produce the penultimate intermediate II-10. Hydrogenation of II-10 yields the final compound II-11. As shown in Scheme II, II-11 contains 2 chiral centers which means there are 4 possible diastereomeric configurations. Methods are known which can provide for the selective synthesis of a single diastereomer or the selective isolation of a single diastereomer from a mixture of the others (*Stereoselective Synthesis of Drugs and Natural Products*, Edited by Vasyl Andrushko and Natalia Andrushko. Published 2013 by John Wiley & Sons, Inc).

Scheme III illustrates a stereoselective synthesis of certain compounds of this invention. Enantioselective addition an aryl- or hetero-aryl (III-2) to III-1, according to the method described in *Org. Biomol. Chem.*, 2012, 10, 1764 provides either S-enantiomer III-3(S) or III-3(R) using chiral ligands (R)-L-1 or (S)-L-2, respectively. Intermediates III-3(S) and III-3(R) can each be carried on to diastereomeric mixtures IV (R,S)/IV (S,S) and IV (R,R)/IV (S,R) respectively. The diastereomers mixtures can be separated under known methods.

An additional method for the synthesis of compounds of this invention is illustrated in Scheme IV. Diketone IV-1 (*Tetrahedron*, 1982, 38, 63) is selectively modified to produce boronate ester IV-3, which can be coupled to bromopyrazole intermediate II-3. The resulting compound, IV-4, is reduced, yielding IV-5. Ketone reduction and activation of the resulting alcohol group of IV-6 provides an intermediate, IV-7, which can be taken on to IV-9 via nucleophilic substitution with NucH (IV-8). Alternatively, the ketone group of IV-5 is suitable for reductive amination with IV-10 yielding IV-11. Both IV-9 and IV-11 can exist in a least 4 different diastereomeric configurations, shown in the scheme. Reaction conditions and pathways can be chosen, based on known stereoselective reaction principles, to favor the formation of one diastereomer over the others. In addition, individual diastereomers of IV-9 and IV-11 are subject to isolation using known conditions.

In Scheme V, oxime V-1, synthesized from IV-5, can be reduced to yield amine V-2. The amine group can be further reacted to provide sulfonamides (V-4) or amides (V-6).

A further method of synthesis is illustrated in Scheme VI. Intermediate IV-5 can be converted to the corresponding epoxide VI-1 using known conditions. This intermediate can be transformed through its reaction with various nucleophiles (NucH, VI-2) to form compounds represented by VI-3. In the event where VI-3 is a sulfide, further modification can be achieved by oxidizing the sulfur atom to the corresponding sulfone VI-5. A second method for forming VI-5 involves reacting IV-5 with the corresponding anion of sulfone of sulfonamide VI-4. VI-5 and VI-3 can exist in at least 4 different diastereomeric configurations, as illustrated in the scheme. Reaction conditions and pathways can be chosen, based on known stereoselective reaction principles, to favor the formation of one diastereomer over the others. In addition, individual diastereomers of VI-3 and VI-5 are subject to isolation using known conditions.

In Scheme VII, Boc-protected VII-I is converted into the corresponding boronate ester, VI-3 and coupled to II-3 according to the methods described in the previous schemes. Following the coupling reaction, VII-4 is hydrogenated to provide VII-5. After removal of the Boc-protecting group, compound VII-6 can be taken on to VII-8 via reaction with an appropriate electrophile or carried on to VII-11 via alkylation or reductive-alkylation.

Scheme VIII illustrates the synthesis of sulfoxide-containing compound VIII-6. Using the methods described above compound VIII-5 is synthesized, which can be oxidized to form VIII-6.

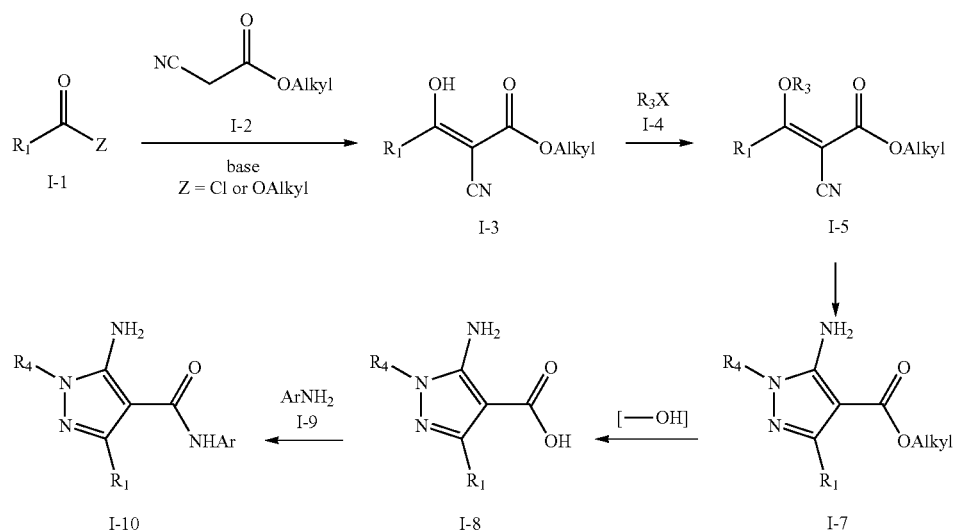
Scheme II
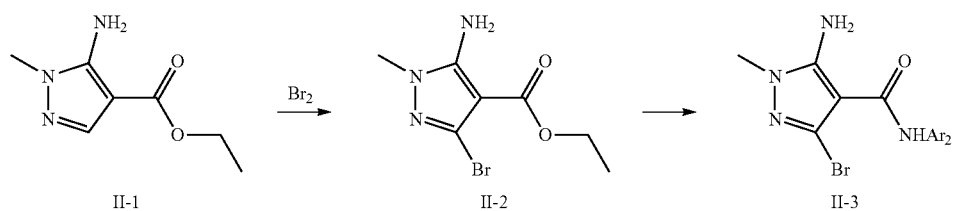
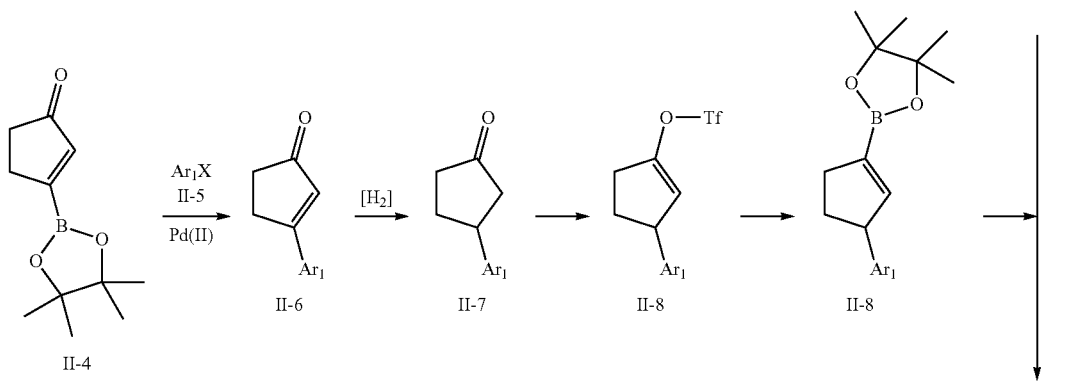
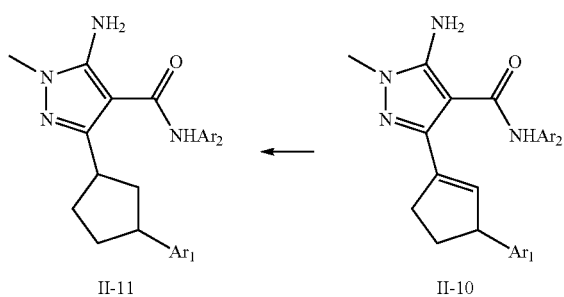

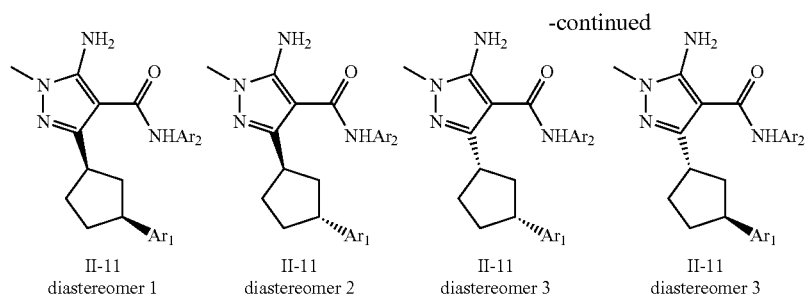
II-11 diastereomer 1    II-11 diastereomer 2    II-11 diastereomer 3    II-11 diastereomer 3
Scheme III
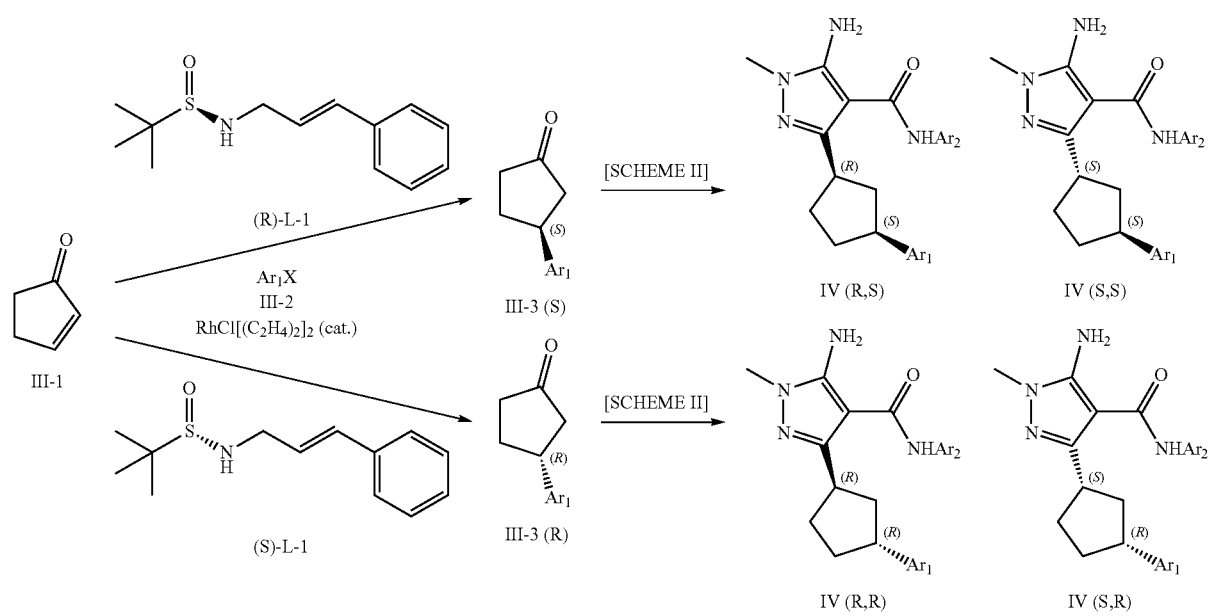
Scheme IV
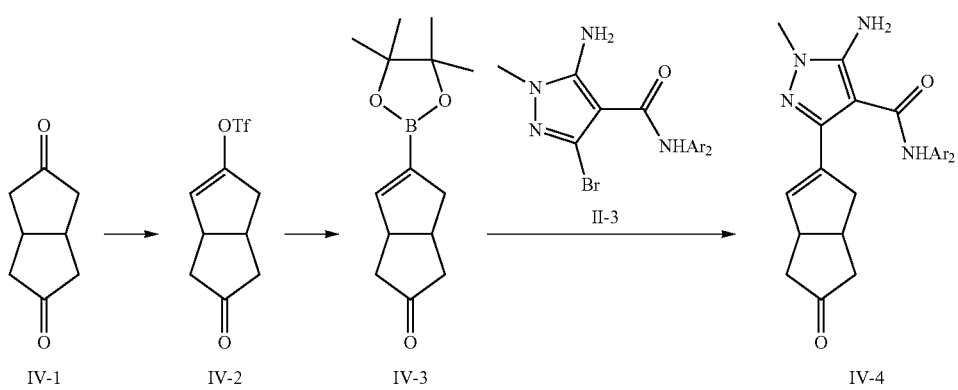

-continued
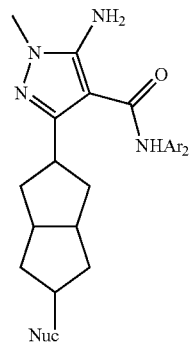 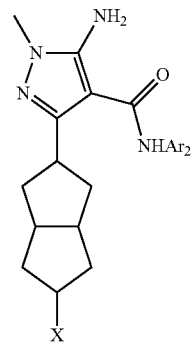 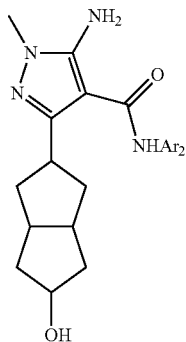 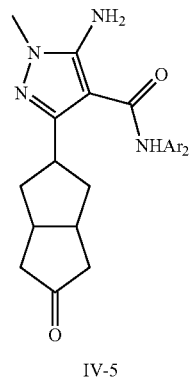
IV-9  
NucH = ROH, RSH, HetH
IV-7  
X = halo, OMs
IV-6
IV-5
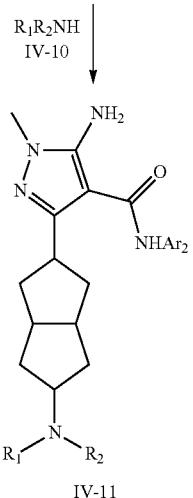
IV-11
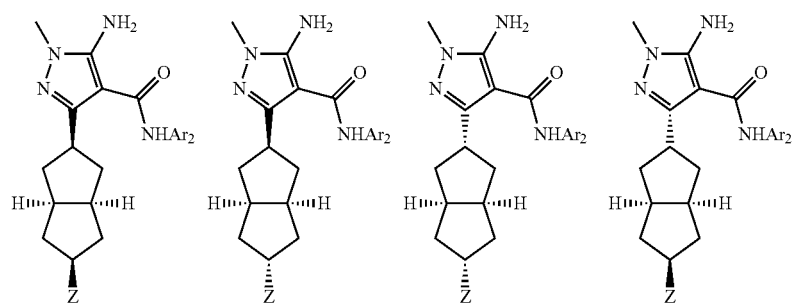

Scheme V
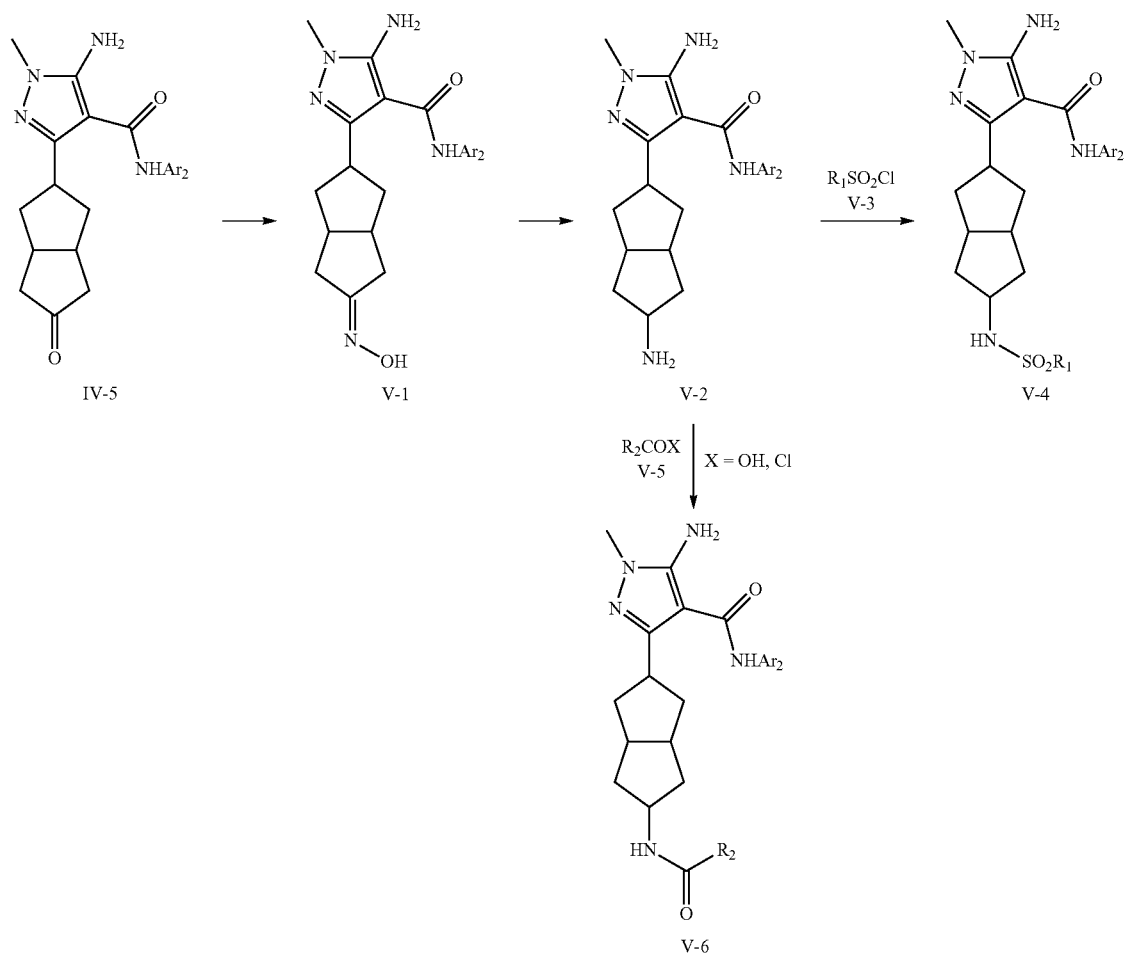
Scheme VI
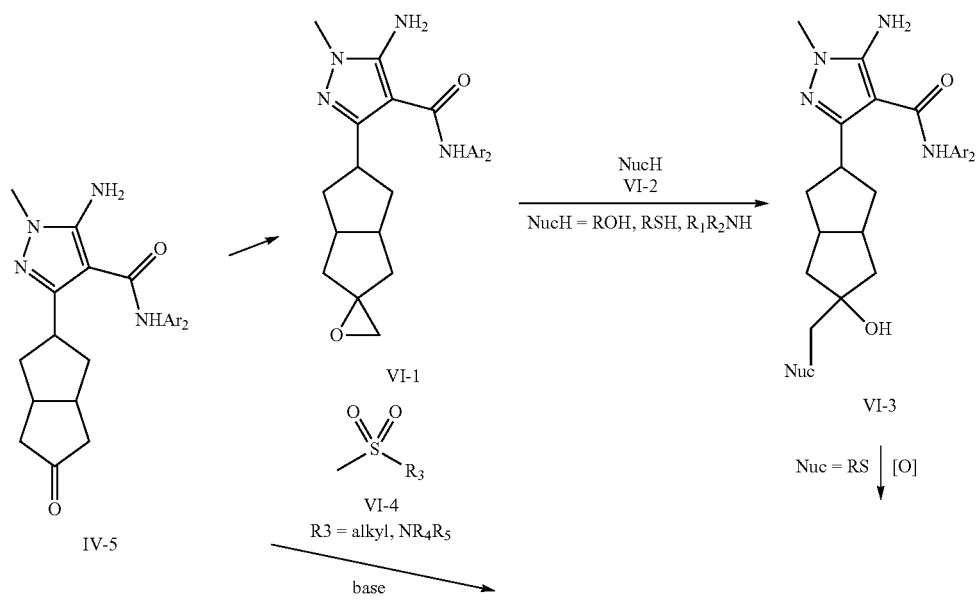

-continued
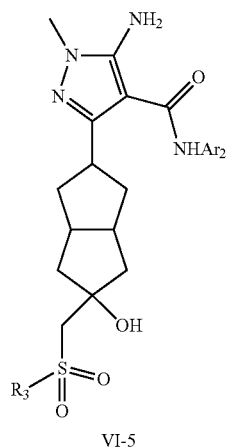
VI-5
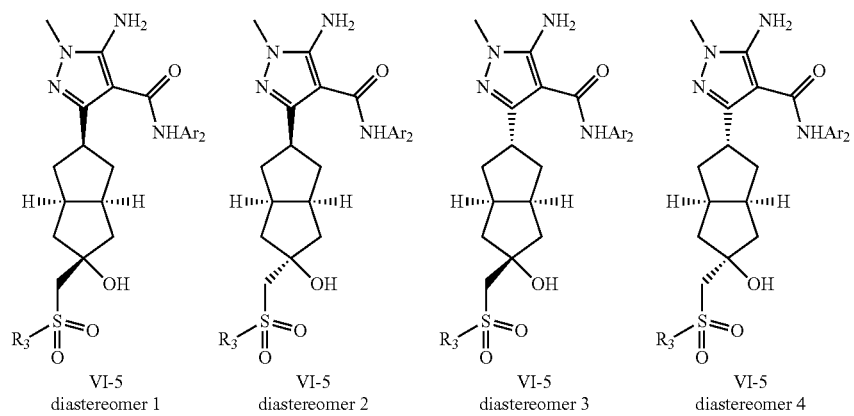
VI-5
diastereomer 1
VI-5
diastereomer 2
VI-5
diastereomer 3
VI-5
diastereomer 4
Scheme VII
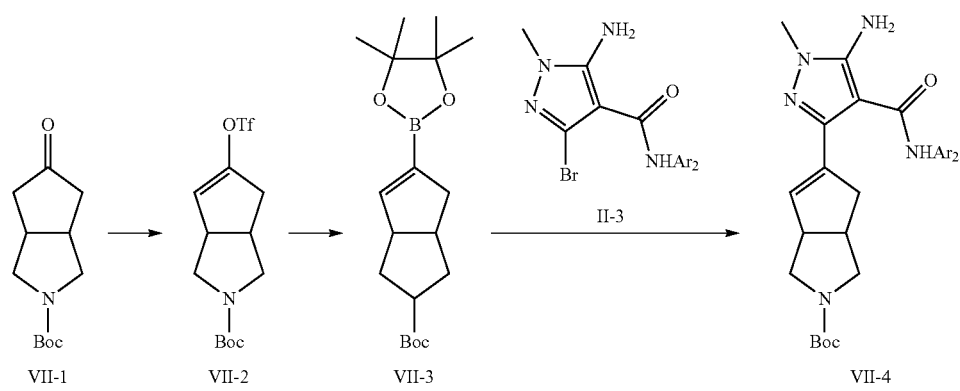
VII-1 → VII-2 → VII-3 → VII-4

-continued
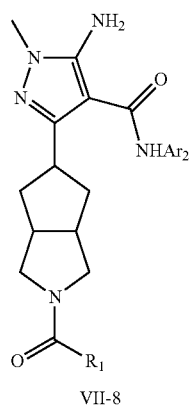 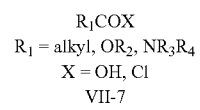 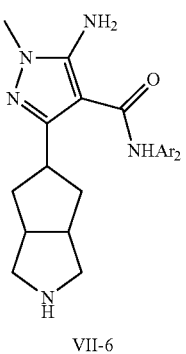 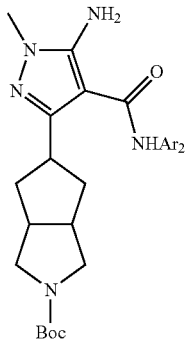
VII-8  　　VII-7  　　VII-6  　　VII-5
R₁COX
R₁ = alkyl, OR₂, NR₃R₄
X = OH, Cl
VII-7
[H]
R₅CHO
(VII-9)
or
R₅X
(VII-10)
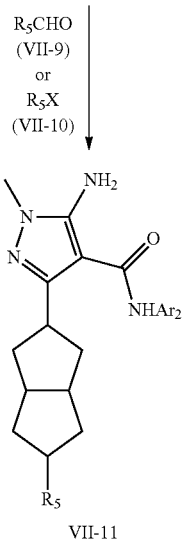
VII-11
Scheme VIII
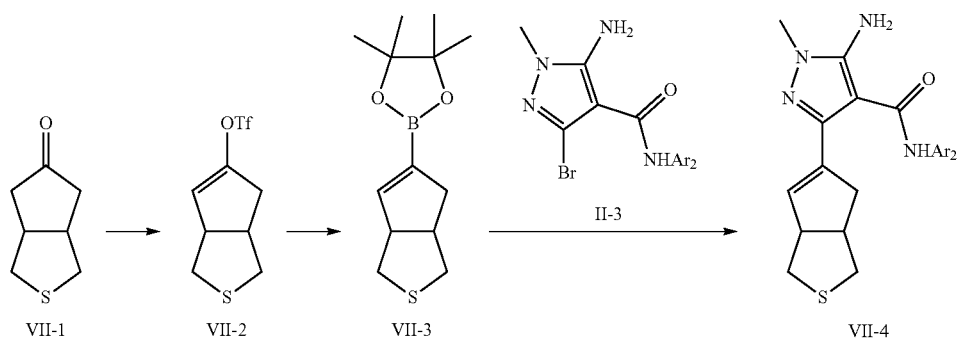
VII-1  　　VII-2  　　VII-3  　　II-3  　　VII-4

-continued

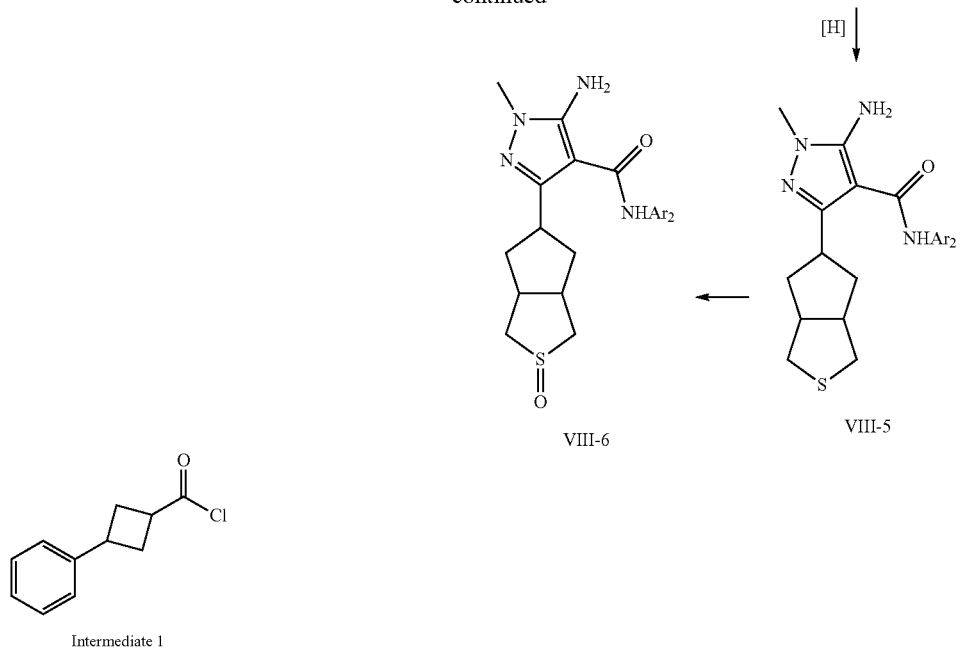

VIII-6   VIII-5

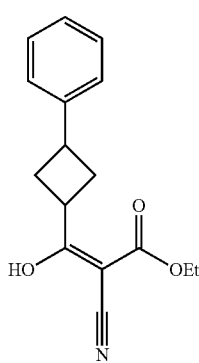

Intermediate 1

3-Phenylcyclobutane-1-carbonyl chloride. A clear solution of 3-phenylcyclobutanecarboxylic acid (1 g, 5.68 mmol, 1 eq) in $SOCl_2$ (5 mL) was stirred at 80° C. for 1 hr. The reaction was concentrated under vacuum to give crude a light-yellow oil. The oil was diluted with DCM (10 mL). The solution was concentrated under vacuum to give 3-phenylcyclobutanecarbonyl chloride (1.1 g, crude) as a light-yellow oil.

Intermediate 2

Ethyl 2-cyano-3-hydroxy-3-(3-phenylcyclobutyl)acrylate. To a solution of ethyl 2-cyanoacetate (1.28 g, 11.30 mmol, 1.21 mL, 2 eq) in THF (20 mL) was added NaH 60% in mineral oil (565.04 mg, 14.13 mmol, 60% purity, 2.5 eq) at 0° C. The reaction was stirred for 1 hr. A solution of 3-phenylcyclobutanecarbonyl chloride (1.1 g, 5.65 mmol, 1 eq) in THF (10 mL) was added dropwise at 0° C. The reaction was warmed to 25° C. and stirred for 16 hr. The reaction was quenched with aq. $NH_4Cl$ (20 mL) and extracted with ethyl acetate (10 mL×2). The organic layers were combined, washed with brine (10 mL), dried over $Na_2SO_4$, filtered and concentrated under vacuum to give ethyl 2-cyano-3-hydroxy-3-(3-phenylcyclobutyl)acrylate (1.8 g, crude) as a brown oil. $^1H$ NMR (400 MHz, CHLOROFORM-d) δ ppm 1.37-1.43 (m, 3H) 2.51-2.74 (m, 3H) 2.76-2.84 (m, 1H) 3.63-3.73 (m, 1H) 3.74-3.87 (m, 1H) 4.33-4.41 (m, 2H) 7.21-7.40 (m, 5H).

Intermediate 3

Ethyl 2-cyano-3-ethoxy-3-(3-phenylcyclobutyl)acrylate. A suspension of ethyl 2-cyano-3-hydroxy-3-(3-phenylcyclobutyl)prop-2-enoate (1.7 g, 6.27 mmol, 1 eq), $Ag_2CO_3$ (4.32 g, 15.66 mmol, 0.710 mL, 2.5 eq) and EtI (4.89 g, 31.33 mmol, 2.51 mL, 5 eq) in DCM (50 mL) was stirred at 25° C. for 16 hr. The reaction was filtered through a pad of Celite®, and the filter cake washed with DCM (10 mL×2). The filtrate was concentrated under vacuum to give crude product (1.8 g) as a yellow oil. The residue was purified by flash chromatography (Combi-Flash®; 12 g SepaFlash® Silica Flash Column, Eluent of 0~5% Ethyl acetate/Petroleum ether gradient @ 20 mL/min) to provide ethyl 2-cyano-3-ethoxy-3-(3-phenylcyclobutyl)acrylate (1.2 g) as a colorless oil. $^1H$ NMR (400 MHz, CHLOROFORM-d) δ ppm 1.29-1.37 (m, 3H) 1.45-1.55 (m, 3H) 2.18 (d, J=7.03 Hz, 1H) 2.25-2.42 (m, 1H) 2.45-2.70 (m, 3H) 3.39-3.49 (m, 1H) 4.16-4.42 (m, 2H) 4.67-4.84 (m, 2H) 7.18-7.35 (m, 5H).

Intermediate 4

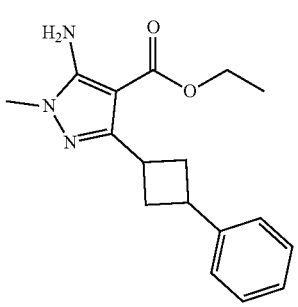

Ethyl 5-amino-1-methyl-3-(3-phenylcyclobutyl)-1H-pyrazole-4-carboxylate. A yellow mixture of ethyl 2-cyano-3-ethoxy-3-(3-phenylcyclobutyl)prop-2-enoate (1.2 g, 4.01 mmol, 1 eq), methylhydrazine-sulfuric acid (577.83 mg, 4.01 mmol, 1 eq) and TEA (1.42 g, 14.03 mmol, 1.95 mL, 3.5 eq) in EtOH (15 mL) was stirred at 70° C. for 1 hr. LCMS showed several new peaks, and 25.1% of desired compound was detected. The reaction was quenched with aq. NH$_4$Cl (10 mL) and extracted with ethyl acetate (10 mL×2). The organic layers were combined and washed with brine (10 mL), dried over Na$_2$SO$_4$, filtered, and concentrated under vacuum to give crude (1.6 g) as a brown oil. The residue was purified by flash silica gel chromatography (Combi-Flash®; 4 g SepaFlash® Silica Flash Column, Eluent of 0~31% Ethyl acetate/Petroleum ether gradient @ 20 mL/min) to give ethyl 5-amino-1-methyl-3-(3-phenylcyclobutyl)pyrazole-4-carboxylate (220 mg, 0.652 mmol, 15.3% yield, 88.7% purity) as a yellow oil. $^1$H NMR (400 MHz, CHLOROFORM-d) δ ppm 1.26-1.42 (m, 3H) 2.36-2.84 (m, 4H) 3.04-3.92 (m, 2H) 4.14-4.33 (m, 2H) 4.92-5.10 (m, 1H) 7.13-7.28 (m, 2H) 7.29-7.36 (m, 3H); LC-MS: 300.2 [M+1]$^+$.

Intermediate 5

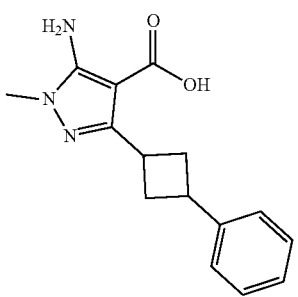

5-Amino-1-methyl-3-(3-phenylcyclobutyl)-1H-pyrazole-4-carboxylic acid. A mixture of ethyl 5-amino-1-methyl-3-(3-phenylcyclobutyl)pyrazole-4-carboxylate (220 mg, 0.652 mmol, 1 eq) and LiOH—H$_2$O (273.43 mg, 6.52 mmol, 10 eq) in THF (3 mL), MeOH (3 mL) and H$_2$O (3 mL) was stirred at 70° C. for 64 hr. The reaction was concentrated under vacuum to remove THF and MeOH. The mixture was adjusted to pH 6 with 1N HCl and extracted with ethyl acetate (50 mL×2). The organic layers were combined, washed with brine (40 mL), dried over Na$_2$SO$_4$, filtered and concentrated under vacuum to give crude 5-amino-1-methyl-3-(3-phenylcyclobutyl)-1H-pyrazole-4-carboxylic acid (200 mg, crude) as a yellow oil. LC-MS: 272.1 [M+1]$^+$.

Intermediate 6

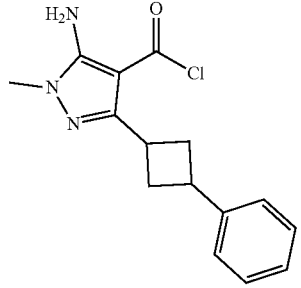

5-Amino-1-methyl-3-(3-phenylcyclobutyl)-1H-pyrazole-4-carbonyl chloride. A solution of 5-amino-1-methyl-3-(3-phenylcyclobutyl)pyrazole-4-carboxylic acid (190 mg, 0.70 mmol) in SOCl$_2$ (3 mL) was stirred at 80° C. for 1 hr. The reaction was concentrated under vacuum to give crude 5-amino-1-methyl-3-(3-phenylcyclobutyl)-1H-pyrazole-4-carbonyl chloride (200 mg) as a yellow oil, which was used to the next step without further purification.

AIA 224A and AIA 224B

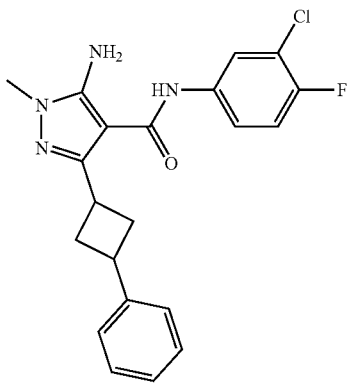

5-Amino-N-(3-chloro-4-fluorophenyl)-1-methyl-3-(3-phenylcyclobutyl)-1H-pyrazole-4-carboxamide, diastereomer 1 and diastereomer 2. To a solution of 5-amino-1-methyl-3-(3-phenylcyclobutyl)pyrazole-4-carbonyl chloride (200 mg, 0.690 mmol) and 3-chloro-4-fluoro-aniline (100.47 mg, 0.690 mmol) in DCM (5 mL) was added Et$_3$N (209.53 mg, 2.07 mmol, 0.288 mL, 3 eq) dropwise at 0° C. under N$_2$. The reaction was warmed to 25° C. and stirred for 15 hr to give a brown solution. The reaction was quenched with aq. NH$_4$Cl (20 mL). The aqueous layer was separated and extracted with DCM (10 mL). The organic layers were combined and washed with brine (10 mL), dried over Na$_2$SO$_4$, filtered and concentrated under vacuum to give crude 5-amino-N-(3-chloro-4-fluorophenyl)-1-methyl-3-(3-phenylcyclobnnutyl)-1H-pyrazole-4-carboxamide (300 mg) as a brown oil. The residue was purified by flash silica gel chromatography (Combi-Flash®; 4 g SepaFlash® Silica Flash Column, Eluent of 0~30% Ethyl acetate/Petroleum ether gradient @ 20 mL/min) to give 5-amino-N-(3-chloro-4-fluoro-phenyl)-1-methyl-3-(3-phenylcyclobutyl) pyrazole-4-carboxamide (100 mg, 0.225 mmol, 32.56% yield, 89.637% purity) as a mixture f 2 diastereomers. The diastereomers were separated by prep-HPLC (column: Xtimate C18 150×25 mm×5 um; mobile phase: [water (0.05% ammonia hydroxide v/v)—ACN]; B %: 52%-92%, 12 min).

5-Amino-N-(3-chloro-4-fluorophenyl)-1-methyl-3-(3-phenylcyclobutyl)-1H-pyrazole-4-carboxamide (AIA-224A); $^1$H NMR (400 MHz, DMSO-d6) δ ppm 2.21-2.33 (m, 2H) 2.62-2.69 (m, 2H) 3.45-3.54 (m, 4H) 3.84-3.98 (m, 1H) 6.10 (s, 2H) 7.11-7.24 (m, 3H) 7.25-7.32 (m, 2H) 7.36 (t, J=9.11 Hz, 1H) 7.57 (ddd, J=9.05, 4.28, 2.69 Hz, 1H) 7.95 (dd, J=6.91, 2.63 Hz, 1H) 8.70 (s, 1H); LC-MS: 399.2 [M+1]$^+$.

5-Amino-N-(3-chloro-4-fluorophenyl)-1-methyl-3-(3-phenylcyclobutyl)-1H-pyrazole-4-carboxamide (AIA-224B); $^1$H NMR (400 MHz, DMSO-d6) δ ppm 2.21-2.33 (m, 2H) 2.62-2.69 (m, 2H) 3.45-3.54 (m, 4H) 3.84-3.98 (m, 1H) 6.10 (s, 2H) 7.11-7.24 (m, 3H) 7.25-7.32 (m, 2H) 7.36 (t, J=9.11 Hz, 1H) 7.57 (ddd, J=9.05, 4.28, 2.69 Hz, 1H) 7.95 (dd, J=6.91, 2.63 Hz, 1H) 8.70 (s, 1H); LC-MS: 399.2 [M+1]$^+$.

were combined, dried over MgSO$_4$, filtered and concentrated under vacuum to give a residue as a yellow solid. The residue was triturated with methyl t-butyl ether (3 mL) for 5 min. 5-Amino-3-bromo-N-(3-chloro-4-fluoro-phenyl)-1-methyl-pyrazole-4-carboxamide (0.1 g, 275.30 umol, 28.46% yield, 95.732% purity) was obtained as a light yellow solid. $^1$H NMR (400 MHz, CHLOROFORM-d) δ ppm 1.57 (s, 3H) 3.64 (s, 3H) 5.53 (br s, 2H) 7.12 (t, J=8.74 Hz, 1H) 7.29-7.41 (m, 1H) 7.80 (dd, J=6.54, 2.63 to Hz, 1H) 8.34 (br s, 1H)

Intermediate 7

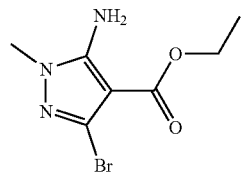

Ethyl 5-amino-3-bromo-1-methyl-1H-pyrazole-4-carboxylate. To a yellow solution of ethyl 5-amino-1-methyl-pyrazole-4-carboxylate (0.206 g, 1.22 mmol, 1 eq) in EtOH (5 mL) was added a solution of sodium acetate (929.89 mg, 11.34 mmol, 9.28 eq) in H$_2$O (8 mL), followed by dropwise addition of Br$_2$ (1.12 g, 7.04 mmol, 362.82 uL, 5.78 eq). The orange suspension was stirred at 15° C. for 3 hr. The reaction mixture was poured into H$_2$O (15 mL). The mixture was extracted with ethyl acetate (3×20 mL). The organic layers were combined and washed with saturated aqueous sodium thiosulfate solution (2×5 mL), dried (Na$_2$SO$_4$), filtered and concentrated under reduced pressure. The solid was triturated with a solution of methyl t-butyl ether: petroleum ether (1:10) (10 mL) for 5 min. Ethyl 5-amino-3-bromo-1-methyl-pyrazole-4-carboxylate (0.24 g, 967.44 umol, 79.45% yield) was obtained as a yellow solid. 1H NMR (400 MHz, CHLOROFORM-d) δ ppm 1.38 (t, J=7.15 Hz, 3H) 3.61 (s, 3H) 4.32 (q, J=7.13 Hz, 2H) 5.14 (br s, 2H).

Intermediate 8

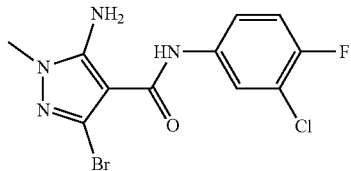

5-Amino-3-bromo-N-(3-chloro-4-fluorophenyl)-1-methyl-1H-pyrazole-4-carboxamide To a colorless solution of 3-chloro-4-fluoro-aniline (281.65 mg, 1.93 mmol, 2 eq) in toluene (6 mL) was added Me$_3$Al (2 M in toluene) (2 M, 1.45 mL, 3 eq) at 0° C. The light brown solution was allowed to warm to 15° C. and stirred for 0.5 hr. To the solution was added ethyl 5-amino-3-bromo-1-methyl-pyrazole-4-carboxylate (0.24 g, 967.44 umol, 1 eq). The brown solution was stirred at 80° C. for 16 hr. Dark brown suspension was observed. The mixture was cooled to 0° C. and quenched with 1 N HCl (2 mL). Brown suspension was observed. The mixture was filtered. The filtrate was diluted with water (10 mL), extracted with EtOAc (15 mL×3). The organic layers Intermediate 9

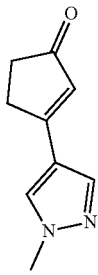

3-(1-Methyl-1H-pyrazol-4-yl)cyclopent-2-en-1-one. A mixture of 3-(4,4,5,5-tetramethyl-1,3,2-dioxaborolan-2-yl)cyclopent-2-en-1-one (5.0 g, 24.0 mmol), 4-bromo-1-methyl-1H-pyrazole (3.9 g, 24.0 mmol), K$_3$PO$_4$ (10.2 mg, 48.0 mmol) and Pd(dppf)Cl$_2$ (880 mg, 1.2 mmol) in dioxane (80 mL) and H$_2$O (20 mL) was stirred at 80° C. overnight under an N2 atmosphere. The solvent was removed under vacuum and the residue was purified by silica gel column chromatography using 1:9 petroleum ether/ethyl acetate to afford 3-(1-methyl-1H-pyrazol-4-yl)cyclopent-2-en-1-one (1.8 g, 46% yield) as a yellow solid. MS Calcd.: 162.1, MS Found: 163.4 [M+1]$^+$.

Intermediate 10

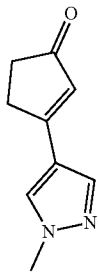

3-(1-Methyl-1H-pyrazol-4-yl)cyclopentanone, enantiomer 1 and enantiomer 2. A mixture of 3-(1-methyl-1H-pyrazol-4-yl)cyclopent-2-en-1-one (1.8 g, 11.1 mmol) and Pd/C (900 mg, 10% purity) in EtOH (50 mL) was degassed and purged with H$_2$ atmosphere 5 times. The mixture was stirred under H$_2$ (5 atm) at 80° C. overnight. The reaction was filtered through a pad of Celite®, and the filter cake washed with EtOH (10 mL×3). The filtrate was concentrated under vacuum and the residue purified by silica gel column chromatography using petroleum 1:1 ether/ethyl acetate to afford 3-(1-methyl-1H-pyrazol-4-yl)cyclopentanone (1.0 g, 56% yield) as a yellow oil. MS Calcd.: 164.1, MS Found: 165.4 [M+1]$^+$. This material was separated by SFC to give provide pure enantiomer 1 and enantiomer 2 of 3-(1-methyl-1H-pyrazol-4-yl) cyclopentanone.

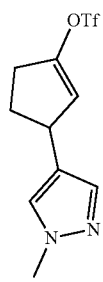

Intermediate 11

3-(1-Methyl-1H-pyrazol-4-yl)cyclopent-1-enyl trifluoromethane sulfonate, enantiomer 1. To a solution of enantiomer 1 of 3-(1-methyl-1H-pyrazol-4-yl)cyclopentanone (400 mg, 2.4 mmol) in THF (10 mL) was added LiHMDS (3.6 mmol, 1 M, 3.6 mL,) at −78° C. The reaction mixture was stirred at −78° C. for 1 h and then treated with a solution of 1,1,1-trifluoro-N-phenyl-N-(trifluoromethylsulfonyl)methanesulfonamide (1.3 g, 3.6 mmol) in THF (5 mL). The reaction mixture was warmed to 30° C. and stirred for 4 h. The reaction mixture was quenched by the addition of NH$_4$Cl (2 mL) at 25° C., diluted with H$_2$O (10 mL) and extracted with EtOAc (20 mL×2). The combined organic layers were washed with brine (20 mL), dried over Na$_2$SO$_4$, filtered and concentrated under reduced pressure. The residue was purified by silica gel column chromatography using 3:1 petroleum ether/ethyl acetate to afford 3-(1-methyl-1H-pyrazol-4-yl)cyclopent-1-enyl trifluoromethane sulfonate, enantiomer 1 (450 mg, 63% yield) as a colorless oil. MS Calcd.: 296.0, MS Found: 297.2 [M+1]$^+$.

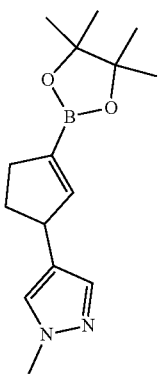

Intermediate 12

1-Methyl-4-(3-(4,4,5,5-tetramethyl-1,3,2-dioxaborolan-2-yl) cyclopent-2-enyl)-1H-pyrazole, enantiomer 1 A mixture of enantiomer 1 of 3-(1-methyl-1H-pyrazol-4-yl)cyclopent-1-enyltrifluoromethane sulfonate (450 mg, 1.5 mmol), 4,4,5,5-tetramethyl-2-(4, 4,5,5-tetramethyl-1,3,2-dioxaborolan-2-yl)-1,3,2-dioxaborolane (580 mg, 2.3 mmol), Pd(dppf)Cl$_2$ (55 mg, 0.075 mmol) and potassium acetate (230 mg, 2.3 mmol) in dioxane (10 mL) was stirred at 80° C. under an N2 atmosphere for 4 h. The reaction was filtered through a pad of Celite, the filter cake washed with EtOAc (10 mL×3). The filtrate was concentrated under vacuum and the residue was purified by silica gel column chromatography using 3:1 petroleum ether/ethyl acetate to afford 1-methyl-4-(3-(4,4,5,5-tetramethyl-1,3,2-dioxaborolan-2-yl) cyclopent-2-enyl)-1H-pyrazole enantiomer 1 (330 mg, 79% yield) as a colorless oil. MS Calcd.: 274.2, MS Found: 275.4 [M+1]$^+$.

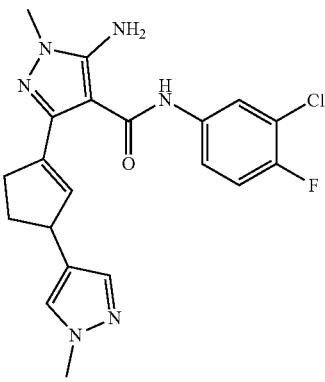

Intermediate 13

5-Amino-N-(3-chloro-4-fluorophenyl)-1-methyl-3-(3-(1-methyl-1H-pyrazol-4-yl)cyclopent-1-enyl)-1H-pyrazole-4-carboxamide enantiomer 1. A mixture of 5-amino-3-bromo-N-(3-chloro-4-fluorophenyl)-1-methyl-1H-pyrazole-4-carboxamide (348 mg, 1.0 mmol), enantiomer 1 of 1-methyl-4-(3-(4,4,5,5-tetramethyl-1,3,2-dioxaborolan-2-yl) cyclopent-2-enyl)-1H-pyrazole (330 mg, 1.2 mmol), K$_3$PO$_4$ (510 mg, 2.4 mmol) and Pd(dppf)Cl$_2$ (44 mg, 0.06 mmol) in dioxane (10 mL) and H$_2$O (2 mL) was stirred at 95° C. for 2 h under an N2 atmosphere. The solvent was removed under vacuum and the residue purified by silica gel to column chromatography using 1:9 petroleum ether/ethyl acetate to afford 5-amino-N-(3-chloro-4-fluorophenyl)-1-methyl-3-(3-(1-methyl-1H-pyrazol-4-yl)cyclopent-1-enyl)-1H-pyrazole-4-carboxamide enantiomer 1 (250 mg, 64% yield) as a white solid. MS Calcd.: 414.1, MS Found: 415.3 [M+1]$^+$.

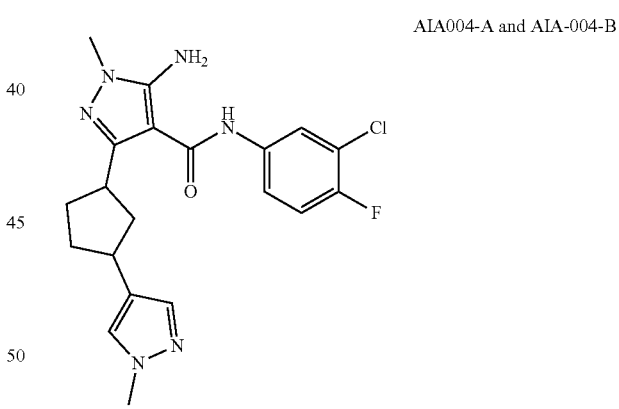

AIA004-A and AIA-004-B

5-Amino-N-(3-chloro-4-fluorophenyl)-1-methyl-3-(3-(1-methyl-1H-pyrazol-4-yl)cyclopentyl)-1H-pyrazole-4-carboxamide, diastereomer 1 (AIA-004A) and diastereomer 2 (AIA-004B). A mixture of enantiomer 1 of 5-amino-N-(3-chloro-4-fluorophenyl)-1-methyl-3-(3-(1-methyl-1H-pyrazol-4-yl)cyclopent-1-enyl)-1H-pyrazole-4-carboxamide (250 mg, 0.6 mmol) and RhCl(PPh$_3$)$_3$ (28 mg, 0.03 mmol) in MeOH (20 mL) was stirred under 10 atm of H$_2$ at 60° C. overnight. The solvent was removed under vacuum and the residue was purified by silica gel column chromatography using 1:9 petroleum ether/ethyl acetate to afford 5-amino-N-(3-chloro-4-fluorophenyl)-1-methyl-3-(3-(1-methyl-1H-pyrazol-4-yl)cyclopentyl)-1H-pyrazole-4-carboxamide as a mixture of diastereomers which were separated by SFC to give diastereomer 1 (AIA-004-A) (20 mg) as a white solid and diastereomer 2 (AIA-004-B) (6 mg) as a white solid. AIA-004-A: (DMSO-$d_6$, 400 MHz): δ 8.91 (s, 1H), 7.91 (dd, J=6.8, 2.4 Hz, 1H), 7.53-7.49 (m, 1H), 7.44 (s, 1H), 7.34 (t, J=9.2 Hz, 1H), 7.24 (s, 1H), 6.02 (s, 2H), 3.77-3.74 (m, 4H), 3.51 (s, 3H), 3.02-2.98 (m, 1H), 2.16-2.11 (m, 1H), 2.08-2.00 (m, 2H), 1.94-1.89 (m, 2H), 1.55-1.50 (m, 1H). AIA-004-B: (DMSO-$d_6$, 400 MHz): δ 8.91 (s, 1H), 7.91 (dd, J=6.8, 2.4 Hz, 1H), 7.52-7.48 (m, 1H), 7.44 (s, 1H), 7.34 (t, J=9.2 Hz, 1H), 7.24 (s, 1H), 6.01 (s, 2H), 3.77-3.74 (m, 4H), 3.51 (s, 3H), 3.02-2.98 (m, 1H), 2.16-2.11 (m, 1H), 2.08-2.00 (m, 2H), 1.94-1.89 (m, 2H), 1.55-1.50 (m, 1H).

AIA004-C and AIA-004-D

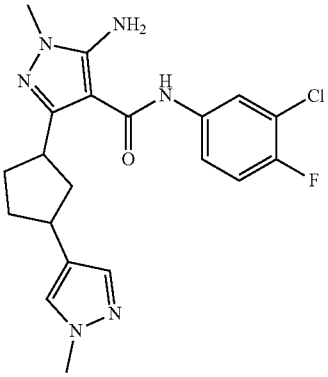

5-Amino-N-(3-chloro-4-fluorophenyl)-1-methyl-3-(3-(1-methyl-1H-pyrazol-4-yl)cyclopentyl)-1H-pyrazole-4-carboxamide, diastereomer 3 (AIA-004C) and diastereomer 4 (AIA-004D). The title compounds were synthesized from enantiomer 2 of 3-(1-methyl-1H-pyrazol-4-yl)cyclopentanone using the same methods described for 5-amino-N-(3-chloro-4-fluorophenyl)-1-methyl-3-(3-(1-methyl-1H-pyrazol-4-yl)cyclopentyl)-1H-pyrazole-4-carboxamide, diastereomer 1 (AIA-004A) and diastereomer 2 (AIA-004B). AIA-004C: (DMSO-$d_6$, 400 MHz): δ 8.90 (s, 1H), 7.91 (dd, J=6.8, 2.4 Hz, 1H), 7.53-7.49 (m, 1H), 7.44 (s, 1H), 7.34 (t, J=9.2 Hz, 1H), 7.24 (s, 1H), 6.01 (s, 2H), 3.78-3.74 (m, 4H), 3.51 (s, 3H), 3.02-2.98 (m, 1H), 2.16-2.11 (m, 1H), 2.08-2.00 (m, 2H), 1.94-1.89 (m, 2H), 1.55-1.50 (m, 1H). AIA-004D: $^1$H-NMR (DMSO-$d_6$, 400 MHz): δ 8.94 (s, 1H), 7.93 (dd, J=6.8, 2.4 Hz, 1H), 7.56-7.52 (m, 1H), 7.45 (s, 1H), 7.35 (t, J=9.2 Hz, 1H), 7.23 (s, 1H), 6.00 (s, 2H), 3.74 (s, 3H), 3.67-3.62 (m, 1H), 3.50 (s, 3H), 2.97-2.93 (m, 1H), 2.28-2.23 (m, 1H), 2.01-1.97 (m, 2H), 1.90-1.86 (m, 1H), 1.78-1.69 (m, 1H), 1.56-1.51 (m, 1H).

Intermediate 14

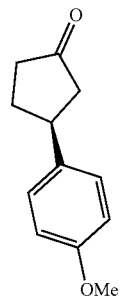

(S)-3-(4-Methoxyphenyl)cyclopentanone. Under a nitrogen atmosphere, a solution of RhCl[(C$_2$H$_4$)$_2$]$_2$ (30 mg, 0.08 mmol), (R)—N-cinnamyl-2-methylpropane-2-sulfinamide (R)-L-1 (Org. Biomol. Chem., 2012, 10, 1764) (38 mg, 0.16 mmol) and (4-methoxyphenyl)boronic acid (1.2 g, 8.0 mmol) in dioxane (10 mL) was stirred at 40° C. for 0.5 h. To this mixture was added cyclopent-2-en-1-one (330 mg, 4.0 mmol) and aqueous K$_3$PO$_4$ (1.6 mL, 1.5 mmol/L, 2.5 mmol). After being stirred at 40° C. for 1 h, the mixture was concentrated under reduced pressure and the residue was purified by silica gel column chromatography using 6:1 petroleum ether/ethyl acetate to afford (S)-3-(4-methoxyphenyl)cyclopentanone (690 mg, 91% yield and 97% ee) as a colorless oil. MS Calcd.: 190.1, MS Found: 191.3 [M+1]$^+$.

Intermediate 15

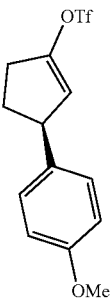

(S)-3-(4-Methoxyphenyl)cyclopent-1-enyl trifluoromethanesulfonate. To a solution of (S)-3-(4-methoxyphenyl)cyclopentanone (690 mg, 3.6 mmol) and Tf$_2$O (1.5 g, 5.4 mmol) in DCM (10 mL) was added 2,6-di-tert-butyl-4-methyl-pyridine (1.5 g, 7.2 mmol) dropwise at 0° C. The reaction was warmed to 40° C. and stirred for 2 h to yield a dark suspension. The reaction was concentrated under vacuum. Petroleum ether (5 mL) was added to the brown solid, the mixture was stirred for 2 min, filtered, and the filter cake washed with petroleum ether (2 mL). The filtrate was concentrated under vacuum to afford (S)-3-(4-methoxyphenyl)cyclopent-1-enyl trifluoromethanesulfonate (1.1 g crude, 92% yield) as a brown oil. MS Calcd.: 322.0, MS Found: 323.0 [M+1]$^+$.

Intermediate 16

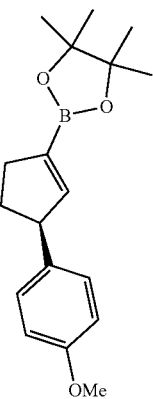

(S)-2-(3-(4-Methoxyphenyl)cyclopent-1-enyl)-4,4,5,5-tetramethyl-1,3,2-dioxaborolane. A mixture of (S)-3-(4-methoxyphenyl)cyclopent-1-enyl trifluoromethanesulfonate (1.1 g, 3.4 mmol), 4,4,5,5-tetramethyl-2-(4, 4,5,5-tetramethyl-1,3,2-dioxaborolan-2-yl)-1,3,2-dioxaborolane (1.3 g, 5.1 mmol), Pd(dppf)Cl$_2$ (125 mg, 0.17 mmol) and potassium acetate (500 mg, 5.1 mmol) in dioxane (10 mL) was stirred at 80° C. under an N$_2$ atmosphere for 4 h. The reaction was filtered through a pad of Celite®, and the filter cake washed with EtOAc (10 mL×3). The filtrate was concentrated under vacuum and the residue purified by silica gel column chromatography using 15:1 petroleum ether/ethyl acetate to afford (S)-2-(3-(4-methoxyphenyl)cyclopent-1-enyl)-4,4,5,5-tetramethyl-1,3,2-dioxaborolane (700 mg, 68% yield) as a yellow oil. MS Calcd.: 300.2, MS Found: 301.3 [M+1]$^+$.

Intermediate 17

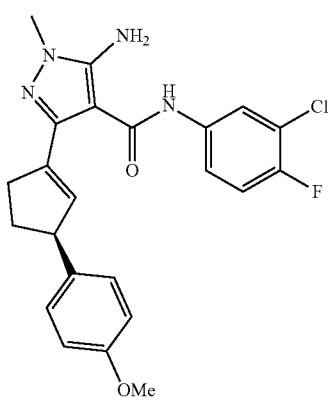

(S)-5-Amino-N-(3-chloro-4-fluorophenyl)-3-(3-(4-methoxyphenyl) cyclopent-1-enyl)-1-methyl-1H-pyrazole-4-carboxamide. A mixture of 5-amino-3-bromo-N-(3-chloro-4-fluorophenyl)-1-methyl-1H-pyrazole-4-carboxamide (348 mg, 1.0 mmol), (S)-2-(3-(4-methoxyphenyl)cyclopent-1-enyl)-4,4,5,5-tetramethyl-1,3,2-dioxaborolane (700 mg, 2.3 mmol), K$_3$PO$_4$ (424 mg, 2.0 mmol) and Pd(dppf)Cl$_2$ (73 mg, 0.1 mmol) in dioxane (10 mL) and H$_2$O (2 mL) was stirred at 95° C. for 2 h under an N$_2$ atmosphere. The solvent was removed under vacuum and the residue purified by silica gel column chromatography using 1:1 petroleum ether/ethyl acetate to afford (S)-5-amino-N-(3-chloro-4-fluorophenyl)-3-(3-(4-methoxyphenyl) cyclopent-1-enyl)-1-methyl-1H-pyrazole-4-carboxamide (300 mg, 68% yield) as a yellow solid. MS Calcd.: 440.1, MS Found: 441.1 [M+1]$^+$.

AIA-003A

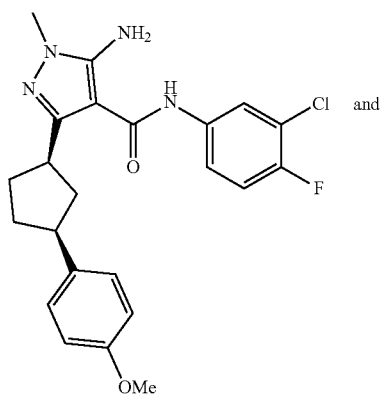

and

AIA-003B

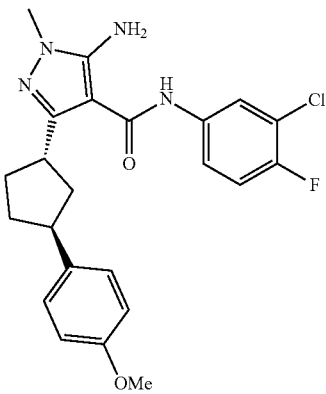

5-Amino-N-(3-chloro-4-fluorophenyl)-3-((1R,3S)-3-(4-methoxyphenyl)cyclopentyl)-1-methyl-1H-pyrazole-4-carboxamide (AIA-003A) and 5-amino-N-(3-chloro-4-fluorophenyl)-3-((1S,3S)-3-(4-methoxyphenyl)cyclopentyl)-1-methyl-1H-pyrazole-4-carboxamide (AIA-003B): A mixture of (S)-5-amino-N-(3-chloro-4-fluorophenyl)-3-(3-(4-methoxyphenyl) cyclopent-1-enyl)-1-methyl-1H-pyrazole-4-carboxamide (300 mg, 0.68 mmol) and RhCl(PPh$_3$)$_3$ (31 mg, 0.034 mmol) in MeOH (20 mL) was stirred at 60° C. overnight under 10 atm of H$_2$. The solvent was removed under vacuum and the residue purified by silica gel column chromatography using 1:1 petroleum ether/ethyl acetate to afford 5-amino-N-(3-chloro-4-fluorophenyl)-3-3-(4-methoxyphenyl)cyclopentyl)-1-methyl-1H-pyrazole-4-carboxamide A mixture if AP-AIA-003A and AIA-003B which were separated by SFC to give 5-amino-N-(3-chloro-4-fluorophenyl)-3-((JR, 3S)-3-(4-methoxyphenyl)cyclopentyl)-1-methyl-1H-pyrazole-4-carboxamide (AIA-003A) (80 mg) as a white solid and 5-amino-N-(3-chloro-4-fluorophenyl)-3-((1S,3S)-3-(4-methoxyphenyl)cyclopentyl)-1-methyl-1H-pyrazole-4-carboxamide (AIA-003 (10 mg) as a white solid. AIA-003-A: (DMSO-d$_6$, 400 MHz): δ 8.97 (s, 1H), 7.93 (dd, J=6.8, 2.8 Hz, 1H), 7.57-7.53 (m, 1H), 7.35 (t, J=9.2 Hz, 1H), 7.17 (d, J=8.8 Hz, 2H), 6.83 (d, J=8.8 Hz, 2H), 6.00 (s, 2H), 3.72-3.67 (m, 4H), 3.52 (s, 3H), 3.08-3.03 (m, 1H), 2.29-2.03 (m, 1H), 2.07-1.99 (m, 2H), 1.95-1.80 (m, 2H), 1.64-1.58 (m, 1H). AIA-003-B: $^1$H-NMR (DMSO-d$_6$, 400 MHz): δ 8.96 (s, 1H), 7.91 (dd, J=6.8, 2.8 Hz, 1H), 7.56-7.52 (m, 1H), 7.34 (t, J=9.2 Hz, 1H), 7.16 (d, J=8.4 Hz, 2H), 6.81 (d, J=8.8 Hz, 2H), 6.03 (s, 2H), 3.85-3.82 (m, 1H), 3.70 (s, 3H), 3.52 (s, 3H), 3.10-3.06 (m, 1H), 2.17-2.05 (m, 3H), 1.99-1.88 (m, 2H), 1.62-1.56 (m, 1H).

AIA-003C

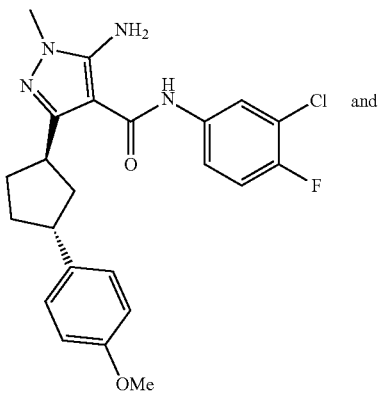

AIA-005A

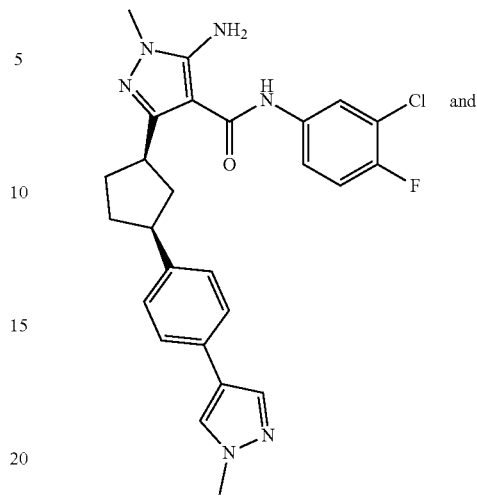

and

AIA-003D

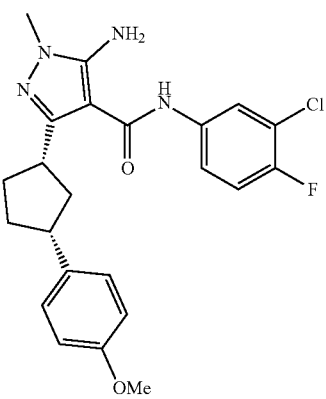

AIA-005B

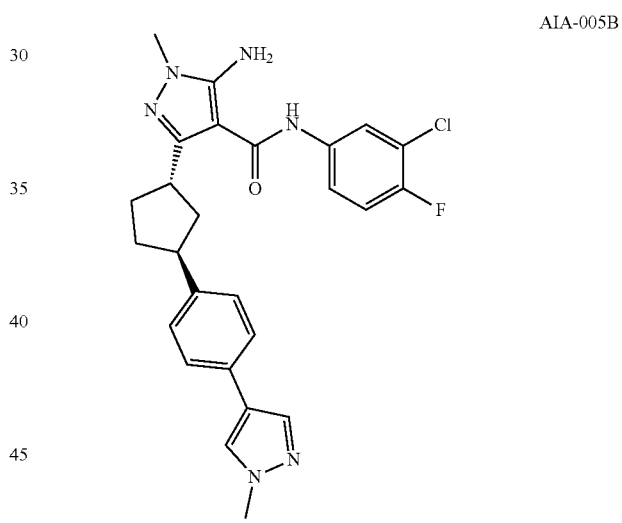

5-Amino-N-(3-chloro-4-fluorophenyl)-3-((1S,3R)-3-(4-methoxyphenyl)cyclopentyl)-1-methyl-1H-pyrazole-4-carboxamide (AIA-003C) and 5-amino-N-(3-chloro-4-fluorophenyl)-3-((1R,3R)-3-(4-methoxyphenyl)cyclopentyl)-1-methyl-1H-pyrazole-4-carboxamide (AIA-003D): The title compounds were synthesized according the procedure described for AIA-003A and AIA-003B using the chiral ligand (S)—N-cinnamyl-2-methylpropane-2-sulfinamide (S)-L-1 (Org. Biomol. Chem., 2012, 10, 1764). AIA-003C: $^1$H-NMR (DMSO-$d_6$, 400 MHz): δ 8.96 (s, 1H), 7.91 (dd, J=6.8, 2.8 Hz, 1H), 7.56-7.52 (m, 1H), 7.34 (t, J=9.2 Hz, 1H), 7.16 (d, J=8.4 Hz, 2H), 6.81 (d, J=8.8 Hz, 2H), 6.03 (s, 2H), 3.86-3.82 (m, 1H), 3.70 (s, 3H), 3.52 (s, 3H), 3.10-3.06 (m, 1H), 2.17-2.05 (m, 3H), 1.99-1.88 (m, 2H), 1.62-1.56 (m, 1H). AIA-003D: (DMSO-$d_6$, 400 MHz): δ 8.97 (s, 1H), 7.93 (dd, J=6.8, 2.8 Hz, 1H), 7.57-7.53 (m, 1H), 7.35 (t, J=9.2 Hz, 1H), 7.17 (d, J=8.8 Hz, 2H), 6.83 (d, J=8.8 Hz, 2H), 6.00 (s, 2H), 3.72-3.67 (m, 4H), 3.52 (s, 3H), 3.08-3.03 (m, 1H), 2.29-2.03 (m, 1H), 2.07-1.99 (m, 2H), 1.95-1.80 (m, 2H), 1.64-1.58 (m, 1H).

5-Amino-N-(3-chloro-4-fluorophenyl)-1-methyl-3-((1R,3S)-3-(4-(1-methyl-1H-pyrazol-4-yl)phenyl)cyclopentyl)-1H-pyrazole-4-carboxamide (AIA-050A) and 5-amino-N-(3-chloro-4-fluorophenyl)-1-methyl-3-((1S,3S)-3-(4-(1-methyl-1H-pyrazol-4-yl)phenyl) cyclopentyl)-1H-pyrazole-4-carboxamide (AIA-050B): The title compounds were synthesized according to the procedure described for AIA-003A and AIA-003B. AIA-050-A: $^1$H-NMR (DMSO-$d_6$, 400 MHz): δ 8.94 (s, 1H), 8.05 (s, 1H), 7.93 (dd, J=7.2, 2.8 Hz, 1H), 7.79 (s, 1H), 7.56-7.52 (m, 1H), 7.43 (d, J=8.4 Hz, 2H), 7.34 (t, J=9.2 Hz, 1H), 7.23 (d, J=8.0 Hz, 2H), 6.04 (s, 2H), 3.88-3.84 (m, 4H), 3.53 (s, 3H), 3.15-3.09 (m, 1H), 2.20-2.08 (m, 3H), 2.03-1.91 (m, 2H), 1.67-1.62 (m, 1H). AIA-050-B: (DMSO-$d_6$, 400 MHz): δ 8.98 (s, 1H), 8.06 (s, 1H), 7.94 (dd, J=6.8, 2.8 Hz, 1H), 7.79 (s, 1H), 7.58-7.54 (m, 1H), 7.45 (d, J=8.4 Hz, 2H), 7.36 (t, J=9.2 Hz, 1H), 7.23 (d, J=8.0 Hz, 2H), 6.01 (s, 2H), 3.85 (s, 3H), 3.73-3.67 (m, 1H), 3.53 (s, 3H), 3.13-3.07 (m, 1H), 2.33-2.26 (m, 1H), 2.09-1.95 (m, 2H), 1.92-1.86 (m, 2H), 1.69-1.63 (m, 1H).

AIA-124-A

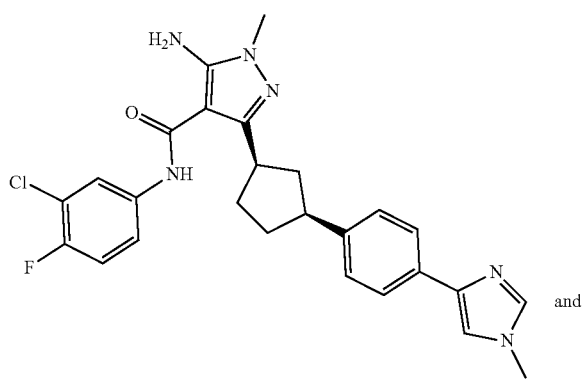

and

AIA-124-B

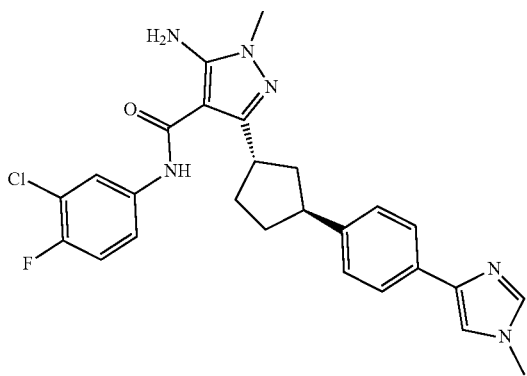

5-Amino-N-(3-chloro-4-fluorophenyl)-1-methyl-3-((1R, 3S)-3-(4-(1-methyl-1H-imidazol-4-yl)phenyl)cyclopentyl)-1H-pyrazole-4-carboxamide (CP-AIA-124-B) and 5-Amino-N-(3-chloro-4-fluorophenyl)-1-methyl-3-((1S, 3S)-3-(4-(1-methyl-1H-imidazol-4-yl)phenyl)cyclopentyl)-1H-pyrazole-4-carboxamide (CP-AIA-124-A). The title compounds were synthesized according to the procedure described for AIA-003A and AIA-003B. CP-AIA-124-A: $^1$H-NMR (DMSO-$d_6$, 400 MHz): δ 8.94 (s, 1H), 7.92 (dd, J=2.4, 6.8 Hz, 1H), 7.60 (t, J=8.0 Hz, 3H), 7.54-7.51 (m, 2H), 7.33 (t, J=9.2 Hz, 1H), 7.21 (d, J=8.4 Hz, 2H), 6.05 (s, 2H), 3.86 (t, J=8.0 Hz, 1H), 3.67 (s, 3H), 3.53 (s, 3H), 3.12 (t, J=8.0 Hz, 1H), 2.20-2.08 (m, 3H), 2.00-1.94 (m, 2H), 1.65 (t, J=8.4 Hz, 1H). CP-AIA-124-B: (DMSO-$d_6$, 400 MHz): δ 8.98 (s, 1H), 7.93 (dd, J=2.4, 6.8 Hz, 1H), 7.65-7.52 (m, 5H), 7.36 (t, J=9.2 Hz, 1H), 7.23 (d, J=8.4 Hz, 2H), 6.02 (s, 2H), 3.71 (t, J=9.6 Hz, 1H), 3.67 (s, 3H), 3.53 (s, 3H), 2.33-2.27 (m, 1H), 2.10-2.04 (m, 2H), 2.02-1.87 (m, 2H), 1.70-1.64 (m, 2H).

Intermediate 18

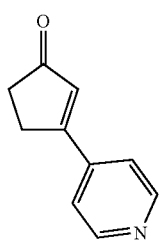

3-(Pyridin-4-yl)cyclopent-2-en-1-one. To a solution of 4-bromopyridine (2 g, 10.29 mmol, 1 eq, HCl) in dioxane (30 mL) and H$_2$O (6 mL) was added 3-(4,4,5,5-tetramethyl-1,3,2-dioxaborolan-2-yl)cyclopent-2-en-1-one (3.21 g, 15.43 mmol, 1.5 eq), Pd(dppf)Cl$_2$ (752.56 mg, 1.03 mmol, 0.1 eq) and K$_3$PO$_4$ (6.55 g, 30.87 mmol, 3 eq). The suspension was degassed and purged with N$_2$ 3 times. The mixture was stirred under N$_2$ at 80° C. for 16 hr. The reaction mixture was filtered, and the filtrate diluted with water (20 mL) and extracted with EtOAc (30 mL×3). The combined organic layers were washed with brine (15 mL×2), dried over Na$_2$SO$_4$, filtered and concentrated under reduced pressure to give a residue, which was purified by flash silica gel chromatography (ISCO®; 40 g SepaFlash® Silica Flash Column, Eluent of 0~100% Ethyl acetate/Petroleum ether gradient @ 40 mL/min) to give 3-(4-pyridyl)cyclopent-2-en-1-one (1.2 g, 7.54 mmol, 73.26% yield), as a yellow solid. $^1$H NMR (400 MHz, CHLOROFORM-d) δ 2.52-2.67 (m, 2H), 3.00 (dt, J=4.85, 2.21 Hz, 2H), 6.65 (d, J=1.76 Hz, 1H), 7.40-7.47 (m, 2H), 8.69 (br d, J=4.41 Hz, 2H).

Intermediates 19-23. Intermediates 19-23 were synthesized according to the procedure described for intermediate 18.

| Intermediate | Structure | Characterization |
|---|---|---|
| 19 | 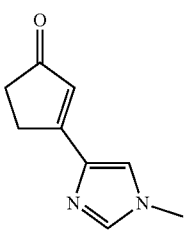 | 3-(1-Methyl-1H-imidazol-4-yl)cyclopent-2-en-1-one<br>$^1$H NMR (400 MHz, CHLOROFORM-d) δ ppm 2.49-2.59 (m, 2H), 2.98 (td, J = 4.85, 1.54 Hz, 1H), 2.96-2.98 (m, 1H), 3.76 (s, 3H), 6.49 (s, 1H), 7.31 (s, 1H), 7.48-7.62 (m, 1H). |

-continued

| Intermediate | Structure | Characterization |
|---|---|---|
| 20 | 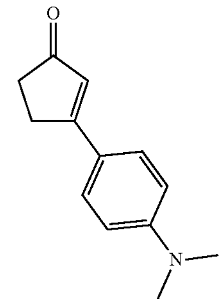 | 3-(4-(Dimethylamino)phenyl)cyclopent-2-en-1-one<br>LCMS: 202.2 [M + 1]$^+$. |
| 21 | 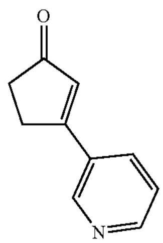 [SMILES: O=C1C=C(c2cccnc2)CC1] | 3-(Pyridin-3-yl)cyclopent-2-en-1-one<br>$^1$H NMR (400 MHz, CHLOROFORM-d) δ ppm 2.58-2.65 (2 H, m), 3.03-3.11 (2 H, m), 6.64 (1 H, t, J = 1.76 Hz), 7.40 (1 H, ddd, J = 7.99, 4.80, 0.66 Hz), 7.93 (1 H, dt, J = 7.94, 1.98 Hz), 8.69 (1 H, dd, J = 4.85, 1.54 Hz), 8.90-8.92 (1 H, m). |
| 22 | 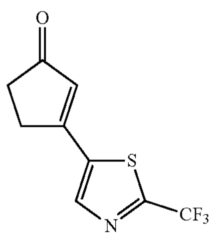 [SMILES: O=C1C=C(c2cnc(C(F)(F)F)s2)CC1] | 3-(2-(Trifluoromethyl)thiazol-5-yl)cyclopent-2-en-1-one<br>MS Calcd.: 233.2, MS Found: 234.0 [M + 1]$^+$ |
| 23 | 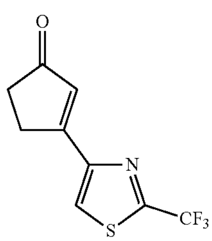 [SMILES: O=C1C=C(c2csc(C(F)(F)F)n2)CC1] | 3-(2-(Trifluoromethyl)thiazol-4-yl)cyclopent-2-enone.<br>MS Calcd.: 233.2; MS Found: 234.4 [M + 1]$^+$. |

Intermediate 24

3-(4-(Dimethylamino)phenyl)cyclopentan-1-one. To a solution of 3-[4-(dimethylamino)phenyl]cyclopent-2-en-1-one (1.05 g, 4.97 mmol, 1 eq) in MeOH (20 mL) was added Pd/C (200 mg, 10% purity) under an $N_2$ atmosphere. The suspension was degassed and purged with $H_2$ 3 times. The mixture was stirred under $H_2$ (40 psi) at 20° C. for 16 hr. The mixture was filtered, and the filtrate concentrated under vacuum to give 3-[4-(dimethylamino)phenyl]cyclopentanone (900 mg, 2.51 mmol, 50.6% yield, 56.7% purity), as a to yellow oil. LCMS: 203.9 [M+1]$^+$.

Intermediates 25-26. Intermediates 25-26 were synthesized according to the procedure described for intermediate 24.

| Intermediate | Structure | Characterization |
|---|---|---|
| 25 | 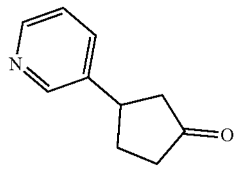 [SMILES: O=C1CCC(c2cccnc2)C1] | 3-(Pyridin-3-yl)cyclopentan-1-one<br>$^1$H NMR (400 MHz, CHLOROFORM-d) δ ppm 1.94-2.07 (1 H, m), 2.29-2.41 (2 H, m), 2.46-2.57 (2 H, m), 2.66-2.78 (1 H, m), 3.38-3.52 (1 H, m), 7.27-7.31 (1 H, m), 7.56-7.60 (1 H, m), 8.52 (1 H, dd, J = 4.74, 1.65 Hz), 8.56 (1 H, d, J = 2.20 Hz). |
| 26 | 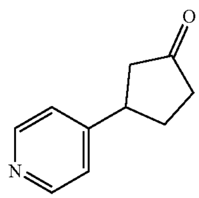 [SMILES: O=C1CCC(c2ccncc2)C1] | 3-(Pyridin-4-yl)cyclopentan-1-one<br>$^1$H NMR (400 MHz, CHLOROFORM-d) δ 1.91-1.95 (m, 1H), 2.17-2.30 (m, 2H), 2.37-2.48 (m, 2H), 2.63 (dd, J = 18.19, 7.61 Hz, 1H), 3.29-3.40 (m, 1H), 7.03-7.18 (m, 2H), 8.37-8.53 (m, 2H). |

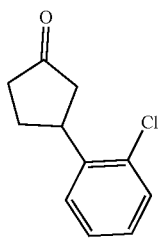

Intermediate 27

3-(2-Chlorophenyl)cyclopentan-1-one. A yellow suspension of (2-chlorophenyl)boronic acid (1.14 g, 7.31 mmol), cyclopent-2-en-1-one (500 mg, 6.09 mmol, 0.510 mL) and [Rh(COD)$_2$Cl]$_2$ (60.06 mg, 0.122 mmol) in 7.7 mL of 10:1 EtOH/H$_2$O was stirred at 50° C. for 50 hr. The yellow suspension was then filtered, and the filtrate concentrated under vacuum. The resulting residue was purified by silica gel chromatography (eluent of 0 to 9.4% EtOAc in petroleum ether gradient) to yield the title compound as a yellow oil. $^1$H NMR (400 MHz, CHLOROFORM-d) δ ppm 1.96-2.07 (1H, m), 2.26-2.49 (4H, m), 2.72 (1H, dd, J=18.19, 7.83 Hz), 3.81-3.90 (1H, m), 7.16-7.22 (1H, m), 7.25-7.28 (2H, m), 7.39 (1H, dt, J=7.77, 0.85 Hz).

Intermediates 28-38 Intermediates 28-38 were synthesized according to the procedure described for intermediate 27.

| Intermediate | structure | Characterization |
|---|---|---|
| 28 | 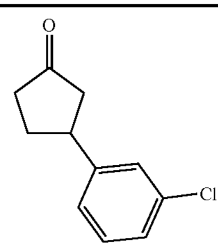 | 3-(3-Chlorophenyl)cyclopentan-1-one<br>$^1$H NMR (400 MHz, CHLOROFORM-d) δ ppm 1.86-2.02 (m, 1H), 2.19-2.58 (m, 4H), 2.59-2.71 (m, 1H), 3.29-3.52 (m, 1H), 7.18-7.38 (m, 4H). |
| 29 | 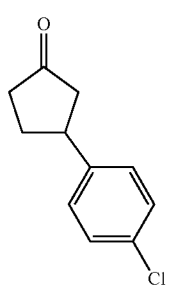 [SMILES: O=C1CCC(c2ccc(Cl)cc2)C1] | 3-(4-Chlorophenyl)cyclopentan-1-one<br>$^1$H NMR (400 MHz, CHLOROFORM-d) δ ppm 1.88-2.03 (m, 1H) 2.22-2.37 (m, 2H) 2.39-2.53 (m, 2H) 2.59-2.73 (m, 1H) 3.40 (tt, J = 10.95, 6.87 Hz, 1H) 7.16-7.22 (m, 2H) 7.29-7.34 (m, 2H) |
| 30 | 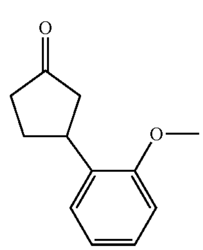 | 3-(2-Methoxyphenyl)cyclopentan-1-one<br>$^1$H NMR (400 MHz, CHLOROFORM-d) δ ppm 2.01-2.13 (m, 1H) 2.27-2.50 (m, 4H) 2.66 (dd, J = 18.40, 8.13 Hz, 1H) 3.66-3.76 (m, 1H) 3.86 (s, 3H) 6.89-6.99 (m, 2H) 7.18-7.28 (m, 2H). |

-continued

| Intermediate | structure | Characterization |
| --- | --- | --- |
| 31 | 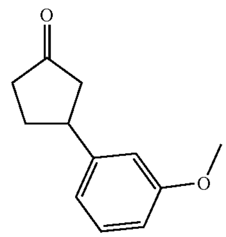 | 3-(3-Methoxyphenyl)cyclopentan-1-one<br>$^1$H NMR (400 MHz, CHLOROFORM-d) δ ppm 1.95-2.08 (m, 1H) 2.27-2.53 (m, 4H) 2.69 (dd, J = 18.10, 7.46 Hz, 1H) 3.42 (ddd, J = 10.85, 6.69, 3.85 Hz, 1H) 3.84 (s, 3H) 6.78-6.90 (m, 3H) 7.26-7.32 (m, 1H). |
| 32 | 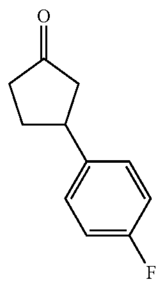 [SMILES: O=C1CCC(c2ccc(F)cc2)C1] | 3-(4-Fluorophenyl)cyclopentan-1-one<br>$^1$H NMR (400 MHz, CHLOROFORM-d) δ ppm 1.88-2.05 (m, 1H) 2.23-2.36 (m, 2H) 2.38-2.51 (m, 2H) 2.66 (dd, J = 17.86, 7.50 Hz, 1H) 3.33-3.47 (m, 1H) 6.97-7.07 (m, 2H) 7.17-7.24 (m, 2H). |
| 33 | 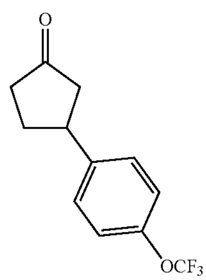 [SMILES: O=C1CCC(c2ccc(OC(F)(F)F)cc2)C1] | 3-(4-(Trifluoromethoxy)phenyl)cyclopentan-1-one<br>$^1$H NMR (400 MHz, CHLOROFORM-d) δ ppm 1.93-2.05 (m, 1H) 2.28-2.40 (m, 2H) 2.43-2.59 (m, 2H) 2.72 (br dd, J = 18.19, 7.61 Hz, 1H) 3.36-3.57 (m, 1H) 7.22 (br d, J = 8.16 Hz, 2H) 7.27-7.36 (m, 2H). |
| 34 | 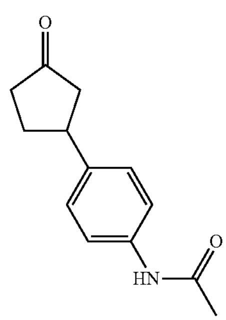 [SMILES: CC(=O)Nc1ccc(C2CCC(=O)C2)cc1] | N-(4-(3-Oxocyclopentyl)phenyl)acetamide<br>$^1$H NMR (400 MHz, CHLOROFORM-d) δ ppm 1.83-1.99 (m, 1H) 2.11 (s, 3H) 2.24 (br dd, J = 18.08, 10.58 Hz, 2H) 2.30-2.46 (m, 2H) 2.58 (br dd, J = 18.30, 7.28 Hz, 1H) 3.24-3.42 (m, 1H) 7.14 (br d, J = 8.38 Hz, 2H) 7.40 (br d, J = 8.38 Hz, 2H); LC-MS: 217.9 [M + 1]$^+$. |
| 35 | 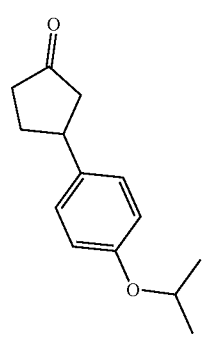 [SMILES: CC(C)Oc1ccc(C2CCC(=O)C2)cc1] | 3-(4-Isopropoxyphenyl)cyclopentan-1-one<br>$^1$H NMR (400 MHz, CHLOROFORM-d) δ ppm 1.34 (d, J = 5.95 Hz, 6H) 1.88-2.02 (m, 1H) 2.23-2.36 (m, 2H) 2.38-2.51 (m, 2H) 2.58-2.71 (m, 1H) 3.27-3.45 (m, 1H) 4.54 (spt, J = 5.92 Hz, 1H) 6.87 (d, J = 8.16 Hz, 2H) 7.15 (s, 2H). |

| Intermediate | structure | Characterization |
|---|---|---|
| 36 | 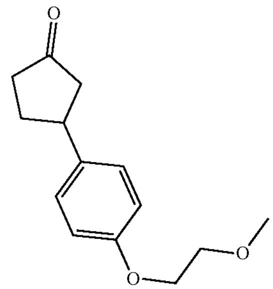 [SMILES: COCCOc1ccc(C2CCC(=O)C2)cc1] | 3-(4-(2-Methoxyethoxy)phenyl)cyclopentan-1-one<br>$^1$H NMR (400 MHz, CHLOROFORM-d) δ ppm 1.87-2.02 (m, 1H), 2.23-2.47 (m, 4H), 2.59-2.77 (m, 1H), 3.31-3.49 (m, 4H), 3.76 (dd, J = 5.40, 4.08 Hz, 2H), 4.07-4.15 (m, 2H), 6.87-6.94 (m, 2H), 7.17 (d, J = 8.60 Hz, 2H); LCMS: 235.0 [M + 1]$^+$. |
| 37 | 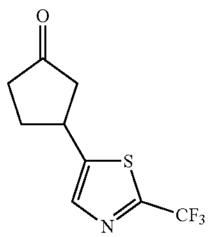 [SMILES: O=C1CCC(c2cnc(C(F)(F)F)s2)C1] | 3-(2-(trifluoromethyl)thiazol-5-yl)cyclopentanone<br>MS Calcd.: 235.2, MS Found: 236.0 [M + 1]$^+$. |
| 38 | 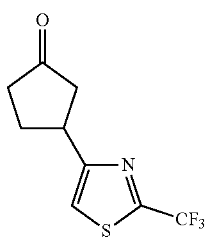 [SMILES: O=C1CCC(c2csc(C(F)(F)F)n2)C1] | 3-(2-(Trifluoromethyl)thiazol-4-yl)cyclopentanone<br>MS Calcd.: 235.0; MS Found: 236.2 [M + 1]$^+$. |

Intermediates 39-55. Intermediates 39-55 were synthesized according to the procedures described for intermediates 11 or 15

| intermediate | structure | Characterization |
|---|---|---|
| 39 | 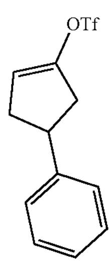 [SMILES: O=S(=O)(OC1=CCC(c2ccccc2)C1)C(F)(F)F] | 4-Phenylcyclopent-1-en-1-yl trifluoromethanesulfonate<br>$^1$H NMR (400 MHz, CHLOROFORM-d) ☐ ppm 2.44-2.63 (m, 1 H) 2.67-2.82 (m, 1 H) 2.86-2.97 (m, 1 H) 2.99-3.08 (m, 1 H) 3.62-3.71 (m, 1 H) 5.71-5.77 (m, 1 H) 7.18-7.28 (m, 2 H) 7.32-7.40 (m, 3 H). |
| 40 | 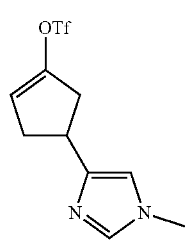 [SMILES: Cn1cnc(C2CC=C(OS(=O)(=O)C(F)(F)F)C2)c1] | 4-(1-Methyl-1H-imidazol-4-yl)cyclopent-1-en-1-yl trifluoromethanesulfonate<br>$^1$H NMR (400 MHz, CHLOROFORM-d) δ ppm 2.40-2.98 (m, 4H), 3.62-3.65 (m, 3H), 3.98 (ddd, J = 8.43, 5.57, 2.76 Hz, 1H), 5.60-5.79 (m, 1H), 6.57-6.70 (m, 1H), 7.33-7.42 (m, 1H). |

| intermediate | structure | Characterization |
|---|---|---|
| 41 | 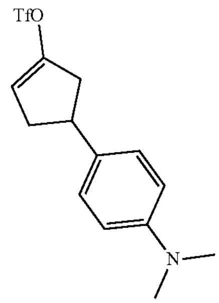 [SMILES: CN(C)c1ccc(C2CC=C(OS(=O)(=O)C(F)(F)F)C2)cc1] | 4-(4-(Dimethylamino)phenyl)cyclopent-1-en-1-yl trifluoromethanesulfonate<br>$^1$H NMR (400 MHz, CHLOROFORM-d) δ ppm 1.83-1.95 (m, 1H), 2.44-2.59 (m, 1H), 2.60-2.81 (m, 2H), 2.91-2.95 (m, 7H), 5.70 (br s, 1H), 6.72 (br d, J = 8.38 Hz, 3H), 7.01-7.19 (m, 2H) |
| 42 | 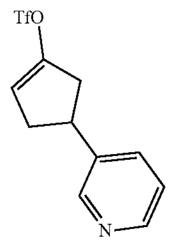 [SMILES: O=S(=O)(OC1=CCC(c2cccnc2)C1)C(F)(F)F] | 4-(Pyridin-3-yl)cyclopent-1-en-1-yl trifluoromethanesulfonate<br>$^1$H NMR (400 MHz, CHLOROFORM-d) δ ppm 1.72-1.80 (m, 1H), 2.38-2.49 (m, 1H), 2.53-2.62 (m, 2H, m, 1H), 3.87 (ddd, J = 8.71, 5.95, 2.98 Hz, 1H), 5.54-5.60 (m, 1H), 7.11-7.14 (m, 1H), 7.35 (dt, J = 7.94, 1.98 Hz, 1H), 8.28-8.38 (m, 1H); LCMS: 294.2 [M + 1]$^+$. |
| 43 | 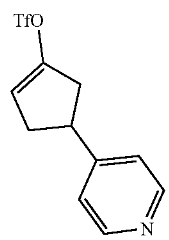 [SMILES: O=S(=O)(OC1=CCC(c2ccncc2)C1)C(F)(F)F] | 4-(Pyridin-4-yl)cyclopent-1-en-1-yl trifluoromethanesulfonate<br>LCMS: 294.2 [M + 1]$^+$. |
| 44 | 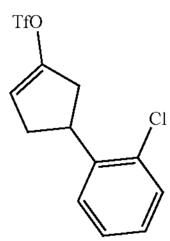 [SMILES: O=S(=O)(OC1=CCC(c2ccccc2Cl)C1)C(F)(F)F] | 4-(2-Chlorophenyl)cyclopent-1-en-1-yl trifluoromethanesulfonate<br>$^1$H NMR (400 MHz, CHLOROFORM-d) δ ppm 2.38-2.52 (m, 1H), 2.63-2.70 (m, 1H), 2.76-2.92 (m, 1H), 2.99 (dddt, J = 16.37, 9.65, 3.36, 1.74, 1.74 Hz, 1H), 3.99-4.11 (m, 1H), 5.63-5.66 (m, 1H), 7.08-7.18 (m, 1H), 7.23-7.32 (m, 1H). |
| 45 | 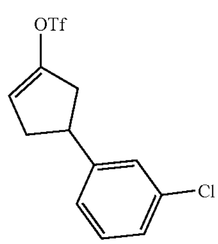 [SMILES: O=S(=O)(OC1=CCC(c2cccc(Cl)c2)C1)C(F)(F)F] | 4-(3-Chlorophenyl)cyclopent-1-en-1-yl trifluoromethanesulfonate<br>$^1$H NMR (400 MHz, CHLOROFORM-d) δ ppm 2.47-2.60 (m, 1H), 2.69-2.74 (m, 1H, 2.85-2.94 (m, 1H, 2.98-3.06 (m, 1H), 3.55-3.67 (m, 1H), 5.70 (d, J = 2.21 Hz), 7.10-7.17 (m, 1H, 7.20-7.26 (m, 3H) |
| 46 | 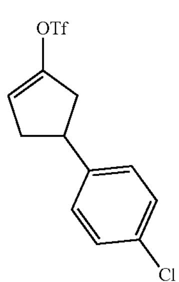 [SMILES: O=S(=O)(OC1=CCC(c2ccc(Cl)cc2)C1)C(F)(F)F] | 4-(3-Chlorophenyl)cyclopent-1-en-1-yl trifluoromethanesulfonate<br>$^1$H NMR (400 MHz, CHLOROFORM-d) δ ppm 1.80-1.95 (m, 1H) 2.43-2.62 (m, 1H) 2.64-2.78 (m, 1H) 2.90 (ddtd, J = 16.41, 9.07, 2.89, 2.89, 1.38 Hz, 1H) 3.03 (dddt, J = 16.19, 9.60, 3.20, 1.57, 1.57 Hz, 1H) 3.62 (tt, J = 9.29, 6.78 Hz, 1H) 3.97 (ddq, J = 8.66, 5.87, 2.77, 2.77, 2.77 Hz, 1H) 5.71 (dq, J = 4.83, 2.32Hz, 1H) 7.09-7.15 (m, 1H) 7.16-7.22 (m, 1H) 7.28-7.33 (m, 2H). |

-continued

| intermediate | structure | Characterization |
| --- | --- | --- |
| 47 | (OTf-cyclopentene with 2-methoxyphenyl) | 4-(2-Methoxyphenyl)cyclopent-1-en-1-yl trifluoromethanesulfonate used in the next reaction without further purification. |
| 48 | (OTf-cyclopentene with 3-methoxyphenyl) | 4-(3-Methoxyphenyl)cyclopent-1-en-1-yl trifluoromethanesulfonate used in the next reaction without further purification. |
| 49 | (OTf-cyclopentene with 4-fluorophenyl) | 4-(4-Fluorophenyl)cyclopent-1-en-1-yl trifluoromethanesulfonate used in the next reaction without further purification. |
| 50 | (OTf-cyclopentene with 4-OCF3-phenyl) | 4-(4-(Trifluoromethoxy)phenyl)cyclopent-1-en-1-yl trifluoromethanesulfonate <br> $^1$H NMR (400 MHz, CHLOROFORM-d) δ ppm 2.45-2.64 (m, 1H) 2.65-2.81 (m, 2H) 2.85-3.10 (m, 1H) 3.60-4.05 (m, 1H) 5.67-5.76 (m, 1H) 7.14-7.23 (m, 3H) 7.27-7.31 (m, 1H). |
| 51 | (OTf-cyclopentene with 4-acetamidophenyl) | 4-(4-Acetamidophenyl)cyclopent-1-en-1-yl trifluoromethanesulfonate <br> LC-MS: 349.9 [M + 1]$^+$. |

-continued

| intermediate | structure | Characterization |
| --- | --- | --- |
| 52 | (structure) | 4-(4-Isopropoxyphenyl)cyclopent-1-en-1-yl trifluoromethanesulfonate<br>$^1$H NMR (400 MHz, CHLOROFORM-d) δ ppm 1.32-1.34 (m, 6H) 2.43-2.77 (m, 3H) 2.80-3.05 (m, 1H) 3.52-3.98 (m, 1H) 4.46-4.60 (m, 1H) 5.62-5.79 (m, 1H) 6.77-6.89 (m, 2H) 7.03-7.21 (m, 2H). |
| 53 | (structure) | 3-(4-(2-Methoxyethoxy)phenyl)cyclopent-1-en-1-yl trifluoromethanesulfonate<br>$^1$H NMR (400 MHz, CHLOROFORM-d) δ ppm 2.36-2.62 (m, 1H), 2.65-2.73 (m, 1H), 2.80-2.92 (m, 1H), 2.93-3.05 (m, 1H), 3.45 (s, 3H), 3.53-3.66 (m, 1H), 3.72-3.79 (m, 2H), 4.07-4.13 (m, 2H), 5.69 (br d, J = 2.01 Hz, 1H), 6.85-6.92 (m, 2H), 7.06-7.20 (m, 2H). |
| 54 | (structure) | 3-(2-(Trifluoromethyl)thiazol-5-yl)cyclopent-1-enyl trifluoromethanesulfonate<br>MS Calcd.: 367.3, MS Found: 367.9 [M + 1]$^+$. |
| 55 | (structure) | 3-(2-(Trifluoromethyl)thiazol-4-yl)cyclopent-1-enyl trifluoromethanesulfonate<br>MS Calcd.: 367.0; MS Found: 368.0 [M + 1]$^+$ |

Intermediates 56-72. Intermediates 56-72 were synthesized according to the procedure described for intermediate 16.

| Intermediate | Structure | Characterization |
|---|---|---|
| 56 | 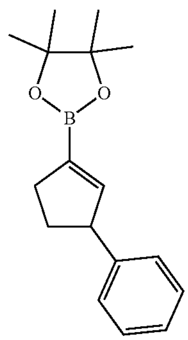 [SMILES: CC1(C)OB(C2=CC(c3ccccc3)CC2)OC1(C)C] | 4,4,5,5-tetramethyl-2-(3-phenylcyclopent-1-en-1-yl)-1,3,2-dioxaborolane<br>$^1$H NMR (400 MHz, CHLOROFORM-d) δ ppm 1.28-1.32 (m, 12 H) 2.36-2.69 (m, 3 H) 2.86-3.00 (m, 1 H) 3.49 (t, J = 8.41 Hz, 1 H) 6.51-6.60 (m, 1 H) 7.15-7.34 (m, 5 H). |
| 57 | 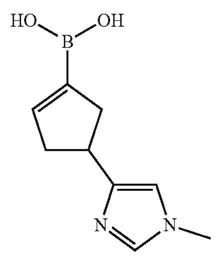 | (4-(1-Methyl-1H-imidazol-4-yl)cyclopent-1-en-1-yl)boronic acid<br>$^1$H NMR (400 MHz, CHLOROFORM-d) δ ppm 1.90 (br s, 1H), 1.92-2.06 (m, 1H), 2.30-2.63 (m, 4H), 3.55 (s, 3H), 3.93 (br s, 1H), 5.52-5.72 (m, 1H), 6.52 (s, 1H), 7.31 (s, 1H). |
| 58 | 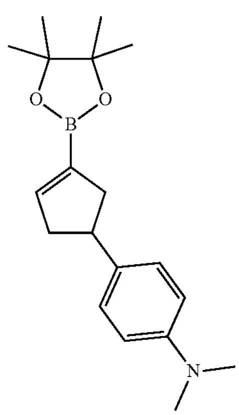 | N,N-Dimethyl-4-(3-(4,4,5,5-tetramethyl-1,3,2-dioxaborolan-2-yl)cyclopent-3-en-1-yl)aniline<br>$^1$H NMR (400 MHz, CHLOROFORM-d) δ ppm 1.27 (br d, J = 4.41 Hz, 12H), 1.60-1.77 (m, 1H), 2.26-2.65 (m, 3H), 2.68-2.95 (m, 7H), 6.44-6.59 (m, 1H), 6.98-7.16 (m, 2H), 7.36-7.40 (m, 2H). |
| 59 | 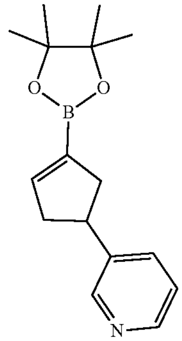 [SMILES: CC1(C)OB(C2=CCC(c3cccnc3)C2)OC1(C)C] | 3-(3-(4,4,5,5-Tetramethyl-1,3,2-dioxaborolan-2-yl)cyclopent-3-en-1-yl)pyridine<br>$^1$H NMR (400 MHz, CHLOROFORM-d) δ ppm 1.26-1.30 (m, 12H), 1.69-1.76 (m, 1H), 2.47-2.57 (m, 2H), 2.59-2.68 (m, 1H), 3.87-3.98 (m, 1H), 6.40-6.58 (m, 1H), 7.19 (dd, J = 7.72, 4.85 Hz, 1H), 7.46 (dt, J = 7.83, 1.82 Hz, 1H), 8.37-8.48 (m, 2H). |

| Intermediate | Structure | Characterization |
|---|---|---|
| 60 | 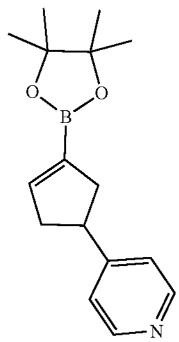 [SMILES: CC1(C)OB(C2=CCC(c3ccncc3)C2)OC1(C)C] | 4-(3-(4,4,5,5-Tetramethyl-1,3,2-dioxaborolan-2-yl)cyclopent-3-en-1-yl)pyridine<br>$^1$H NMR (400 MHz, DMSO-$d_6$) δ ppm 1.80 (s, 12H), 2.20-2.31 (m, 1H), 2.95-3.00 (m, 2H), 4.36-4.58 (m, 1H), 6.84-7.04 (m, 1H), 7.68-7.78 (m, 2H), 8.97-9.02 (m, 2H); LCMS: 272.3 [M + 1]$^+$. |
| 61 | 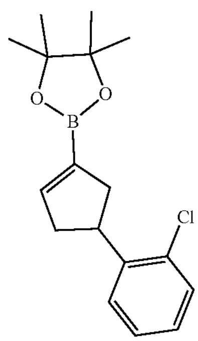 [SMILES: CC1(C)OB(C2=CCC(c3ccccc3Cl)C2)OC1(C)C] | 2-(4-(2-Chlorophenyl)cyclopent-1-en-1-yl)-4,4,5,5-tetramethyl-1,3,2-dioxaborolane<br>$^1$H NMR (400 MHz, CHLOROFORM-d) δ ppm 1.29 (d, J = 7.50 Hz, 12H), 2.39-2.64 (m, 3H), 2.89-3.00 (m, 1H), 3.90-3.98 (m, 1H), 6.46-6.58 (m, 1H), 7.07-7.20 (m, 3H), 7.33 (d, J = 7.50 Hz, 1H). |
| 62 | 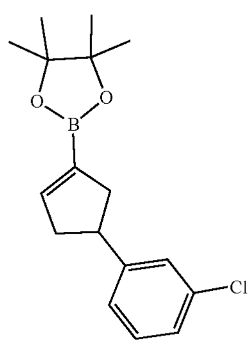 [SMILES: CC1(C)OB(C2=CCC(c3cccc(Cl)c3)C2)OC1(C)C] | 2-(4-(3-Chlorophenyl)cyclopent-1-en-1-yl)-4,4,5,5-tetramethyl-1,3,2-dioxaborolane<br>$^1$H NMR (400 MHz, CHLOROFORM-d) δ ppm 1.29 (13H, d, J = 4.63 Hz), 2.34-2.69 (m, 3H), 2.85-2.98 (m, 1H), 3.38-3.52 (m, 1H), 6.47-6.56 (m, 1H), 7.04-7.12 (m, 1H), 7.13-7.22 (m, 3H). |
| 63 | 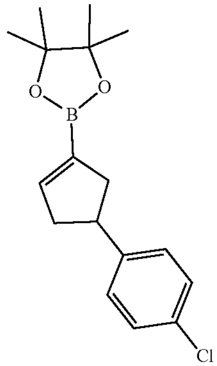 [SMILES: CC1(C)OB(C2=CCC(c3ccc(Cl)cc3)C2)OC1(C)C] | 2-(4-(4-Chlorophenyl)cyclopent-1-en-1-yl)-4,4,5,5-tetramethyl-1,3,2-dioxaborolane<br>$^1$H NMR (400 MHz, CHLOROFORM-d) δ ppm 1.30 (d, J = 4.03 Hz, 12H) 1.71 (ddt, J = 12.55, 8.91, 7.18, 7.18 Hz, 1H) 2.23-2.71 (m, 3H) 2.82-3.02 (m, 1H) 3.36-3.53 (m, 1H) 3.87-3.97 (m, 1H) 6.43-6.59 (m, 1H) 7.09-7.19 (m, 2H) 7.21-7.26 (m, 2H). |

-continued

| Intermediate | Structure | Characterization |
|---|---|---|
| 64 | 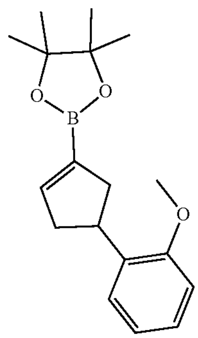 [SMILES: COc1ccccc1C1CC=C(B2OC(C)(C)C(C)(C)O2)C1] | 2-(4-(2-Methoxyphenyl)cyclopent-1-en-1-yl)-4,4,5,5-tetramethyl-1,3,2-dioxaborolane<br>$^1$H NMR (400 MHz, CHLOROFORM-d) δ ppm 1.25-1.34 (m, 12H) 2.37-2.63 (m, 3H) 2.71-2.98 (m, 1H) 3.77-3.88 (m, 3H) 4.29-4.35 (m, 1H) 6.53-6.59 (m, 1H) 6.80-6.93 (m, 2H) 7.09-7.22 (m, 2H). |
| 65 | 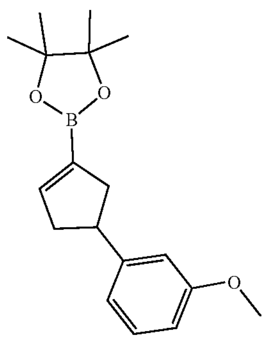 | 2-(4-(3-Methoxyphenyl)cyclopent-1-en-1-yl)-4,4,5,5-tetramethyl-1,3,2-dioxaborolane<br>$^1$H NMR (400 MHz, CHLOROFORM-d) δ ppm 1.24-1.32 (m, 12H) 2.34-2.71 (m, 3H) 2.85-2.99 (m, 1H) 3.46 (t, J = 8.28 Hz, 1H) 3.76-3.83 (m, 3H) 6.51-6.58 (m, 1H) 6.70-6.86 (m, 3H) 7.17-7.24 (m, 1H). |
| 66 | 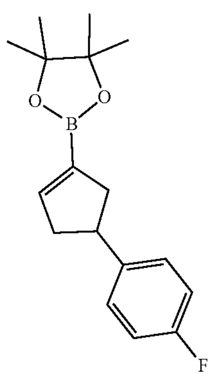 [SMILES: CC1(C)OB(C2=CCC(c3ccc(F)cc3)C2)OC1(C)C] | 2-(4-(4-Fluorophenyl)cyclopent-1-en-1-yl)-4,4,5,5-tetramethyl-1,3,2-dioxaborolane<br>$^1$H NMR (400 MHz, CHLOROFORM-d) δ ppm 1.22-1.30 (m, 12H) 2.33-2.68 (m, 3H) 2.78-2.99 (m, 1H) 3.37-3.51 (m, 1H) 6.43-6.56 (m, 1H) 6.88-6.99 (m, 2H) 7.06-7.21 (m, 2H). |
| 67 | 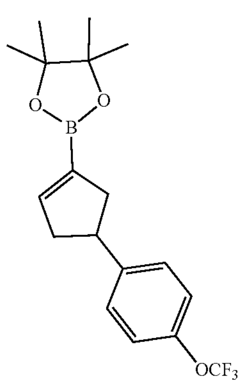 [SMILES: CC1(C)OB(C2=CCC(c3ccc(OC(F)(F)F)cc3)C2)OC1(C)C] | 4,4,5,5-Tetramethyl-2-(4-(4-(trifluoromethoxy)phenyl)cyclopent-1-en-1-yl)-1,3,2-dioxaborolane<br>$^1$H NMR (400 MHz, CHLOROFORM-d) δ ppm 1.30 (d, J = 3.51 Hz, 12H) 1.73 (ddt, J = 12.64, 8.82, 7.09, 7.09 Hz, 1H) 2.35-2.60 (m, 2H) 2.86-3.01 (m, 1H) 3.43-3.99 (m, 1H) 6.42-6.62 (m, 1H) 7.09-7.15 (m, 2H) 7.17-7.21 (m, 1H) 7.22-7.26 (m, 1H). |

-continued

| Intermediate | Structure | Characterization |
|---|---|---|
| 68 | 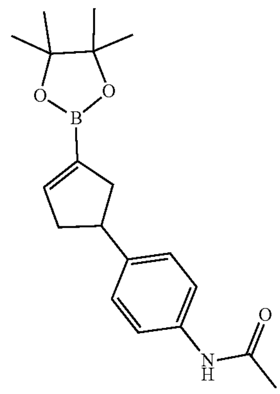 [SMILES: CC(=O)Nc1ccc(C2CC=C(B3OC(C)(C)C(C)(C)O3)C2)cc1] | N-(4-(3-(4,4,5,5-Tetramethyl-1,3,2-dioxaborolan-2-yl)cyclopent-3-en-1-yl)phenyl)acetamide<br>LC-MS: 328.1 [M + 1]⁺. |
| 69 | 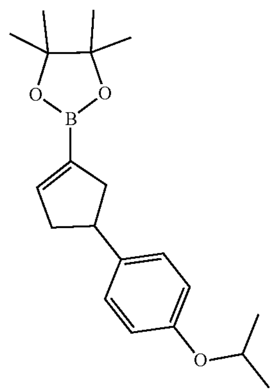 [SMILES: CC(C)Oc1ccc(C2CC=C(B3OC(C)(C)C(C)(C)O3)C2)cc1] | 2-(4-(4-Isopropoxyphenyl)cyclopent-1-en-1-yl)-4,4,5,5-tetramethyl-1,3,2-dioxaborolane<br>¹H NMR (400 MHz, CHLOROFORM-d) δ ppm 1.29-1.34 (m, 12H) 1.70-2.43 (m, 1H) 2.45-2.66 (m, 2H) 2.80-2.99 (m, 1H) 3.33-3.96 (m, 1H) 4.50 (dt, J = 12.18, 6.15 Hz, 1H) 6.49-6.58 (m, 1H) 6.80 (d, J = 8.60 Hz, 2H) 7.04-7.17 (m, 2H). |
| 70 | 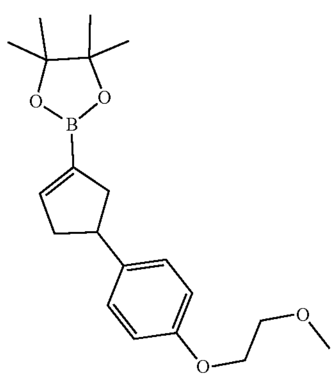 | 2-(4-(4-(2-Methoxyethoxy)phenyl)cyclopent-1-en-1-yl)-4,4,5,5-tetramethyl-1,3,2-dioxaborolane<br>¹H NMR (400 MHz, CHLOROFORM-d) δ ppm 1.31 (d, J = 3.31 Hz, 12H), 2.32-2.70 (m, 3H), 2.80-3.02 (m, 1H), 3.36-3.51 (m, 3H), 3.76 (dd, J = 5.51, 3.97 Hz, 2H), 3.87-3.98 (m, 1H), 4.07-4.14 (m, 2H), 6.47-6.63 (m, 1H), 6.86 (br d, J = 8.60 Hz, 2H), 7.07-7.20 (m, 2H);<br>LCMS: 345.1 [M + 1]⁺. |
| 71 | 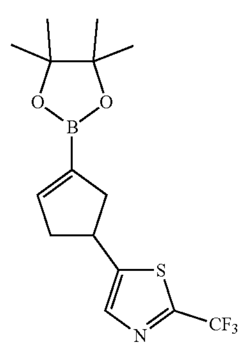 [SMILES: CC1(C)OB(C2=CCC(c3cnc(C(F)(F)F)s3)C2)OC1(C)C] | 5-(3-(4,4,5,5-Tetramethyl-1,3,2-dioxaborolan-2-yl)cyclopent-2-enyl)-2-(trifluoromethyl)thiazole<br>MS Calcd.: 345.2, MS Found: 346.1 [M + 1]⁺. |

-continued

| Intermediate | Structure | Characterization |
|---|---|---|
| 72 | 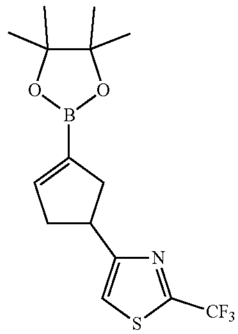 [SMILES: CC1(C)OB(C2=CCC(c3csc(C(F)(F)F)n3)C2)OC1(C)C] | 4-(3-(4,4,5,5-Tetramethyl-1,3,2-dioxaborolan-2-yl)cyclopent-2-enyl)-2-(trifluoromethyl) thiazole<br>MS Calcd.: 345.1; MS Found: 346.4 [M + 1]+. |

Intermediates 73-89. Intermediates 73-89 were synthesized according to the procedure described for intermediate 18.

| Intermediate | Structure | Characterization |
|---|---|---|
| 73 | 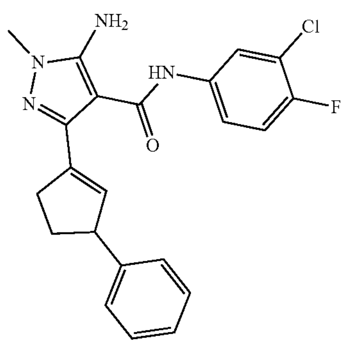 [SMILES: Cn1nc(C2=CC(c3ccccc3)CC2)c(C(=O)Nc2ccc(F)c(Cl)c2)c1N] | 5-Amino-N-(3-chloro-4-fluorophenyl)-1-methyl-3-(3-phenylcyclopent-1-en-1-yl)-1H-pyrazole-4-carboxamide<br>LC-MS: 411.1 [M + 1]+. |
| 74 | 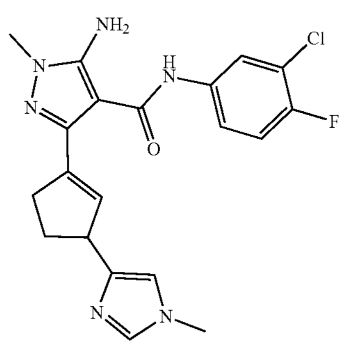 [SMILES: Cn1cnc(C2C=C(c3nn(C)c(N)c3C(=O)Nc3ccc(F)c(Cl)c3)CC2)c1] | 5-Amino-N-(3-chloro-4-fluorophenyl)-1-methyl-3-(4-(1-methyl-1H-imidazol-4-yl)cyclopent-1-en-1-yl)-1H-pyrazole-4-carboxamide<br>LCMS: 437.0 [M + 23]+. |

| Intermediate | Structure | Characterization |
|---|---|---|
| 75 | 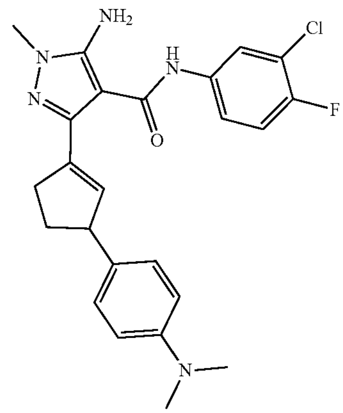 [SMILES: CN(C)c1ccc(C2C=C(c3nn(C)c(N)c3C(=O)Nc3ccc(F)c(Cl)c3)CC2)cc1] | 5-Amino-N-(3-chloro-4-fluorophenyl)-3-(4-(4-(dimethylamino)phenyl)cyclopent-1-en-1-yl)-1-methyl-1H-pyrazole-4-carboxamide LCMS: 476.0 [M + 1]+. |
| 76 | 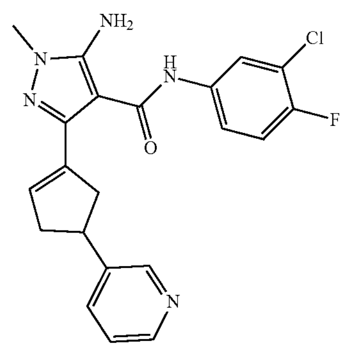 [SMILES: Cn1nc(C2=CCC(c3cccnc3)C2)c(C(=O)Nc2ccc(F)c(Cl)c2)c1N] | 5-Amino-N-(3-chloro-4-fluorophenyl)-1-methyl-3-(4-(pyridin-3-yl)cyclopent-1-en-1-yl)-1H-pyrazole-4-carboxamide LCMS: 412.0 [M + 1]+. |
| 77 | 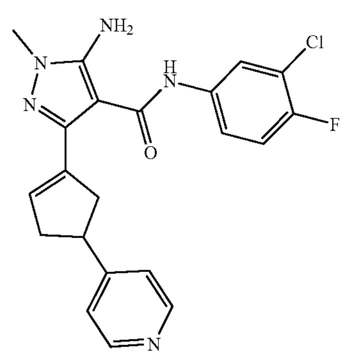 [SMILES: Cn1nc(C2=CCC(c3ccncc3)C2)c(C(=O)Nc2ccc(F)c(Cl)c2)c1N] | 5-Amino-N-(3-chloro-4-fluorophenyl)-1-methyl-3-(4-(pyridin-4-yl)cyclopent-1-en-1-yl)-1H-pyrazole-4-carboxamide LCMS: 412.0 [M + 1]+. |
| 78 | 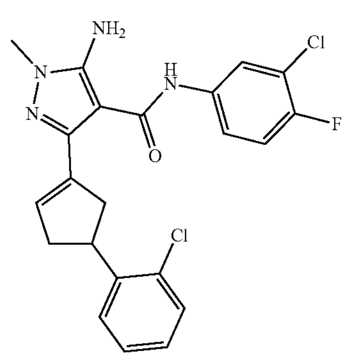 [SMILES: Cn1nc(C2=CCC(c3ccccc3Cl)C2)c(C(=O)Nc2ccc(F)c(Cl)c2)c1N] | 5-Amino-N-(3-chloro-4-fluorophenyl)-3-(4-(2-chlorophenyl)cyclopent-1-en-1-yl)-1-methyl-1H-pyrazole-4-carboxamide LCMS: 445.0 [M + 1]+. |

| Intermediate | Structure | Characterization |
|---|---|---|
| 79 | 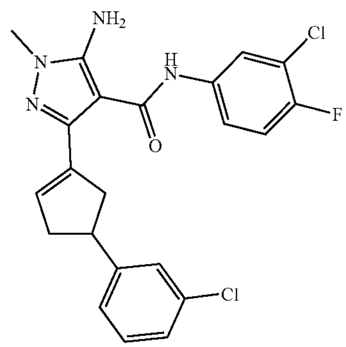 [SMILES: Cn1nc(C2=CCC(c3cccc(Cl)c3)C2)c(C(=O)Nc2ccc(F)c(Cl)c2)c1N] | 5-Amino-N-(3-chloro-4-fluorophenyl)-3-(4-(3-chlorophenyl)cyclopent-1-en-1-yl)-1-methyl-1H-pyrazole-4-carboxamide LCMS: 445.0 [M + 1]⁺. |
| 80 | 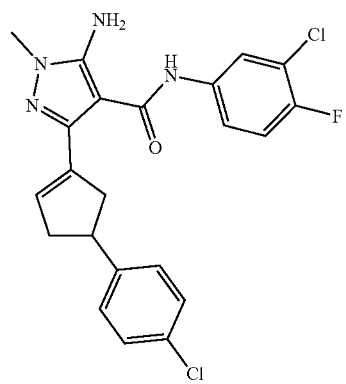 [SMILES: Cn1nc(C2=CCC(c3ccc(Cl)cc3)C2)c(C(=O)Nc2ccc(F)c(Cl)c2)c1N] | 5-Amino-N-(3-chloro-4-fluorophenyl)-3-(4-(4-chlorophenyl)cyclopent-1-en-1-yl)-1-methyl-1H-pyrazole-4-carboxamide used in next reaction without further purification |
| 81 | 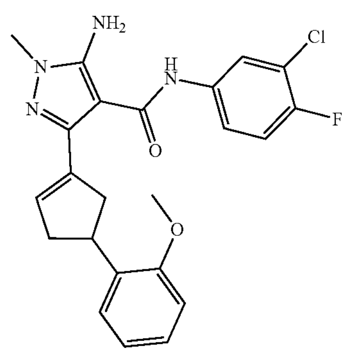 [SMILES: COc1ccccc1C1CC=C(c2nn(C)c(N)c2C(=O)Nc2ccc(F)c(Cl)c2)C1] | 5-Amino-N-(3-chloro-4-fluorophenyl)-3-(4-(2-methoxyphenyl)cyclopent-1-en-1-yl)-1-methyl-1H-pyrazole-4-carboxamide LCMS: 441.0 [M + 1]⁺. |
| 82 | 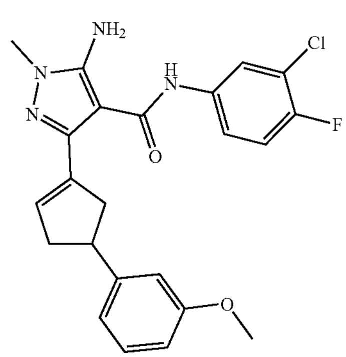 [SMILES: COc1cccc(C2CC=C(c3nn(C)c(N)c3C(=O)Nc3ccc(F)c(Cl)c3)C2)c1] | 5-Amino-N-(3-chloro-4-fluorophenyl)-3-(4-(3-methoxyphenyl)cyclopent-1-en-1-yl)-1-methyl-1H-pyrazole-4-carboxamide LCMS: 441.0 [M + 1]⁺. |

| Intermediate | Structure | Characterization |
|---|---|---|
| 83 | 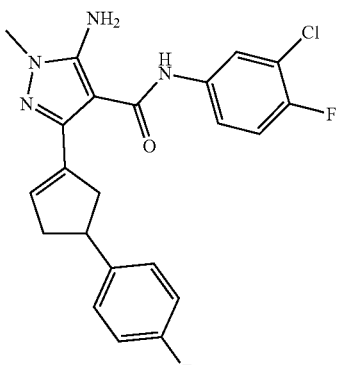 | 5-Amino-N-(3-chloro-4-fluorophenyl)-3-(4-(4-fluorophenyl)cyclopent-1-en-1-yl)-1-methyl-1H-pyrazole-4-carboxamide LCMS: 429.0 [M + 1]$^+$. |
| 84 | 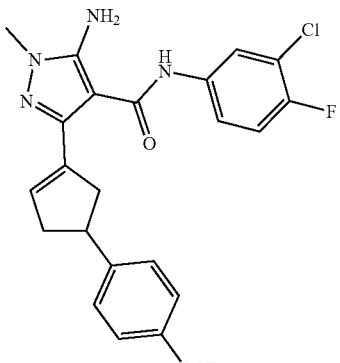 | 5-Amino-N-(3-chloro-4-fluorophenyl)-1-methyl-3-(4-(4-(trifluoromethoxy)phenyl)cyclopent-1-en-1-yl)-1H-pyrazole-4-carboxamide LCMS: 495.0 [M + 1]$^+$. |
| 85 | 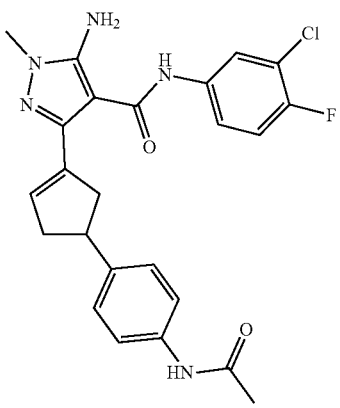 [SMILES: CC(=O)Nc1ccc(C2CC=C(c3nn(C)c(N)c3C(=O)Nc3ccc(F)c(Cl)c3)C2)cc1] | 3-(4-(4-Acetamidophenyl)cyclopent-1-en-1-yl)-5-amino-N-(3-chloro-4-fluorophenyl)-1-methyl-1H-pyrazole-4-carboxamide LCMS 490.2 [M + 23]$^+$. |
| 86 | 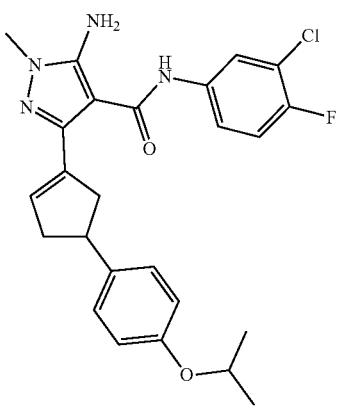 [SMILES: CC(C)Oc1ccc(C2CC=C(c3nn(C)c(N)c3C(=O)Nc3ccc(F)c(Cl)c3)C2)cc1] | 5-Amino-N-(3-chloro-4-fluorophenyl)-3-(4-(4-isopropoxyphenyl)cyclopent-1-en-1-yl)-1-methyl-1H-pyrazole-4-carboxamide LCMS: 469.0 [M + 1]$^+$. |

| Intermediate | Structure | Characterization |
|---|---|---|
| 87 | 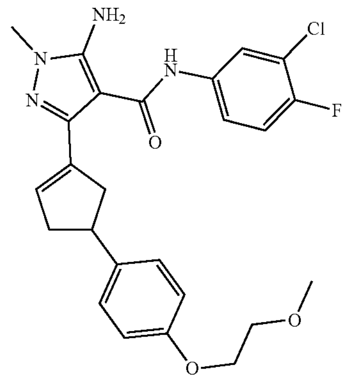 [SMILES: COCCOc1ccc(C2CC=C(c3nn(C)c(N)c3C(=O)Nc3ccc(F)c(Cl)c3)C2)cc1] | 5-Amino-N-(3-chloro-4-fluorophenyl)-3-(4-(4-(2-methoxyethoxy)phenyl)cyclopent-1-en-1-yl)-1-methyl-1H-pyrazole-4-carboxamide LCMS: 485.0 [M + 1]⁺. |
| 88 | 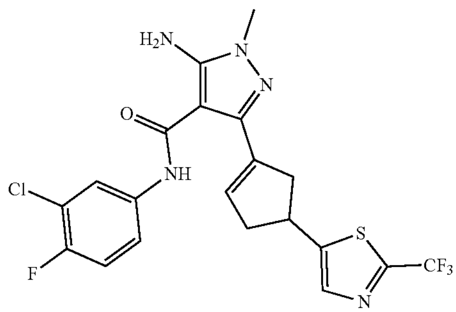 [SMILES: Cn1nc(C2=CCC(c3cnc(C(F)(F)F)s3)C2)c(C(=O)Nc2ccc(F)c(Cl)c2)c1N] | 5-Amino-N-(3-chloro-4-fluorophenyl)-1-methyl-3-(3-(2-(trifluoromethypthiazol-5-yl)cyclopent-1-enyl)-1H-pyrazole-4-carboxamide MS Calcd.: 485.9, MS Found: 486.1 [M + 1]⁺ |
| 89 | 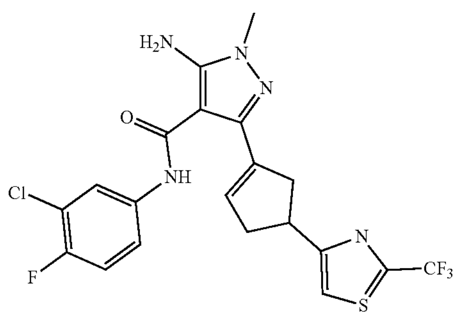 | 5-Amino-N-(3-chloro-4-fluorophenyl)-1-methyl-3-(3-(2-(trifluoromethypthiazol-4-yl)cyclo pent-1-enyl)-1H-pyrazole-4-carboxamide MS Calcd.: 485.1; MS Found: 486.3 [M + 1]⁺ |

AIA-202A, AIA-202B, AIA-202C and CP-202D

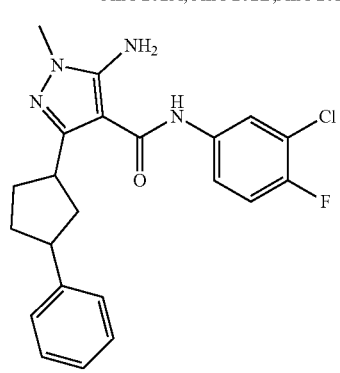

5-Amino-N-(3-chloro-4-fluorophenyl)-1-methyl-3-(3-phenylcyclopentyl)-1H-pyrazole-4-carboxamide diastereomer 1 (AIA-202A), diastereomer 2 (AIA-202B), diastereomer 3 (AIA-202C), diastereomer 4 (AIA-202D). A brown solution of 5-amino-N-(3-chloro-4-fluoro-phenyl)-1-methyl-3-(3-phenylcyclopenten-1-yl)pyrazole-4-carboxamide (400 mg, 0.801 mmol, 1 eq) and RhCl(PPh₃)₃ (37.05 mg, 0.040 mmol, 0.05 eq) in MeOH (20 mL) was stirred under 50 Psi of H₂ at 45° C. for 16 hr. The reaction was concentrated under vacuum to give a crude brown oil. The residue was purified by flash silica gel chromatography (CombiFlash®; 4 g SepaFlash® Silica Flash Column, Eluent of 0~5.5% MeOH/DCM gradient @20 mL/min) followed by SFC to provide 4 diastereomers of 5-amino-N-(3-chloro-4-fluoro-phenyl)-1-methyl-3-(3-phenylcyclopentyl)pyrazole-4-carboxamide. AIA-202A: ¹H NMR (400 MHz, DMSO-d6) δ ppm 1.67 (dt, J=9.87, 4.91 Hz, 1H) 1.86-1.99 (m, 2H) 2.01-2.12 (m, 2H) 2.26-2.35 (m, 1H) 3.07-3.16 (m, 1H) 3.52 (s, 3H) 3.66-3.76 (m, 1H) 6.01 (s, 2H) 7.14-7.22 (m, 1H) 7.24-7.38 (m, 5H) 7.56 (ddd, J=9.05, 4.34, 2.63 Hz, 1H) 7.94 (d, J=6.71 Hz, 1H) 8.99 (s, 1H); LC-MS: 413.3 [M+1]⁺; and de: 100%. AIA-202B: ¹H NMR (400 MHz, DMSO-d6) δ ppm 1.60-1.74 (m, 1H) 1.85-2.01 (m, 2H) 2.01-2.13 (m, 2H) 2.31 (br dd, J=12.05, 6.27 Hz, 1H) 3.05-3.20 (m, 1H) 3.48-3.56 (m, 3H) 3.65-3.79 (m, 1H) 6.01 (s, 2H) 7.05-7.22 (m, 1H) 7.24-7.39 (m, 5H) 7.47-7.74 (m, 1H) 7.94 (d, J=6.59 Hz, 1H) 8.98 (s, 1H); LC-MS: 413.3 [M+1]⁺; and de: 100%.

AIA-202C: $^1$H NMR (400 MHz, DMSO-d6) δ ppm 1.59-1.70 (m, 1H) 1.91-2.04 (m, 2H) 2.07-2.23 (m, 3H) 3.10-3.23 (m, 1H) 3.53 (s, 3H) 3.82-3.90 (m, 1H) 6.04 (s, 2H) 7.12-7.19 (m, 1H) 7.24-7.37 (m, 5H) 7.54 (ddd, J=9.02, 4.31, 2.57 Hz, 1H) 7.91 (d, J=6.74 Hz, 1H) 8.94 (s, 1H); LC-MS: 413.3 [M+1]$^+$; and de: 97.6%. AIA-202D: $^1$H NMR (400 MHz, DMSO-d6) δ ppm 1.12-1.33 (m, 4H) 1.57-1.72 (m, 1H) 1.90-2.02 (m, 2H) 2.04-2.20 (m, 3H) 2.26-2.39 (m, 1H) 3.07-3.21 (m, 1H) 3.53 (d, J=1.47 Hz, 3H) 3.71 (br s, 1H) 3.79-3.91 (m, 1H) 5.96-6.09 (m, 2H) 7.13-7.38 (m, 7H) 7.45-7.59 (m, 1H) 7.86-7.96 (m, 1H) 8.91-9.00 (m, 1H); LC-MS: 413.3 [M+1]$^+$.

TABLE 1

| The compounds in table 1 were synthesized according to the procedure described for CP-AIA-202A-D | |
|---|---|
| Compound | Structure and Characterization |
| CP-AIA-280 | 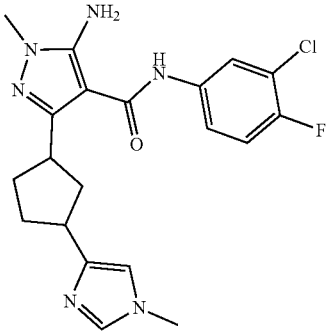 [SMILES: Cn1cnc(C2CCC(c3nn(C)c(N)c3C(=O)Nc3ccc(F)c(Cl)c3)C2)c1]<br>5-Amino-N-(3-chloro-4-fluoro-phenyl)-1-methyl-3-[3-(1-methylimidazol-4-yl)cyclopentyl]pyrazole-4-carboxamide. $^1$H NMR (400 MHz, CHLOROFORM-d) δ 1.81-1.92 (m, 1H), 2.01 (ddd, J = 12.36, 10.10, 8.41 Hz, 1H), 2.12-2.36 (m, 3H), 2.39-2.51 (m, 1H), 3.30-3.46 (m, 1H), 3.62 (d, J = 15.81 Hz, 6H), 5.34-5.43 (m, 2H), 6.63 (s, 1H), 7.08 (t, J = 8.91 Hz, 1H), 7.29-7.36 (m, 1H), 7.58 (ddd, J = 8.97, 4.20, 2.64 Hz, 1H), 7.66 (dd, J = 6.65, 2.64 Hz, 1H), 7.89 (s, 1H); LCMS: 439.0 [M + 23]$^+$. |
| CP-AIA-293 | 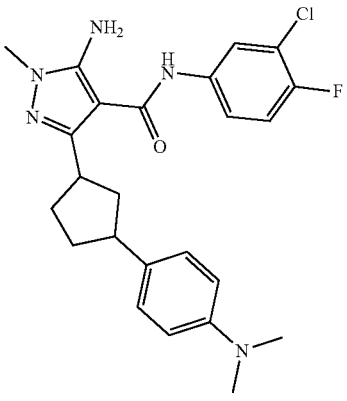 [SMILES: CN(C)c1ccc(C2CCC(c3nn(C)c(N)c3C(=O)Nc3ccc(F)c(Cl)c3)C2)cc1]<br>5-Amino-N-(3-chloro-4-fluorophenyl)-3-(3-(4-(dimethylamino)phenyl)cyclopentyl)-1-methyl-1H-pyrazole-4-carboxamide $^1$H NMR (400 MHz, CHLOROFORM-d) δ 1.79-1.96 (m, 1H), 2.05-2.39 (m, 4H), 2.44 (dt, J = 12.86, 6.49 Hz, 1H), 2.89-2.97 (m, 6H), 3.06-3.23 (m, 1H), 3.30-3.52 (m, 1H), 3.61 (s, 3H), 5.21-5.39 (m, 2H), 6.62-6.81 (m, 2H), 7.02-7.24 (m, 3H), 7.32 (ddd, J = 8.91, 4.02, 2.64 Hz, 1H), 7.37 (s, 1H), 7.68-7.80 (m, 1H); LCMS: 456.2 [M + 1]$^+$. |

TABLE 1-continued

The compounds in table 1 were synthesized according to the procedure described for CP-AIA-202A-D

| Compound | Structure and Characterization |
| --- | --- |
| CP-AIA-270 | 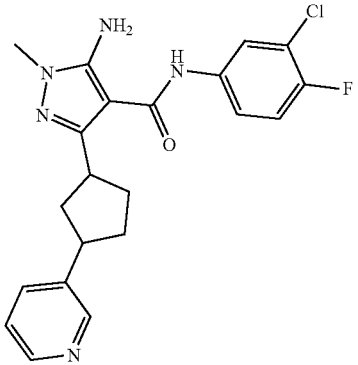 [SMILES: Cn1nc(C2CCC(c3cccnc3)C2)c(C(=O)Nc2ccc(F)c(Cl)c2)c1N]<br>5-Amino-N-(3-chloro-4-fluorophenyl)-1-methyl-3-(3-(pyridin-3-yl)cyclopentyl)-1H-pyrazole-4-carboxamide |
| CP-AIA-271 | 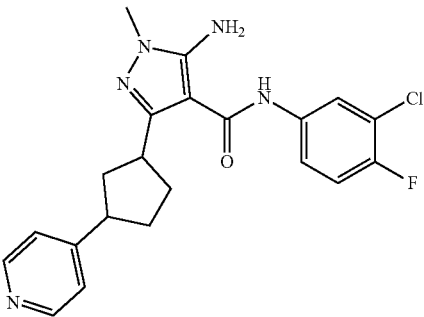 [SMILES: Cn1nc(C2CCC(c3ccncc3)C2)c(C(=O)Nc2ccc(F)c(Cl)c2)c1N]<br>5-Amino-N-(3-chloro-4-fluorophenyl)-1-methyl-3-(3-(pyridin-4-yl)cyclopentyl)-1H-pyrazole-4-carboxamide. $^1$H NMR (400 MHz, CHLOROFORM-d) δ 1.86-2.05 (m, 1H), 2.13-2.42 (m, 4H), 2.43-2.57 (m, 1H), 3.14-3.26 (m, 1H), 3.41-3.51 (m, 1H), 3.61 (s, 3H), 5.27 (s, 2H), 7.12 (t, J = 8.66 Hz, 1H), 7.24 (br s, 2H), 7.30-7.36 (m, 2H), 7.71 (dd, J = 6.40, 2.64 Hz, 1H), 8.51 (br d, J = 5.02 Hz, 2H); LCMS: 414.0 [M + 1]$^+$. |
| CP-ATA-272 | 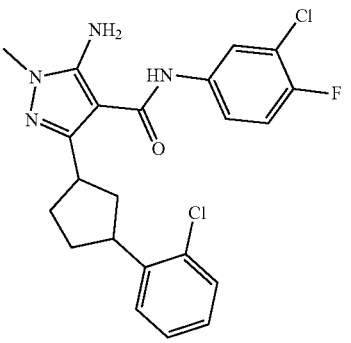 [SMILES: Cn1nc(C2CCC(c3ccccc3Cl)C2)c(C(=O)Nc2ccc(F)c(Cl)c2)c1N]<br>5-Amino-N-(3-chloro-4-fluorophenyl)-3-(3-(2-chlorophenyl)cyclopentyl)-1-methyl-1H-pyrazole-4-carboxamide. $^1$H NMR (400 MHz, DMSO-d6) δ ppm 1.65 (1 H, td, J = 9.70, 5.51 Hz), 1.84-1.96 (2 H, m), 2.01-2.12 (2 H, m), 2.25-2.32 (1 H, m), 3.46-3.53 (4 H, m), 3.65-3.79 (1 H, m), 5.96-6.03 (2 H, m), 7.15-7.20 (1 H, m), 7.25-7.38 (3 H, m), 7.43 (1 H, dd, J = 7.83, 1.65 Hz), 7.54 (1 H, ddd, J = 8.99, 4.24, 2.65 Hz), 7.91 (1 H, dd, J = 6.84, 2.65 Hz), 8.92-8.97 (1 H, m); LCMS: 446.9 [M + 1]$^+$. |

TABLE 1-continued

The compounds in table 1 were synthesized according to the procedure described for CP-AIA-202A-D

| Compound | Structure and Characterization |
|---|---|
| CP-AIA-273 | 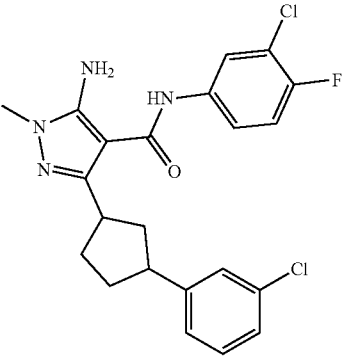 [SMILES: Cn1nc(C2CCC(c3cccc(Cl)c3)C2)c(C(=O)Nc2ccc(F)c(Cl)c2)c1N]<br>5-Amino-N-(3-chloro-4-fluorophenyl)-3-(3-(3-chlorophenyl)cyclopentyl)-1-methyl-1H-pyrazole-4-carboxamide. $^1$H NMR (400 MHz, DMSO-d6) δ ppm 1.57-1.68 (1 H, m), 1.84-1.96 (2 H, m), 1.98-2.10 (2 H, m), 2.25-2.33 (1 H, m), 3.07-3.17 (1 H, m), 3.50 (3 H, s), 3.62-3.86 (1 H, m), 5.92-6.05 (2 H, m), 7.15-7.37 (5 H, m), 7.53 (1 H, ddd, J = 9.04, 4.41, 2.65 Hz), 7.91 (1 H, dd, J = 6.95, 2.54 Hz), 8.97 (1 H, s); LCMS: 446.9 [M + 1]$^+$. |
| CP-ATA-274 | 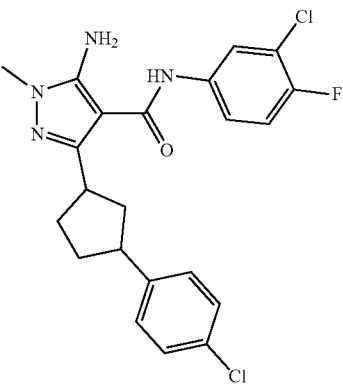 [SMILES: Cn1nc(C2CCC(c3ccc(Cl)cc3)C2)c(C(=O)Nc2ccc(F)c(Cl)c2)c1N]<br>5-Amino-N-(3-chloro-4-fluorophenyl)-3-(3-(4-chlorophenyl)cyclopentyl)-1-methyl-1H-pyrazole-4-carboxamide. $^1$H NMR (400 MHz, DMSO-d6) δ ppm 1.62 (td, J = 9.98, 5.18 Hz, 1 H) 1.82-1.96 (m, 2 H) 2.00-2.11 (m, 2 H) 2.24-2.35 (m, 1 H) 3.04-3.19 (m, 1 H) 3.51 (s, 3 H) 3.62-3.87 (m, 1 H) 5.95-6.08 (m, 2 H) 7.26-7.38 (m, 5 H) 7.50-7.57 (m, 1 H) 7.85-7.95 (m, 1 H) 8.91-9.02 (m, 1 H); LCMS: 446.9 [M + 1]$^+$. |

TABLE 1-continued

The compounds in table 1 were synthesized according to the procedure described for CP-AIA-202A-D

| Compound | Structure and Characterization |
| --- | --- |
| CP-AIA-275A | 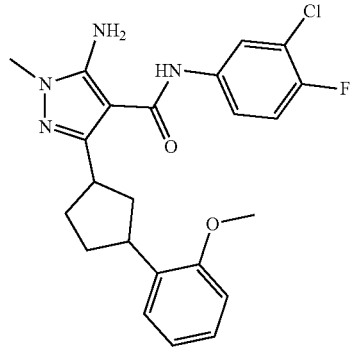 [SMILES: COc1ccccc1C1CCC(c2nn(C)c(N)c2C(=O)Nc2ccc(F)c(Cl)c2)C1]
5-Amino-N-(3-chloro-4-fluorophenyl)-3-(3-(2-methoxyphenyl)cyclopentyl)-1-methyl-1H-pyrazole-4-carboxamide, diastereomer 1 (CP-AIA-275A) $^1$H NMR (400 MHz, CHLOROFORM-d) δ ppm 1.85-1.91 (m, 1 H) 2.09-2.32 (m, 5 H) 3.36-3.45 (m, 1 H) 3.53 (s, 3 H) 3.55-3.62 (m, 1 H) 3.73 (s, 3 H) 5.25 (s, 2 H) 6.82-6.90 (m, 2 H) 6.97 (d, J = 8.60 Hz, 1 H) 7.01-7.05 (m, 1 H) 7.14-7.19 (m, 2 H) 7.23 (s, 1 H) 7.54 (dd, J = 6.62, 2.65 Hz, 1 H); LC-MS: 443.0 [M + 1]$^+$. |
| CP-AIA-275B | 5-Amino-N-(3-chloro-4-fluorophenyl)-3-(3-(2-methoxyphenyl)cyclopentyl)-1-methyl-1H-pyrazole-4-carboxamide, diastereomer 2 (CP-AIA-275B). $^1$H NMR (400 MHz, DMSO-d6) δ ppm 1.61 (br d, J = 10.04 Hz, 1 H) 1.78-2.11 (m, 4 H) 2.18-2.25 (m, 1 H) 3.40-3.47 (m, 1 H) 3.51 (s, 2 H) 3.48-3.56 (m, 1 H) 3.66-3.78 (m, 4 H) 6.03 (s, 2 H) 6.88 (t, J = 7.50 Hz, 1 H) 6.92 (d, J = 7.77 Hz, 1 H) 7.15 (t, J = 7.77 Hz, 1 H) 7.23 (d, J = 7.20 Hz, 1 H) 7.36 (t, J = 9.14 Hz, 1 H) 7.53-7.58 (m, 1 H) 7.93 (d, J = 6.56 Hz, 1 H) 8.92-8.96 (m, 1 H); LC-MS: 443.0 [M + 1]$^+$. |
| CP-AIA-275C/CP-AIA-D | 5-Amino-N-(3-chloro-4-fluorophenyl)-3-(3-(2-methoxyphenyl)cyclopentyl)-1-methyl-1H-pyrazole-4-carboxamide, mixture of diastereomer 3 and 4 (CP-AIA-275C, CP-AIA0275D) $^1$H NMR (400 MHz, DMSO-d6) δ ppm 1.61 (br dd, J = 9.79, 5.52 Hz, 1 H) 1.80-2.10 (m, 4 H) 2.18-2.26 (m, 1 H) 3.45-3.61 (m, 4 H) 3.63-3.84 (m, 4 H) 6.03 (br s, 2 H) 6.84-6.94 (m, 2 H) 7.11-7.18 (m, 1 H) 7.23 (d, J = 7.53 Hz, 1 H) 7.36 (t, J = 9.21 Hz, 1 H) 7.48-7.59 (m, 1 H) 7.93 (dd, J = 6.78, 2.26 Hz, 1H) 8.94 (br s, 1 H); LC-MS: 443.0 [M + 1]$^+$. |
| AIA-276D | 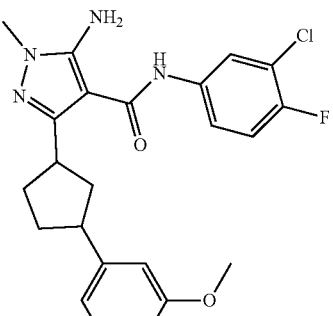
5-Amino-N-(3-chloro-4-fluorophenyl)-3-(3-(3-methoxyphenyl)cyclopentyl)-1-methyl-1H-pyrazole-4-carboxamide, single diastereomer (AIA-276D). $^1$H NMR (400 MHz, DMSO-d6) δ ppm 1.64 (dt, J = 9.65, 4.77 Hz, 1 H) 1.84-2.06 (m, 4 H) 2.26 (dt, J = 12.62, 6.59 Hz, 1 H) 3.02-3.11 (m, 1 H) 3.49 (s, 3 H) 3.64-3.74 (m, 4 H) 5.98 (s, 2 H) 6.70 (d, J = 8.41 Hz, 1 H) 6.79 (s, 1 H) 6.81 (d, J = 7.69 Hz, 1 H) 7.16 (t, J = 7.53 Hz, 1 H) 7.33 (t, J = 9.15 Hz, 1 H) 7.53 (ddd, J = 8.99, 4.35, 2.54 Hz, 1 H) 7.90 (d, J = 6.57 Hz, 1 H) 8.96 (s, 1 H); LC-MS: 443.0 [M + 1]$^+$. |

TABLE 1-continued

The compounds in table 1 were synthesized according to the procedure described for CP-AIA-202A-D

| Compound | Structure and Characterization |
| --- | --- |
| AIA-281 | 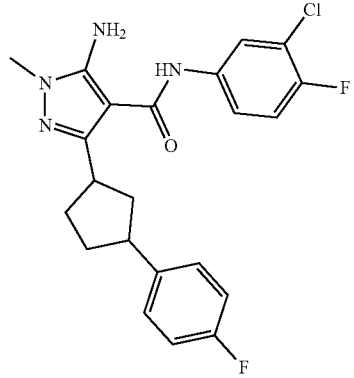 [SMILES: Cn1nc(C2CCC(c3ccc(F)cc3)C2)c(C(=O)Nc2ccc(F)c(Cl)c2)c1N]<br>5-Amino-N-(3-chloro-4-fluorophenyl)-3-(3-(4-fluorophenyl)cyclopentyl)-1-methyl-1H-pyrazole-4-carboxamide. $^1$H NMR (400 MHz, DMSO-d6) δ ppm 1.60 (td, J = 10.03, 5.07 Hz, 1 H) 1.81-1.95 (m, 2 H) 1.96-2.11 (m, 2 H) 2.23-2.31 (m, 1 H) 3.05-3.15 (m, 1 H) 3.50 (s, 3 H) 3.64-3.87 (m, 1 H) 5.96-6.02 (m, 2 H) 7.02-7.09 (m, 2 H) 7.24-7.36 (m, 3 H) 7.49-7.55 (m, 1 H) 7.87-7.92 (m, 1 H) 8.89-8.97 (m, 1 H); LC-MS: 431.0 [M + 1]$^+$. |
| AIA-292 | 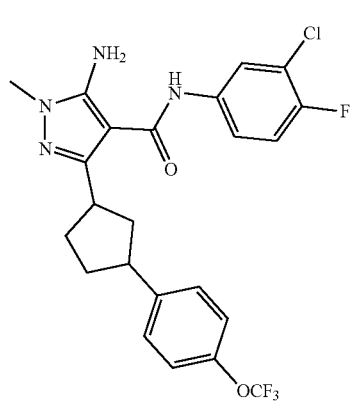 [SMILES: Cn1nc(C2CCC(c3ccc(OC(F)(F)F)cc3)C2)c(C(=O)Nc2ccc(F)c(Cl)c2)c1N]<br>5-Amino-N-(3-chloro-4-fluorophenyl)-1-methyl-3-(3-(4-(trifluoromethoxy)phenyl)cyclopentyl)-1H-pyrazole-4-carboxamide. $^1$H NMR (400 MHz, DMSO-d6) δ ppm 1.59-1.76 (m, 1 H) 1.86-2.02 (m, 2 H) 2.03-2.16 (m, 2 H) 2.28-2.35 (m, 1 H) 3.10-3.27 (m, 1 H) 3.54 (s, 3 H) 3.67-3.81 (m, 1 H) 5.99-6.07 (m, 2 H) 7.24-7.31 (m, 2 H) 7.34-7.45 (m, 3 H) 7.52-7.62 (m, 1 H) 7.89-7.98 (m, 1 H) 8.94-9.05 (m, 1 H); LCMS: 497.0 [M + 1]$^+$. |

TABLE 1-continued

The compounds in table 1 were synthesized according to the procedure described for CP-AIA-202A-D

| Compound | Structure and Characterization |
|---|---|
| AIA-294 | 3-(3-(4-Acetamidophenyl)cyclopentyl)-5-amino-N-(3-chloro-4-fluorophenyl)-1-methyl-1H-pyrazole-4-carboxamide. $^1$H NMR (400 MHz, DMSO-d6) δ ppm 1.59 (dt, J = 9.70, 4.85 Hz, 1 H) 1.77-1.93 (m, 2 H) 1.93-2.04 (m, 5 H) 2.19-2.27 (m, 1 H) 2.97-3.09 (m, 1 H) 3.45-3.52 (m, 3 H) 3.66 (br dd, J = 9.59, 7.61 Hz, 1 H) 5.93-6.03 (m, 2 H) 7.08-7.20 (m, 2 H) 7.32 (t, J = 9.10 Hz, 1 H) 7.39-7.46 (m, 2 H) 7.52 (ddd, J = 8.99, 4.35, 2.54 Hz, 1 H) 7.90 (d, J = 6.59 Hz, 1 H) 8.92-9.22 (m, 1 H) 9.77-9.82 (m, 1 H); LC-MS: 470.0 [M + 1]$^+$. |
| AIA-296 | 5-Amino-N-(3-chloro-4-fluorophenyl)-3-(3-(4-isopropoxyphenyl)cyclopentyl)-1-methyl-1H-pyrazole-4-carboxamide. $^1$H NMR (400 MHz, DMSO-d6) δ ppm 1.25 (d, J = 6.17 Hz, 6 H) 1.56-1.67 (m, 1 H) 1.80-1.98 (m, 2 H) 2.00-2.16 (m, 2 H) 2.21-2.33 (m, 1 H) 2.99-3.12 (m, 1 H) 3.53 (s, 3 H) 3.65-3.76 (m, 1 H) 4.48-4.61 (m, 1 H) 5.98-6.07 (m, 2 H) 6.76-6.86 (m, 2 H) 7.11-7.19 (m, 2 H) 7.31-7.42 (m, 1 H) 7.52-7.60 (m, 1 H) 7.90-7.98 (m, 1 H) 8.93-9.01 (m, 1 H). LCMS: 471.0 [M + 1]$^+$. |

TABLE 1-continued

The compounds in table 1 were synthesized according to the procedure described for CP-AIA-202A-D

| Compound | Structure and Characterization |
|---|---|
| AIA297 | 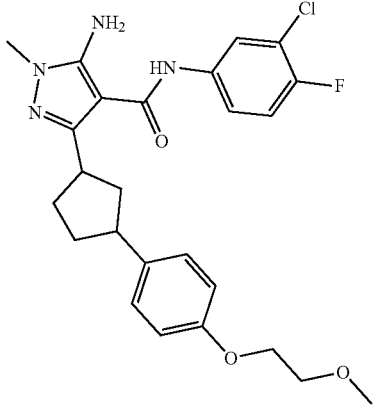<br>5-Amino-N-(3-chloro-4-fluorophenyl)-3-(3-(4-(2-methoxyethoxy)phenyl)cyclopentyl)-1-methyl-1H-pyrazole-4-carboxamide. $^1$H NMR (400 MHz, DMSO-d6) δ 1.51-1.69 (m, 1H), 1.80-2.15 (m, 4H), 2.20-2.31 (m, 1H), 2.97-3.16 (m, 1H), 3.29 (s, 3H), 3.51 (s, 3H), 3.59-3.89 (m, 3H), 4.00-4.32 (m, 2H), 5.93-6.10 (m, 2H), 6.76-6.88 (m, 2H), 7.10-7.23 (m, 2H), 7.29-7.43 (m, 1H), 7.48-7.61 (m, 1H), 7.86-8.01 (m, 1H), 8.88-9.06 (m, 1H); LCMS: 487.0 [M + 1]$^+$. |
| AIA-354 | 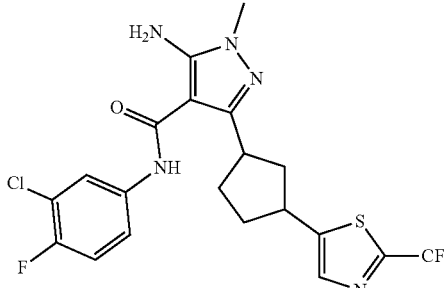<br>5-Amino-N-(3-chloro-4-fluorophenyl)-1-methyl-3-((1R,3R)-3-(2-(trifluoromethyl)thiazol-5-yl)cyclopentyl)-1H-pyrazole-4-carboxamide. $^1$H-NMR (DMSO-d$_6$, 400 MHz): δ 9.03 (s, 1H), 7.93 (d, J = 9.6 Hz, 2H), 7.55 (t, J = 4.8 Hz, 1H), 7.36 (t, J = 8.8 Hz, 1H), 6.02 (s, 2H), 3.79-3.71 (m, 2H), 3.61-3.51 (m, 1H), 3.46 (s, 2H), 2.25-1.68 (m, 5H), 1.29 (s, 1H). |
| AIA-355 | 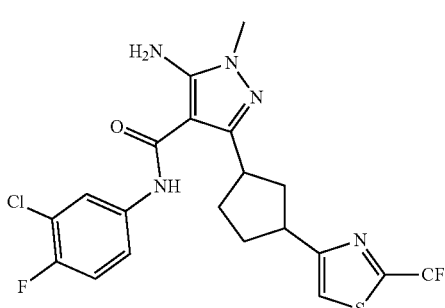<br>5-Amino-N-(3-chloro-4-fluorophenyl)-1-methyl-3-(3-(2-(trifluoromethyl)thiazol-4-yl)cyclopentyl)-1H-pyrazole-4-carboxamide. MS Calcd.: 487.1; MS Found: 488.2 [M + 1]$^+$; $^1$H NMR (DMSO-d6, 400 MHz): δ 8.99 (s, 1H), 7.94-7.91 (m, 1H), 7.84 (s, 1H), 7.57-7.53 (m, 1H), 7.38-7.32 (m, 1H), 6.01 (s, 2H), 3.73-3.69 (m, 1H), 3.56-3.51 (m, 3H), 3.43-3.38 (m, 1H), 2.37-2.32 (m, 1H), 2.12-2.03 (m, 2H), 2.00-1.90 (m, 2H), 1.89-1.77 (m, 1H). |

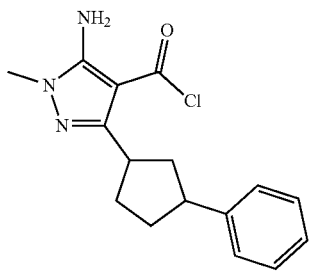

Intermediate 90

5-Amino-1-methyl-3-(3-phenylcyclopentyl)-1H-pyrazole-4-carbonyl chloride. A solution of 5-amino-1-methyl-3-(3-phenylcyclopentyl)pyrazole-4-carboxylic acid (50 mg, 0.175 mmol, 1 eq) in $SOCl_2$ (2 mL) was stirred at 80° C. for 1 hr. The reaction was concentrated under vacuum to give 5-amino-1-methyl-3-(3-phenylcyclopentyl)pyrazole-4-carbonyl chloride (50 mg, crude), as a yellow oil. The crude was used to the next step without further purification.

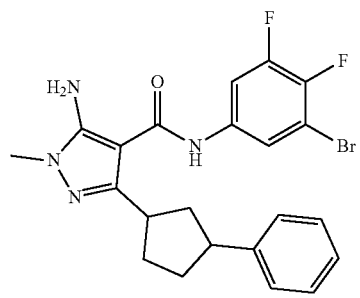

AIA-278

5-Amino-N-(3-bromo-4,5-difluorophenyl)-1-methyl-3-(3-phenylcyclopentyl)-1H-pyrazole-4-carboxamide. To a solution of 5-amino-1-methyl-3-(3-phenylcyclopentyl)pyrazole-4-carbonyl chloride (50 mg, 0.165 mmol, 1 eq) and 3-bromo-4,5-difluoro-aniline (51.35 mg, 0.247 mmol, 0.032 mL, 1.5 eq) in DCM (3 mL) was added dropwise $Et_3N$ (33.31 mg, 0.329 mmol, 0.046 mL, 2.0 eq) at 0° C. The reaction was warmed to 25° C. and stirred for 2 hr. The reaction was diluted with DCM (20 mL) and washed with aq. $NH_4Cl$ (10 mL), brine (10 mL), dried over $Na_2SO_4$, filtered and concentrated under vacuum to give the crude product as a brown oil. The crude product was purified by Prep-HPLC (column: Gemini 150×25 5 u; mobile phase: [water (0.05% ammonia hydroxide v/v)—ACN]; B %: 55%-85%, 10 min). The desired fraction was dried by lyophilization to obtain 5-amino-N-(3-bromo-4,5-difluoro-phenyl)-1-methyl-3-(3-phenylcyclopentyl)pyrazole-4-carboxamide (7.5 mg, 0.015 mmol, 9.30% yield, 96.97% purity), as a gray solid. $^1$H NMR (400 MHz, DMSO-d6) δ ppm 1.65-1.78 (m, 1H) 1.95-2.21 (m, 4H) 2.22-2.39 (m, 1H) 3.13-3.24 (m, 1H) 3.56-3.61 (m, 3H) 3.75 (br t, J=8.71 Hz, 1H) 6.09-6.16 (m, 2H) 7.17-7.26 (m, 1H) 7.29-7.36 (m, 4H) 7.79-7.89 (m, 2H) 9.08-9.17 (m, 1H); LC-MS: 475.0 $[M+1]^+$.

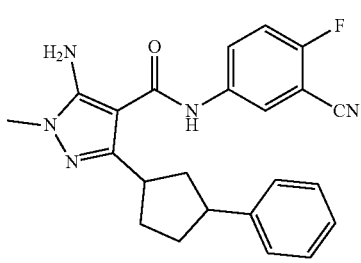

AIA-279

5-Amino-N-(3-cyano-4-fluorophenyl)-1-methyl-3-(3-phenylcyclopentyl)-1H-pyrazole-4-carboxamide. The title compound was synthesized according to the procedure described for AIA-278. $^1$H NMR (400 MHz, DMSO-d6) δ ppm 1.63-1.69 (m, 1H) 1.89-2.14 (m, 4H) 2.15-2.32 (m, 1H) 3.07-3.23 (m, 1H) 3.47-3.55 (m, 3H) 3.65-3.77 (m, 1H) 6.02-6.20 (m, 2H) 7.13-7.21 (m, 1H) 7.24-7.31 (m, 4H) 7.44-7.53 (m, 1H) 7.93 (tdd, 1H) 8.08-8.17 (m, 1H) 9.06-9.15 (m, 1H); LC-MS: 404.0 $[M+1]^+$.

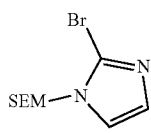

Intermediate 91

2-Bromo-1-((2-(trimethylsilyl)ethoxy)methyl)-1H-imidazole. To a solution of 2-bromo-imidazole (10.0 g, 68.0 mmol) in acetone (100 mL) was added $K_2CO_3$ (23.5 g, 170.0 mmol) and SEMCl (13.6 g, 81.6 mmol). The reaction mixture was stirred at room temperature overnight. The mixture was filtered through a pad of Celite®, and the filtrate concentrated to give the crude product which was purified by silica gel column chromatography using 10:1 petroleum ether/ethyl acetate to afford 2-bromo-1-42-(trimethylsilyl)ethoxy)methyl)-1H-imidazole (12.0 g, 63.7%) as yellow oil. MS Calcd.: 276.0, MS Found: 277.1 $[M+1]^+$.

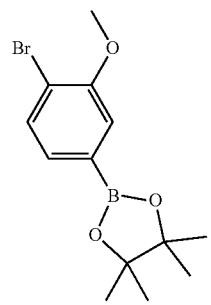

Intermediate 92

2-(4-Bromo-3-methoxyphenyl)-4,4,5,5-tetramethyl-1,3,2-dioxaborolane. A mixture of 1-bromo-4-iodo-2-methoxybenzene (8.0 g, 25.6 mmol), $pin_2B_2$ (6.8 g, 26.9 mmol), Pd(dppf)$Cl_2$ (940.0 mg, 1.3 mmol) and potassium acetate (6.3 g, 64.0 mmol) in dioxane (100 mL) was stirred at 80° C. under an $N_2$ atmosphere overnight. The reaction was filtered through a pad of Celite® and the filter cake washed with EtOAc (50 mL×3). The filtrate was concentrated under vacuum and the residue purified by silica gel column chromatography using 15:1 petroleum ether/ethyl acetate to afford 2-(4-bromo-3-methoxyphenyl)-4,4,5,5-tetramethyl-1,3,2-dioxaborolane (6.0 g, 75.0%) as a yellow oil. MS Calcd.: 312.0; $^1$H-NMR (CDCl$_3$, 400 MHz): δ 7.53 (d, J=7.6 Hz, 1H), 7.28-7.25 (m, 2H), 3.93 (s, 3H), 1.34 (s, 12H).

Intermeidate 93

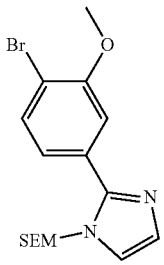

2-(4-Bromo-3-methoxyphenyl)-1-((2-(trimethylsilyl)ethoxy)methyl)-1H-imidazole. To a solution of 2-(4-bromo-3-methoxyphenyl)-4,4,5,5-tetramethyl-1,3,2-dioxaborolane (6.0 g, 19.2 mmol) in dioxane/H$_2$O (60 mL, v/v=5:1) was added 2-bromo-1-((2-(trimethylsilyl)ethoxy)methyl)-1H-imidazole (5.9 g, 21.1 mmol), Pd(dppf)Cl$_2$ (1.4 g, 1.9 mmol) and Na$_2$CO$_3$ (5.1 g, 48.0 mmol). The reaction was stirred at 90° C. under an N$_2$ atmosphere overnight. The solvent was removed, and water added, and the mixture extracted with EtOAc (50 mL×3). The combined organic layers were dried over Na$_2$SO$_4$ then concentrated to give the crude product, which was purified by silica gel column chromatography using 10:1 petroleum ether/ethyl acetate to afford 2-(4-bromo-3-methoxyphenyl)-1-((2-(trimethylsilyl)ethoxy)methyl)-1H-imidazole (1.5 g, 20.4%) as a gray solid. MS Calcd.: 382.1, MS Found: 383.2 [M+1]$^+$.

Intermidate 94

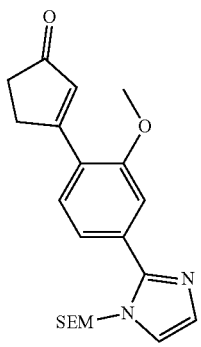

3-(2-Methoxy-4-(1-((2-(trimethylsilyl)ethoxy)methyl)-1H-imidazol-2-yl)phenyl)cyclopent-2-enone. To a solution of 2-(4-bromo-3-methoxyphenyl)-1-((2-(trimethylsilyl)ethoxy)methyl)-1H-imidazole (1.5 g, 3.9 mmol) in dioxane/H$_2$O (60 mL, v/v=5:1) was added 3-(4,4,5,5-tetramethyl-1,3,2-dioxaborolan-2-yl)cyclopent-2-en-1-one (1.0 g, 4.7 mmol), Pd(dppf)Cl$_2$ (500.0 mg, 0.4 mmol) and K$_3$PO$_4$ (2.1 g, 9.8 mmol). The reaction was stirred at 90° C. under an N$_2$ atmosphere overnight. The solvent was removed, water added, and the mixture extracted with EtOAc (50 mL×3). The combined organic layers were dried over Na$_2$SO$_4$ and concentrated to give the crude product, which was purified by silica gel column chromatography using 10:1 petroleum ether/ethyl acetate to afford 3-(2-methoxy-4-(1-((2-(trimethylsilyl)ethoxy)methyl)-1H-imidazol-2-yl)phenyl)cyclopent-2-enone (1.0 g, 66.7%) as a gray solid. MS Calcd.: 384.2, MS Found: 385.3 [M+1]$^+$.

Intermediate 95

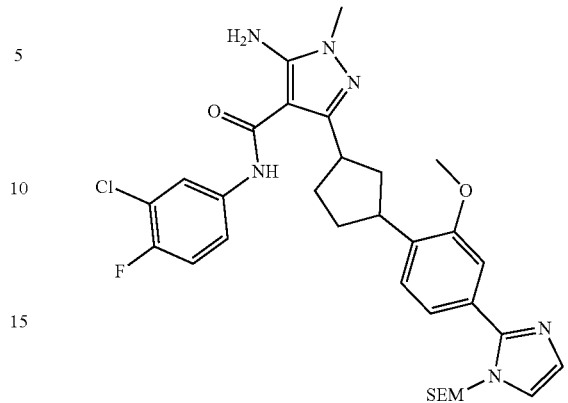

5-Amino-N-(3-chloro-4-fluorophenyl)-3-(3-(2-methoxy-4-(1-((2-(trimethylsilyl)ethoxy)methyl)-1H-imidazol-2-yl)phenyl)cyclopentyl)-1-methyl-1H-pyrazole-4-carboxamide. The title compound was synthesized according the procedure described above. MS Calcd.: 638.2, MS Found: 639.3 [M+1]$^+$.

AIA-352-1 and AIA-352-2

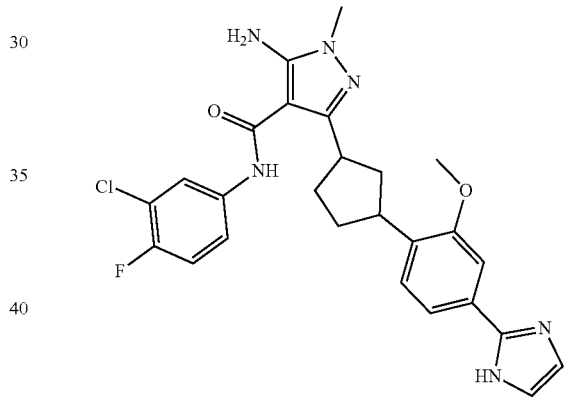

3-(3-(4-(1H-Imidazol-2-yl)-2-methoxyphenyl)cyclopentyl)-5-amino-N-(3-chloro-4-fluorophenyl)-1-methyl-1H-pyrazole-4-carboxamide. Diastereomer 1 (AIA-352-1) and Diastereomer 2 (AIA-352-2). A mixture of 5-amino-N-(3-chloro-4-fluorophenyl)-3-(3-(2-methoxy-4-(1-((2-(trimethylsilyl)ethoxy)methyl)-1H-imidazol-2-yl)phenyl)cyclopentyl)-1-methyl-1H-pyrazole-4-carboxamide (230.0 mg, 0.4 mmol) and TFA (2 mL) in DCM (10 mL) was stirred at room temperature overnight. The solvent was removed and ammonium hydroxide (2 mL) added. The resulting mixture was stirred 15 minutes at room temperature. The solvent was removed to give the crude product which was purified by prep-HPLC to afford AIA-352-1 (11 mg, 5.4%) and AIA-352-2 (7 mg, 3.4%) AIA-352-1: $^1$H-NMR (DMSO-d$_6$, 400 MHz): δ 12.42 (s, 1H), 8.93 (s, 1H), 7.92 (dd, J=6.8, 2.4 Hz, 1H), 7.49-7.44 (m, 3H), 7.33-7.27 (m, 2H), 7.22 (s, 1H), 6.98 (s, 1H), 6.03 (s, 2H), 3.90-3.86 (m, 1H), 3.84 (s, 3H), 3.53 (s, 3H), 3.45-3.39 (m, 1H), 2.14-1.92 (m, 5H), 1.68-1.63 (m, 1H). AIA-352-2: $^1$H-NMR (DMSO-d$_6$, 400 MHz): δ 12.43 (s, 1H), 8.94 (s, 1H), 7.94 (dd, J=6.8, 2.8 Hz, 1H), 7.58-7.54 (m, 1H), 7.51-7.45 (m, 2H), 7.36 (t, J=8.8 Hz, 1H), 7.28 (d, J=8.0 Hz, 1H), 7.22 (s, 1H), 6.98 (s, 1H), 6.03 (s, 2H), 3.83 (s, 3H), 3.73-3.67 (m, 1H), 3.52 (s, 3H), 3.46-3.38 (m, 1H), 2.27-2.20 (m, 1H), 2.07-1.83 (m, 4H), 1.65-1.60 (m, 1H).

TABLE 2

The compounds in table 2 were synthesized according to the procedure described for AIA-352-1 and AIA-352-2

| Compound | Structure and Characterization |
| --- | --- |
| AIA-365-1 | 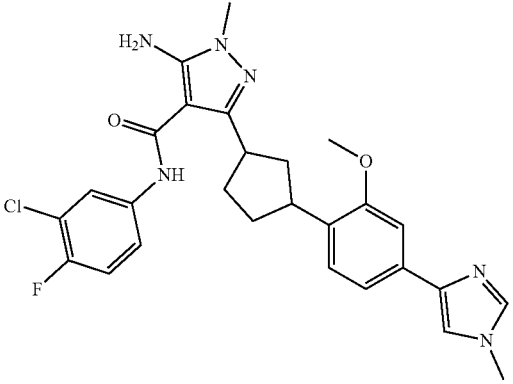 [SMILES: COc1cc(-c2cn(C)cn2)ccc1C1CCC(c2nn(C)c(N)c2C(=O)Nc2ccc(F)c(Cl)c2)C1] 5-Amino-N-(3-chloro-4-fluorophenyl)-3-(3-(2-methoxy-4-(1-methyl-1H-imidazol-4-yl)phenyl)cyclopentyl)-1-methyl-1H-pyrazole-4-carboxamide. Diastereomer 1 (AIA-365-1). MS Calcd.: 522.2; MS Found: 523.3 [M + 1]$^+$. $^1$H-NMR (DMSO-d$_6$, 400 MHz): δ 8.89 (s, 1H), 7.90 (dd, J = 6.8, 2.4 Hz, 1H), 7.57 (s, 1 H), 7.53 (s, 1 H), 7.48-7.44 (m, 1H), 7.32-7.26 (m, 2H), 7.22-7.15 (m, 2H), 6.01 (s, 2H), 3.81-3.79 (m, 1H), 3.76 (s, 3H), 3.65 (s, 3H), 3.50 (s, 3H), 3.40-3.33 (m, 1H), 2.10-1.91 (m, 5H), 1.64-1.59 (m, 1H). |
| AIA-365-2 | 5-Amino-N-(3-chloro-4-fluorophenyl)-3-(3-(2-methoxy-4-(1-methyl-1H-imidazol-4-yl)phenyl)cyclopentyl)-1-methyl-1H-pyrazole-4-carboxamide. Diastereomer 2 (AIA-365-2). MS Calcd.: 522.2; MS Found: 523.3 [M + 1]$^+$. $^1$H-NMR (DMSO-d$_6$, 400 MHz): δ 8.93 (s, 1H), 7.94 ((dd, J = 6.8, 2.4 Hz, 1H), 7.58-7.53 (m, 3H), 7.38-7.30 (m, 2H), 7.26-7.17 (m, 2 H), 6.03(s, 2H), 3.80 (s, 3H), 3.70-3.68 (m, 1H), 3.67 (s, 3H), 3.52 (s, 3H), 3.40-3.35 (m, 1H), 2.33-2.32 (m, 1H), 2.02-1.90 (m, 4H), 1.62-1.58 (m, 1H). |
| AIA-366-1 | 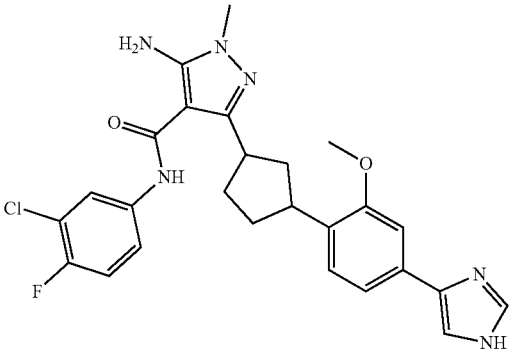 [SMILES: COc1cc(-c2c[nH]cn2)ccc1C1CCC(c2nn(C)c(N)c2C(=O)Nc2ccc(F)c(Cl)c2)C1] 3-(3-(4-(1H-Imidazol-4-yl)-2-methoxyphenyl)cyclopentyl)-5-amino-N-(3-chloro-4-fluorophenyl)-1-methyl-1H-pyrazole-4-carboxamide. Diastereomer 1 (AIA-366-1). MS Calcd.: 508.2; MS Found: 509.3 [M + 1]$^+$. $^1$H-NMR (DMSO-d$_6$, 400 MHz): δ 12.2 (s, 1H), 8.93 (s, 1H), 7.92 (dd, J = 6.8, 2.4 Hz, 1H), 7.67 (s, 1H), 7.56-7.46 (m, 2H), 7.40-7.18 (m, 4H), 6.03 (s, 2H), 3.84-3.83 (m, 1H), 3.80 (s, 3H), 3.52 (s, 3H), 3.43-3.38 (m, 1H), 2.12-1.91 (m, 5H), 1.65-1.60 (m, 1H). |
| AIA-366-2 | 3-(3-(4-(1H-Imidazol-4-yl)-2-methoxyphenyl)cyclopentyl)-5-amino-N-(3-chloro-4-fluorophenyl)-1-methyl-1H-pyrazole-4-carboxamide. Diastereomer 2 (AIA-366-2). MS Calcd.: 508.2; MS Found: 509.3 [M + 1]$^+$. $^1$H-NMR (DMSO-d$_6$, 400 MHz): δ 12.2 (s, 1H), 8.93 (s, 1H), 7.97 (dd, J = 6.8, 2.4 Hz, 1H), 7.93 (s, 1H), 7.54-7.38 (m, 2H), 7.36-7.20 (m, 4H), 6.03 (s, 2H), 3.83 (s, 3H), 3.80-3.79 (m, 1H), 3.71 (s, 3H), 3.49-3.46 (m, 1H), 2.25-2.18 (m, 1H), 2.02-1.85 (m, 4H), 1.63-1.52 (m, 1H). |

TABLE 2-continued

The compounds in table 2 were synthesized according to the procedure described for AIA-352-1 and AIA-352-2

| Compound | Structure and Characterization |
|---|---|
| AIA-367-1 | 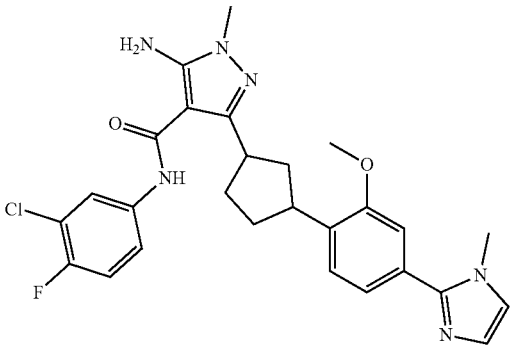 [SMILES: COc1cc(-c2nccn2C)ccc1C1CCC(c2nn(C)c(N)c2C(=O)Nc2ccc(F)c(Cl)c2)C1]<br>5-Amino-N-(3-chloro-4-fluorophenyl)-3-(3-(2-methoxy-4-(1-methyl-1H-imidazol-2-yl)phenyl)cyclopentyl)-1-methyl-1H-pyrazole-4-carboxamide. Diastereomer 1 (AIA-367-1). MS Calcd.: 522.2; MS Found: 523.3 [M + 1]$^+$. $^1$H-NMR (DMSO-d$_6$, 400 MHz): δ 8.95 (s, 1H), 7.93 (dd, J = 7.2, 2.8 Hz, 1H), 7.49-7.46 (m, 1 H), 7.36-7.31 (m, 2 H), 7.22 (s, 1H), 7.18-7.14 (m, 2H), 6.94 (s, 1H), 6.03 (s, 2H), 3.85-3.83 (m, 1H), 3.82 (s, 3H), 3.73 (s, 3H), 3.53(s, 3H), 3.49-3.44 (m, 1H), 2.13-1.97 (m, 5H), 1.67-1.58 (m, 1H). |
| AIA-367-2 | 5-Amino-N-(3-chloro-4-fluorophenyl)-3-(3-(2-methoxy-4-(1-methyl-1H-imidazol-2-yl)phenyl)cyclopentyl)-1-methyl-1H-pyrazole-4-carboxamide. Diastereomer 2 (AIA-367-2). MS Calcd.: 522.2; MS Found: 523.3 [M + 1]$^+$. $^1$H-NMR (DMSO-d$_6$, 400 MHz): δ 8.92 (s, 1H), 7.92 ((dd, J = 7.2, 2.8 Hz, 1H), 7.56-7.53 (m, 1H), 7.36-7.31 (m, 2H), 7.21-7.15 (m, 3 H), 6.92 (s, 1H), 6.01 (s, 2H), 3.82 (s, 3H), 3.77 (s, 3H), 3.72-3.68 (m, 1H), 3.50 (s, 3H), 3.45-3.40 (m, 1H), 2.25-2.22 (m, 1H), 2.05-1.98 (m, 2H), 1.92-1.86 (m, 2H), 1.65-1.58 (m, 1H). |
| AIA-369 | 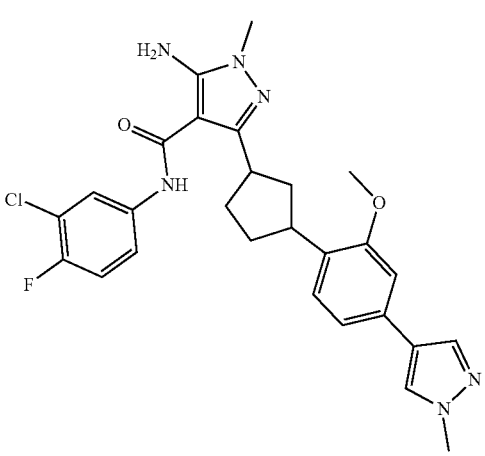 [SMILES: COc1cc(-c2cnn(C)c2)ccc1C1CCC(c2nn(C)c(N)c2C(=O)Nc2ccc(F)c(Cl)c2)C1]<br>5-Amino-N-(3-chloro-4-fluorophenyl)-3-(3-(2-methoxy-4-(1-methyl-1H-pyrazol-4-yl)phenyl)cyclopentyl)-1-methyl-1H-pyrazole-4-carboxamide (AIA-369). MS Calcd.:522.2, MS Found: 523.3 [M + 1]$^+$; $^1$H-NMR (CD$_3$OD, 400 MHz): δ 7.91 (s, 1H), 7.74-7.84 (m, 2H), 7.42-7.45 (m, 0.7H), 7.03-7.24(m, 4.3 H), 3.81-3.91 (m, 6H), 3.46-3.73 (m, 5H), 1.74-2.36 (m, 6H). |

TABLE 2-continued

The compounds in table 2 were synthesized according to the procedure described for AIA-352-1 and AIA-352-2

| Compound | Structure and Characterization |
| --- | --- |
| AIA-370 | 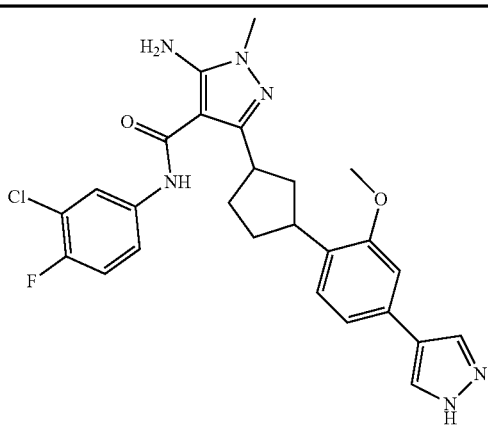

5-Amino-N-(3-chloro-4-fluorophenyl)-3-(3-(2-methoxy-4-(1H-pyrazol-4-yl)phenyl) cyclopentyl)-1-methyl-1H-pyrazole-4-carboxamide (AIA-370): MS Calcd.: 508.1, MS Found: 509.2 [M + 1]$^+$; $^1$H-NMR (CD$_3$OD, 400 MHz): δ 7.92 (s, 1H), 7.82-7.84 (m, 2H), 7.42-7.46 (m, 1 H), 7.03-7.25(m, 4 H), 3.85 (s, 3H), 3.64-3.68 (m, 1H), 3.57 (s, 3H), 3.52 (m, 1H), 2.34-2.37 (m, 2H), 1.77-2.19(m, 4H). |
| AIA-371 | 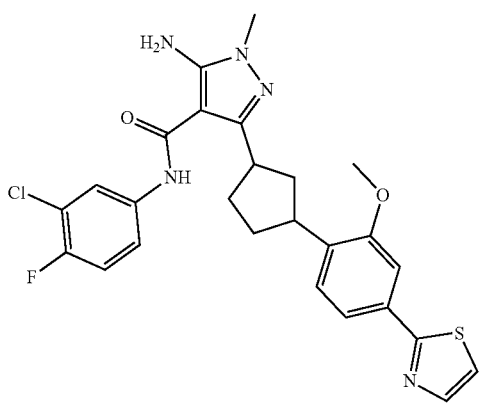 [SMILES: COc1cc(-c2nccs2)ccc1C1CCC(c2nn(C)c(N)c2C(=O)Nc2ccc(F)c(Cl)c2)C1]

5-Amino-N-(3-chloro-4-fluorophenyl)-3-(3-(2-methoxy-4-(thiazol-2-yl)phenyl)cyclopentyl)-1-methyl-1H-pyrazole-4-carboxamide. MS Calcd.: 525.14; MS Found: 526.3 [M + 1]$^+$; $^1$H NMR (DMSO-d$_6$, 400 MHz): δ 8.95 (brs, 1H), 7.95-7.89 (m, 2H), 7.76 (d, J = 3.2 Hz, 1H), 7.58-7.42 (m, 3H), 7.38-7.29 (m, 2H), 6.04 (s, 2H), 3.89-3.68 (m, 4H), 3.53-3.42 (m, 4H), 2.28-1.91 (m, 5H), 1.67-1.58 (m, 1H). |
| AIA-372 | 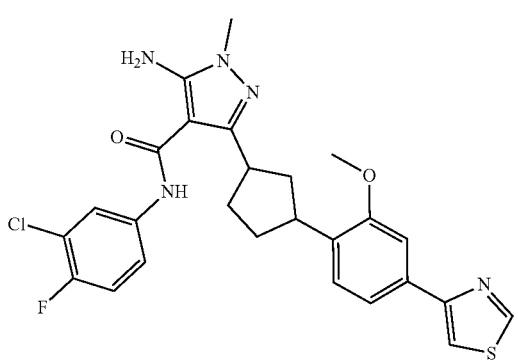 [SMILES: COc1cc(-c2cscn2)ccc1C1CCC(c2nn(C)c(N)c2C(=O)Nc2ccc(F)c(Cl)c2)C1]

5-Amino-N-(3-chloro-4-fluorophenyl)-3-(3-(2-methoxy-4-(thiazol-4-yl)phenyl)cyclopentyl)-1-methyl-1H-pyrazole-4-carboxamide. MS Calcd.: 525.1; MS Found: 526.3 [M + 1]$^+$; $^1$H NMR (DMSO-d6 + D$_2$O, |

TABLE 2-continued

The compounds in table 2 were synthesized according to the procedure described for AIA-352-1 and AIA-352-2

| Compound | Structure and Characterization |
|---|---|
| | 400 MHz): δ 9.12 (m, 1H), 8.08-8.07 (m, 1H), 7.89-7.84 (m, 1H), 7.54-7.46 (m, 3H), 7.35-7.25 (m, 2H), 3.81-3.79 (m, 3H), 3.69-3.62 (m, 1H), 3.49-3.48 (m, 3H), 3.42-3.37 (m, 1H), 2.23-2.20 (m, 1H), 2.06-1.82 (m, 4H), 1.63-1.60 (m, 1H). |

Intermediate 96

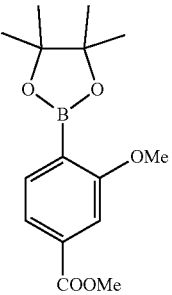

Methyl 3-methoxy-4-(4,4,5,5-tetramethyl-1,3,2-dioxaborolan-2-yl)benzoate. A mixture of methyl 4-bromo-3-methoxybenzoate (3.0 g, 12.2 mmol), 4,4,5,5-tetramethyl-2-(4,4,5,5-tetramethyl-1,3,2-dioxaborolan-2-yl)-1,3,2-dioxaborolane (4.8 g, 19 mmol), Pd(dppf)Cl$_2$ (450 mg, 0.6 mmol) and potassium acetate (1.9 g, 19.0 mmol) in dioxane (50 mL) was stirred at 80° C. under an N$_2$ atmosphere for 4 h. The reaction was filtered through a pad of Celite®, and the filter cake washed with EtOAc (10 mL×3). The filtrate was concentrated under vacuum and the residue purified by silica gel column chromatography using 15:1 petroleum ether/ethyl acetate to afford methyl 3-methoxy-4-(4,4,5,5-tetramethyl-1,3,2-dioxaborolan-2-yl)benzoate (2.5 g, 70% yield) as a white solid. MS Calcd.: 292.1, MS Found: 293.4 [M+1]$^+$.

Intermediate 97

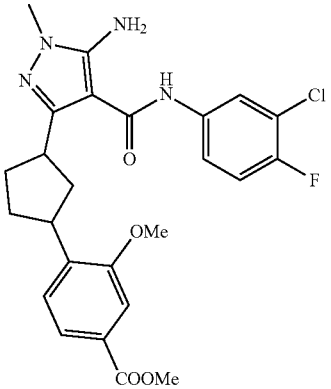

Methyl 3-methoxy-4-(3-oxocyclopent-1-enyl)benzoate. A mixture of methyl 3-methoxy-4-(4,4,5,5-tetramethyl-1,3,2-dioxaborolan-2-yl)benzoate (2.5 g, 8.6 mmol), 3-bromocyclopent-2-en-1-one (1.3 g, 8.6 mmol), Pd(PPh$_3$)$_4$ (500 mg, 0.43 mmol) and potassium carbonate (1.8 g, 12.9 mmol) in dioxane (50 mL) and water (10 mL) was stirred at 100° C. under an N$_2$ atmosphere for 4 h. The reaction was filtered through a pad of Celite® and the filter cake washed with EtOAc (10 mL×3). The filtrate was concentrated under vacuum and the residue purified by silica gel column chromatography using 3:1 petroleum ether/ethyl acetate to afford methyl 3-methoxy-4-(3-oxocyclopent-1-enyl)benzoate (1.8 g, 86% yield) as a yellowish solid. MS Calcd.: 246.1, MS Found: 247.4 [M+1]$^+$.

Intermediate 98

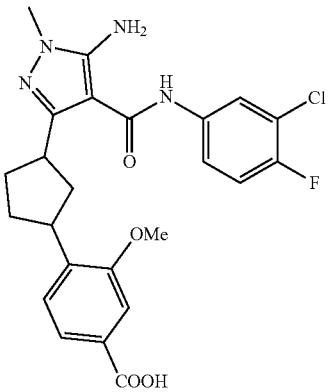

Methyl 4-(3-(5-amino-4-(3-chloro-4-fluorophenylcarbamoyl)-1-methyl-1H-pyrazol-3-yl)cyclopentyl)-3-methoxybenzoate. The title compound was synthesized from methyl 3-methoxy-4-(3-oxocyclopent-1-enyl)benzoate and 5-amino-3-bromo-N-(3-chloro-4-fluorophenyl)-1-methyl-1H-pyrazole-4-carboxamide according to the procedure described above. MS Calcd.: 500.2, MS Found: 501.3 [M+1]$^+$.

Intermediate 99

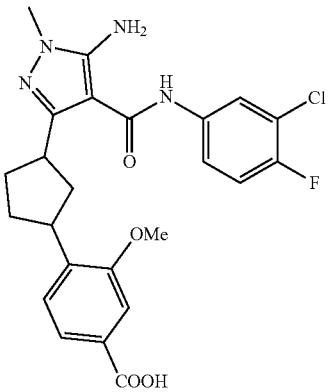

4-(3-(5-Amino-4-(3-chloro-4-fluorophenylcarbamoyl)-1-methyl-1H-pyrazol-3-yl)cyclopentyl)-3-methoxybenzoic acid. A mixture of methyl 4-(3-(5-amino-4-(3-chloro-4-fluorophenylcarbamoyl)-1-methyl-1H-pyrazol-3-yl)cyclopentyl)-3-methoxybenzoate (800 mg, 1.6 mmol) and LiOH—H$_2$O (670 mg, 16.0 mmol) in THF/H$_2$O=1:1 (10 mL) was heated at 60° C. overnight. The reaction was neutralized with 2N HCl, and the solvent removed under vacuum. The residue was purified by silica gel column chromatography using ethyl acetate to afford 4-(3-(5-amino-4-(3-chloro-4-fluorophenylcarbamoyl)-1-methyl-1H-pyrazol-3-yl)cyclopentyl)-3-methoxybenzoic acid. (700 mg, 90% yield) as a white solid. MS Calcd.: 486.1, MS Found: 487.3 [M+1]$^+$.

by SFC to give AIA-150-C(30 mg) as a white solid and AIA-150-D (30 mg) as a white solid. AIA-150-C: $^1$H-NMR (DMSO-d$_6$, 400 MHz): δ 8.94 (s, 1H), 7.93 (dd, J=6.8, 2.4 Hz, 1H), 7.91 (brs, 1H), 7.58-7.54 (m, 1H), 7.44-7.41 (m, 2H), 7.36 (t, J=9.2 Hz, 1H), 7.30-7.27 (m, 2H), 6.03 (s, 2H), 3.81 (s, 3H), 3.73-3.69 (m, 1H), 3.52 (s, 3H), 3.46-3.41 (m, 1H), 2.27-2.20 (m, 1H), 2.08-2.00 (m, 2H), 1.99-1.83 (m, 2H), 1.65-1.59 (m, 1H). AIA-150-D: $^1$H-NMR (DMSO-d$_6$, 400 MHz): δ 8.94 (s, 1H), 7.93 (dd, J=6.8, 2.4 Hz, 1H), 7.91 (brs, 1H), 7.58-7.54 (m, 1H), 7.44-7.41 (m, 2H), 7.36 (t, J=9.2 Hz, 1H), 7.30-7.27 (m, 2H), 6.03 (s, 2H), 3.81 (s, 3H), 3.73-3.69 (m, 1H), 3.52 (s, 3H), 3.46-3.41 (m, 1H), 2.27-2.20 (m, 1H), 2.08-2.00 (m, 2H), 1.99-1.83 (m, 2H), 1.65-1.59 (m, 1H).

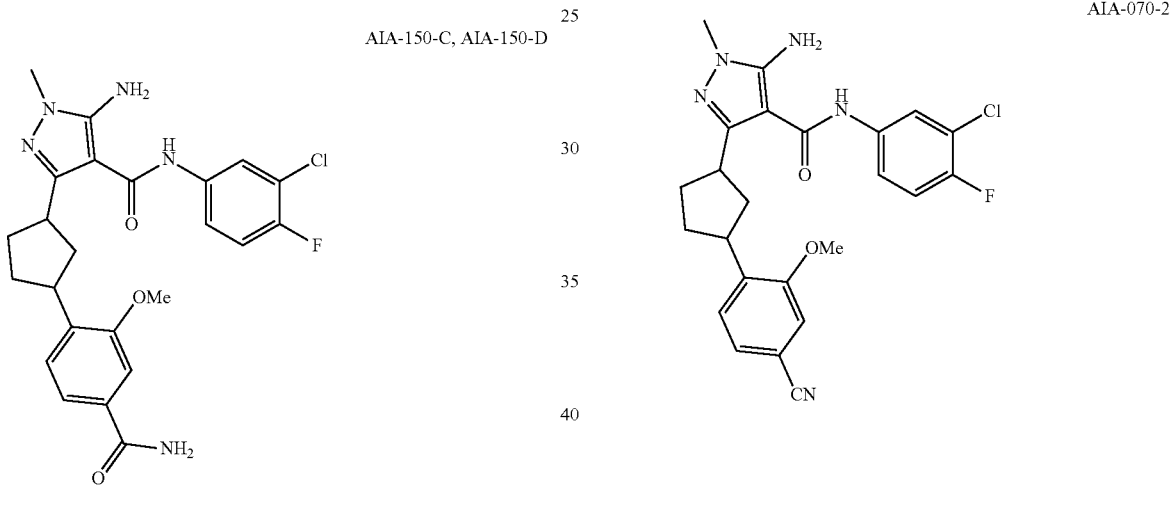

AIA-150-C, AIA-150-D

AIA-070-2

5-Amino-3-(3-(4-carbamoyl-2-methoxyphenyl)cyclopentyl)-N-(3-chloro-4-fluorophenyl)-1-methyl-1H-pyrazole-4-carboxamide. Diastereomer 1 (AP-AIA-150-C), Diastereomer 2 (AIA-150-D). A mixture of 4-(3-(5-amino-4-(3-chloro-4-fluorophenylcarbamoyl)-1-methyl-1H-pyrazol-3-yl)cyclopentyl)-3-methoxybenzoic acid (700 mg, 1.4 mmol), HCOONH$_4$ (180 mg, 2.9 mmol), HATU (1.1 g, 2.9 mmol) and TEA (300 mg, 2.9 mmol) in DMF (5 mL) was stirred at room temperature overnight. The reaction was quenched with water (20 mL) then extracted with EtOAc (20 mL×3). The organic layer was concentrated under reduce pressure and the resulting residue purified by silica gel column chromatography using ethyl acetate to afford AIA-150-1 (30 mg, 4% yield) as a white solid and AIA-150-2 (300 mg, 43% yield) as a white solid. MS Calcd.: 485.2, MS Found: 486.3 [M+1]$^+$. 100 mg of AIA-150-2 was separated 5-Amino-N-(3-chloro-4-fluorophenyl)-3-(3-(4-cyano-2-methoxyphenyl)cyclopentyl)-1-methyl-1H-pyrazole-4-carboxamide To a solution of AIA-150-2 (150 mg, 0.3 mmol) in pyridine (5 mL) was added POCl$_3$ (140 mg, 0.9 mmol) and the mixture stirred at −40° C. for 10 min. The reaction was quenched with water (10 mL) and extracted with EtOAc (10 mL×3). The combined organic layers were concentrated under vacuum. The resulting residue was purified by silica gel column chromatography using 1:1 petroleum ether/ethyl acetate to afford 5-amino-N-(3-chloro-4-fluorophenyl)-3-(3-(4-cyano-2-methoxyphenyl)cyclopentyl)-1-methyl-1H-pyrazole-4-carboxamide (7 mg, 5% yield) as a white solid. MS Calcd.: 467.2, MS Found: 468.2 [M+1]$^+$. $^1$H-NMR (DMSO-d$_6$, 400 MHz): δ 8.94 (s, 1H), 7.93 (dd, J=6.8, 2.4 Hz, 1H), 7.58-7.54 (m, 1H), 7.44 (d, J=8.0 Hz, 1H), 7.38-7.33 (m, 3H), 6.03 (s, 2H), 3.83 (s, 3H), 3.74-3.70 (m, 1H), 3.51 (s, 3H), 3.48-3.43 (m, 1H), 2.28-2.22 (m, 1H), 2.08-2.00 (m, 2H), 1.99-1.83 (m, 2H), 1.65-1.59 (m, 1H).

TABLE 3

The compounds in table 3 were synthesized according to the procedure described for AIA-150-C and AIA-150-D

| Compound | Structure and Characterization |
|---|---|
| AIA-387-1 | 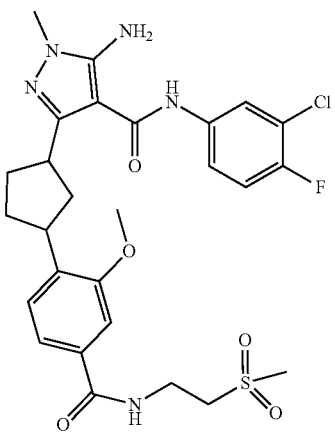 [SMILES: COc1cc(C(=O)NCCS(C)(=O)=O)ccc1C1CCC(c2nn(C)c(N)c2C(=O)Nc2ccc(F)c(Cl)c2)C1]<br>5-Amino-N-(3-chloro-4-fluorophenyl)-3-(3-(2-methoxy-4-42-(methylsulfonyl)ethyl)carbamol)phenyl)cyclopentyl)-1-methyl-1H-pyrazole-4-carboxamide. Diastereomer 1 (AIA-387-1). $^1$H-NMR (D$_2$O/DMSO-d$_6$, 400 MHz): δ 7.83-7.85 (m, 1H), 7.46-7.50 (m, 1H), 7.28-7.35 (m, 4H), 3.76(s, 3H), 3.62-3.65 (m, 3H), 3.46(s, 3H), 3.31-3.38 (m, 3H), 2.97 (s, 3H), 2.17-2.21 (m, 1H), 1.78-2.02(m, 4H), 1.57-1.61 (m, 1H). |
| AIA-387-2 | 5-Amino-N-(3-chloro-4-fluorophenyl)-3-(3-(2-methoxy-4-((2-(methylsulfonyl)ethyl)carbamoyl)phenyl)cyclopentyl)-1-methyl-1H-pyrazole-4-carboxamide. Diastereomer 2 (AIA-387-2). $^1$H-NMR (D$_2$O/DMSO-d$_6$, 400 MHz): δ 7.82-7.84 (m, 1H), 7.45-7.49 (m, 1H), 7.28-7.34 (m, 4H), 3.61-3.65 (m, 3H), 3.46(s, 3H), 3.30-3.38 (m, 3H), 2.97 (s, 3H), 2.17-2.20 (m, 1H), 1.77-2.01(m, 4H), 1.57-1.61 (m, 1H). |
| AIA-388 | 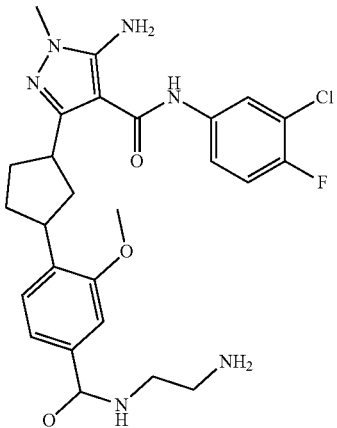 [SMILES: COc1cc(C(O)NCCN)ccc1C1CCC(c2nn(C)c(N)c2C(=O)Nc2ccc(F)c(Cl)c2)C1]<br>5-Amino-3-(3-(4-((2-aminoethyl)carbamoyl)-2-methoxyphenyl)cyclopentyl)-N-(3-chloro-4-fluorophenyl)-1-methyl-1H-pyrazole-4-carboxamide. MS Calcd.: 528.2, MS Found: 529.3 [M + 1]$^+$. $^1$H-NMR (D$_2$O/DMSO-d$_6$, 400 MHz): δ 7.83-7.85 (m, 1H), 7.47-7.51 (m, 1H), 7.27-7.37 (m, 4H), 3.78 (s, 3H), 3.62-3.66(m, 1H), 3.47(s, 3H), 3.37-3.42 (m, 1H), 3.17-3.25 (m, 2H), 3.03-3.06 (m, 1H), 2.56-2.63 (m, 1H), 2.19-2.22 (m, 1H), 1.77-2.06(m, 4H), 1.57-1.61 (m, 1H). |

AIA-262

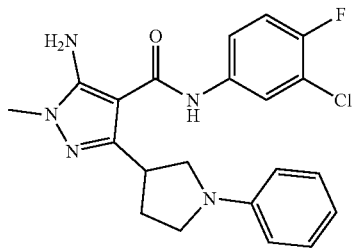

5-Amino-N-(3-chloro-4-fluorophenyl)-1-methyl-3-(1-phenylpyrrolidin-3-yl)-1H-pyrazole-4-carboxamide. A mixture of 5-amino-N-(3-chloro-4-fluoro-phenyl)-1-methyl-3-pyrrolidin-3-yl-pyrazole-4-carboxamide (100 mg, 0.296 mmol, 1 eq), bromobenzene (46.48 mg, 0.296 mmol, 0.031 mL, 1 eq), $Pd_2(dba)_3$ (8.13 mg, 0.009 mmol, 0.03 eq), XPhos (4.23 mg, 0.009 mmol, 0.03 eq) and NaOtBu (85.35 mg, 0.888 mmol, 3 eq) in dioxane (3 mL) was stirred at 105° C. for 2 hr under $N_2$. A brown suspension was observed. The reaction was continued by stirring at 105° C. for 2 hr under $N_2$. Ethyl acetate (10 mL) and water (10 mL) were added to the reaction. The aqueous layer was separated and extracted with ethyl acetate (10 mL). The organic layers were combined and washed with brine (10 mL), dried over $Na_2SO_4$, filtered and concentrated under vacuum to give 5-amino-N-(3-chloro-4-fluoro-phenyl)-1-methyl-3-(1-phenylpyrrolidin-3-yl)pyrazole-4-carboxamide (150 mg, crude) as a brown oil. The residue was purified by prep-TLC (1:1 Petroleum ether/EtOAc) to give 5-amino-N-(3-chloro-4-fluoro-phenyl)-1-methyl-3-(1-phenylpyrrolidin-3-yl)pyrazole-4-carboxamide (5 mg, crude) as a yellow oil, which was purified by prep-HPLC (column: Gemini 150×25 5 u; mobile phase: [water (0.05% ammonia hydroxide v/v)—ACN]; B %: 50%-80%, 10 min) to give 5-amino-N-(3-chloro-4-fluoro-phenyl)-1-methyl-3-(1-phenylpyrrolidin-3-yl) pyrazole-4-carboxamide (1.8 mg, 0.004 mmol, 36.00% yield, 100% purity), as a yellow solid. $^1$H NMR (400 MHz, CHLOROFORM-d) □ ppm 2.35-2.57 (m, 2H) 3.13-3.23 (m, 1H) 3.46-3.60 (m, 4H) 3.75-3.82 (m, 2H) 5.47 (br s, 2H) 6.75 (br d, J=7.72 Hz, 2H) 6.80-6.98 (m, 2H) 7.11 (ddd, J=8.99, 4.02, 2.65 Hz, 1H) 7.25-7.32 (m, 2H) 7.39-7.48 (m, 1H) 8.66 (br s, 1H); LC-MS: 414.0 $[M+1]^+$.

was purified by silica gel column chromatography using 8:1 petroleum ether/ethyl acetate to afford 5-oxo-1,3a,4,5,6,6a-hexahydropentalen-2-yl trifluoromethanesulfonate (36.0 g, 46% yield) as a yellow oil. $^1$H NMR (400 MHz, CHLOROFORM-d) δ ppm 2.17 (ddd, J=19.14, 7.34, 1.63 Hz, 1H) 2.26-2.34 (m, 1H) 2.40-2.56 (m, 2H) 2.58-2.67 (m, 1H) 3.00-3.14 (m, 2H) 3.50-3.57 (m, 1H) 5.63 (q, J=1.92 Hz, 1H).

Intermediate 101

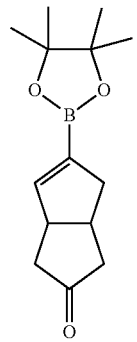

5-(4,4,5,5-Tetramethyl-1,3,2-dioxaborolan-2-yl)-3,3a,6,6a-tetrahydropentalen-2(1H)-one. A mixture of 5-oxo-1,3a,4,5,6,6a-hexahydropentalen-2-yltrifluoromethanesulfonate (110.0 g, 407.0 mmol), 4,4,5,5-tetramethyl-2-(4, 4,5,5-tetramethyl-1,3,2-dioxaborolan-2-yl)-1,3,2-dioxaborolane (108.5 g, 427.4 mmol), $Pd(dppf)Cl_2$ (8.9 g, 12.2 mmol) and potassium acetate (119.7 g, 1221.0 mmol) in dioxane (1000 ml) was stirred at 80° C. under an $N_2$ atmosphere for 2 h. The reaction mixture was filtered through a pad of Celite® and the filter cake was washed with EtOAc (250 mL×3). The filtrate was concentrated under vacuum and the residue was purified by silica gel column chromatography using 8:1 petroleum ether/ethyl acetate to afford 5-(4,4,5,5-tetramethyl-1,3,2-dioxaborolan-2-yl)-3,3a,6,6a-tetrahydropentalen-2(1H)-one (90.0 g, 89% yield) as a yellow oil. $^1$H NMR (400 MHz, CHLOROFORM-d) δ ppm 1.28 (s, 13H) 1.95-2.07 (m, 1H) 2.24-2.55 (m, 4H) 2.79 (ddt, J=16.48, 7.58, 2.64, 2.64 Hz, 1H) 2.93-3.05 (m, 1H) 3.41-3.54 (m, 1H) 6.37 (q, J=2.08 Hz, 1H).

Intermediate 100

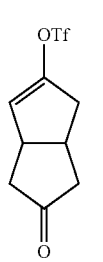

5-Oxo-1,3a,4,5,6,6a-hexahydropentalen-2-yl trifluoromethanesulfonate. To a solution of 1,3,3a,4,6,6a-hexahydropentalene-2,5-dione (40.0 g, 289.5 mmol) and pyridine (24.0 g, 304.0 mmol) in DCM (600 ml) was added $Tf_2O$ (89.8 g, 318.5 mmol) dropwise at room temperature. The mixture was stirred at room temperature for 3 h. Brine (300 mL) was added and the aqueous layer extracted with DCM (200 mL×3). The organic layer was separated, dried over $Na_2SO_4$ and concentrated to give the crude product which Intermediate 102

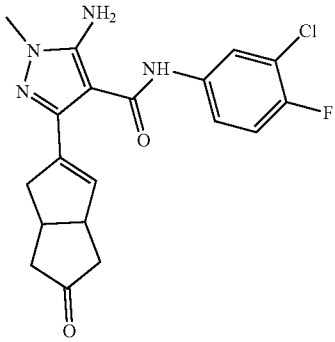

5-Amino-N-(3-chloro-4-fluorophenyl)-1-methyl-3-(5-oxo-1,3a,4,5,6,6a-hexahydropentalen-2-yl)-1H-pyrazole-4-carboxamide. A mixture of 5-amino-3-bromo-N-(3-chloro-4-fluorophenyl)-1-methyl-1H-pyrazole-4-carboxamide (68.6 g, 197.5 mmol), 5-(4,4,5,5-tetramethyl-1,3,2-dioxaborolan-2-yl)-3,3a,6,6a-tetrahydropentalen-2(1H)-one (70.0 g, 282.1 mmol), Pd(dppf)Cl$_2$ (10.1 g, 13.8 mmol) and Na$_2$CO$_3$ (41.9 g, 395.0 mmol) in dioxane (1200 mL) and H$_2$O (150 mL) was stirred at 80° C. overnight under N$_2$. The mixture was a brown suspension. The solvent was evaporated under vacuum. The residue was purified by silica gel column chromatography using 1:2 petroleum ether/ethyl acetate to afford 5-amino-N-(3-chloro-4-fluorophenyl)-1-methyl-3-(5-oxo-1,3a,4,5,6,6a-hexahydropentalen-2-yl)-1H-pyrazole-4-carboxamide (55.0 g, 72% yield) as a yellow solid. MS Calcd.: 388.1, MS Found: 389.0 [M+1]$^+$. $^1$H NMR (400 MHz, CHLOROFORM-d) δ ppm 2.19 (dd, J=19.20, 5.26 Hz, 1H) 2.33 (br d, J=18.83 Hz, 1H) 2.55-2.79 (m, 3H) 3.15-3.28 (m, 2H) 3.63 (s, 3H) 3.66 (s, 1H) 3.68-3.77 (m, 1H) 5.24-5.45 (m, 2H) 6.05 (d, J=1.71 Hz, 1H) 6.95-7.20 (m, 2H) 7.47-7.58 (m, 1H) 7.68-7.86 (m, 2H); LCMS: 389.0 [M+1]$^+$.

AIA-002

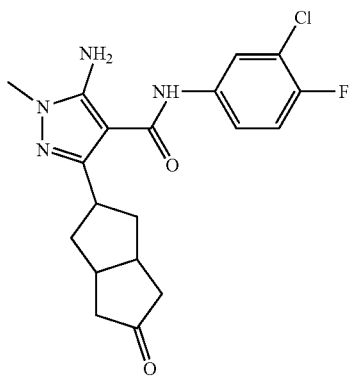

5-Amino-N-(3-chloro-4-fluorophenyl)-1-methyl-3-(5-oxooctahydropentalen-2-yl)-1H-pyrazole-4-carboxamide. To a solution of 5-(4,4,5,5-tetramethyl-1,3,2-dioxaborolan-2-yl)-3,3a,6,6a-tetrahydropentalen-2(1H)-one (5.0 g, 12.9 mmol) in EtOAc (500 ml) was added Pd/C (2.5 g, 10% w/w Pd). The mixture was stirred at 40° C. for 2 h under Hz. The mixture was filtered and evaporated under vacuum to give the target compound (4.6 g, 92%) as white solid. The crude was used directly without any further purification. MS Calcd.: 390.1; MS Found: 391.0 [M+1]$^+$. $^1$H NMR (400 MHz, CHLOROFORM-d) δ ppm 1.85-2.01 (m, 2H) 2.07-2.29 (m, 2H) 2.41-2.67 (m, 4H) 2.83-3.06 (m, 2H) 3.32-3.50 (m, 1H) 3.54-3.61 (m, 3H) 5.15-5.32 (m, 2H) 7.12 (t, J=8.74 Hz, 1H) 7.27-7.35 (m, 2H) 7.65-7.83 (m, 1H); LCMS: 391.2 [M+1]$^+$.

AIA-290

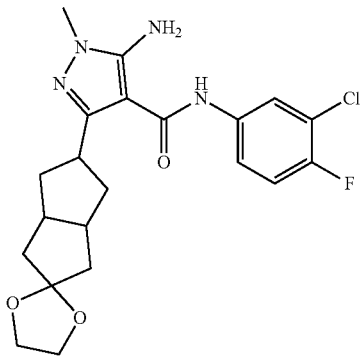

5-Amino-N-(3-chloro-4-fluorophenyl)-3-(hexahydro-1H-spiro[pentalene-2,2'-[1,3]dioxolan]-5-yl)-1-methyl-1H-pyrazole-4-carboxamide. To a pale brown solution of 5-amino-N-(3-chloro-4-fluoro-phenyl)-1-methyl-3-(5-oxo-2,3,3a,4,6,6a-hexahydro-1H-pentalen-2-yl)pyrazole-4-carboxamide (30 mg, 0.071 mmol, 1 eq) and ethylene glycol (4.39 mg, 0.0708 mmol, 1 eq) in toluene (3 mL) was added p-TsOH (12.19 mg, 0.0708 mmol, 1.0 eq). The mixture was stirred at 110° C. for 16 hr. The mixture was diluted with EtOAc (10 mL), washed with saturated NaHCO$_3$ solution (10 mL), dried over Na$_2$SO$_4$, filtered and concentrated under vacuum to give a residue. The residue was purified by prep-TLC (SiO$_2$, 10:1 DCM: MeOH). The compound 5-amino-N-(3-chloro-4-fluoro-phenyl)-1-methyl-3-spiro[1,3-dioxolane-2,5'-2,3,3a,4,6,6a-hexahydro-1Hpentalene]-2'-yl-pyrazole-4-carboxamide (30 mg, 0.0659 mmol, 55.9% yield, 95.6% purity) was obtained as a colorless gum, and further purified by prep-HPLC (Base). $^1$H NMR (400 MHz, CHLOROFORM-d) δ ppm 1.74 (2H, br dd, J=13.45, 4.85 Hz), 1.81-1.92 (2H, m), 2.00-2.10 (2H, m), 2.30-2.42 (2H, m), 2.60-2.74 (2H, m), 3.07-3.19 (1H, m), 3.60 (3H, s), 3.85-3.95 (4H, m), 5.28 (2H, s), 7.11 (1H, t, J=8.71 Hz), 7.27-7.33 (2H, m), 7.72 (1H, dd, J=6.62, 2.65 Hz); LCMS: 435.0 [M+1]$^+$.

Intermediate 103

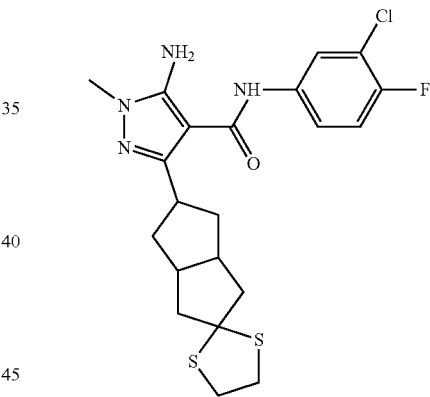

5-Amino-N-(3-chloro-4-fluorophenyl)-3-(hexahydro-1H-spiro[pentalene-2,2'-[1,3]dithiolan]-5-yl)-1-methyl-1H-pyrazole-4-carboxamide. To a mixture of 5-amino-N-(3-chloro-4-fluoro-phenyl)-1-methyl-3-(5-oxo-2,3,3a,4,6,6a-hexahydro-1H-pentalen-2-yl)pyrazole-4-carboxamide (0.2 g, 0.512 mmol, 1 eq) and ethane-1,2-dithiol (77.13 mg, 0.819 mmol, 0.069 mL, 1.6 eq) in DCM (5 mL) was added BF$_3$.Et$_2$O (290.51 mg, 2.05 mmol, 0.253 mL, 4 eq). The mixture was stirred at 25° C. for 3 hr. The mixture was washed with H$_2$O (15 mL) three times, then brine (20 mL). The organic layer was dried over Na$_2$SO$_4$ and evaporated under vacuum to give a yellow solid. The yellow solid was purified by flash silica gel chromatography (combi Flash®; 4 g SepaFlash® Silica Flash Column, Eluent of 0~41.4% Ethyl acetate/Petroleum ether gradient @ 18 mL/min). 5-Amino-N-(3-chloro-4-fluoro-phenyl)-1-methyl-3-spiro[1,3-dithiolane-2,5'-2,3,3a,4,6,6a-hexahydro-1H-pentalene]-2'-yl-pyrazole-4-carboxamide (190 mg, 0.397 mmol, 77.58% yield, 97.580% purity), was obtained as a yellow solid. LCMS: 467.0 [M+1]$^+$.

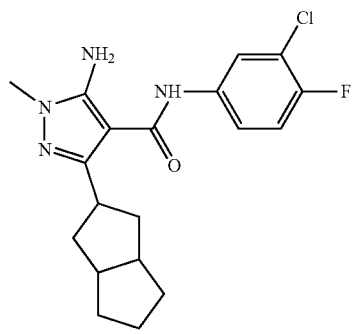

AIA-232

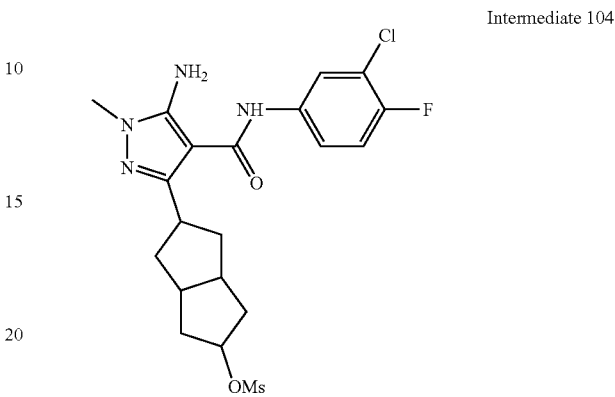

Intermediate 104

7.91 (dd, J=6.8, 2.8 Hz, 1H), 7.53-7.49 (m, 1H), 7.34 (t, J=9.2 Hz, 1H), 5.96 (s, 2H), 4.45 (d, J=3.2 Hz, 1H), 4.04-4.02 (m, 1H), 3.49 (s, 3H), 3.45-3.39 (m, 1H), 2.38-2.32 (m, 2H), 2.17-2.11 (m, 2H), 1.92-1.89 (m, 2H), 1.62-1.54 (m, 2H), 1.30-1.24 (m, 2H)

5-Amino-N-(3-chloro-4-fluorophenyl)-1-methyl-3-(octahydropentalen-2-yl)-1H-pyrazole-4-carboxamide. To a solution of Raney-Ni (100 mg, 1.17 mmol) in EtOH (10 mL) was added 5-amino-N-(3-chloro-4-fluoro-phenyl)-1-methyl-3-spiro[1,3-dithiolane-2,5'-2,3,3a,4,6,6a-hexahydro-1H-pentalene]-2'-yl-pyrazole-4-carboxamide (50 mg, 0.078 mmol, 1 eq). The mixture was stirred at 80° C. for 4 hr. The mixture was filtered, and the filtrate was evaporated under vacuum to give a yellow gum. The crude product was purified by Prep-HPLC (column: Gemini 150×25 5 u; mobile phase: [water (0.05% ammonium hydroxide v/v)—ACN]; B %: 55%-85%, 10 min) to yield 3-(1,2,3,3a,4,5,6,6a-octahydropentalen-2-yl)-5-amino-N-(3-chloro-4-fluoro-phenyl)-1-methyl-pyrazole-4-carboxamide (10 mg, 0.0265 mmol, 16.9% yield, 100% purity) as a white solid. $^1$H NMR (400 MHz, DMSO-d6) δ ppm 1.16-1.29 (m, 2H) 1.36 (br s, 2H) 1.41-1.54 (m, 4H) 2.07-2.18 (m, 2H) 2.43 (br s, 2H) 3.26-3.34 (m, 1H) 3.48 (s, 3H) 5.95 (s, 2H) 7.34 (t, J=9.15 Hz, 1H) 7.51 (ddd, J=9.04, 4.41, 2.65 Hz, 1H) 7.91 (dd, J=6.84, 2.65 Hz, 1H) 8.97 (s, 1H); LCMS: 376.9 [M+1]$^+$.

5-(5-Amino-4-((3-chloro-4-fluorophenyl)arbamoyl)-1-methyl-1H-pyrazol-3-yl)octahydropentalen-2-yl methanesulfonate To a mixture of AIA-026 (400 mg, 1 mmol) and TEA (204 mg, 2 mmol) in DCM (20 mL) was added MsCl (172 mg, 1.5 mmol) and the mixture stirred at 25° C. for 4 h. The reaction was concentrated under vacuum and the residue purified by silica gel column chromatography using 5-10% ethyl acetate/petroleum ether to give 5-(5-amino-4-((3-chloro-4-fluorophenyl)carbamoyl)-1-methyl-1H-pyrazol-3-yl)octahydropentalen-2-yl methanesulfonate (311 mg, 65% yield) as a pale white solid. MS Calcd.: 470.9; MS Found: 471.7 [M+1]$^+$.

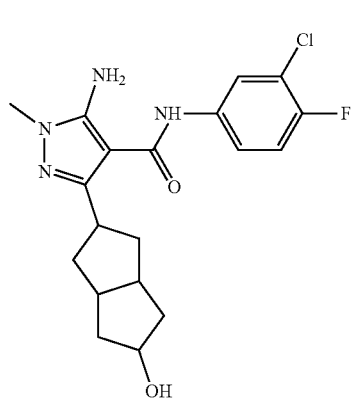 [SMILES: CCSC1CC2CC(c3nn(C)c(N)c3C(=O)Nc3ccc(F)c(Cl)c3)CC2C1]

AIA-026

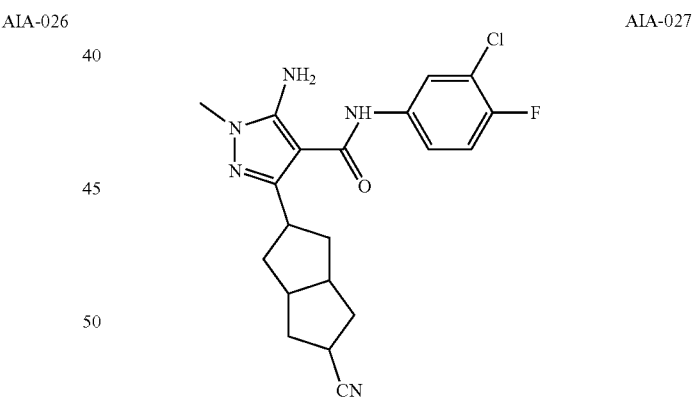

AIA-027

5-Amino-N-(3-chloro-4-fluorophenyl)-3-(5-hydroxyoctahydropentalen-2-yl)-1-methyl-1H-pyrazole-4-carboxamide. To a suspension of AIA-002 (39 mg, 0.1 mmol, 1 eq) in THF/MeOH (1 mL/1 mL) was added NaBH$_4$ (6 mg, 0.15 mmol, 1.5 eq) in portions. The reaction was stirred at RT for 30 minutes. A yellow solution was observed. The reaction was quenched with water and exacted with ethyl acetate (10 mL×2). The organic phase was concentrated under vacuum and the residue purified by prep-HPLC to give 5-amino-N-(3-chloro-4-fluorophenyl)-3-(5-hydroxyoctahydropentalen-2-yl)-1-methyl-1H-pyrazole-4-carboxamide (28 mg, 71% yield) as white solid. MS Calcd.: 392.1; MS Found: 393.0 [M+1]$^+$. $^1$H-NMR (DMSO-d$_6$, 400 MHz): δ 8.93 (s, 1H), 5-Amino-N-(3-chloro-4-fluorophenyl)-3-(5-cyanooctahydropentalen-2-yl)-1-methyl-1H-pyrazole-4-carboxamide To a solution of 5-(5-amino-4-((3-chloro-4-fluorophenyl)carbamoyl)-1-methyl-1H-pyrazol-3-yl)octahydropentalen-2-yl methanesulfonate (46.7 mg, 0.10 mmol) in acetonitrile (5 mL) was added TMSCN (100 mg, 1.01 mmol) and TBAF (100 mg, 0.38 mmol) and the resulting mixture stirred at 70° C. for 4 h. The mixture was concentrated in vacuo and the residue purified by prep-HPLC to afford 5-amino-N-(3-chloro-4-fluorophenyl)-3-(5-cyanooctahydropentalen-2-yl)-1-methyl-1H-pyrazole-4-carboxamide (6.7 mg, 16% yield) as a white solid. MS Calcd.: 401.8; MS Found: 402.7 [M+1]$^+$. V$^1$H-NMR (DMSO-d$_6$, 400 MHz): δ 8.96 (s, 1H), 7.91 (dd, J=6.8, 2.8 Hz, 1H), 7.53-7.49 (m, 1H), 7.34 (t, J=9.2 Hz, 1H), 5.97 (s, 2H), 3.48 (s, 3H), 3.31-3.29 (m, 1H), 2.93-2.88 (m, 1H), 2.60-2.57 (m, 2H), 2.17-2.11 (m, 2H), 1.85-1.73 (m, 4H), 1.30-1.22 (m, 2H)

AIA-028

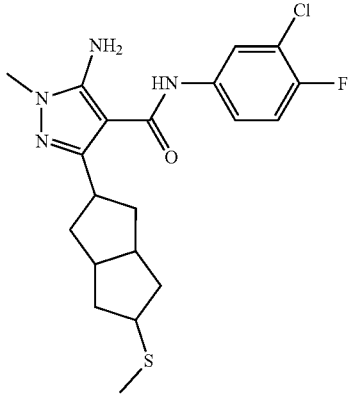

5-Amino-N-(3-chloro-4-fluorophenyl)-1-methyl-3-(5-(methylthio)octahydropentalen-2-yl)-1H-pyrazole-4-carboxamide. A mixture of 5-(5-amino-4-((3-chloro-4-fluorophenyl)carbamoyl)-1-methyl-1H-pyrazol-3-yl) octahydropentalen-2-yl methanesulfonate (46 mg, 0.1 mmol) and MeSNa (28 mg, 0.4 mmol) in DMF (4 mL) was stirred at 70° C. for 4 h. H$_2$O (10 mL) was added to the mixture. The solution was extracted with ethyl acetate (10 mL×3). The combined organic layers were dried over Na$_2$SO$_4$, concentrated then purified by silica gel column chromatography using 5-30% ethyl acetate/petroleum ether to afford 5-amino-N-(3-chloro-4-fluorophenyl)-1-methyl-3-(5-(methylthio)octahydropentalen-2-yl)-1H-pyrazole-4-carboxamide (10 mg, 23% yield) as a pale-white solid. MS Calcd.: 422.13; MS Found: 423.2 [M+1]$^+$. $^1$H-NMR (DMSO-d$_6$, 400 MHz): δ 8.96 (s, 1H), 7.91 (d, J=4.8, 1H), 7.52-7.50 (m, 1H), 7.34 (t, J=9.2 Hz, 1H), 5.96 (s, 2H), 3.48 (s, 3H), 3.05-3.02 (m, 1H), 2.45-2.50 (m, 3H), 2.16-2.14 (m, 2H), 2.00 (s, 3H), 1.76-1.72 (m, 2H), 1.50-1.48 (m, 2H), 1.31-1.25 (m, 2H)

TABLE 4

The compounds in table 4 were synthesized according to the procedure described for 5-amino-N-(3-chloro-4-fluorophenyl)-1-methyl-3-(5-(methylthio)octahydropentalen-2-yl)-1H-pyrazole-4-carboxamide

| Compound | Structure and characterization |
| --- | --- |
| AIA-029 | 5-Amino-N-(3-chloro-4-fluorophenyl)-3-(5-(ethylthio)octahydropentalen-2-yl)-1-methyl-1H-pyrazole-4-carboxamide. MS Calcd.: 436.9; MS Found: 437.7 [M + 1]$^+$. |
| AIA-048 | 3-(5-(1H-Pyrazol-1-yl)octahydropentalen-2-yl)-5-amino-N-(3-chloro-4-fluorophenyl)-1-methyl-1H-pyrazole-4-carboxamide. $^1$H NMR |

TABLE 4-continued

The compounds in table 4 were synthesized according to the procedure described for 5-amino-N-(3-chloro-4-fluorophenyl)-1-methyl-3-(5-(methylthio)octahydropentalen-2-yl)-1H-pyrazole-4-carboxamide

| Compound | Structure and characterization |
|---|---|
|  | (DMSO-d$_6$, 400 MHz): δ 8.98 (s, 1H), 7.92 (dd, J = 6.8, 2.4 Hz, 1H), 7.77 (d, J = 2.0 Hz, 1H), 7.55-7.51 (m, 1H), 7.43 (d, J = 4.0 Hz, 1H), 7.40-7.33 (m, 1H), 6.19 (t, J = 2.0 Hz, 1H), 5.99 (s, 2H), 4.77-4.69 (m, 1H), 3.51 (s, 3H), 3.38-3.35 (m, 1H), 2.68-2.59 (m, 2H), 2.26-2.20 (m, 2H), 2.11-2.04 (m, 2H), 1.86-1.82 (m, 2H), 1.45-1.37 (m, 2H); MS Calcd.: 442.2; MS Found: 443.2 [M + 1]$^+$. |
| AIA-058 | 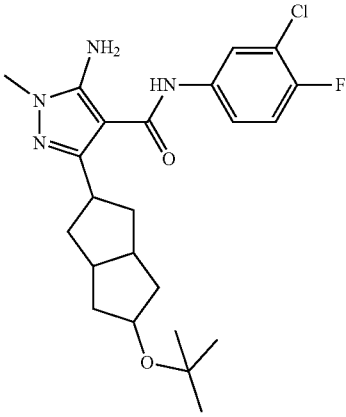 [SMILES: Cn1nc(C2CC3CC(OC(C)(C)C)CC3C2)c(C(=O)Nc2ccc(F)c(Cl)c2)c1N] 5-Amino-3-(5-(tert-butoxy)octahydropentalen-2-yl)-N-(3-chloro-4-fluorophenyl)-1-methyl-1H-pyrazole-4-carboxamide. MS Calcd.: 448.2; MS Found: 449.4 [M + 1]$^+$. |
| AIA-101 | 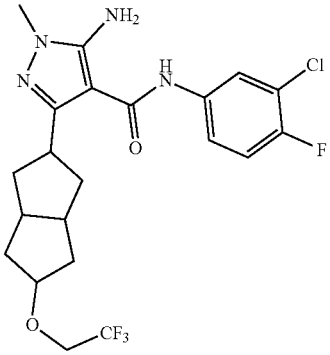 [SMILES: Cn1nc(C2CC3CC(OCC(F)(F)F)CC3C2)c(C(=O)Nc2ccc(F)c(Cl)c2)c1N] 5-Amino-N-(3-chloro-4-fluorophenyl)-1-methyl-3-(5-(2,2,2-trifluoroethoxy)octahydropentalen-2-yl)-1H-pyrazole-4-carboxamide. MS Calcd.: 474.1; MS Found: 475.2 [M + 1]$^+$. |
| Intermediate 105 | 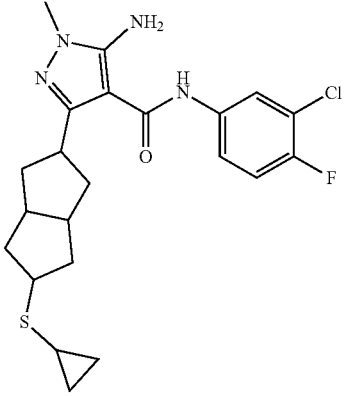 [SMILES: Cn1nc(C2CC3CC(SC4CC4)CC3C2)c(C(=O)Nc2ccc(F)c(Cl)c2)c1N] |

TABLE 4-continued

The compounds in table 4 were synthesized according to the procedure described for 5-amino-N-(3-chloro-4-fluorophenyl)-1-methyl-3-(5-(methylthio)octahydropentalen-2-yl)-1H-pyrazole-4-carboxamide

| Compound | Structure and characterization |
|---|---|
| AIA-170 | 5-Amino-N-(3-chloro-4-fluorophenyl)-3-(5-(cyclopropylthio)octahydropentalen-2-yl)-1-methyl-1H-pyrazole-4-carboxamide. MS Calcd.: 448.1; MS Found: 449.2 [M + 1]+. |

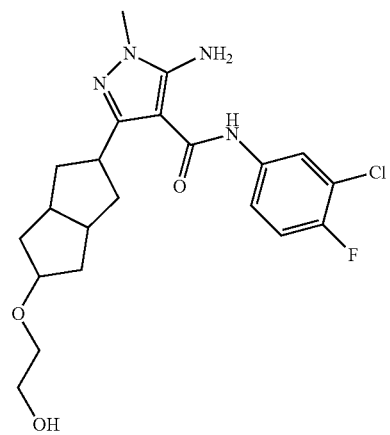 [SMILES: Cn1nc(C2CC3CC(OCCO)CC3C2)c(C(=O)Nc2ccc(F)c(Cl)c2)c1N]

5-Amino-N-(3-chloro-4-fluorophenyl)-3-(5-(2-hydroxyethoxy)octahydropentalen-2-yl)-1-methyl-1H-pyrazole-4-carboxamide. MS Calcd.: 436.2; MS Found: 437.3 [M + 1]+; $^1$H NMR (DMSO-d6, 400 MHz): δ 8.94 (s, 1H), 7.89 (dd, J = 7.2, 2.4 Hz, 1H), 7.51-7.47 (m, 1H), 7.33 (t, J = 9.2 Hz, 1H), 5.95 (s, 2H), 4.50 (t, J = 5.6 Hz, 1H), 3.92 (t, J = 5.6 Hz, 1H) 3.47 (s, 3H) 3.44-3.40 (m, 2H), 3.38-3.31 (m, 5H), 2.15-2.12 (m, 2H), 1.59-1.57 (m, 4H), 1.32-1.24 (m, 2H).

AIA-030

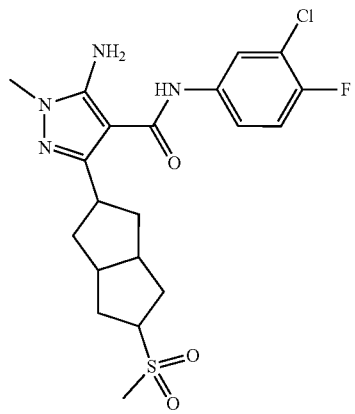 [SMILES: CCS(=O)(=O)C1CC2CC(c3nn(C)c(N)c3C(=O)Nc3ccc(F)c(Cl)c3)CC2C1]

5-Amino-N-(3-chloro-4-fluorophenyl)-1-methyl-3-(5-(methylsulfonyl)octahydropentalen-2-yl)-1H-pyrazole-4-carboxamide. To a solution of 5-amino-N-(3-chloro-4-fluorophenyl)-1-methyl-3-(5-(methylthio)octahydropentalen-2-yl)-1H-pyrazole-4-carboxamide (35 mg, 0.08 mmol) in DCM (5 mL) was added m-CPBA (14 mg, 0.08 mmol), and the resulting mixture stirred at 25° C. for 1 h. The solvent was removed under vacuum and the residue purified by prep-HPLC to afford 5-amino-N-(3-chloro-4-fluorophenyl)-1-methyl-3-(5-(methylsulfonyl)octahydropentalen-2-yl)-1H-pyrazole-4-carboxamide (6 mg, 17% yield) as a white solid. MS Calcd.: 454.12; MS Found: 455.3 [M+1]+. $^1$H-NMR (DMSO-d$_6$, 400 MHz): δ 8.96 (s, 1H), 7.91 (dd, J=6.8, 2.8 Hz, 1H), 7.53-7.49 (m, 1H), 7.34 (t, J=9.2 Hz, 1H), 5.98 (s, 2H), 3.69-3.66 (m, 1H), 3.49 (s, 3H), 3.35-3.34 (m, 1H), 2.92 (s, 3H), 2.67-2.62 (m, 2H), 2.21-2.15 (m, 2H), 1.90-1.83 (m, 2H), 1.78-1.73 (m, 2H), 1.39-1.31 (m, 2H).

AIA-074

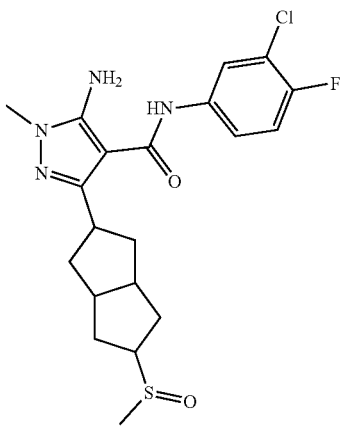

5-Amino-N-(3-chloro-4-fluorophenyl)-1-methyl-3-(5-(methylsulfinyl)octahydropentalen-2-yl)-1H-pyrazole-4-carboxamide. To a solution of 5-amino-N-(3-chloro-4-fluorophenyl)-1-methyl-3-(5-(methylthio)octahydropentalen-2-yl)-1H-pyrazole-4-carboxamide (50 mg, 0.11 mmol) in DCM (5 mL) was added m-CPBA (10 mg, 0.05 mmol), and the resulting mixture was stirred at 25° C. for 1 h. The solvent was removed in vacuo and the residue purified by prep-HPLC to afford 5-amino-N-(3-chloro-4-fluorophenyl)-1-methyl-3-(5-(methylsulfinyl)octahydropentalen-2-yl)-1H-pyrazole-4-carboxamide (8 mg, 15% yield) as a white solid. MS Calcd.: 438.13; MS Found: 439.3 [M+1]$^+$. $^1$H-NMR (DMSO-d$_6$, 400 MHz): δ 8.96 (s, 1H), 7.92 (dd, J=7.2, 2.8 Hz, 1H), 7.54-7.50 (m, 1H), 7.34 (t, J=8.8 Hz, 1H), 5.97 (s, 2H), 3.49 (s, 3H), 3.37-3.31 (m, 1H), 3.31-3.12 (m, 1H), 2.60-2.58 (m, 2H), 2.50-2.47 (m, 3H), 2.21-2.17 (m, 2H), 1.93-1.90 (m, 1H), 1.68-1.62 (m, 3H), 1.40-1.32 (m, 2H)

TABLE 5

The compounds in table 5 were synthesized according to the procedure described for 5-amino-N-(3-chloro-4-fluorophenyl)-1-methyl-3-(5-(methylsulfonyl)octahydropentalen-2-yl)-1H-pyrazole-4-carboxamide and 5-amino-N-(3-chloro-4-fluorophenyl)-1-methyl-3-(5-(methylsulfinyl)octahydropentalen-2-yl)-1H-pyrazole-4-carboxamide.

| Example | Structure and characterization |
|---|---|
| AIA-031 | 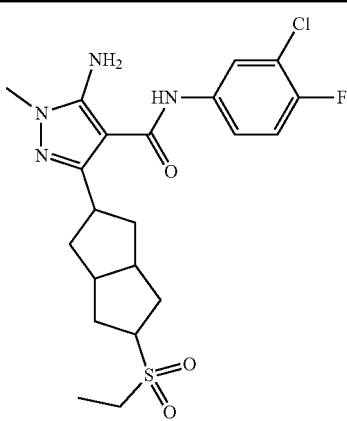 5-Amino-N-(3-chloro-4-fluorophenyl)-3-(5-(ethylsulfonyl)octahydropentalen-2-yl)-1-methyl-1H-pyrazole-4-carboxamide: MS Calcd.: 468.9; MS Found: 469.7 [M + 1]$^+$. $^1$H-NMR (DMSO-d$_6$, 400 MHz): δ 8.95 (s, 1H), 7.90 (dd, J = 6.8, 2.8 Hz, 1H), 7.50-7.47 (m, 1H), 7.32 (t, J = 9.2 Hz, 1H), 5.95 (s, 2H), 3.64-3.62 (m, 1H), 3.47 (s, 3H), 3.33-3.32 (m, 1H), 3.02 (q, J = 7.6 Hz, 2H), 2.65-2.61 (m, 2H), 2.18-2.12 (m, 2H), 1.86-1.82 (m, 2H), 1.75-1.71 (m, 2H), 1.39-1.31 (m, 2H), 1.18 (t, J = 7.6 Hz, 3H) |
| AIA-075 | 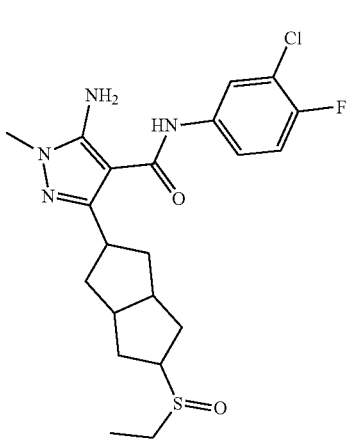 [SMILES: CCS(=O)C1CC2CC(c3nn(C)c(N)c3C(=O)Nc3ccc(F)c(Cl)c3)CC2C1] 5-Amino-N-(3-chloro-4-fluorophenyl)-3-(5-(ethylsulfinyl)octahydropentalen-2-yl)-1-methyl-1H-pyrazole-4-carboxamide: MS Calcd.: 452.9; MS Found: 453.7 [M + 1]$^+$. $^1$H-NMR (DMSO-d$_6$, 400 MHz): δ 8.95 (s, 1H), 7.90 (dd, J = 6.8, 2.4 Hz, 1H), 7.51-7.47 (m, 1H), 7.32 (t, J = 8.8 Hz, 1H), 5.95 (s, 2H), 3.46 (s, 3H), 3.34-3.29 (m, 1H), 3.14-3.12 (m, 1H), 2.70-2.65 (m, 1H), 2.58-2.51 (m, 3H), 2.18-2.14 (m, 2H), 1.91-1.86 (m, 1H), 1.66-1.58 (m, 3H), 1.38-1.30 (m, 2H), 1.15 (t, J = 7.4) |

TABLE 5-continued

The compounds in table 5 were synthesized according to the procedure described for 5-amino-N-(3-chloro-4-fluorophenyl)-1-methyl-3-(5-(methylsulfonyl)octahydropentalen-2-yl)-1H-pyrazole-4-carboxamide and 5-amino-N-(3-chloro-4-fluorophenyl)-1-methyl-3-(5-(methylsulfinyl)octahydropentalen-2-yl)-1H-pyrazole-4-carboxamide.

| Example | Structure and characterization |
|---|---|
| AIA-105 | 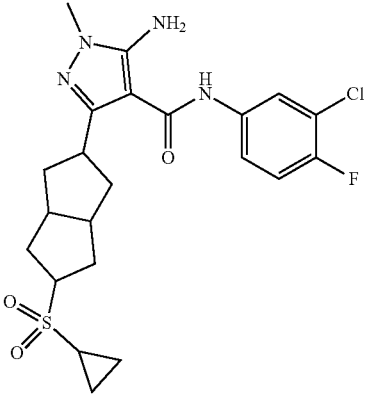 [SMILES: Cn1nc(C2CC3CC(S(=O)(=O)C4CC4)CC3C2)c(C(=O)Nc2ccc(F)c(Cl)c2)c1N]<br>5-Amino-N-(3-chloro-4-fluorophenyl)-3-(5-(cyclopropylsulfonyl)octahydropentalen-2-yl)-1-methyl-1H-pyrazole-4-carboxamide. MS Calcd.: 480.1; MS Found: 481.2 [M + 1]+. |
| AIA-285 | 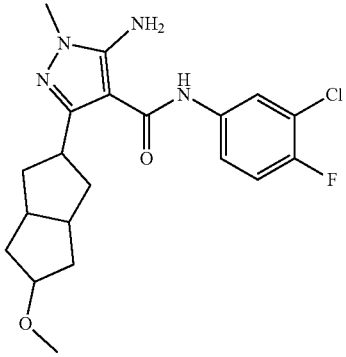 |

5-Amino-N-(3-chloro-4-fluorophenyl)-3-(5-methoxyoctahydropentalen-2-yl)-1-methyl-1H-pyrazole-4-carboxamide. To a solution of 5-amino-N-(3-chloro-4-fluoro-phenyl)-3-(5-hydroxy-1,2,3,3a,4,5,6,6a-octahydropentalen-2-yl)-1-methylpyrazole-4-carboxamide (50 mg, 0.127 mmol, 1 eq) in DCM (3 mL) was added trimethyloxonium-tetrafluoroborate (37.65 mg, 0.255 mmol, 2.0 eq) and N1,N1,N8,N8-tetramethylnaphthalene-1,8-diamine (54.55 mg, 0.255 mmol, 2.0 eq). The mixture was stirred at 25° C. for 16 hr under $N_2$. Additional to trimethyloxonium-tetrafluoroborate (37.65 mg, 0.255 mmol, 2.0 eq) was added and stirring continued for 48 hr under $N_2$. Water (10 mL) was added to the reaction mixture. The aqueous layer was extracted with ethyl acetate (10 mL×2). The combined organic layers were dried over $Na_2SO_4$, filtered and concentrated to give a pale residue. The residue was purified by prep-TLC ($SiO_2$, 1:1 petroleum ether:ethyl acetate) to give crude product (25 mg). The crude product was further purified by prep-HPLC. Column: Gemini 150×25 5 u; mobile phase: [water (0.05% ammonia hydroxide v/v)—ACN]; B %: 40%-70%, 10 min. The desired fraction was dried by lyophilization to provide 5-amino-N-(3-chloro-4-fluoro-phenyl)-3-(5-methoxy-1,2,3,3a,4,5,6,6a-octahydropentalen-2-yl)-1-methyl-pyrazole-4-carboxamide (10.8 mg, 0.027 mmol, 20.9% yield, 100% purity) as a white solid. $^1$H NMR (400 MHz, CHLOROFORM-d) δ ppm 1.60-1.64 (m, 2H) 1.81-1.93 (m, 2H) 2.06 (ddd, J=13.40, 8.10, 5.62 Hz, 2H) 2.33 (br d, J=5.95 Hz, 2H) 2.49-2.62 (m, 2H) 3.11 (tt, J=11.85, 5.79 Hz, 1H) 3.28 (s, 3H) 3.57 (s, 3H) 3.84 (quin, J=6.01 Hz, 1H) 5.25 (s, 2H) 7.10 (t, J=8.71 Hz, 1H) 7.26-7.30 (m, 1H) 7.30 (s, 1H) 7.70 (dd, J=6.50, 2.76 Hz, 1H); LC-MS: 406.9 [M+1]+.

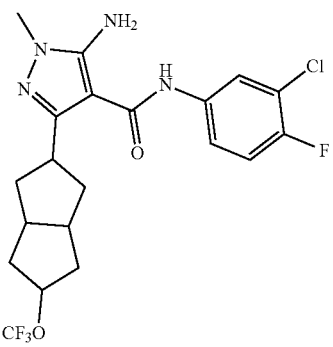

5-Amino-N-(3-chloro-4-fluorophenyl)-1-methyl-3-(5-(trifluoromethoxy)octahydropentalen-2-yl)-1H-pyrazole-4-carboxamide. A mixture of AIA-026 (100 mg, 0.25 mmol), 1-(trifluoromethyl)-1λ$^3$-benzo[d][1,2]iodaoxol-3(1H)-one (157 mg, 0.5 mmol) and zinc bis(trifluoromethylsulfonyl)imide (306 mg, 0.5 mmol) in DCM (15 mL) was stirred at RT for 8 h. Water was added and the mixture was extracted with DCM (20 mL×3). The organic layer was dried and concentrated. The resulting residue was purified by silica gel column chromatography (using 20-60% ethyl acetate/petroleum ether) and prep-HPLC to give 5-amino-N-(3-chloro-4-fluorophenyl)-1-methyl-3-(5-(trifluoromethoxy)octahydropentalen-2-yl)-1H-pyrazole-4-carboxamide (5 mg, 4.3%) as a white solid. MS Calcd.: 460.1; MS Found: 461.3 [M+1]⁺. ¹H-NMR (DMSO-d$_6$, 400 MHz): δ 8.97 (s, 1H), 7.91 (dd, J=6.8, 2.4 Hz, 1H), 7.54-7.50 (m, 1H), 7.34 (t, J=3.2 Hz, 1H), 5.96 (s, 2H), 4.79 (t, J=6.0 Hz, 1H), 3.46 (t, J=6.0 Hz, 4H), 2.22-2.09 (m, 5H), 1.65-1.51 (m, 5H).

AIA-286

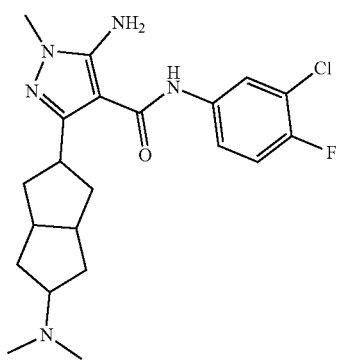

5-Amino-N-(3-chloro-4-fluorophenyl)-3-(5-(dimethylamino)octahydropentalen-2-yl)-1-methyl-1H-pyrazole-4-carboxamide. To a mixture of 5-amino-N-(3-chloro-4-fluoro-phenyl)-1-methyl-3-(5-oxo-2,3,3a,4,6,6a-hexahydro-1H-pentalen-2-yl)pyrazole-4-carboxamide (54.21 mg, 0.128 mmol, 1 eq), N-methylmethanamine-hydrochloride (12.52 mg, 0.154 mmol, 1.2 eq), TEA (19.42 mg, 0.192 mmol, 0.027 mL, 1.5 eq) and MgSO$_4$ (76.99 mg, 0.640 mmol, 5 eq) in DCM (3 mL) was added sodium triacetoxyborohydride (54.23 mg, 0.256 mmol, 2 eq) portion wise at 25° C. AcOH (catalytic amount) was added to the mixture which was stirred for 16 hr. The reaction was diluted with DCM (10 mL) and washed with aq. NaHCO$_3$ (10 mL). The aqueous layer was separated and extracted with ethyl acetate (10 mL). The organic layers were combined and washed with brine (10 mL), dried over Na$_2$SO$_4$, filtered and concentrated to give crude product as a yellow oil. The crude product was purified by Prep-HPLC (column: Phenomenex Gemini C18 250×50 10 u; mobile phase: [water (0.225% FA)—ACN]; B %: 28%-58%, 11.2 min) to give 5-amino-N-(3-chloro-4-fluorophenyl)-3-(5-(dimethylamino)octahydropentalen-2-yl)-1-methyl-1H-pyrazole-4-carboxamide, (8 mg, 0.017 mmol, 13.42% yield, 100% purity, FA salt), as a white solid. ¹H NMR (400 MHz, DMSO-d6) δ ppm 1.18-1.31 (m, 2H) 1.47 (td, J=11.86, 8.16 Hz, 2H) 2.05-2.24 (m, 4H) 2.32 (s, 6H) 2.37-2.44 (m, 2H) 2.52-2.55 (m, 1H) 2.73-2.89 (m, 1H) 3.50-3.50 (m, 3H) 5.98 (br s, 2H) 7.35 (t, J=9.04 Hz, 1H) 7.49-7.54 (m, 1H) 7.90 (d, J=6.56 Hz, 1H) 8.27 (s, 1H) 9.00 (s, 1H); LC-MS: 420.0 [M+1]⁺.

TABLE 6

The compounds in table 6 were synthesized according to the procedure described for 5-amino-N-(3-chloro-4-fluorophenyl)-3-(5-(dimethylamino)octahydropentalen-2-yl)-1-methyl-1H-pyrazole-4-carboxamide

| Compound | Structure and characterization |
| --- | --- |
| AIA-012 | 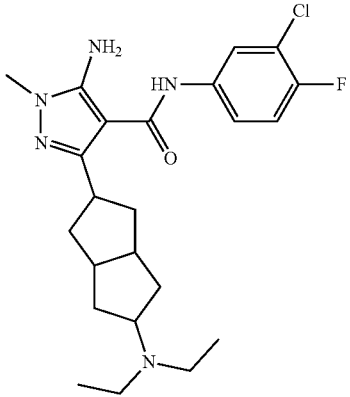 [SMILES: CCN(CC)C1CC2CC(c3nn(C)c(N)c3C(=O)Nc3ccc(F)c(Cl)c3)CC2C1]<br>5-Amino-N-(3-chloro-4-fluorophenyl)-3-(5-(diethylamino)octahydropentalen-2-yl)-1-methyl-1H-pyrazole-4-carboxamide. MS Calcd.: 447.9; MS Found: 448.7 [M + 1]⁺. ¹H-NMR (DMSO-d$_6$, 400 MHz): δ 8.96 (s, 1H), 7.91 (dd, J = 6.8, 2.8 Hz, 1H), 7.53-7.49 (m, 1H), 7.34 (t, J = 9.2 Hz, 1H), 5.95 (s, 2H), 3.54-3.51 (m, 1H), 3.49 (s, 3H), 2.94-2.91 (m, 1H), 2.37 (s, 2H), 2.18-2.13 (m, 2H), 1.98 (s, 2H), 1.48-1.40 (m, 2H), 1.09-1.08 (m, 2H), 0.90 (s, 6H) |

TABLE 6-continued

The compounds in table 6 were synthesized according to the procedure described for 5-amino-N-(3-chloro-4-fluorophenyl)-3-(5-(dimethylamino)octahydropentalen-2-yl)-1-methyl-1H-pyrazole-4-carboxamide

| Compound | Structure and characterization |
| --- | --- |

AIA-013

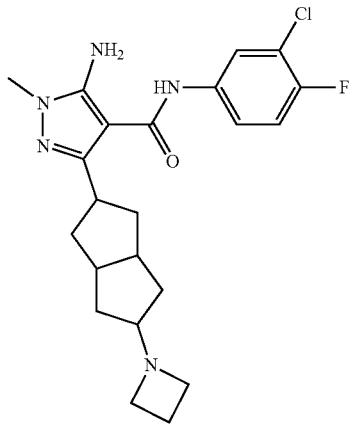 [SMILES: Cn1nc(C2CC3CC(N4CCC4)CC3C2)c(C(=O)Nc2ccc(F)c(Cl)c2)c1N]

5-Amino-3-(5-(azetidin-1-yl)octahydropentalen-2-yl)-N-(3-chloro-4-fluorophenyl)-1-methyl-1H-pyrazole-4-carboxamide. MS Calcd.: 431.9; MS Found: 432.7 [M + 1]$^+$. H-NMR (DMSO-d$_6$, 400 MHz): δ 8.93 (s, 1H), 7.91 (dd, J = 6.8, 2.4 Hz, 1H), 7.52-7.48 (m, 1H), 7.34 (t, J = 9.2 Hz, 1H), 5.95 (s, 2H), 3.49 (s, 3H), 3.45-3.42 (m, 1H), 2.99 (t, J = 6.8 Hz, 4H), 2.61-2.58 (m, 1H), 2.40-2.38 (m, 2H), 2.14-2.07 (m, 2H), 1.87-1.03 (m, 2H), 1.78-1.71 (m, 2H), 1.55-1.47 (m, 2H), 1.08-1.01 (m, 2H)

AIA-040

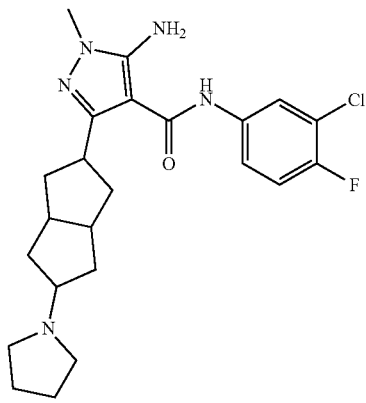 [SMILES: Cn1nc(C2CC3CC(N4CCCC4)CC3C2)c(C(=O)Nc2ccc(F)c(Cl)c2)c1N]

5-Amino-N-(3-chloro-4-fluorophenyl)-1-methyl-3-(5-(pyrrolidin-1-yl)octahydropentalen-2-yl)-1H-pyrazole-4-carboxamide MS Calcd.: 445.2; MS Found: 446.3 [M + 1]$^+$; 448.3 [M + 2 + 1]$^+$; $^1$H NMR (DMSO-d$_6$, 400 MHz): 1H-NMR (DMSO-d$_6$, 400 MHz): δ 8.95 (s, 1H), 7.90 (dd, J = 6.8, 2.4 Hz, 1H), 7.50 (dq, J = 8.8, 4.4 Hz, 1H), 7.34 (t, J = 9.2 Hz, 1H), 5.95 (s, 2H), 3.52-3.49 (m, 1H), 3.49 (s, 3H), 2.44-2.38 (m, 7H), 2.18-2.12 (m, 2H), 2.03-1.97 (m, 2H), 1.65-1.58 (m, 4H), 1.49-1.41 (m, 2H), 1.20-1.12 (m, 2H).

TABLE 6-continued

The compounds in table 6 were synthesized according to the procedure described for 5-amino-N-(3-chloro-4-fluorophenyl)-3-(5-(dimethylamino)octahydropentalen-2-yl)-1-methyl-1H-pyrazole-4-carboxamide

| Compound | Structure and characterization |
| --- | --- |

AIA-041

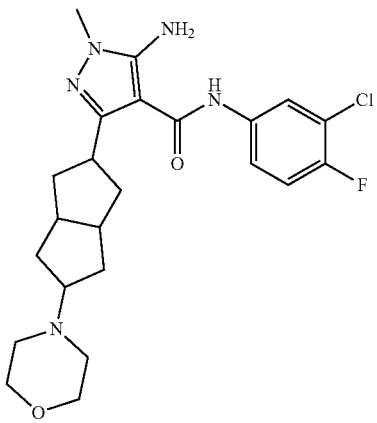 [SMILES: Cn1nc(C2CC3CC(N4CCOCC4)CC3C2)c(C(=O)Nc2ccc(F)c(Cl)c2)c1N]

5-Amino-N-(3-chloro-4-fluorophenyl)-1-methyl-3-(5-morpholinooctahydropentalen-2-yl)-1H-pyrazole-4-carboxamide
$^1$H-NMR (DMSO-$d_6$, 400 MHz): δ 8.95 (s, 1H), 7.88 (dd, J = 6.8, 2.8 Hz, 1H), 7.49 (dq, J = 8.8, 4.0 Hz, 1H), 7.32 (t, J = 8.8 Hz, 1H), 5.94 (s, 2H), 3.52 (t, J = 4.4 Hz, 5H), 3.47 (s, 3H), 2.48-2.45 (m, 1H), 2.39-2.33 (m, 6H), 2.17-2.11 (m, 2H), 2.05-1.98 (m, 2H) , 1.47-1.40 (m, 2H) , 1.12-1.04 (m, 2H); MS Calcd.: 461.2; MS Found: 462.3 [M + 1]$^+$; 464.3 [M + 2 + 1]$^+$.

AIA-246

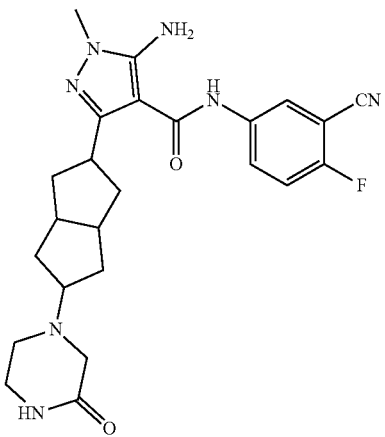 [SMILES: Cn1nc(C2CC3CC(N4CCNC(=O)C4)CC3C2)c(C(=O)Nc2ccc(F)c(C#N)c2)c1N]

5-Amino-N-(3-cyano-4-fluorophenyl)-1-methyl-3-(5-(3-oxopiperazin-1-yl)octahydropentalen-2-yl)-1H-pyrazole-4-carboxamide MS Calcd.: 465.2; MS Found: 466.1 [M + 1]$^+$. $^1$H-NMR (DMSO-$d_6$, 400 MHz): δ 9.09 (s, 1H), 8.10 (dd, J = 5.6, 2.8 Hz, 1H), 7.91-7.87 (m, 1H), 7.70 (s, 1H), 7.47 (t, J = 9.2 Hz, 1H), 6.00 (s, 2H), 3.55-3.52 (m, 1H), 3.49 (s, 3H), 3.11 (s, 2H), 2.90 (s, 2H), 2.62-2.52 (m, 3H), 2.42-2.36 (m, 2H), 2.19-2.13 (m, 2H), 2.08-2.02 (m, 2H), 1.50-1.43 (m, 2H), 1.17-1.09 (m, 2H).

TABLE 6-continued

The compounds in table 6 were synthesized according to the procedure described for 5-amino-N-(3-chloro-4-fluorophenyl)-3-(5-(dimethylamino)octahydropentalen-2-yl)-1-methyl-1H-pyrazole-4-carboxamide

| Compound | Structure and characterization |
|---|---|
| AIA-199 | 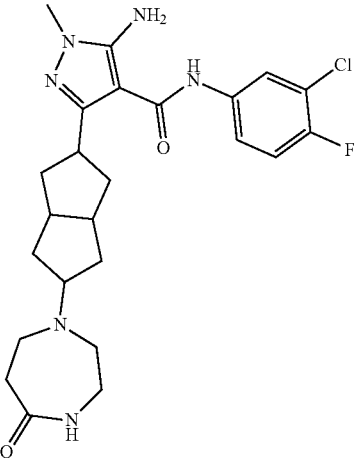 [SMILES: Cn1nc(C2CC3CC(N4CCNC(=O)CC4)CC3C2)c(C(=O)Nc2ccc(F)c(Cl)c2)c1N]<br>5-Amino-N-(3-chloro-4-fluorophenyl)-1-methyl-3-(5-(5-oxo-1,4-diazepan-1-yl)octahydropentalen-2-yl)-1H-pyrazole-4-carboxamide. MS Calcd.: 488.2; MS Found: 489.3 [M + 1]$^+$; 1H NMR (DMSO-d6, 400 MHz): δ 7.79 (dd, J = 6.8, 2.8 Hz, 1H), 7.42-7.39 (m, 1H), 7.18 (t, J = 8.8 Hz, 1H), 3.55 (s, 3H), 3.54-3.51 (m, 1H), 3.30-3.27 (m, 2H), 2.93-2.87 (m, 1H), 2.72-2.68 (m, 4H), 2.59-2.48 (m, 4H), 2.34-2.28 (m, 2H), 2.21-2.15 (m, 2H), 1.61-1.53 (m, 2H), 1.33-1.25 (m, 2H). |

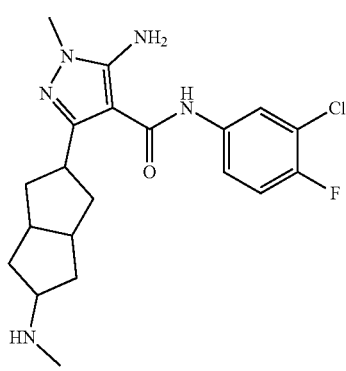

AIA-102

5-Amino-N-(3-chloro-4-fluorophenyl)-1-methyl-3-(5-(methylamino)octahydropentalen-2-yl)-1H-pyrazole-4-carboxamide. To a solution of AIA-002 (300 mg, 0.7 mmol) in Ti(OiPr)$_4$ (5 mL) was added MeNH$_2$ (100 mg, 1.05 mmol). The mixture was stirred at 40° C. for 1 h. The mixture was diluted with MeOH (5 mL), NaBH$_4$ (100 mg, 1.4 mmol) was added, and stirring continued at room temperature for 1 h. The mixture was quenched with water then filtered and concentrated in vacuo. The residue was purified by column chromatography using 10:3 H$_2$O/MeCN to afford crude compound (200 mg, 64.3%) as a white solid. This material was further purified by pre-HPLC to yield 5-amino-N-(3-chloro-4-fluorophenyl)-1-methyl-3-(5-(methylamino)octahydropentalen-2-yl)-1H-pyrazole-4-carboxamide as a white solid. $^1$H NMR (DMSO-d$_6$, 400 MHz): δ 8.94 (s, 1H), 7.90 (dd, J=2.8, 2.4 Hz, 1H), 7.51-7.49 (m, 1H), 7.34 (t, J=8.8, 9.2 Hz, 1H), 5.95 (s, 2H), 3.52-3.47 (m, 5H), 2.87 (s, 1H), 2.37 (s, 2H), 2.22 (s, 3H), 2.17-2.12 (m, 2H), 2.02 (t, J=5.6 Hz, 2H), 1.48-1.46 (m, 2H), 1.03-1.01 (m, 2H); MS Calcd.: 405.1; MS Found: 406.2 [M+1]$^+$.

TABLE 7

The compounds in table 7 were synthesized according to the procedure described for
5-amino-N-(3-chloro-4-fluorophenyl)-1-methyl-3-(5-
(methylamino)octahydropentalen-2-yl)-1H-pyrazole-4-carboxamide

| Compound | Structure and characterization |
|---|---|
| AIA-160 | 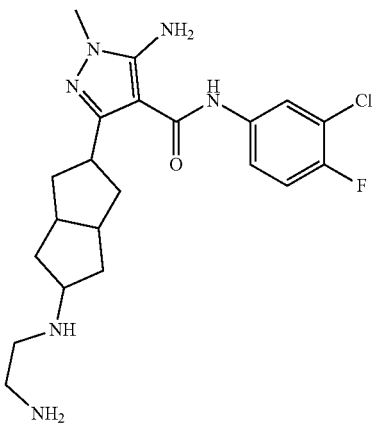 [SMILES: Cn1nc(C2CC3CC(NCCN)CC3C2)c(C(=O)Nc2ccc(F)c(Cl)c2)c1N]<br>5-Amino-3-(5-((2-aminoethyl)amino)octahydropentalen-2-yl)-N-(3-chloro-4-fluorophenyl)-1-methyl-1H-pyrazole-4-carboxamide. MS Calcd.: 434.2, MS Found: 435.3 [M + 1]$^+$. |
| AIA-103 | 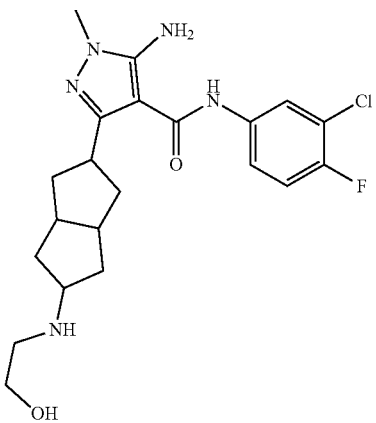 [SMILES: Cn1nc(C2CC3CC(NCCO)CC3C2)c(C(=O)Nc2ccc(F)c(Cl)c2)c1N]<br>5-Amino-N-(3-chloro-4-fluorophenyl)-3-(5-((2-hydroxyethyl)amino)octahydropentalen-2-yl)-1-methyl-1H-pyrazole-4-carboxamide. $^1$H-NMR (DMSO-d$_6$, 400 MHz): δ 8.96 (s, 1H), 7.91 (dd, J = 6.8, 2.4 Hz, 1H), 7.53-7.49 (m, 1H), 7.35 (t, J = 9.2 Hz, 1H), 5.97 (s, 2H), 4.42-4.39 (m, 1H), 3.52-3.47 (m, 4H), 3.42-3.38 (m, 2H), 3.02-2.97 (m, 1H), 2.55-2.52 (m, 2H), 2.37-2.33 (m, 2H), 2.18-2.12 (m, 2H), 2.07-2.01 (m, 2H), 1.52-1.44 (m, 2H), 1.06-0.98 (m, 2H); MS Calcd.: 435.2, MS Found: 436.3 [M + 1]$^+$. |
| AIA-079 | 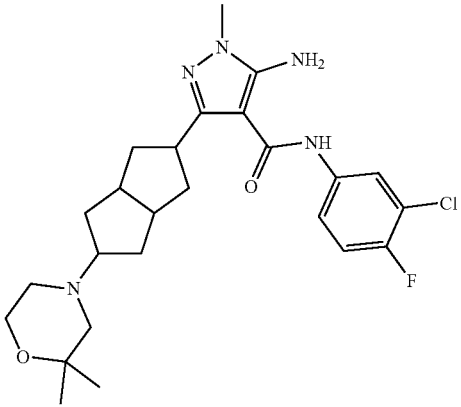 [SMILES: Cn1nc(C2CC3CC(N4CCOC(C)(C)C4)CC3C2)c(C(=O)Nc2ccc(F)c(Cl)c2)c1N] |

TABLE 7-continued

The compounds in table 7 were synthesized according to the procedure described for 5-amino-N-(3-chloro-4-fluorophenyl)-1-methyl-3-(5-(methylamino)octahydropentalen-2-yl)-1H-pyrazole-4-carboxamide

| Compound | Structure and characterization |
| --- | --- |

5-Amino-N-(3-chloro-4-fluorophenyl)-3-(5-(2,2-dimethylmorpholino)octahydropentalen-2-yl)-1-methyl-1H-pyrazole-4-carboxamide. MS Calcd.: 489.2; MS Found: 490.3 [M + 1]⁺. ¹H-NMR (CDCl₃, 400 MHz): δ 7.71 (dd, J = 6.4, 2.8 Hz, 1H), 7.29 (t, J = 4 Hz, 1H), 7.11 (t, J = 8.8 Hz, 1H), 5.26 (s, 2H), 3.72 (t, J = 4.8 Hz, 2H), 3.58 (s, 3H), 3.25-3.16 (m, 1H), 2.57-2.50 (m, 3H), 2.39-2.31 (m, 4H), 2.22 (s, 2H), 2.15-2.09 (m, 2H), 1.84-1.76 (m, 2H), 1.37-1.30 (m, 2H), 1.23 (s, 6H)

AIA-202

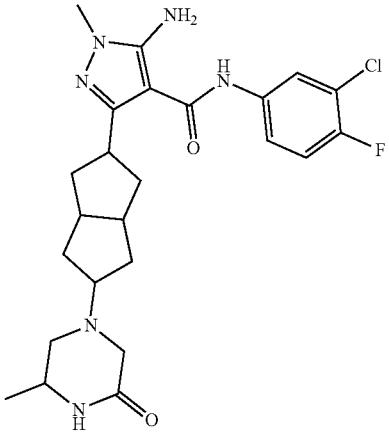 [SMILES: CC1CN(C2CC3CC(c4nn(C)c(N)c4C(=O)Nc4ccc(F)c(Cl)c4)CC3C2)CC(=O)N1]

5-Amino-N-(3-chloro-4-fluorophenyl)-1-methyl-3-(5-(3-methyl-5-oxopiperazin-1-yyl)octahydropentalen-2-yl)-1H-pyrazole-4-carboxamide. MS Calcd.: 488.2; MS Found: 489.4 [M + 1]⁺. ¹H-NMR (DMSO-d₆, 400 MHz): δ 8.95 (s, 1H), 7.89-7.87 (dd, J = 6.8, 2.4 Hz, 1H), 7.51 (s, 1H), 7.50-7.47 (m, 1H), 7.32 (t, J = 8.8 Hz, 2H), 5.95 (s, 2H), 3.53-3.47 (m, 4H), 3.39-3.36 (m, 1H), 3.01 (d, J = 16 Hz, 1H), 2.78-2.68 (m, 2H), 2.57-2.53 (m,1H), 2.37-2.33 (m, 2H), 2.17-2.12 (m, 2H), 2.06-1.96 (m,3H), 1.48-1.43 (m, 2H), 1.12-1.02 (m, 2H), 1.01 (d, J = 6.4 Hz, 3H).

AIA-082

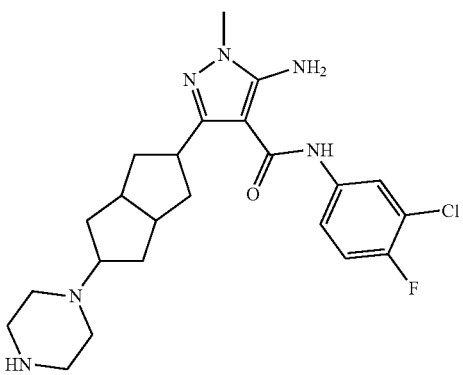 [SMILES: Cn1nc(C2CC3CC(N4CCNCC4)CC3C2)c(C(=O)Nc2ccc(F)c(Cl)c2)c1N]

5-Amino-N-(3-chloro-4-fluorophenyl)-1-methyl-3-(5-(piperazin-1-yl)octahydropentalen-2-yl)-1H-pyrazole-4-carboxamide. MS Calcd.: 460.2; MS Found: 461.3 [M + 1]⁺. ¹H-NMR (DMSO-d₆, 400 MHz): δ 8.97 (s, 1H), 7.90 (dd, J = 6.8, 2.4 Hz, 1H), 7.52-7.49 (m, 1H), 7.34 (t, J = 9.2 Hz, 1H), 5.96 (s, 2H), 3.54-3.49 (m, 4H), 3.28-3.14 (m, 2H), 2.64 (s, 3H), 2.44-2.22 (m, 6H), 2.17-2.09 (m, 2H), 2.04-2.01 (m, 2H), 1.48-1.39 (m, 2H), 1.10-1.07 (m, 2H).

TABLE 7-continued

The compounds in table 7 were synthesized according to the procedure described for 5-amino-N-(3-chloro-4-fluorophenyl)-1-methyl-3-(5-(methylamino)octahydropentalen-2-yl)-1H-pyrazole-4-carboxamide

| Compound | Structure and characterization |
| --- | --- |
| AIA-203 | 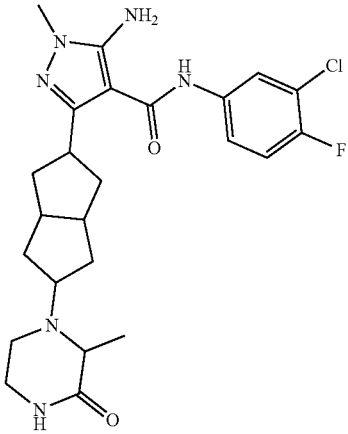 [SMILES: CC1C(=O)NCCN1C1CC2CC(c3nn(C)c(N)c3C(=O)Nc3ccc(F)c(Cl)c3)CC2C1]<br>5-Amino-N-(3-chloro-4-fluorophenyl)-1-methyl-3-(5-(2-methyl-3-oxopiperazin-1-yl)octahydropentalen-2-yl)-1H-pyrazole-4-carboxamide. MS Calcd.: 488.2; MS Found: 489.4 [M + 1]$^+$. $^1$H NMR (DMSO-d$_6$, 400 MHz): δ 8.95 (s, 1H), 7.90-7.87 (dd, J = 7.2, 2.4 Hz, 1H), 7.55 (2, 1H), 7.51-7.47 (m, 1H), 7.35-7.30 (t, J = 8.8 Hz, 2H), 5.95 (s, 2H), 3.53-3.50 (m, 1H), 3.47 (s, 3H), 3.19-3.14 (m, 2H), 3.04-2.95 (m, 2H), 2.80-2.75 (m, 1H), 2.60-2.56 (m, 1H), 2.43-2.30 (m, 2H), 2.15-2.12 (m, 2H), 2.00 (s, 2H), 1.48-1.40 (m, 2H), 1.14-1.06 (m, 5H). |
| AIA-211 | 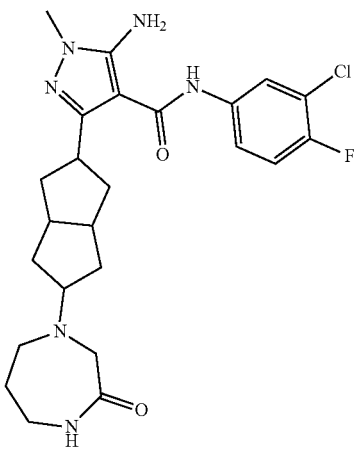 [SMILES: Cn1nc(C2CC3CC(N4CCCNC(=O)C4)CC3C2)c(C(=O)Nc2ccc(F)c(Cl)c2)c1N]<br>5-Amino-N-(3-chloro-4-fluorophenyl)-1-methyl-3-(5-(3-oxo-1,4-diazepan-l-yl)octahydropentalen-2-yl)-1H-pyrazole-4-carboxamide. MS Calcd.: 488.2; MS Found: 489.2 [M + 1]$^+$; $^1$H NMR (DMSO-d$_6$, 400 MHz): 8.96 (s, 1H), 7.91 (dd, J = 6.8, 2.4 Hz, 1H), 7.54-7.48 (m, 2H), 7.34 (t, J = 9.2 Hz, 1H), 5.97 (s, 2H), 3.56-3.52 (m, 1H), 3.50 (s, 3H), 3.29 (s, 2H), 3.10-3.09 (m, 2H), 3.02-2.94 (m, 1H), 2.89-2.88 (m, 2H), 2.38-2.32 (m, 2H), 2.19-2.10 (m, 4H), 1.54 (s, 2H), 1.48-1.41 (m, 2H), 1.10-1.02 (m, 2H) |

AIA-043

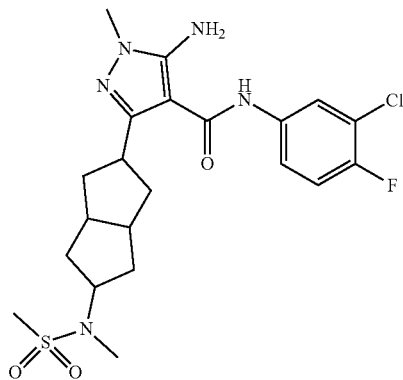

5-Amino-N-(3-chloro-4-fluorophenyl)-1-methyl-3-(5-(N-methylmethylsulfon amido)octahydropentalen-2-yl)-1H-pyrazole-4-carboxamide. To a solution of 5-amino-N-(3-chloro-4-fluorophenyl)-1-methyl-3-(5-(methylamino) octahydropentalen-2-yl)-1H-pyrazole-4-carboxamide (100 mg, 0.2 mmol) in DCM (10 mL) were added TEA (50 mg, 0.4 mmol) and MSCl (28 mg, 0.2 mmol). The mixture was stirred at room temperature for 2 h. The mixture was quenched with MeOH and concentrated in vacuo. The residue was purified by pre-HPLC to afford 5-amino-N-(3-chloro-4-fluorophenyl)-1-methyl-3-(5-(N-methylmethyl-sulfon amido)octahydropentalen-2-yl)-1H-pyrazole-4-carboxamide (10.5 mg, 8.8%) as a white solid. $^1$H NMR (DMSO-$d_6$, 400 MHz): δ 8.96 (s, 1H), 7.90 (dd, J=2.4, 2.8 Hz, 1H), 7.54-7.50 (m, 1H), 7.34 (t, J=2.8, 10.0 Hz, 1H), 5.97 (s, 2H), 4.06-4.00 (m, 1H), 3.57-3.52 (m, 4H), 2.83 (s, 3H), 2.67 (s, 3H), 2.42-2.32 (m, 2H), 2.20-2.14 (m, 2H), 1.90-1.84 (m, 2H), 1.55-1.48 (m, 2H), 1.43-1.35 (m, 2H); MS Calcd.: 483.1; MS Found: 484.2 [M+1]$^+$.

AIA-047

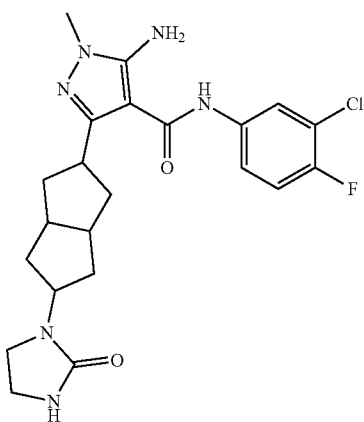

5-Amino-N-(3-chloro-4-fluorophenyl)-1-methyl-3-(5-(2-oxoimidazolidin-1-yl) octahydropentalen-2-yl)-1H-pyrazole-4-carboxamide. A solution of 5-amino-3-(5-((2-amino-ethyl)amino)octahydropentalen-2-yl)-N-(3-chloro-4-fluorophenyl)-1-methyl-1H-pyrazole-4-carboxamide (120 mg, 0.28 mmol), CDI (68 mg, 0.42 mmol) and DIPEA (108 mg, 0.84 mmol) in DCM (10 mL) was stirred at room temperature overnight. The mixture was concentrated in vacuo and the residue purified by Prep-HPLC to afford 5-amino-N-(3-chloro-4-fluorophenyl)-1-methyl-3-(5-(2-oxoimidazolidin-1-yl) octahydropentalen-2-yl)-1H-pyrazole-4-carboxamide (20 mg, 15%) as a white solid. $^1$H-NMR (DMSO-$d_6$, 400 MHz): δ 8.96 (s, 1H), 7.91 (dd, J=6.8, 2.4 Hz, 1H), 7.54-7.50 (m, 1H), 7.35 (t, J=9.2 Hz, 1H), 6.17 (s, 1H), 5.98 (s, 2H), 4.06-4.00 (m, 1H), 3.57-3.54 (m, 1H), 3.32-3.17 (m, 7H), 2.43-2.37 (m, 2H), 2.21-2.16 (m, 2H), 1.82-1.76 (m, 2H), 1.52-1.44 (m, 2H), 1.37-1.29 (m, 2H); MS Calcd.: 460.2; MS Found: 461.3 [M+1]$^+$.

AIA-046

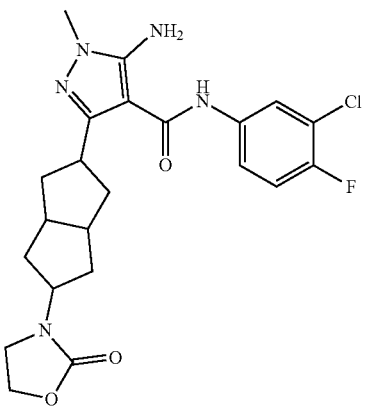

5-Amino-N-(3-chloro-4-fluorophenyl)-1-methyl-3-(5-(2-oxooxazolidin-3-yl) octahydro pentalen-2-yl)-1H-pyrazole-4-carboxamide. A solution of 5-amino-N-(3-chloro-4-fluorophenyl)-3-(5-((2-hydroxy ethyl)amino) octahydropentalen-2-yl)-1-methyl-1H-pyrazole-4-carboxamide (110 mg, 0.25 mmol), CDI (62 mg, 0.38 mmol) and DIPEA (97 mg, 0.75 mmol) in DCM (10 mL) was stirred at room temperature overnight. The mixture was concentrated in vacuo and the residue purified by Prep-HPLC to afford 5-amino-N-(3-chloro-4-fluorophenyl)-1-methyl-3-(5-(2-oxooxazolidin-3-yl) octahydro pentalen-2-yl)-1H-pyrazole-4-carboxamide (20 mg, 17%) as a white solid. $^1$H-NMR (DMSO-$d_6$, 400 MHz): δ 8.99 (s, 1H), 7.91 (dd, J=6.8, 2.4 Hz, 1H), 7.54-7.50 (m, 1H), 7.35 (t, J=9.2 Hz, 1H), 5.99 (s, 2H), 4.24 (t, J=7.6 Hz, 2H), 4.02-3.97 (m, 1H), 3.58-3.48 (m, 6H), 2.44-2.40 (m, 2H), 2.22-2.16 (m, 2H), 1.93-1.87 (m, 2H), 1.54-1.47 (m, 2H), 1.43-1.35 (m, 2H); MS Calcd.: 461.2; MS Found: 462.3 [M+1]$^+$.

AIA-032

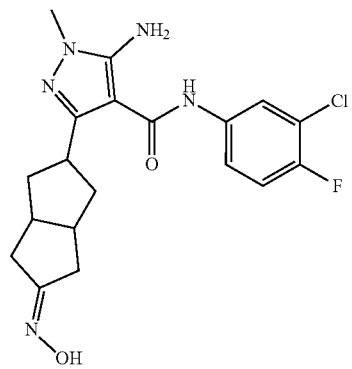

5-Amino-N-(3-chloro-4-fluorophenyl)-3-(5-(hydroxy-imino)octahydropentalen-2-yl)-1-methyl-1H-pyrazole-4-carboxamide. To a solution of AIA-002 (800 mg, 2.1 mmol)

in mixed solvent (THF:EtOH=10:10 mL) was added NH$_2$OH—HCl (440 mg, 6.3 mmol) and NaOAc (1.2 g, 14.7 mmol). The mixture was stirred at room temperature overnight, then filtered and concentrated in vacuo. The residue was purified by silica gel column chromatography using 10:1 DCM/MeOH to afford 5-amino-N-(3-chloro-4-fluorophenyl)-3-(5-(hydroxyimino)octahydropentalen-2-yl)-1-methyl-1H-pyrazole-4-carboxamide (800 mg, 96.0%) as white solid); MS Calcd.: 405.1; MS Found: 406.2 [M+1]$^+$.

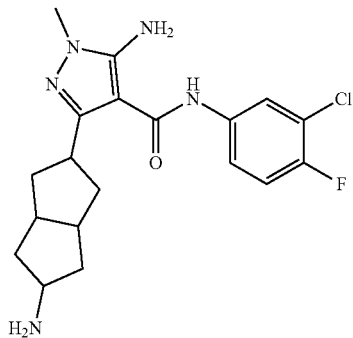

AIA-073

5-Amino-3-(5-aminooctahydropentalen-2-yl)-N-(3-chloro-4-fluorophenyl)-1-methyl-1H-pyrazole-4-carboxamide. To a solution of 5-amino-N-(3-chloro-4-fluorophenyl)-3-(5-(hydroxyimino)octahydropentalen-2-yl)-1-methyl-1H-pyrazole-4-carboxamide (300 mg, 0.4 mmol) in MeOH (15 mL) was added NiCl$_2$6H$_2$O (23 mg, 0.08 mmol). The mixture was stirred at −30° C. for 0.5 h. To this was added NaBH$_4$ (94 mg, 2 mmol) and the mixture stirred for 1 h and allowed to return to room temperature. The mixture was quenched with water and extracted with ethyl acetate. The organic layer was concentrated in vacuo to afford crude compound as a light-yellow solid which was purified by Prep-HPLC to afford 5-amino-3-(5-aminooctahydropentalen-2-yl)-N-(3-chloro-4-fluorophenyl)-1-methyl-1H-pyrazole-4-carboxamide (10 mg, 10% yield) as a white solid. $^1$H NMR (DMSO-d$_6$, 400 MHz): δ 8.96 (s, 1H), 7.90 (dd, J=2.8, 2.4 Hz, 1H), 7.53-7.49 (m, 1H), 7.34 (t, J=9.2, 9.2 Hz, 1H), 5.97 (s, 2H), 3.49-3.33 (m, 5H), 3.14-3.11 (m, 1H), 2.34 (d, J=5.6 Hz, 2H), 2.17-2.12 (m, 2H), 1.99-1.93 (m, 2H), 1.57-1.42 (m, 2H), 1.23 (s, 1H), 1.02-0.95 (m, 2H); MS Calcd.: 391.1; MS Found: 392.2 [M+1]$^+$.

AIA-042

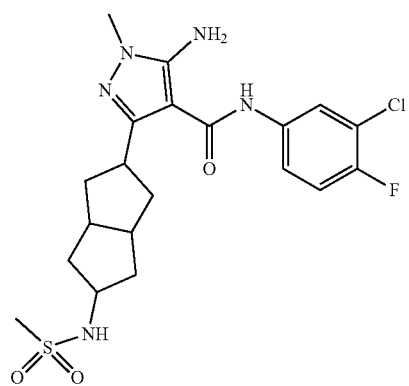

5-Amino-N-(3-chloro-4-fluorophenyl)-1-methyl-3-(5-(methylsulfonamido)octahydropentalen-2-yl)-1H-pyrazole-4-carboxamide. To a solution of 5-amino-3-(5-aminooctahydropentalen-2-yl)-N-(3-chloro-4-fluorophenyl)-1-methyl-1H-pyrazole-4-carboxamide (200 mg, 0.2 mmol) in DCM (10 mL) was added TEA (52 mg, 0.4 mmol) and MsCl (39 mg, 0.2 mmol). The mixture was stirred at room temperature for 2 h. The solvent was removed, and the residue was purified by prep-HPLC to afford 5-amino-N-(3-chloro-4-fluorophenyl)-1-methyl-3-(5-(methylsulfonamido)octahydropentalen-2-yl)-1H-pyrazole-4-carboxamide (19.3 mg, 16.8%) as a white solid. $^1$H NMR (DMSO-d$_6$, 400 MHz): δ ppm 8.96 (s, 1H), 7.90 (dd, J=2.4, 4.0 Hz, 1H), 7.53-7.49 (m, 1H), 7.34 (t, J=8.8, 9.2 Hz, 1H), 7.10 (d, J=7.6 Hz, 1H), 5.97 (s, 2H), 3.60-3.50 (m, 2H), 3.47 (s, 3H), 2.87 (s, 3H), 2.34 (t, J=8.0 Hz, 2H), 2.20-2.11 (m, 4H), 1.48-1.40 (m, 2H), 1.23-1.16 (m, 2H); MS Calcd.: 469.1; MS Found: 470.2 [M+1]$^+$.

AIA-086

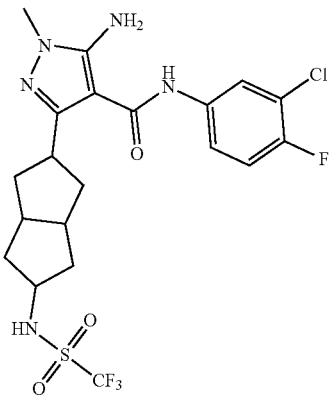

5-Amino-N-(3-chloro-4-fluorophenyl)-1-methyl-3-(5-((trifluoromethyl)sulfonamido)octahydropentalen-2-yl)-1H-pyrazole-4-carboxamide. The title compound was synthesized according to the procedure described for 5-amino-N-(3-chloro-4-fluorophenyl)-1-methyl-3-(5-(methylsulfonamido)octahydropentalen-2-yl)-1H-pyrazole-4-carboxamide. $^1$H NMR (DMSO-d$_6$, 400 MHz): δ 9.46 (s, 1H), 8.97 (s, 1H), 7.89 (dd, J=2.4, 2.4 Hz, 1H), 7.53-7.49 (m, 1H), 7.34 (t, J=9.2 Hz, 1H), 5.98 (s, 2H), 3.74 (s, 1H), 3.54-3.33 (m, 4H), 2.39-2.37 (m, 2H), 2.21-2.09 (m, 4H), 1.48-1.40 (m, 2H), 1.32-1.24 (m, 2H); MS Calcd.: 523.1; MS Found: 524.2 [M+1]$^+$.

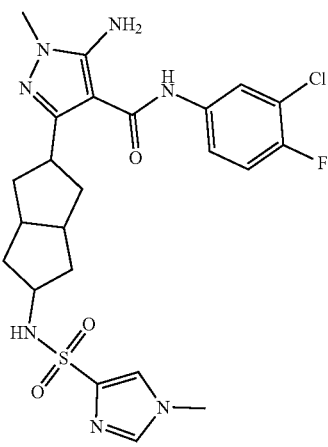

AIA-087

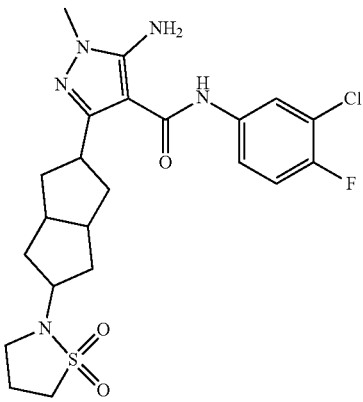

AIA-044

Amino-N-(3-chloro-4-fluorophenyl)-1-methyl-3-(5-((1-methyl-1H-imidazole)-4-sulfonamido)octahydropentalen-2-yl)-1H-pyrazole-4-carboxamide The title compound was synthesized according to the procedure described for 5-amino-N-(3-chloro-4-fluorophenyl)-1-methyl-3-(5-(methylsulfonamido)octahydropentalen-2-yl)-1H-pyrazole-4-carboxamide. MS Calcd.: 535.1; MS Found: 536.2 [M+1]⁺. ¹H NMR (DMSO-d₆, 400 MHz): δ 8.95 (s, 1H), 7.88 (dd, J=2.4, 2.4 Hz, 1H), 7.74 (s, 1H), 7.65 (d, J=0.8 Hz, 1H), 7.52-7.47 (m, 2H), 7.33 (t, J=9.2, 9.2 Hz, 1H), 5.96 (s, 2H), 3.68 (s, 3H), 3.49-3.43 (m, 5H), 2.23 (t, J=4.8, 8.4 Hz, 2H), 2.14-2.07 (m, 2H), 1.92-1.85 (m, 2H), 1.37 (dd, J=12.4, 12.0 Hz, 2H), 1.11 (t, J=12.0, 11.6 Hz, 2H).

5-Amino-N-(3-chloro-4-fluorophenyl)-3-(5-(1,1-dioxidoisothiazolidin-2-yl)octahydropentalen-2-yl)-1-methyl-1H-pyrazole-4-carboxamide. To a solution of 5-amino-N-(3-chloro-4-fluorophenyl)-3-(5-((3-chloropropyl)sulfonamido)octahydropentalen-2-yl)-1-methyl-1H-pyrazole-4-carboxamide (100 mg, 0.2 mmol) in DMF (5 mL) was added NaH (13 mg, 0.6 mmol). The mixture was stirred at room temperature for 1 h then quenched with water and extracted with ethyl acetate. The organic layer was concentrated in vacuo. The residue was purified by pre-HPLC to afford 5-amino-N-(3-chloro-4-fluorophenyl)-3-(5-(1,1-dioxidoisothiazolidin-2-yl)octahydropentalen-2-yl)-1-methyl-1H-pyrazole-4-carboxamide (47.3 mg, 51% yield) as a white solid. ¹H NMR (DMSO-d₆, 400 MHz): δ 8.97 (s, 1H), 7.90 (dd, J=2.8, 2.4 Hz, 1H), 7.53-7.49 (m, 1H), 7.34 (t, J=9.2, 9.2 Hz, 1H), 5.97 (s, 2H), 3.55-3.49 (m, 5H), 3.17-3.13 (m, 4H), 2.41-2.39 (m, 2H), 2.21-2.14 (m, 4H), 2.06-1.99 (m, 2H), 1.52-1.44 (m, 2H), 1.41-1.33 (m, 2H); MS Calcd.: 495.1; MS Found: 496.2 [M+1]⁺

Intermediate 106

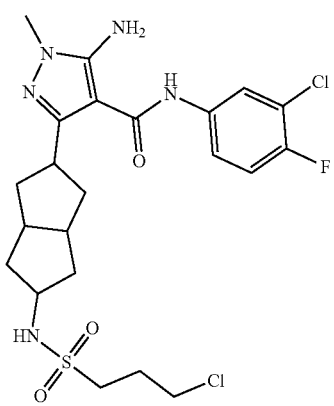

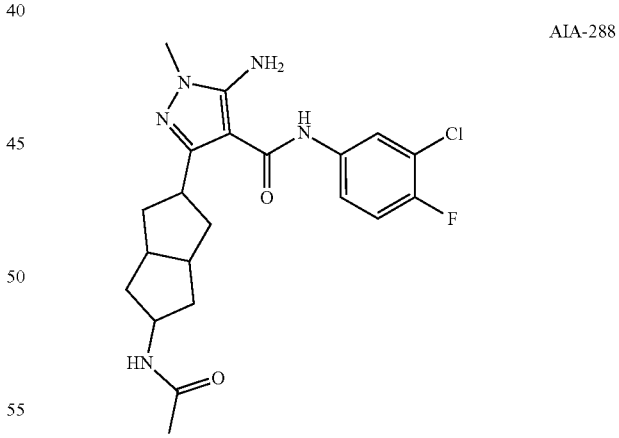

AIA-288

5-Amino-N-(3-chloro-4-fluorophenyl)-3-(5-((3-chloropropyl)sulfonamido)octahydropentalen-2-yl)-1-methyl-1H-pyrazole-4-carboxamide: The title compound was synthesized according to the procedure described for 5-amino-N-(3-chloro-4-fluorophenyl)-1-methyl-3-(5-(methylsulfonamido)octahydropentalen-2-yl)-1H-pyrazole-4-carboxamide. MS Calcd.: 531.1; MS Found: 532.2 [M+1]⁺.

3-(5-Acetamidooctahydropentalen-2-yl)-5-amino-N-(3-chloro-4-fluorophenyl)-1-methyl-1H-pyrazole-4-carboxamide The title compound was synthesized according to the procedure described for 5-amino-N-(3-chloro-4-fluorophenyl)-1-methyl-3-(5-(methylsulfonamido)octahydropentalen-2-yl)-1H-pyrazole-4-carboxamide ¹H NMR (400 MHz, CHLOROFORM-d) δ ppm 1.19-1.31 (2H, m), 1.71-1.83 (2H, m), 1.95 (3H, s), 2.28-2.42 (4H, m), 2.52-2.63 (2H, m), 3.23 (1H, dt, J=11.30, 5.71 Hz), 3.58 (3H, s), 4.24-4.37 (1H, m), 5.25 (2H, s), 5.49-5.58 (1H, m), 7.11

(1H, t, J=8.77 Hz), 7.22-7.25 (2H, m), 7.71 (1H, dd, J=6.39, 2.21 Hz); LCMS: 434.0 [M+1]⁺.

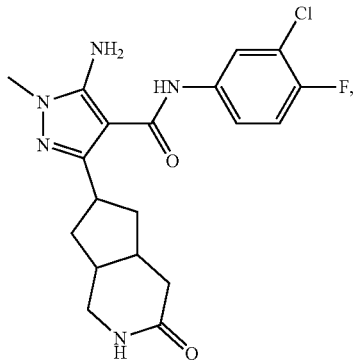

AIA-033A, AIA-033B

5-Amino-N-(3-chloro-4-fluorophenyl)-1-methyl-3-(3-oxooctahydro-1H-cyclopenta[c]pyridin-6-yl)-1H-pyrazole-4-carboxamide. Diastereomer 1 (AIA-033A) and Diastereomer 2(AIA-033B). A mixture of 5-amino-N-(3-chloro-4-fluorophenyl)-3-(5-(hydroxyimino)octahydropentalen-2-yl)-1-methyl-1H-pyrazole-4-carboxamide (90 mg, 0.22 mmol), TsCl (90 mg, 1.47 mmol), Na₂CO₃ (90 mg, 0.85 mmol) in H₂O (5 mL)/acetone (5 mL) was stirred at 80° C. for 4 h. The reaction mixture was concentrated in vacuo and the residue was purified by chiral-HPLC to afford AIA-033A and AIA-03-B. AIA-033-A (20 mg, 22% yield) as a white solid. MS Calcd.: 405.14; MS Found: 406.3 [M+1]⁺; (DMSO-d₆, 400 MHz): δ 8.95 (s, 1H), 7.91 (dd, J=6.8, 2.4 Hz, 1H), 7.52-7.45 (m, 2H), 7.32 (t, J=9.2 Hz, 1H), 5.95 (s, 2H), 3.47 (s, 3H), 3.38-3.35 (m, 1H), 3.16-3.12 (m, 1H), 2.84-2.81 (m, 1H), 2.42-2.41 (m, 1H), 2.31-2.21 (m, 2H), 2.09-2.04 (m, 2H), 1.96-1.91 (m, 1H), 1.48-1.45 (m, 1H), 1.29-1.27 (m, 1H). AIA-033-B (20 mg, 22% yield) as a white solid. MS Calcd.: 405.14; MS Found: 406.3 [M+1]⁺. ¹H-NMR (DMSO-d₆, 400 MHz): δ 8.95 (s, 1H), 7.91 (dd, J=6.8, 2.4 Hz, 1H), 7.52-7.45 (m, 2H), 7.32 (t, J=9.2 Hz, 1H), 5.95 (s, 2H), 3.47 (s, 3H), 3.38-3.35 (m, 1H), 3.16-3.12 (m, 1H), 2.84-2.81 (m, 1H), 2.42-2.41 (m, 1H), 2.31-2.21 (m, 2H), 2.09-2.04 (m, 2H), 1.96-1.91 (m, 1H), 1.48-1.45 (m, 1H), 1.30-1.27 (m, 1H).

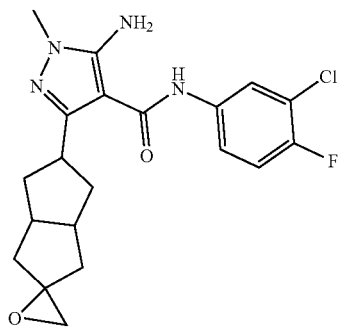

Intermediate 107

5-Amino-N-(3-chloro-4-fluorophenyl)-3-(hexahydro-1'H-spiro[oxirane-2,2'-pentalene]-5'-yl)-1-methyl-1H-pyrazole-4-carboxamide. To a solution of potassium 2-methylpropan-2-olate (230 mg, 2.05 mmol) in THF (30 mL) was added trimethylsulfoxonium iodide (450 mg, 2.05 mmol). The mixture was stirred at RT for 1 h under N₂. AIA-002 (200 mg, 0.53 mmol) was then added to the mixture and stirring continued at 60° C. for 5 h under an N₂ atmosphere. The solvent was removed under vacuum and the product purified by silica gel column chromatography using 1:1 ethyl acetate/petroleum ether to afford 5-amino-N-(3-chloro-4-fluorophenyl)-3-(hexahydro-1'H-spiro[oxirane-2,2'-pentalene]-5'-yl)-1-methyl-1H-pyrazole-4-carboxamide. (200 mg, 96.6%) as yellow solid. MS Calcd.: 404.1; MS Found: 405.2 [M+1]⁺.

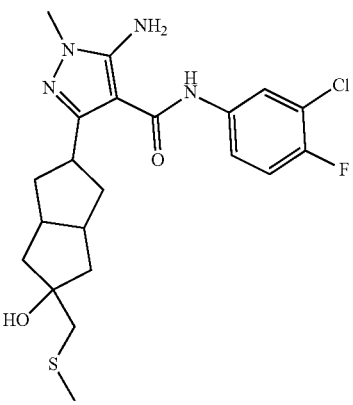

AIA-225

5-Amino-N-(3-chloro-4-fluorophenyl)-3-(5-hydroxy-5-(methylthiomethyl)octahydropentalen-2-yl)-1-methyl-1H-pyrazole-4-carboxamide. To a solution of 5-amino-N-(3-chloro-4-fluorophenyl)-3-(hexahydro-1'H-spiro[oxirane-2,2'-pentalene]-5'-yl)-1-methyl-1H-pyrazole-4-carboxamide (200 mg, 0.495 mmol) in THF/H₂O (6 mL/2 mL) was added NaSMe (138.6 mg, 1.98 mmol). The mixture was stirred at RT overnight. The solvent was removed and the crude product purified by silica gel column chromatography using 3:1 petroleum ether/ethyl acetate to afford 5-amino-N-(3-chloro-4-fluorophenyl)-3-(5-(100 mg, 44.7%) as yellow solid. MS Calcd.: 452.1; MS Found: 452.2 [M+1]⁺.

TABLE 8

The compounds int table 8 were synthesized according to the procedure described for 5-amino-N-(3-chloro-4-fluorophenyl)-3-(5-hydroxy-5-(methylthiomethyl)octahydropentalen-2-yl)-1-methyl-1H-pyrazole-4-carboxamide

| Compound | Structure and characterization |
| --- | --- |
| Intermediate 108 | 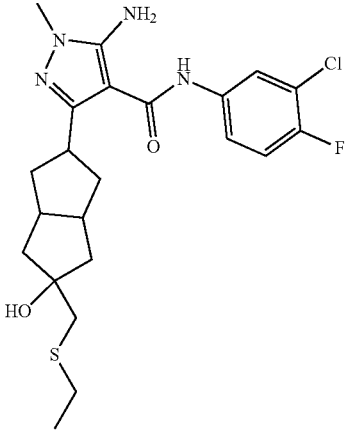 [SMILES: CCSCC1(O)CC2CC(c3nn(C)c(N)c3C(=O)Nc3ccc(F)c(Cl)c3)CC2C1]<br>5-Amino-N-(3-chloro-4-fluorophenyl)-3-(5-((ethylthio)methyl)-5-hydroxyoctahydropentalen-2-yl)-1-methyl-1H-pyrazole-4-carboxamide. MS Calcd.: 466.1; MS Found: 467.2 [M + 1]⁺. |
| Intermediate 109 | 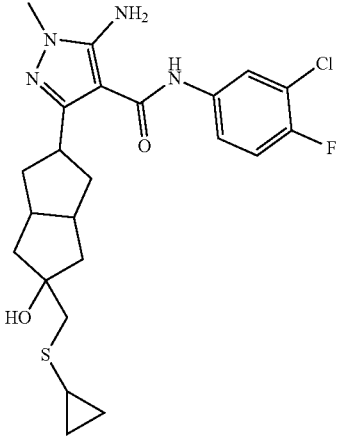 [SMILES: Cn1nc(C2CC3CC(O)(CSC4CC4)CC3C2)c(C(=O)Nc2ccc(F)c(Cl)c2)c1N]<br>5-Amino-N-(3-chloro-4-fluorophenyl)-3-(5-((cyclopropylthio)methyl)-5-hydroxyoctahydropentalen-2-yl)-1-methyl-1H-pyrazole-4-carboxamide. MS Calcd.: 478.2; MS Found: 479.3 [M + 1]⁺. |
| AIA-258-1 | 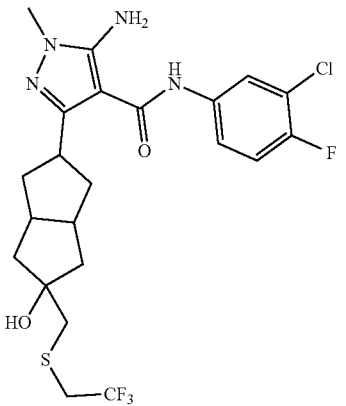 [SMILES: Cn1nc(C2CC3CC(O)(CSCC(F)(F)F)CC3C2)c(C(=O)Nc2ccc(F)c(Cl)c2)c1N]<br>5-Amino-N-(3-chloro-4-fluorophenyl)-3-(5-hydroxy-5-(((2,2,2-trifluoroethyl)thio)methyl)octahydropentalen-2-yl)-1-methyl-1H- |

TABLE 8-continued

The compounds int table 8 were synthesized according to the procedure described for 5-amino-N-(3-chloro-4-fluorophenyl)-3-(5-hydroxy-5-(methylthiomethyl)octahydropentalen-2-yl)-1-methyl-1H-pyrazole-4-carboxamide

| Compound | Structure and characterization |
|---|---|
| | pyrazole-4-carboxamide. Diastereomer 1. MS Calcd.: 520.1; MS Found: 521.2 [M + 1]⁺. AIA-258-1: ¹H NMR (DMSO-d6, 400 MHz): δ 8.94 (s, 1H), 7.91 (dd, J = 6.8, 2.4 Hz, 1H), 7.54-7.50 (m, 1H), 7.35 (t, J = 9.2 Hz, 1H), 5.97 (s, 2H), 4.47 (s, 1H) 3.58-3.45 (m, 6H), 2.86 (s, 2H), 2.67-2.62 (m, 2H), 2.18-2.11 (m, 2H), 1.89-1.84 (m, 2H), 1.44-1.32 (m, 4H). |
| AIA-258-2 | 5-Amino-N-(3-chloro-4-fluorophenyl)-3-(5-hydroxy-5-(((2,2,2-trifluoroethyl)thio)methyl)octahydropentalen-2-yl)-1-methyl-1H-pyrazole-4-carboxamide. Diastereomer 2. ¹H NMR(DMSO-d6, 400 MHz): δ 8.94 (s, 1H), 7.91 (dd, J = 6.8, 2.8 Hz, 1H), 7.53-7.49 (m, 1H), 7.34 (t, J = 8.8 Hz, 1H), 5.97 (s, 2H), 4.60 (s, 1H) 3.54-3.46 (m, 5H), 3.42-3.39 (m, 1H), 2.79 (s, 2H), 2.42-2.41 (m, 2H), 2.14-2.10 (m, 2H), 1.92-1.87 (m, 2H), 1.65-1.63 (m, 2H), 1.51-1.47 (m, 2H). |
| AIA-283-1 | 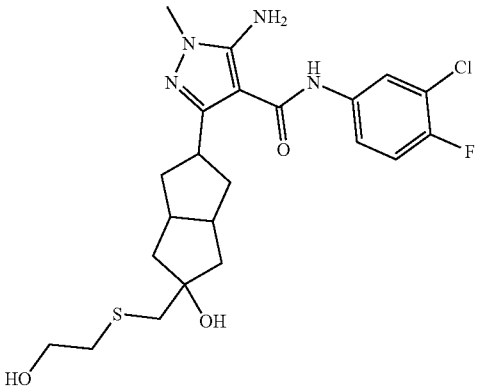 [SMILES: Cn1nc(C2CC3CC(O)(CSCCO)CC3C2)c(C(=O)Nc2ccc(F)c(Cl)c2)c1N]<br>5-Amino-N-(3-chloro-4-fluorophenyl)-3-(5-hydroxy-5-(((2-hydroxyethyl)thio)methyl)octahydropentalen-2-yl)-1-methyl-1H-pyrazole-4-carboxamide. Diastereomer 1. MS Calcd.: 483.0; MS Found: 484.1 [M + 1]⁺. ¹H NMR (CDCl₃, 400 MHz): δ 7.74-7.72 (m, 1H), 7.30-7.26 (m, 2H), 7.11 (t, J=8.4 Hz, 1H), 5.28 (s, 2H), 3.80-3.77 (m, 2H), 3.59 (s, 3H), 3.29-3.24 (m, 2H), 2.92-2.79 (m, 6H), 2.41-2.35 (m, 2H), 2.10-2.04 (m, 2H), 1.75-1.60 (m, 2H), 1.50-1.46 (m, 2H). |
| AIA-283-2 | 5-Amino-N-(3-chloro-4-fluorophenyD-3-(5-hydroxy-5-(((2-hydroxyethyl)thio)methyl)octahydropentalen-2-yl)-1-methyl-1H-pyrazole-4-carboxamide. Diastereomer 2. ¹H NMR (DMSO-d₆, 400 MHz): δ 8.94(s, 1H), 7.92-7.90 (m, 1H), 7.51-7.50 (m, 1H), 7.35 (t, J = 9.2 Hz, 1H), 5.98 (s, 2H), 4.76-4.74 (m, 1H), 3.42 (s, 1H), 3.52-3.49 (m, 6H), 2.62-2.57 (m, 4H), 2.42 (s, 2H), 2.13-2.10 (m, 2H), 1.91-1.86 (m, 2H), 1.67-1.65 (m, 2H), 1.46-1.44 (m, 2H). |
| AIA-284-1 | 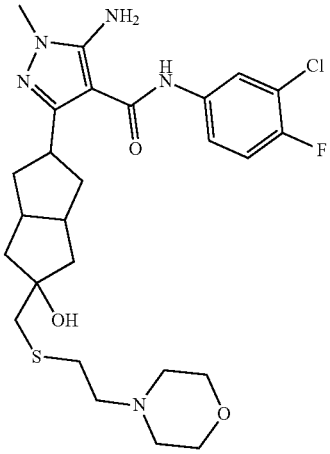 [SMILES: Cn1nc(C2CC3CC(O)(CSCCN4CCOCC4)CC3C2)c(C(=O)Nc2ccc(F)c(Cl)c2)c1N]<br>5-Amino-N-(3-chloro-4-fluorophenyl)-3-(5-hydroxy-5-(((2-morpholinoethyl)thio)methyl)octahydropentalen-2-yl)-1-methyl-1H-pyrazole-4-carboxamide. Diastereomer 1. MS Calcd.: 551.2; |

TABLE 8-continued

The compounds int table 8 were synthesized according to the procedure described for 5-amino-N-(3-chloro-4-fluorophenyl)-3-(5-hydroxy-5-(methylthiomethyl)octahydropentalen-2-yl)-1-methyl-1H-pyrazole-4-carboxamide

| Compound | Structure and characterization |
| --- | --- |
|  | MS Found: 552.3 [M + 1]$^+$. $^1$H NMR (DMSO-d$_6$, 400 MHz) δ 8.94 (s, 1H), 7.91 (dd, J = 6.8, 2.0 Hz, 1H), 7.53-7.49 (m, 1H), 7.37-7.32 (m, 1H), 5.98 (s, 2H), 4.48 (s, 1H), 3.56-3.53 (m, 4H), 3.49 (s, 3H), 3.42-3.38 (m, 1H), 2.66-2.62 (m, 4H), 2.47-2.36 (m, 8H), 2.15-2.08 (m, 2H), 1.90-1.85 (m, 2H), 1.68-1.65 (m, 2H), 1.46-1.43 (m, 2H). |
| AIA-284-2 | 5-Amino-N-(3-chloro-4-fluorophenyl)-3-(5-hydroxy-5-(((2-morpholinoethyl)thio)methyl)octahydropentalen-2-yl)-1-methyl-1H-pyrazole-4-carboxamide. Diastereomer 2. $^1$H NMR (DMSO-d$_6$, 400 MHz) δ 8.95 (s, 1H), 7.91 (dd, J = 6.8, 2.4 Hz, 1H), 7.54-7.50 (m, 1H), 7.37-7.33 (m, 1H) 5.98 (s, 2H), 4.37 (s, 1H), 3.59-3.53 (m, 5H), 3.51-3.49 (s, 3H), 2.68-2.61 (m, 6H), 2.51-2.30 (m, 6H), 2.17-2.11 (m, 2H), 1.83-1.78 (m, 2H), 1.43-1.23 (m, 4H). |
| AIA-262-1 | ![structure] |
|  | 5-Amino-3-(5-((tert-butylthio)methyl)-5-hydroxyoctahydropentalen-2-yl)-N-(3-chloro-4-fluorophenyl)-1-methyl-1H-pyrazole-4-carboxamide. Diastereomer 1. MS Calcd.: 494.19; MS Found: 495.3 [M + 1]$^+$. $^1$H-NMR (DMSO, 400 MHz): δ 8.94 (s, 1H), 7.90-7.93 (dd, J = 7.2, 2.8 Hz, 1H), 7.54-7.50 (m, 1H), 7.35 (t, J = 9.2 Hz, 1H), 5.96 (s, 2H), 4.29 (s, 1H), 3.55-3.52 (m, 1H), 3.49 (s, 3H), 2.66-2.51 (m, 4H), 2.16-2.08 (m, 2H), 1.79-1.74 (m, 2H), 1.42-1.34 (m, 4H), 1.24 (s, 9H). |
| AIA-262-2 | 5-Amino-3-(5-((tert-butylthio)methyl)-5-hydroxyoctahydropentalen-2-yl)-N-(3-chloro-4-fluorophenyl)-1-methyl-1H-pyrazole-4-carboxamide.Diastereomer 2. $^1$H-NMR (DMSO, 400 MHz): δ 8.92 (s, 1H), 7.92-7.90 (dd, J = 6.8, 2.4 Hz, 1H), 7.53-7.49 (m, 1H), 7.35 (t, J = 9.2 Hz, 1H), 5.97 (s, 2H), 4.33 (s, 1H), 3.49 (s, 3H), 3.43-3.34 (m, 1H), 2.61 (s, 2H), 2.45-2.44 (m, 2H), 2.14-2.08 (m, 2H), 1.92-1.87 (m, 2H), 1.72-1.34 (m, 2H), 1.46-1.40 (m, 2H), 1.24 (s, 9H). |

TABLE 8-continued

The compounds int table 8 were synthesized according to the procedure described for 5-amino-N-(3-chloro-4-fluorophenyl)-3-(5-hydroxy-5-(methylthiomethyl)octahydropentalen-2-yl)-1-methyl-1H-pyrazole-4-carboxamide

| Compound | Structure and characterization |
|---|---|
| AIA-295-2B | 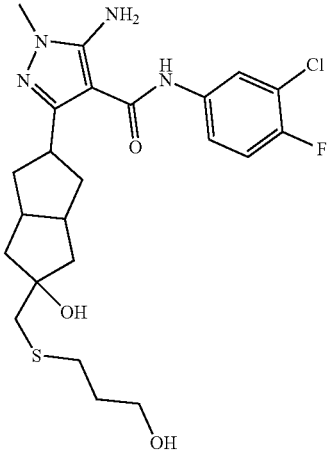 [SMILES: Cn1nc(C2CC3CC(O)(CSCCCO)CC3C2)c(C(=O)Nc2ccc(F)c(Cl)c2)c1N] |
| | 5-Amino-N-(3-chloro-4-fluorophenyl)-3-(5-hydroxy-5-(((3-hydroxypropypthio)methyl)octahydropentalen-2-yl)-1-methyl-1H-pyrazole-4-carboxamide Diastereomer 1. MS Calcd.: 496.17; MS Found: 497.13 [M + 1]+. |
| AIA-295-2B | 5-Amino-N-(3-chloro-4-fluorophenyl)-3-(5-hydroxy-5-(((3-hydroxypropypthio)methyl)octahydropentalen-2-yl)-1-methyl-1H-pyrazole-4-carboxamide Diastereomer 2. MS Calcd.: 496.17; MS Found: 497.13 [M + 1]+. |

AIA-227-1

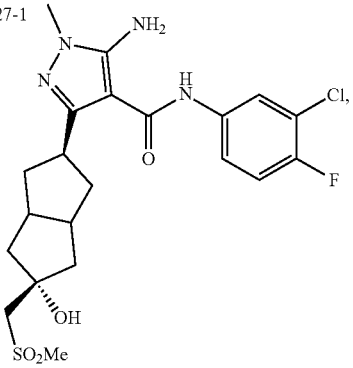

CP-AIA-227-1

AIA-227-2

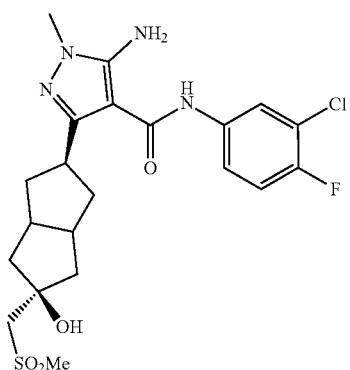

CP-AIA-227-2

5-Amino-N-(3-chloro-4-fluorophenyl)-3-((2r,5r)-5-hydroxy-5-(methylsulfonylmethyl)octahydropentalen-2-yl)-1-methyl-1H-pyrazole-4-carboxamide (AIA-227-1) and 5-Amino-N-(3-chloro-4-fluorophenyl)-3-((2s,5s)-5-hydroxy-5-(methylsulfonylmethyl)octahydropentalen-2-yl)-1-methyl-1H-pyrazole-4-carboxamide (AIA-227-2). To a solution of 5-amino-N-(3-chloro-4-fluorophenyl)-3-(5-hydroxy-5-(100 mg, 0.22 mmol) in DCM (5 mL) was added m-CPBA (114.8 mg, 0.66 mmol). The mixture was stirred at RT overnight. The solvent was removed and the crude material purified by silica gel column chromatography using 3:1 DCM/MeOH to afford AIA-227 (40 mg, 37.3%) as white solid. MS Calcd.: 484.1; MS Found: 484.3 [M+1]$^+$. AIA-227 was separated by SFC to give AIA-227-1 (4 mg) as a white solid and AIA-227-2 (4 mg) as a white solid. AIA-227-1: (DMSO, 400 MHz): δ 8.95 (s, 1H), 7.91 (dd, J=6.8, 2.4 Hz, 1H), 7.54-7.50 (m, 1H), 7.35 (t, J=9.2 Hz, 1H), 5.97 (s, 2H), 4.79 (s, 1H), 3.59-3.53 (m, 1H), 3.49 (s, 3H), 3.35 (s, 2H), 2.97 (s, 3H), 2.67-2.60 (m, 2H), 2.18-2.12 (m, 2H), 2.07-2.02 (m, 2H), 1.45-1.36 (m, 4H). AIA-227-2: (DMSO, 400 MHz): δ 8.94 (s, 1H), 7.91 (dd, J=2.8, 2.4 Hz, 1H), 7.53-7.49 (m, 1H), 7.34 (t, J=9.2 Hz, 1H), 5.97 (s, 2H), 4.87 (s, 1H), 3.49 (s, 3H), 3.43-3.35 (m, 1H), 3.25 (s, 2H), 2.97 (s, 3H), 2.49 (s, 2H), 2.15-2.09 (m, 2H), 2.02-1.97 (m, 2H), 1.73-1.60 (m, 4H).

TABLE 9

The compounds in table 9 were synthesized according to the procedure described for 5-amino-N-(3-chloro-4-fluorophenyl)-3-((2r,5r)-5-hydroxy-5-(methylsulfonylmethyl)octahydropentalen-2-yl)-1-methyl-1H-pyrazole-4-carboxamide (AIA-227-1) and 5-amino-N-(3-chloro-4-fluorophenyl)-3-((2s,5s)-5-hydroxy-5-(methylsulfonylmethyl)octahydropentalen-2-yl)-1-methyl-1H-pyrazole-4-carboxamide (AIA-227-2).

| Compound | Structure and characterization |
| --- | --- |
| AIA-250-1 | 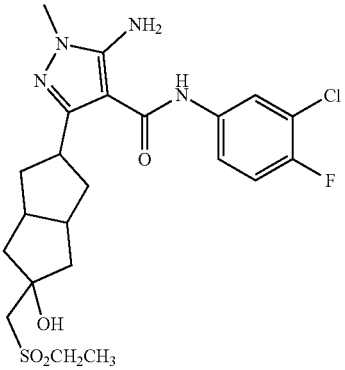<br>5-Amino-N-(3-chloro-4-fluorophenyl)-3-(5-((ethylsulfonyl)nethyl)-5-hydroxyoctahydropentalen-2-yl)-1-methyl-1H-pyrazole-4-carboxamide. Diastereomer 1. $^1$H-NMR (DMSO, 400 MHz): δ 8.95 (s, 1H), 7.91 (dd, J = 6.8, 2.4 Hz, 1H), 7.54-7.50 (m, 1H), 7.35 (t, J = 9.2 Hz, 1H), 5.98 (s, 2H), 4.77 (s, 1H), 3.58-3.55 (m,1H), 3.49 (s, 3H), 3.31 (s, 2H), 3.11 (q, J = 7.2 Hz, 2H), 2.63-2.61 (m, 2H), 2.18-2.12 (m, 2H), 2.06-2.02 (m, 2H), 1.47-1.36 (m, 4H), 1.20 (t, J = 7.6 Hz, 3H). |
| AIA-250-2 | 5-Amino-N-(3-chloro-4-fluorophenyl)-3-(5-((ethylsulfonyl)methyl)-5-hydroxyortahydropentalen-2-yl)-1-methyl-1H-pyrazole-4-carboxamide. Diastereomer 2. $^1$H-NMR (DMSO, 400 MHz): δ 8.94 (s, 1H), 7.91 (dd, J = 7.2, 2.8 Hz, 1H), 7.53-7.49 (m, 1H), 7.35 (t, J = 9.2 Hz, 1H), 5.97 (s, 2H), 4.87 (s, 1H), 3.49 (s, 3H), 3.41-3.37 (m, 1H), 3.21 (s, 2H), 3.11 (q, J = 7.6 Hz, 2H), 2.49 (s, 2H), 2.15-2.09 (m, 2H), 2.03-1.98 (m, 2H), 1.73-1.60 (m, 4H), 1.20 (t, J = 7.6 Hz, 3H). |

TABLE 9-continued

The compounds in table 9 were synthesized according to the procedure described for 5-amino-N-(3-chloro-4-fluorophenyl)-3-((2r,5r)-5-hydroxy-5-(methylsulfonylmethyl)octahydropentalen-2-yl)-1-methyl-1H-pyrazole-4-carboxamide (AIA-227-1) and 5-amino-N-(3-chloro-4-fluorophenyl)-3-((2s,5s)-5-hydroxy-5-(methylsulfonylmethyl)octahydropentalen-2-yl)-1-methyl-1H-pyrazole-4-carboxamide (AIA-227-2).

| Compound | Structure and characterization |
|---|---|
| AIA-252-1 | 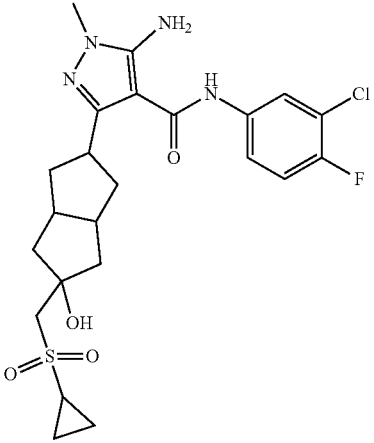 [SMILES: Cn1nc(C2CC3CC(O)(CS(=O)(=O)C4CC4)CC3C2)c(C(=O)Nc2ccc(F)c(Cl)c2)c1N]<br>5-Amino-N-(3-chloro-4-fluorophenyl)-3-(5-((cyclopropylsulfonyl)methyl)-5-hydroxyortahydropentalen-2-yl)-1-methyl-1H-pyrazole-4-carboxamide. Diastereomer 1. $^1$H-NMR (DMSO, 400 MHz): δ 8.95 (s, 1H), 7.90-7.93(dd, J = 6.8, 2.4 Hz, 1H), 7.55-7.51 (m, 1H), 7.35 (t, J = 9.2 Hz, 1H), 5.98 (s, 2H), 4.73 (s, 1H), 3.60-3.54 (m, 1H), 3.49 (s, 3H), 3.37 (s, 2H), 2.79-2.72 (m, 1H), 2.68-2.61 (m, 2H), 2.19-2.13 (m, 2H), 2.09-2.04 (m, 2H), 1.50-1.37 (m, 4H), 0.97 (d, J = 6.4 Hz, 4H). |
| AIA-252-2 | 5-Amino-N-(3-chloro-4-fluorophenyl)-3-(5-((cyclopropylsulfonyl)methyl)-5-hydroxyortahydropentalen-2-yl)-1-methyl-1H-pyrazole-4-carboxamide. Diastereomer 2. MS Calcd.: 510.2; MS Found: 511.2 [M + H]$^+$. $^1$H-NMR (DMSO, 400 MHz): δ 8.94 (s, 1H), 7.92 (d, J = 6.0 Hz, 1H), 7.53-7.50 (m, 1H), 7.35 (t, J = 9.2 Hz, 1H), 5.97 (s, 2H), 4.80 (s, 1H), 3.49 (s, 3H), 3.41-3.36 (m, 1H), 3.28 (s, 2H), 2.78-2.75 (m, 1H), 2.60 (m, 2H), 2.13-2.11 (m, 2H), 2.04-2.01 (m, 2H), 1.76-1.64 (m, 4H), 0.96 (d, J = 6.0 Hz, 4H). |
| AIA-266-1 | 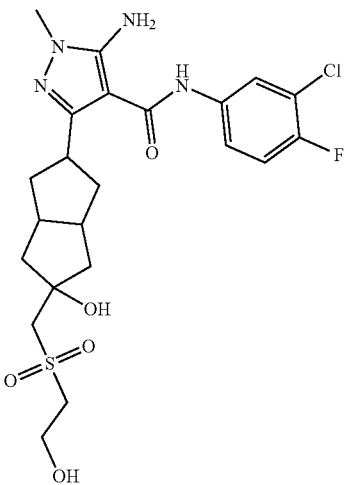 [SMILES: Cn1nc(C2CC3CC(O)(CS(=O)(=O)CCO)CC3C2)c(C(=O)Nc2ccc(F)c(Cl)c2)c1N]<br>5-Amino-N-(3-chloro-4-fluorophenyl)-3-(5-hydroxy-5-(((2-hydroxyethyl)sulfonyl)methyl)octahydropentalen-2-yl)-1-methyl-1H-pyrazole-4-carboxamide. Diastereomer 1. MS Calcd.: 515.0; MS Found: 515.15 [M + 1]$^+$; $^1$H NMR (DMSO-d$_6$, 400 MHz): δ 8.96 (s, 1H), 7.93-7.90 (m, 1H), 7.55-7.51 (m, 1H), 7.35 (t, J = 9.2 Hz, 1H), 5.55 (s, 1H), 5.02 (t, J = 5.6 Hz, 1H), 4.76 (s, 1H), 3.78 (dd, J = 11.6, 5.6 Hz, 1H), 3.58-3.55 (m, 1H), 3.49 (s, 3H), 3.38 (s, 2H), 3.28 (t, J = 6.4 Hz, 2H), 2.26 (s, 2H), 2.17-2.01 (m, 4H), 1.48-1.39 (m, 4H). |

TABLE 9-continued

The compounds in table 9 were synthesized according to the procedure described for 5-amino-N-(3-chloro-4-fluorophenyl)-3-((2r,5r)-5-hydroxy-5-(methylsulfonylmethyl)octahydropentalen-2-yl)-1-methyl-1H-pyrazole-4-carboxamide (AIA-227-1) and 5-amino-N-(3-chloro-4-fluorophenyl)-3-((2s,5s)-5-hydroxy-5-(methylsulfonylmethyl)octahydropentalen-2-yl)-1-methyl-1H-pyrazole-4-carboxamide (AIA-227-2).

| Compound | Structure and characterization |
|---|---|
| AIA-266-2 | 5-Amino-N-(3-chloro-4-fluorophenyl)-3-(5-hydroxy-5-(((2-hydroxyethyl)sulfonyl)methyl)octahydropentalen-2-yl)-1-methyl-1H-pyrazole-4-carboxamide. Diastereomer 2. MS Calcd.: 515.0; MS Found: 515.15 [M + 1]$^+$; $^1$H NMR (DMSO-d$_6$, 400 MHz): δ 8.95 (s, 1H), 7.93-7.90 (m, 1H), 7.53-7.49 (m, 1H), 7.35 (t, J = 8.8 Hz, 1H), 5.98 (s, 2H), 5.02-4.99 (m, 1H), 4.82 (s, 1H), 3.80-3.76 (m, 2H), 3.49 (s, 3H), 3.42-3.40 (m, 2H), 3.37-3.28 (m, 5H), 2.13-1.98 (m, 4H), 1.74-1.61 (m, 4H). |
| AIA-260-1 | 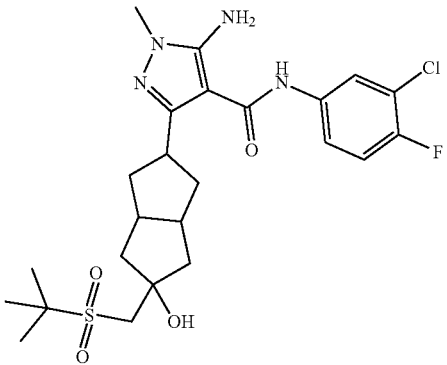 [SMILES: Cn1nc(C2CC3CC(O)(CS(=O)(=O)C(C)(C)C)CC3C2)c(C(=O)Nc2ccc(F)c(Cl)c2)c1N]<br>5-Amino-3-(5-((tert-butylsulfonyl)methyl)-5-hydroxyoctahydropentalen-2-yl)-N-(3-chloro-4-fluorophenyl)-1-methyl-1H-pyrazole-4-carboxamide. Diastereomer 1. MS Calcd.: 526.18; MS Found: 527.2 [M + H]$^+$. $^1$H-NMR (CDCl$_3$, 400 MHz): δ 7.68-7.66 (dd, J = 6.4, 2.4 Hz, 1H), 7.23-7.17 (m, 2H), 7.04 (t, J = 8.8 Hz, 1H), 5.20 (s, 2H), 3.66 (s, 1H), 3.51 (s, 3H), 3.24-3.20 (m, 1H), 3.17 (s, 2H),2.88-2.83 (m, 2H), 2.36-2.28 (m, 4H), 1.70-1.51 (m, 4H), 1.35 (s, 9H). |
| AIA-260-2 | 5-Amino-3-(5-((tert-butylsulfonyl)methyl)-5-hydroxyoctahydropentalen-2-yl)-N-(3-chloro-4-fluorophenyl)-1-methyl-1H-pyrazole-4-carboxamide. Diastereomer 2. MS Calcd.: 526.18; MS Found: 527.2 [M + H]$^+$. $^1$H-NMR ((CD$_3$)$_2$CO, 400 MHz): δ 8.14 (s, 1H), 8.03-8.00 (dd, J = 6.8, 2.4 Hz, 2H), 7.58-7.54 (t, J = 8.8 Hz, 1H), 5.90 (s, 2H), 3.96 (s, 1H), 3.56 (s, 3H), 3.45-3.39 (m, 1H), 3.35 (s, 2H),2.71-2.69 (m, 2H), 2.32-2.26 (m, 2H), 2.17-2.11 (m, 2H), 2.01-1.85 (m, 2H), 1.88-1.83 (dd, J = 13.2, 2.8 Hz, 2H), 1.38 (s, 9H). |

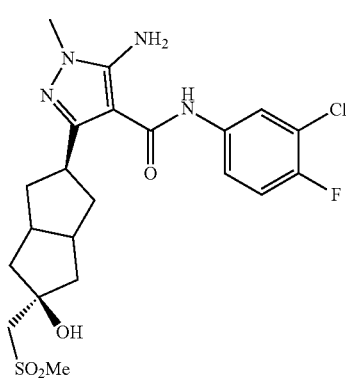

AIA-227-2

Alternative synthesis of 5-amino-N-(3-chloro-4-fluorophenyl)-3-((2s,5s)-5-hydroxy-5-(methylsulfonylmethyl)octahydropentalen-2-yl)-1-methyl-1H-pyrazole-4-carboxamide. To a solution of dimethylsulfone (77.0 g, 818.7 mmol) in THF (800 mL) was added n-BuLi (327.5 mL, 818.7 mmol, 2.5M) dropwise at −78° C. The resulting solution was allowed to warm to −20° C. and stirred for 1 hour. The reaction was cooled to −78° C., and a solution of AIA-002 (40.0 g, 102.3 mmol) in anhydrous tetrahydrofuran (1200 mL) was added over 2 hours. The mixture was warmed to RT and stirred for an additional 4 hours. The reaction mixture was quenched with saturated aqueous ammonium chloride solution (200 mL). The solvent was removed, followed by dilution with water, extraction with ethyl acetate (3×200 mL), drying over Na$_2$SO$_4$, filtration, and concentration to give the crude product. The crude product was purified by column chromatography using 0-5% methanol in DCM and basic prep-HPLC to afford 5-amino-N-(3-chloro-4-fluorophenyl)-3-((2s,5s)-5-hydroxy-5-(methylsulfonylmethyl)octahydropentalen-2-yl)-1-methyl-1H-pyrazole-4-carboxamide (26.0 g, 52.4%) as a white solid. MS Calcd.: 484.1, MS Found: 485.2 [M+1]$^+$; $^1$H NMR (DMSO-d$_6$, 400 MHz): δ 8.96 (s, 1H), 7.92 (dd, J=6.8, 2.8 Hz, 1H), 7.54-7.50 (m, 1H), 7.35 (t, J=8.8 Hz, 1H), 5.98 (s, 2H), 4.88 (s, 1H), 3.49 (s, 3H), 3.42-3.37 (m, 1H), 3.25 (s, 2H), 2.97 (s, 3H), 2.15-2.10 (m, 2H), 2.03-1.97 (m, 2H), 1.73-1.60 (m, 4H).

Intermediate 110

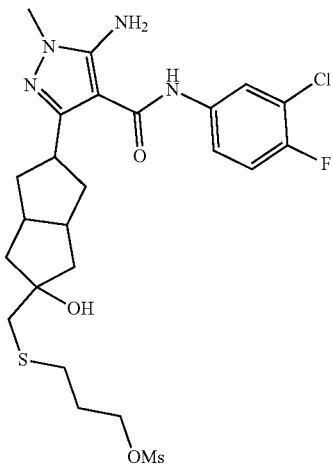

3-(((5-(5-Amino-4-((3-chloro-4-fluorophenyl)carbamoyl)-1-methyl-1H-pyrazol-3-yl)-2-hydroxyoctahydropentalen-2-yl)methyl)thio)propyl methanesulfonate Diastereomer 1. A solution of 5-amino-N-(3-chloro-4-fluorophenyl)-3-(5-hydroxy-5-(((3-hydroxypropyl)thio)methyl)octahydropentalen-2-yl)-1-methyl-1H-pyrazole-4-carboxamide Diastereomer 1 (AIA-295-2A) (198.8 mg, 0.4 mmol) in DCM (15 mL) was added TEA (121.4 mg, 1.2 mmol) and MsCl (91.6 mg, 0.8 mmol). The mixture was stirred at room temperature for 1 h. After completion of the reaction, the mixture was quenched with H$_2$O and extracted with DCM. The organic layer was removed under reduced pressure, and the residue was purified by column chromatography to afford 3-(((5-(5-amino-4-((3-chloro-4-fluorophenyl)carbamoyl)-1-methyl-1H-pyrazol-3-yl)-2-hydroxyoctahydropentalen-2-yl)methyl)thio)propyl methanesulfonate diastereomer 1 (200.0 mg, 86.9%) as a white solid. MS Calcd.: 574.15; MS Found: 575.2 [M+1]$^+$.

Intermediate 111

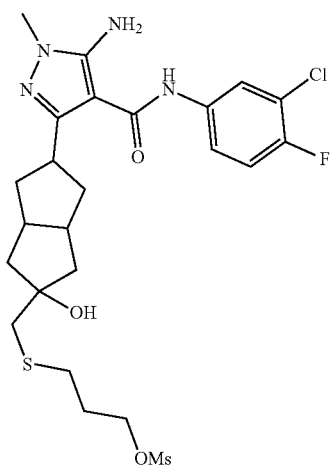

3-(((5-(5-Amino-4-((3-chloro-4-fluorophenyl)carbamoyl)-1-methyl-1H-pyrazol-3-yl)-2-hydroxyoctahydropentalen-2-yl)methyl)thio)propyl methanesulfonate Diastereomer 2. A solution of 5-amino-N-(3-chloro-4-fluorophenyl)-3-(5-hydroxy-5-(((3-hydroxypropyl)thio)methyl)octahydropentalen-2-yl)-1-methyl-1H-pyrazole-4-carboxamide Diastereomer 2 (AIA-295-2B) (452.3 mg, 0.91 mmol) in DCM (15 mL) was added TEA (276.2 mg, 2.73 mmol) and MsCl (208.5 mg, 1.82 mmol). The mixture was stirred at room temperature for 1 h. After completion of the reaction, the mixture was quenched with H$_2$O and extracted with DCM. The organic layer was removed under reduced pressure, and the residue was purified by column chromatography to afford 3-(((5-(5-amino-4-((3-chloro-4-fluorophenyl)carbamoyl)-1-methyl-1H-pyrazol-3-yl)-2-hydroxyoctahydropentalen-2-yl)methyl)thio)propyl methanesulfonate diastereomer 2 (460.0 mg, 87.9%) as a white solid. MS Calcd.: 574.15; MS Found: 575.2 [M+1]$^+$.

Intermediate 112

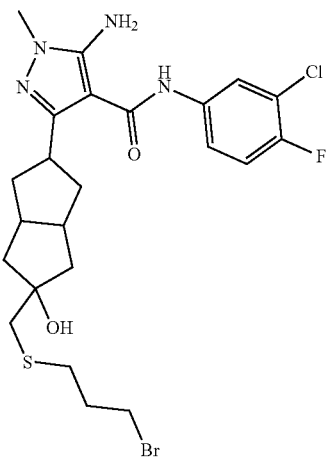

5-Amino-3-(5-(((3-bromopropyl)thio)methyl)-5-hydroxyoctahydropentalen-2-yl)-N-(3-chloro-4-fluorophenyl)-1-methyl-1H-pyrazole-4-carboxamide. Diastereomer 1. A mixture of 3-(((5-(5-amino-4-((3-chloro-4-fluorophenyl)carbamoyl)-1-methyl-1H-pyrazol-3-yl)-2-hydroxyoctahydropentalen-2-yl)methyl)thio)propyl methanesulfonate diastereomer 1 (201.3 mg, 0.35 mmol) and LiBr (76.4 mg, 0.88 mmol) in NMP was stirred at 80° C. After completion of the reaction, the mixture was purified by Prep-HPLC to afford 5-amino-3-(5-(((3-bromopropyl)thio)methyl)-5-hydroxyoctahydropentalen-2-yl)-N-(3-chloro-4-fluorophenyl)-1-methyl-1H-pyrazole-4-carboxamide, diastereomer 1 (120 mg, 61.2%) as a white solid. MS Calcd.: 558.09; MS Found: 559.13 [M+1]$^+$.

Intermediate 113

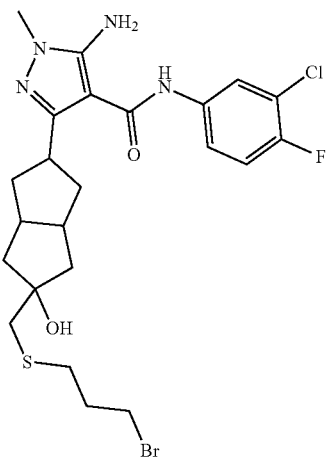

5-Amino-3-(5-(((3-bromopropyl)thio)methyl)-5-hydroxyoctahydropentalen-2-yl)-N-(3-chloro-4-fluorophenyl)-1-methyl-1H-pyrazole-4-carboxamide. Diastereomer 2. A mixture of 3-(((5-(5-amino-4-((3-chloro-4-fluorophenyl)carbamoyl)-1-methyl-1H-pyrazol-3-yl)-2-hydroxyoctahydropentalen-2-yl)methyl)thio)propyl methanesulfonate diastereomer 2 (460.1 mg, 0.8 mmol) and LiBr (173.7 mg, 2.0 mmol) in NMP was stirred at 80° C. After completion of the reaction, the mixture was purified by Pre-HPLC to afford 5-amino-3-(5-(((3-bromopropyl)thio)methyl)-5-hydroxyoctahydropentalen-2-yl)-N-(3-chloro-4-fluorophenyl)-1-methyl-1H-pyrazole-4-carboxamide, diastereomer 2. (200 mg, 44.6%) as a white solid. MS Calcd.: 558.09; MS Found: 559.1 [M+1]$^+$, 561.2 [M+2+H]$^+$.

Intermediate 114

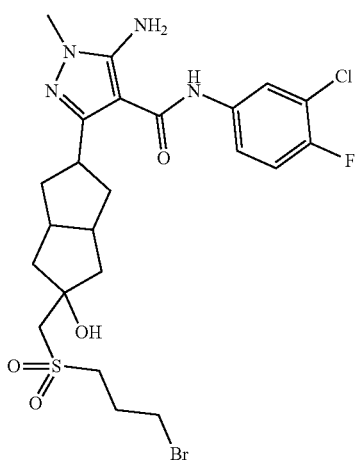

5-Amino-3-(5-(((3-bromopropyl)sulfonyl)methyl)-5-hydroxyoctahydropentalen-2-yl)-N-(3-chloro-4-fluorophenyl)-1-methyl-1H-pyrazole-4-carboxamide. Diastereomer 1. A mixture of 5-amino-3-(5-(((3-bromopropyl)thio)methyl)-5-hydroxyoctahydropentalen-2-yl)-N-(3-chloro-4-fluorophenyl)-1-methyl-1H-pyrazole-4-carboxamide, diastereomer 1 (117.6 mg, 0.21 mmol) and m-CPBA (108.7 mg, 0.63 mmol) in DCM was stirred at room temperature for 2 h. After completion of the reaction, the mixture was quenched with NaHCO$_3$ and extracted with DCM. The organic layer was removed under reduced pressure, and the residue purified by column chromatography to afford 5-amino-3-(5-(((3-bromopropyl)sulfonyl)methyl)-5-hydroxyoctahydropentalen-2-yl)-N-(3-chloro-4-fluorophenyl)-1-methyl-1H-pyrazole-4-carboxamide, diastereomer 1 (60 mg, 48.3%) as a white solid. MS Calcd.: 590.08; MS Found: 591.13 [M+1]$^+$.

Intermediate 115

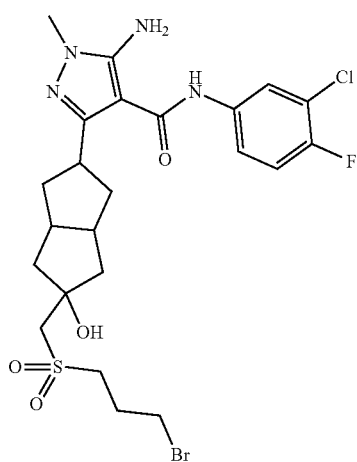

5-Amino-3-(5-(((3-bromopropyl)sulfonyl)methyl)-5-hydroxyoctahydropentalen-2-yl)-N-(3-chloro-4-fluorophenyl)-1-methyl-1H-pyrazole-4-carboxamide. Diastereomer 2. A mixture of 5-amino-3-(5-(((3-bromopropyl)thio)methyl)-5-hydroxyoctahydropentalen-2-yl)-N-(3-chloro-4-fluorophenyl)-1-methyl-1H-pyrazole-4-carboxamide, diastereomer 1 (117.6 mg, 0.21 mmol) and m-CPBA (108.7 mg, 0.63 mmol) in DCM was stirred at room temperature for 2 h. After completion of the reaction, the mixture was quenched with NaHCO$_3$ and extracted with DCM. The organic layer was removed under reduced pressure, and the residue purified by column chromatography to afford 5-amino-3-(5-(((3-bromopropyl)sulfonyl)methyl)-5-hydroxyoctahydropentalen-2-yl)-N-(3-chloro-4-fluorophenyl)-1-methyl-1H-pyrazole-4-carboxamide, diastereomer 1 (150 mg, 72.4%) as a white solid. MS Calcd.: 590.08; MS Found: 591.1 [M+1]$^+$, 593.2 [M+2+H]$^+$.

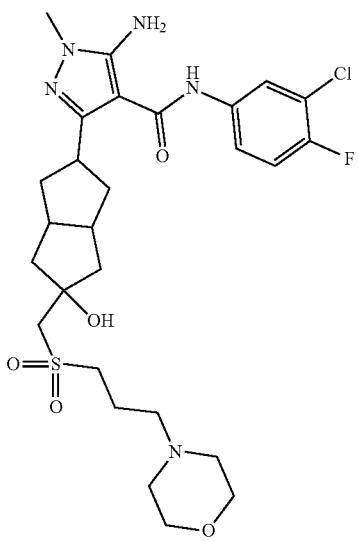

AIA-295-1

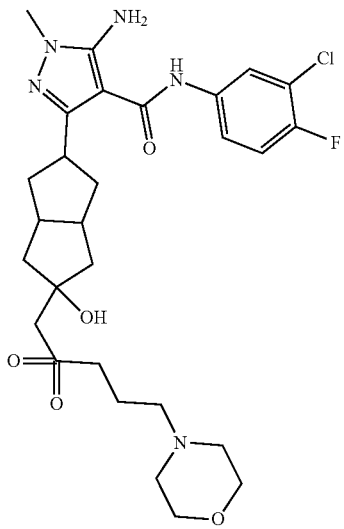

AIA-295-B

5-Amino-N-(3-chloro-4-fluorophenyl)-3-(5-hydroxy-5-(((3-morpholinopropyl)sulfonyl)methyl)octahydropentalen-2-yl)-1-methyl-1H-pyrazole-4-carboxamide. Diastereomer 1 (AIA-295-1). A mixture of 5-amino-3-(5-(((3-bromopropyl)sulfonyl)methyl)-5-hydroxyoctahydropentalen-2-yl)-N-(3-chloro-4-fluorophenyl)-1-methyl-1H-pyrazole-4-carboxamide, diastereomer 1 (50.0 mg, 0.08 mmol), morpholine (14.0 mg, 0.16 mmol) and $K_2CO_3$ (22.1 mg, 0.16 mmol) in ACN was stirred at 80° C. After completion of the reaction, the mixture was quenched with $H_2O$ and extracted with DCM. The organic layer was removed under reduced pressure, and the residue purified by Prep-HPLC to afford 5-amino-N-(3-chloro-4-fluorophenyl)-3-(5-hydroxy-5-(((3-morpholinopropyl)sulfonyl)methyl)octahydropentalen-2-yl)-1-methyl-1H-pyrazole-4-carboxamide, diastereomer 1 (AIA-295-1) (10.0 mg, 21.3%) as a white solid. MS Calcd.: 597.22; MS Found: 598.22 [M+1]$^+$; $^1$H NMR (DMSO-$d_6$, 400 MHz) of AIA-295-1: δ 8.95 (S, 1H), 7.92-7.90 (m, 1H), 7.53-7.51 (m, 1H), 7.38-7.33 (t, J=8.6 Hz, 1H), 5.98 (S, 2H), 4.89 (S, 1H), 3.60 (S, 4H), 3.60 (S, 3H), 3.42-3.38 (m, 1H), 3.28-3.10 (m, 4H), 2.64-2.57 (m, 2H), 2.42-2.33 (m, 6H), 2.14-2.11 (m, 2H), 2.03-1.96 (m, 2H), 1.87-1.83 (m, 2H), 1.73-1.58 (m, 4H).

5-Amino-N-(3-chloro-4-fluorophenyl)-3-(5-hydroxy-5-(((3-morpholinopropyl)sulfonyl)methyl)octahydropentalen-2-yl)-1-methyl-1H-pyrazole-4-carboxamide. Diastereomer 2 (AIA-295-B). A mixture of 5-amino-3-(5-(((3-bromopropyl)sulfonyl)methyl)-5-hydroxyoctahydropentalen-2-yl)-N-(3-chloro-4-fluorophenyl)-1-methyl-1H-pyrazole-4-carboxamide, diastereomer 1 2 (50.0 mg, 0.08 mmol), morpholine (14.0 mg, 0.16 mmol) and $K_2CO_3$ (22.1 mg, 0.16 mmol) in ACN was stirred at 80° C. After completion of the reaction, the mixture was quenched with $H_2O$ and extracted with DCM. The organic layer was removed under reduced pressure, and the residue purified by Prep-HPLC to afford 5-amino-N-(3-chloro-4-fluorophenyl)-3-(5-hydroxy-5-(((3-morpholinopropyl)sulfonyl)methyl)octahydropentalen-2-yl)-1-methyl-1H-pyrazole-4-carboxamide, diastereomer 1 (AIA-295-B) (33 mg, 55.2%) as a white solid. MS Calcd.: 597.22; MS Found: 598.2 [M+1]$^+$; $^1$H NMR (DMSO-$d_6$, 400 MHz): δ 8.95 (s, 1H), 7.91 (dd, J=2.4 Hz, 6.8 Hz, 1H), 7.54-7.50 (m, 1H), 7.35 (t, J=9.2 Hz, 1H), 5.97 (s, 2H), 4.78 (s, 1H), 3.57-3.54 (m, 5H), 3.49 (s, 3H), 3.32 (brs, 2H), 3.16-3.12 (m, 2H), 2.63-2.61 (m, 2H), 2.36-2.33 (m, 6H), 2.18-2.11 (m, 2H), 2.06-2.01 (m, 2H), 1.85-1.81 (m, 2H), 1.47-1.36 (m, 4H).

TABLE 10

The compounds in table 10 were synthesized according to the procedure described for 5-Amino-N-(3-chloro-4-fluorophenyl)-3-(5-hydroxy-5-(((3-morpholinopropyl)sulfonyl)methyl)octahydropentalen-2-yl)-1-methyl-1H-pyrazole-4-carboxamide, diastereomers 1 and 2.

Compound   Structure and characterization

AIA-349

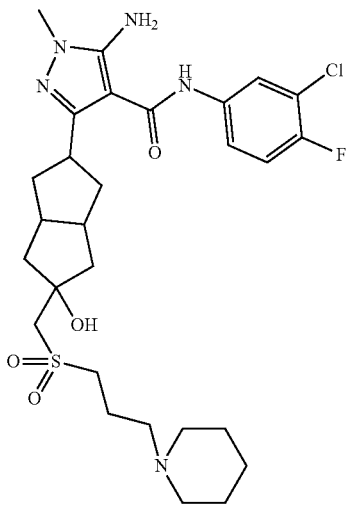 [SMILES: Cn1nc(C2CC3CC(O)(CS(=O)(=O)CCCN4CCCCC4)CC3C2)c(C(=O)Nc2ccc(F)c(Cl)c2)c1N]

5-Amino-N-(3-chloro-4-fluorophenyl)-3-(5-hydroxy-5-(((3-(piperidin-1-yl)propyl)sulfonyl)methyl)octahydropentalen-2-yl)-1-methyl-1H-pyrazole-4-carboxamide, Diastereomer 1. (AIA-349). MS Calcd.: 595.24; MS Found: 596.2 [M + 1]$^+$; $^1$H NMR (DMSO-d$_6$, 400 MHz): δ 8.91 (s, 1H), 7.89 (dd, J = 2.8 Hz, 7.2Hz , 1H), 7.50-7.47 (m, 1H), 7.32 (t, J = 9.2 Hz, 1H), 5.95 (s, 2H), 4.85 (s, 1H), 3.46 (s, 3H), 3.40-3.34(m, 2H), 3.20 (s, 1H), 3.20-3.08 (m, 2H), 2.40 (m, 1H), 2.29-2.26 (m, 6H), 2.13-2.08 (m, 2H), 2.00-1.95 (m, 2H), 1.83-1.76 (m, 2H), 1.73-1.55 (m, 4H), 1.47-1.42 (m, 4H), 1.35-1.34 (m, 2H).

AIA-349-B

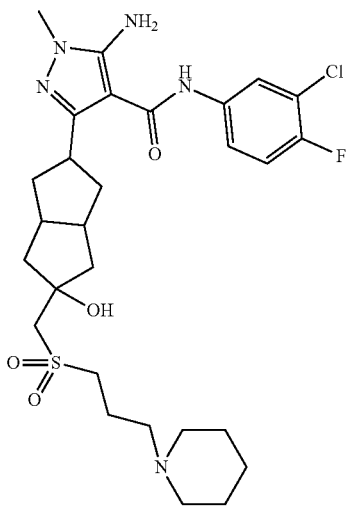 [SMILES: Cn1nc(C2CC3CC(O)(CS(=O)(=O)CCCN4CCCCC4)CC3C2)c(C(=O)Nc2ccc(F)c(Cl)c2)c1N]

5-Amino-N-(3-chloro-4-fluorophenyl)-3-(5-hydroxy-5-(((3-(piperidin-1-yl)propyl)sulfonyl)methyl)octahydropentalen-2-yl)-1-methyl-1H-pyrazole-4-carboxamide, Diastereomer 2. (AIA-349-B). MS Calcd.: 595.24; MS Found: 596.2 [M + 1]$^+$; $^1$H NMR (DMSO-d$_6$, 400 MHz): δ 8.95 (s, 1H), 7.91 (dd, J = 2.8 Hz, 6.8 Hz, 1H), 7.54-7.50 (m, 1H), 7.35 (s, J = 9.2 Hz, 1H), 5.98 (s, 2H), 4.78 (s, 1H), 3.56-3.55 (m, 1H), 3.49 (s, 3H), 3.33 (brs, 2H), 3.14-3.10 (m, 2H), 2.62-2.60 (m, 2H), 2.32-2.28 (m, 6H), 2.16-2.13 (m, 2H), 2.06-2.01 (m, 2H), 1.83-1.79 (m, 2H), 1.50-1.36 (m, 10H).

TABLE 10-continued

The compounds in table 10 were synthesized according to the procedure described for 5-Amino-N-(3-chloro-4-fluorophenyl)-3-(5-hydroxy-5-(((3-morpholinopropyl)sulfonyl)methyl)octahydropentalen-2-yl)-1-methyl-1H-pyrazole-4-carboxamide, diastereomers 1 and 2.

| Compound | Structure and characterization |
|---|---|
| AIA-350 | 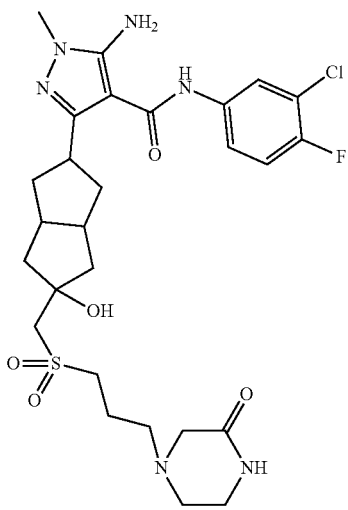 [SMILES: Cn1nc(C2CC3CC(O)(CS(=O)(=O)CCCN4CCNC(=O)C4)CC3C2)c(C(=O)Nc2ccc(F)c(Cl)c2)c1N]<br>5-Amino-N-(3-chloro-4-fluorophenyl)-3-(5-hydroxy-5-(((3-(3-oxopiperazin-1-yl)propyl)sulfonyl)methyl)octahydropentalen-2-yl)-1-methyl-1H-pyrazole-4-carboxamide. Diastereomer 1 (AIA-350). MS Calcd.: 610.21; MS Found: 611.2 [M + 1]$^+$; $^1$H NMR (CDCl$_3$, 400 MHz) δ 7.80 (dd, J = 2.4 Hz, 6.8 Hz, 1H), 7.43-7.39 (m, 1H), 7.19 (t, J = 8.8 Hz, 1H), 4.72 (brs, 1H), 4.60 (s, 1H), 3.55 (s, 3H), 3.47-3.37(m, 2H), 3.25 (brs, 6H), 3.12 (s, 2H), 2.69-2.63 (m, 4H), 2.59-2.55 (m, 2H), 2.31-2.26 (m, 2H), 2.18-2.13(m, 2H), 2.05-1.97 (m, 2H), 1.84-1.74 (m, 4H). |
| AIA-350-b | 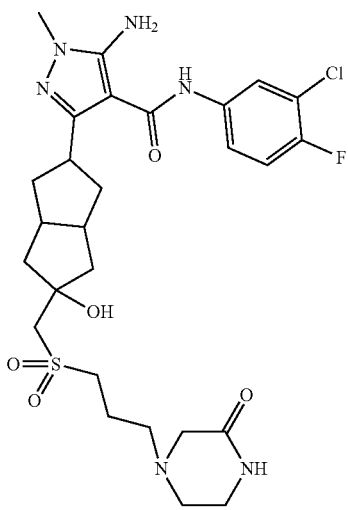 [SMILES: Cn1nc(C2CC3CC(O)(CS(=O)(=O)CCCN4CCNC(=O)C4)CC3C2)c(C(=O)Nc2ccc(F)c(Cl)c2)c1N]<br>5-Amino-N-(3-chloro-4-fluorophenyl)-3-(5-hydroxy-5-(((3-(3-oxopiperazin-1-yl)propyl)sulfonyl)methyl)octahydropentalen-2-yl)-1-methyl-1H-pyrazole-4-carboxamide. Diastereomer 2 (AIA-350-b): MS Calcd.: 610.21; MS Found: 611.2 [M + 1]$^+$; $^1$H NMR (DMSO-d$_6$, 400 MHz) δ 8.96 (s, 1H), 7.90 (dd, J = 2.4 Hz, 7.2 Hz, 1H), 7.73 (s, 1H), 7.54-7.50 (m, 1H), 7.35 (t, J = 9.2 Hz, 1H), 5.97 (s, 2H), 4.81 (s, 1H), 3.57-3.53 (m, 1H), 3.48 (s, 3H), 3.34 (s, 2H), 3.16-3.12 (m, 4H), 2.89 (s, 2H), 2.63-2.62 (m, 2H), 2.54-2.51 (m, 2H), 2.44-2.41 (m, 2H), 2.18-2.12 (m, 2H), 2.07-2.01 (m, 2H), 1.86-1.82 (m, 2H), 1.46-1.39 (m, 4H). |

TABLE 10-continued

The compounds in table 10 were synthesized according to the procedure described for 5-Amino-N-(3-chloro-4-fluorophenyl)-3-(5-hydroxy-5-(((3-morpholinopropyl)sulfonyl)methyl)octahydropentalen-2-yl)-1-methyl-1H-pyrazole-4-carboxamide, diastereomers 1 and 2.

| Compound | Structure and characterization |
| --- | --- |

AIA-351-1

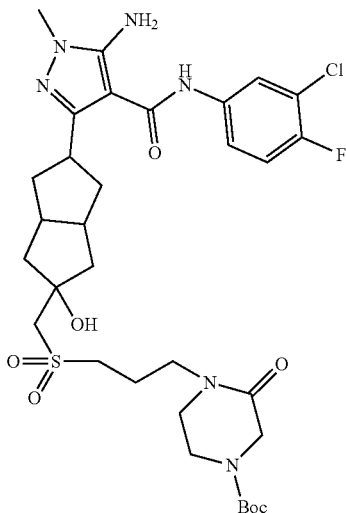 [SMILES: Cn1nc(C2CC3CC(O)(CS(=O)(=O)CCCN4CCN(C(=O)OC(C)(C)C)CC4=O)CC3C2)c(C(=O)Nc2ccc(F)c(Cl)c2)c1N]

tert-Butyl 4-(3-((45-(5-amino-4-((3-chloro-4-fluorophenyl)carbamoyl)-1-methyl-1H-pyrazol-3-yl)-2-hydroxyortahydropentalen-2-yl)methyl)sulfonyl)propyl)-3-oxopiperazine-1-carboxylate. Diastereomer 1 (AIA-351-1). MS Calcd.: 710.27; MS Found: 711.3 [M + 1]$^+$.

AIA-269-1

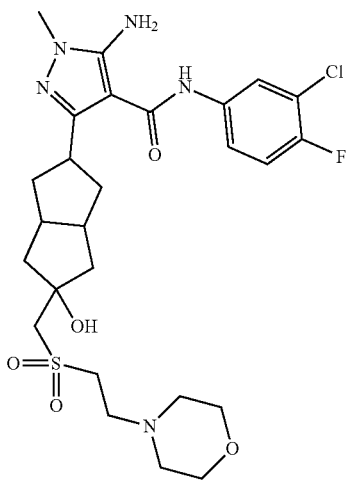 [SMILES: Cn1nc(C2CC3CC(O)(CS(=O)(=O)CCN4CCOCC4)CC3C2)c(C(=O)Nc2ccc(F)c(Cl)c2)c1N]

5-Amino-N-(3-chloro-4-fluorophenyl)-3-(5-hydroxy-5-(((2-morpholinoethyl)sulfonyl)methyl)octahydropentalen-2-yl)-1-methyl-1H-pyrazole-4-carboxamide. Diastereomer 1. (AIA-269-1): MS Calcd.: 583.20; MS Found: 584.20 [M + 1]$^+$; $^1$H NMR (DMSO-d$_6$, 400 MHz) δ 7.80 (dd, J = 6.4, 2.4, 1H), 7.43-7.39 (m, 1H), 7.18 (t, J = 9.2, 1H), 4.91 (s, 1H), 3.69-3.66 (m, 4H), 3.46 (s, 3H), 3.47-3.36 (m, 7H), 2.85-2.82 (m, 2H), 2.64-2.51 (m, 7H), 2.33-2.27 (m, 2H), 2.19-2.14 (m, 2H), 1.84-1.74 (m, 4H).

AIA-351-A

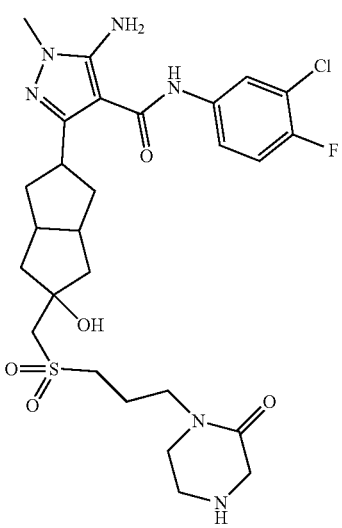

5-Amino-N-(3-chloro-4-fluorophenyl)-3-(5-hydroxy-5-(((3-(2-oxopiperazin-1-yl)propyl)sulfonyl)methyl)octahydropentalen-2-yl)-1-methyl-1H-pyrazole-4-carboxamide. A solution of tert-Butyl 4-(3-(((5-(5-amino-4-((3-chloro-4-fluorophenyl)carbamoyl)-1-methyl-1H-pyrazol-3-yl)-2-hydroxyoctahydropentalen-2-yl)methyl)sulfonyl)propyl)-3-oxopiperazine-1-carboxylate, diastereomer 1 (50.0 mg, 0.08 mmol) in HCl/CH$_3$OH (5 mL), was stirred at r.t. for 1 h, After the reaction was completed, the solvent was removed under reduced pressure, and the resulting residue purified by Prep-HPLC to afford 5-amino-N-(3-chloro-4-fluorophenyl)-3-(5-hydroxy-5-(((3-(2-oxopiperazin-1-yl)propyl)sulfonyl)methyl)octahydropentalen-2-yl)-1-methyl-1H-pyrazole-4-carboxamide. (10.0 mg, 47.6%) as a white solid. MS Calcd.: 610.21; MS Found: 611.1 [M+1]$^+$; $^1$H NMR (DMSO-d$_6$, 400 MHz): δ 8.92 (s, 1H), 7.89 (dd, J=2.8 Hz, 7.2 Hz, 1H), 7.51-7.47 (m, 1H), 7.33 (t, J=5.2 Hz, 1H), 5.95 (s, 2H), 4.96-4.94 (m, 1H), 4.87 (s, 1H), 3.47 (s, 3H), 3.45-3.36 (m, 3H), 3.33-3.32 (m, 1H), 3.29-3.28 (m, 1H), 3.18-3.12 (m, 5H), 2.83-2.82 (m, 2H), 2.47 (brs, 2H), 2.14-2.09 (m, 2H), 2.02-1.93 (m, 2H), 1.70-1.59 (m, 4H), 1.16 (d, J=6.8 Hz, 3H).

AIA-259-A, AIA-259-B

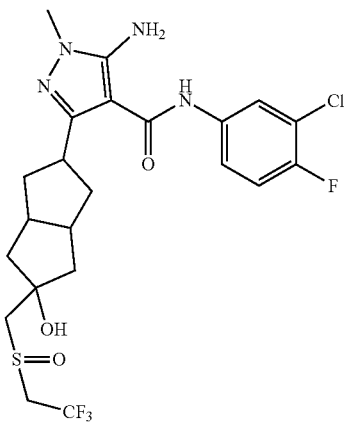

5-Amino-N-(3-chloro-4-fluorophenyl)-3-((2r,5r)-5-hydroxy-5-((2,2,2-trifluoroethylsulfinyl) methyl)octahydropentalen-2-yl)-1-methyl-1H-pyrazole-4-carboxamide Diastereomer 1 (AIA-259-A), Diastereomer 2 (AIA-259-B). To a solution of 5-amino-N-(3-chloro-4-fluorophenyl)-3-(5-hydroxy-5-(((2,2,2-trifluoroethyl)thio)methyl)octahydropentalen-2-yl)-1-methyl-1H-pyrazole-4-carboxamide, diastereomer 1 (100 mg, 0.2 mmol) in dry DCM (10 mL) was added m-CPBA (99 mg, 0.6 mmol), and the mixture stirred at RT for 4 hours. The solvent was removed under reduced pressure, and the residue purified by prep-HPLC to afford AIA-259-1 This was purified further by chiral-HPLC to give AIA-259-A (9 mg) and AIA-259-B (12 mg). AIA-259-A: $^1$H NMR (DMSO-d6, 400 MHz): δ 8.95 (s, 1H), 7.91 (dd, J=6.8, 2.4 Hz, 1H), 7.54-7.51 (m, 1H), 7.35 (t, J=9.2 Hz, 1H), 5.98 (s, 2H), 4.91 (s, 1H) 4.06-3.89 (m, 2H), 3.59-3.56 (m, 1H), 3.49 (s, 3H), 3.16 (dd, J=28.8, 13.6 Hz, 2H), 2.68-2.62 (m, 2H), 2.18-2.14 (m, 2H), 2.08-2.00 (m, 1H), 1.92-1.89 (m, 1H) 1.49-1.37 (m, 4H). AIA-259-B: $^1$H NMR (DMSO-d6, 400 MHz): δ 8.95 (s, 1H), 7.91 (dd, J=6.8, 2.4 Hz, 1H), 7.54-7.50 (m, 1H), 7.35 (t, J=9.2 Hz, 1H), 5.98 (s, 2H), 4.91 (s, 1H) 4.03-3.89 (m, 2H), 3.58-3.56 (m, 1H), 3.49 (s, 3H), 3.22-3.11 (m, 2H), 2.68-2.62 (m, 2H), 2.18-2.14 (m, 2H), 2.08-2.00 (m, 2H), 1.92-1.89 (m, 2H), 1.49-1.37 (m, 4H).

AIA-259-C, AIA-259-D

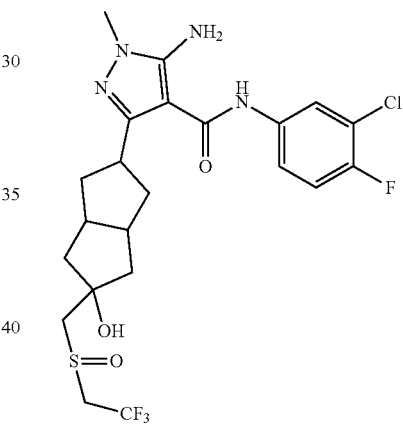

5-Amino-N-(3-chloro-4-fluorophenyl)-3-((2r,5r)-5-hydroxy-5-((2,2,2-trifluoroethylsulfinyl) methyl)octahydropentalen-2-yl)-1-methyl-1H-pyrazole-4-carboxamide Diastereomer 3 (AIA-259-C), Diastereomer 4 (AIA-259-D). To a solution of 5-amino-N-(3-chloro-4-fluorophenyl)-3-(5-hydroxy-5-(((2,2,2-diastereomer 2 (200 mg, 0.4 mmol) in dry DCM (10 mL) was added m-CPBA (331 mg, 1.9 mmol), and the mixture was stirred at RT for 4 hours. After the starting material was consumed completely, the solvent was removed under reduced pressure, and the residue was purified by prep-HPLC to afford AIA-259-2 which was further purified by chiral-HPLC to give AIA-259-C (6 mg) and AIA-259-D (6 mg). AIA-259-C: $^1$H NMR (DMSO-d6, 400 MHz): δ 8.96 (s, 1H), 7.92 (dd, J=7.2, 2.8 Hz, 1H), 7.54-7.50 (m, 1H), 7.35 (t, J=9.2 Hz, 1H), 5.98 (s, 2H), 4.99 (s, 1H) 4.05-3.90 (m, 2H), 3.49 (s, 3H), 3.45-3.39 (m, 1H), 3.10 (dd, J=16.8, 13.2 Hz, 2H), 2.33-2.32 (m, 2H), 2.14-2.12 (m, 2H), 2.07-2.02 (m, 1H), 1.89-1.82 (m, 1H), 1.69-1.56 (m, 4H). AIA-259-D: $^1$H NMR (DMSO-d6, 400 MHz): δ 8.96 (s, 1H), 7.91 (dd, J=6.8, 2.4 Hz, 1H), 7.54-7.50 (m, 1H), 7.35 (t, J=9.2 Hz, 1H), 5.98 (s, 2H), 4.99 (s, 1H) 4.02-3.90 (m, 2H), 3.49 (s, 3H), 3.44-3.37 (m, 1H), 3.10 (dd, J=16.8, 13.6

Hz, 2H), 2.44-2.33 (m, 2H), 2.14-2.12 (m, 2H), 2.07-2.02 (m, 1H), 1.88-1.82 (m, 1H), 1.69-1.56 (m, 4H).

5-Amino-N-(3-chloro-4-fluorophenyl)-3-(5-hydroxy-5-(isopropoxymethyl)octahydropentalen-2-yl)-1-methyl-1H-pyrazole-4-carboxamide. Diastereomer 1 (AIA-339-1), Diastereomer 2 (AIA-339-2). A mixture of 5-amino-N-(3-chloro-4-fluorophenyl)-3-(hexahydro-1'H-spiro[oxirane-2,2'-pentalen]-5'-yl)-1-methyl-1H-pyrazole-4-carboxamide (420 mg crude, 1.0 mmol) and sodium propan-2-olate (410 mg, 5.0 mmol) in iPrOH (20 mL) was stirred at reflux overnight. The reaction mixture was purified by Prep-HPLC to afford AIA-339-1 (9 mg, 2%) as a white solid and compound AIA-339-2 (10 mg, 2%) as a white solid. AIA-339-1: MS Calcd.: 464.20; MS Found: 465.3 [M+H]$^+$. $^1$H-NMR (d$_6$-DMSO, 400 MHz): δ 8.92 (s, 1H), 7.90 (dd, J=6.8, 2.4 Hz, 1H), 7.52-7.48 (m, 1H), 7.33 (t, J=9.2 Hz, 1H), 5.95 (s, 2H), 4.07 (s, 1H), 3.52-3.45 (m, 5H), 3.20 (s, 2H), 2.63-2.60 (m, 2H), 2.13-2.09 (m, 2H), 1.67-1.61 (m, 2H), 1.39-1.34 (m, 4H), 1.05 (d, J=6.0 Hz, 6H). AIA-339-2: MS Calcd.: 464.20; MS Found: 465.3 [M+H]$^+$. $^1$H-NMR (d$_6$-DMSO, 400 MHz): δ 8.90 (s, 1H), 7.89 (dd, J=6.8, 2.8 Hz, 1H), 7.51-7.46 (m, 1H), 7.32 (t, J=9.2 Hz, 1H), 5.95 (s, 2H), 4.13 (s, 1H), 3.51-3.47 (m, 4H), 3.38-3.35 (m, 1H), 3.15 (s, 2H), 2.40-2.39 (m, 2H), 2.13-2.06 (m, 2H), 1.80-1.86 (m, 2H), 1.72-1.66 (m, 2H), 1.34-1.30 (m, 2H), 1.05 (d, J=6.4 Hz, 6H).

AIA-339-1, AIA-339-2

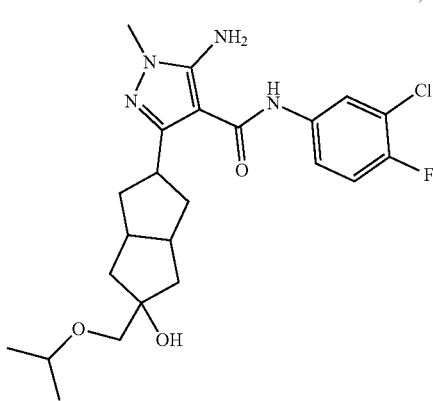

TABLE 11

The compounds in table 11 were synthesized according to the procedure described for 5-amino-N-(3-chloro-4-fluorophenyl)-3-(5-hydroxy-5-(isopropoxymethypoctahydropentalen-2-yl)-1-methyl-1H-pyrazole-4-carboxamide

| Compound | Structure and characterization |
|---|---|
| AIA-254 | 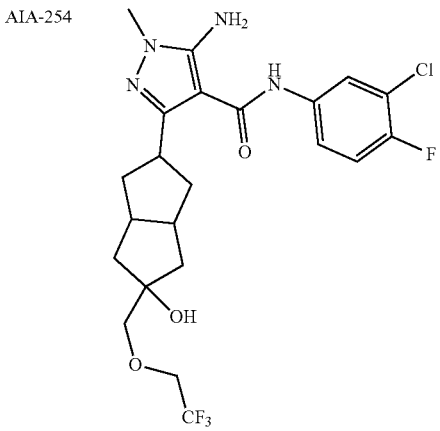<br>5-Amino-N-(3-chloro-4-fluorophenyl)-3-((2s,5s)-5-hydroxy-5-((2,2,2-trifluoroethoxy)methyl)octahydropentalen-2-yl)-1-methyl-1H-pyrazole-4-carboxamide MS Calcd.: 504.1; MS Found: 505.1 [M + 1]$^+$. $^1$H NMR (DMSO-d$_6$, 400 MHz): δ 8.93 (s, 1H), 7.91 (dd, J = 7.2, 2.8 Hz, 1H), 7.53-7.49 (m, 1H), 7.34 (t, J = 9.2 Hz, 1H), 5.97 (s, 2H), 4.46 (s, 1H), 4.08 (q, J = 9.2 Hz, 2H), 3.49 (s, 3H), 3.42 (s, 2H), 3.40-3.37 (m, 1H), 2.45-2.41 (m, 2H), 2.16-2.09 (m, 2H), 1.87-1.82 (m, 2H), 1.71-1.63 (m, 2H), 1.41-1.36 (m, 2H); |

TABLE 11-continued

The compounds in table 11 were synthesized according to the procedure described for 5-amino-N-(3-chloro-4-fluorophenyl)-3-(5-hydroxy-5-(isopropoxymethyoctahydropentalen-2-yl)-1-methyl-1H-pyrazole-4-carboxamide

| Compound | Structure and characterization |
|---|---|
| AIA-168-A | 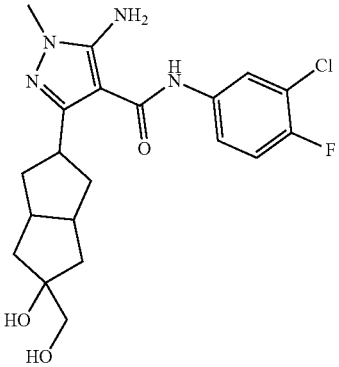 [SMILES: Cn1nc(C2CC3CC(O)(CO)CC3C2)c(C(=O)Nc2ccc(F)c(Cl)c2)c1N]<br>5-Amino-N-(3-chloro-4-fluorophenyl)-3-(5-hydroxy-5-(hydroxymethyl)octahydropentalen-2-yl)-1-methyl-1H-pyrazole-4-carboxamide. Diastereomer 1 (AIA-168-A). $^1$H NMR (DMSO-d$_6$, 400 MHz): δ 8.92 (brs, 1H), 7.89 (dd, 1H, J = 6.8 Hz, 2.8 Hz, 1H), 7.52-7.48 (m, 1H), 7.33 (t, J = 9.2 Hz, 1H), 5.95 (brs, 2H), 4.50 (t, J = 5.6 Hz, 1H), 4.00 (brs, 1H), 3.50-3.47 (m, 4H), 3.22 (d, J = 5.6 Hz, 2H), 2.65-2.61 (m, 2H), 2.14-2.08 (m, 2H), 1.62-1.57 (m, 2H), 1.40-1.31 (m, 4H). AIA-168-A MS Calcd.: 422.2; MS Found: 423.3 [M + 1]$^+$. |
| AIA-168-B | 5-Amino-N-(3-chloro-4-fluorophenyl)-3-(5-hydroxy-5-(hydroxymethyl)octahydropentalen-2-yl)-1-methyl-1H-pyrazole-4-carboxamide. Diastereomer 2 (AIA-168-B). $^1$H NMR (DMSO-d$_6$, 400 MHz): δ 8.90 (brs, 1H), 7.89 (dd, 1H, J = 6.8 Hz, 2.8 Hz, 1H), 7.51-7.47 (m, 1H), 7.92 (t, J = 9.2 Hz, 1H), 6.00 (brs, 2H), 4.44 (t, J = 5.6 Hz, 1H), 4.07 (brs, 1H), 3.47 (s, 3H), 3.39-3.34 (m, 1H), 3.17 (d, J = 5.6 Hz, 2H), 2.42-2.36 (m, 2H), 2.13-2.09 (m, 2H), 1.85-1.80 (m, 2H), 1.70-1.65 (m, 2H), 1.31-1.27 (m, 2H). |
| AIA-225-A | 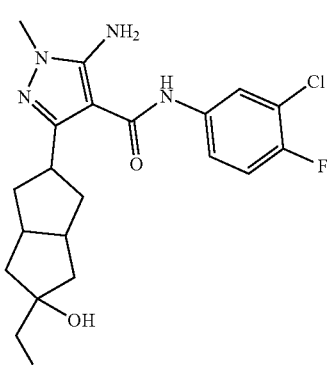<br>5-Amino-N-(3-chloro-4-fluorophenyl)-3-(5-hydroxy-5-(methoxymethyl)octahydropentalen-2-yl)-1-methyl-1H-pyrazole-4-carboxamide. Diastereomer 1. $^1$H-NMR (DMSO, 400 MHz): δ 8.94 (s, 1H), 7.91 (dd, J = 2.4, 2.8 Hz, 1H), 7.54-7.50 (m, 1H), 7.34 (t, J = 9.2 Hz, 1H), 5.97 (s, 2H), 4.22 (s, 1H), 3.56-3.52 (m, 1H), 3.48 (s, 3H), 3.28 (s, 3H), 3.20 (s, 2H), 2.67-2.60 (m, 2H), 2.15-2.12 (m, 2H), 1.71-1.66 (m, 2H), 1.41-1.34 (m, 4H). |
| AIA-225-B | 5-Amino-N-(3-chloro-4-fluorophenyl)-3-(5-hydroxy-5-(methoxymethyl)octahydropentalen-2-yl)-1-methyl-1H-pyrazole-4-carboxamide. Diastereomer 2. $^1$H-NMR (DMSO, 400 MHz): δ 8.92 (s, 1H), 7.91 (dd, J = 2.8, 2.8 Hz, 1H), 7.53-7.49 (m, 1H), 7.34 (t, J = 9.2 Hz, 1H), 5.97 (s, 2H), 4.27 (s, 1H), 3.49 (s, 3H), 3.40-3.36 (m, 1H), 3.25 (s, 3H), 3.15(s, 2H), 2.45-2.41 (m, 2H), 2.14-2.08 (m, 2H), 1.85-1.79 (m, 2H), 1.73-1.65 (m, 2H), 1.37 (dd, J = 2.8, 3.2 Hz, 2H). |

TABLE 11-continued

The compounds in table 11 were synthesized according to the procedure described for 5-amino-N-(3-chloro-4-fluorophenyl)-3-(5-hydroxy-5-(isopropoxymethypoctahydropentalen-2-yl)-1-methyl-1H-pyrazole-4-carboxamide

| Compound | Structure and characterization |
|---|---|
| AIA-363-1 | 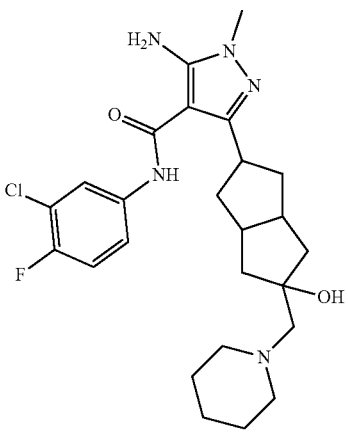 [SMILES: Cn1nc(C2CC3CC(O)(CN4CCCCC4)CC3C2)c(C(=O)Nc2ccc(F)c(Cl)c2)c1N]<br>5-Amino-N-(3-chloro-4-fluorophenyl)-3-(5-hydroxy-5-(piperidin-1-ylmethyl)octahydropentalen-2-yl)-1-methyl-1H-pyrazole-4-carboxamide. Diastereomer 1 (AIA-363-1) $^1$H NMR (DMSO-$d_6$, 400 MHz): δ 8.92 (s, 1H), 7.89 (dd, J = 7.2, 2.8 Hz, 1H), 7.52-7.48 (m, 1H), 7.33 (t, J = 9.2 Hz, 1H), 5.95 (s, 2H), 3.90 (s, 1H), 3.55-3.49 (m, 1H), 3.46 (s, 3H), 2.65-2.59 (m, 2H), 2.41-2.35 (m, 4H), 2.25 (s, 2H), 2.14-2.08 (m, 2H), 1.71-1.66 (m, 2H), 1.45-1.25 (m, 10H). |
| AIA-363-2 | 5-Amino-N-(3-chloro-4-fluorophenyl)-3-(5-hydroxy-5-(piperidin-1-ylmethyl)octahydropentalen-2-yl)-1-methyl-1H-pyrazole-4-carboxamide. Diastereomer 2 (AIA-363-2) $^1$H NMR (DMSO-$d_6$, 400 MHz): δ 8.92 (s, 1H), 7.90 (dd, J = 7.2, 2.8 Hz, 1H), 7.52-7.48 (m, 1H), 7.34 (t, J = 9.2 Hz, 1H), 5.97 (s, 2H), 4.08 (s, 1H), 3.49 (s, 3H), 3.43-3.36 (m, 1H), 2.43-2.32 (m, 6H), 2.20 (s, 2H), 2.15-2.08 (m, 2H), 1.86-1.81 (m, 2H), 1.69-1.61 (m, 2H), 1.47-1.45 (m, 4H), 1.35-1.31 (m, 4H). |
| AIA-364-1 | 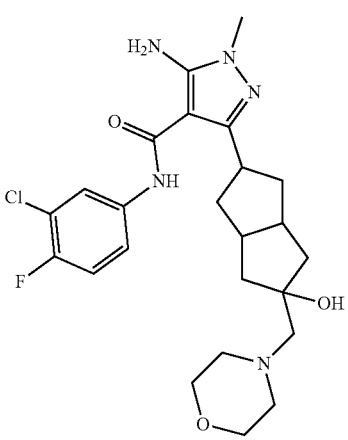 [SMILES: Cn1nc(C2CC3CC(O)(CN4CCOCC4)CC3C2)c(C(=O)Nc2ccc(F)c(Cl)c2)c1N]<br>5-Amin o-N-(3-chloro-4-fluorophenyl)-3-(5-hydroxy-5-(morpholinomethyl)octahydropentalen-2-yl)-1-methyl-1H-pyrazole-4-carboxamide Diastereomer 1 (AIA-364-1). $^1$H NMR (DMSO-$d_6$, 400 MHz): δ 8.92 (s, 1H), 7.90 (dd, J = 6.8, 2.4 Hz, 1H), 7.52-7.48 (m, 1H), 7.33 (t, J = 9.2 Hz, 1H), 5.95 (s, 2H), 3.96 (s, 1H), 3.53-3.50 (m, 5H), 3.46 (s, 3H), 2.65-2.59 (m, 2H), 2.45-2.44 (m, 4H), 2.31-2.30 (m, 2H), 2.14-2.08 (m, 2H), 1.77-1.72 (m, 2H), 1.41-1.25 (m, 4H). |
| AIA-364-2 | 5-Amino-N-(3-chloro-4-fluorophenyl)-3-(5-hydroxy-5-(morpholinomethyl)octahydropentalen-2-yl)-1-methyl-1H-pyrazole-4-carboxamide Diastereomer 2 (AIA-364-2). $^1$H NMR (DMSO-$d_6$, 400 MHz): δ 8.93 (s, 1H), 7.90 (dd, J = 6.8, 2.8 Hz, 1H), 7.52-7.48 (m, 1H), 7.34 (t, J = 9.2 Hz, 1H), 5.97 (s, 2H), 4.18 (s, 1H), 3.55-3.52 (m, 4H), 3.49 (s, 3H), 3.42-3.37 (m, 1H), 2.49-2.46 (m, 4H), 2.36-2.32 (m, 2H), 2.22 (s, 2H), 2.16-2.11 (m, 2H), 1.91-1.86 (m, 2H), 1.66-1.58 (m, 2H), 1.37-1.32 (m, 2H). |

AIA-217-3

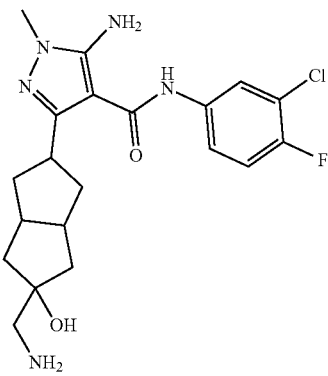

5-Amino-3-(5-(aminomethyl)-5-hydroxyoctahydropentalen-2-yl)-N-(3-chloro-4-fluorophenyl)-1-methyl-1H-pyrazole-4-carboxamide. To a solution of 5-amino-N-(3-chloro-4-fluorophenyl)-3-(hexahydro-1'H-spiro[oxirane-2,2'-pentalen]-5'-yl)-1-methyl-1H-pyrazole-4-carboxamide (200 mg, 0.495 mmol) in THF (5 mL) was added NH$_4$OH (5 mL). The mixture was stirred at room temperature overnight. The solvent was removed and purified by silica gel column chromatography using ethyl acetate to afford 5-amino-3-(5-(aminomethyl)-5-hydroxyoctahydropentalen-2-yl)-N-(3-chloro-4-fluorophenyl)-1-methyl-1H-pyrazole-4-carboxamide (80 mg, 38.4%) as white solid. MS Calcd.: 421.1; MS Found: 422.3 [M+1]$^+$ AIA-218-1 and AIA-218-2

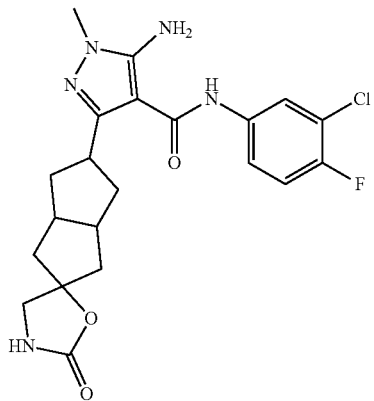

5-Amino-N-(3-chloro-4-fluorophenyl)-1-methyl-3-(2-oxohexahydro-1'H-Spiro[oxazolidine-5,2'-pentalen]-5'-yl)-1H-pyrazole-4-carboxamide. Diastereomer 1 (CP-AIA-218-1). Diastereomer 2(CP-AIA-218-2): To a solution of 5-amino-3-(5-(aminomethyl)-5-hydroxyoctahydropentalen-2-yl)-N-(3-chloro-4-fluorophenyl)-1-methyl-1H-pyrazole-4-carboxamide (80 mg, 0.19 mmol) in DCM (6 mL) was added CDI (43 mg, 0.266 mmol). The mixture was stirred at room temperature for 4 h. The solvent was removed and purified by silica gel column chromatography using DCM/ MeOH=3/1 to afford CP-AIA-218 (40 mg, 47.1%) as white solid. MS Calcd.: 447.1; MS Found: 448.2 [M+1]$^+$. CP-AIA-218 was separated by SFC to give CP-AIA-218-1 (4 mg) as a white solid and CP-AIA-218-2 (4 mg) as a white solid. CP-AIA-218-1: $^1$H-NMR (DMSO, 400 MHz): δ 8.95 (s, 1H), 7.92 (dd, J=2.4, 2.4 Hz, 1H), 7.55-7.51 (m, 1H), 7.37-7.33 (m, 2H), 5.98 (s, 2H), 3.62-3.56 (m, 1H), 3.49 (s, 3H), 3.38 (s, 2H), 2.67-2.61 (m, 2H), 2.22-2.10 (m, 4H), 1.55 (dd, J=8.0, 7.2 Hz, 2H), 1.50-1.42 (m, 2H). CP-AIA-218-2: $^1$H-NMR (DMSO, 400 MHz): δ 8.96 (s, 1H), 7.91 (dd, J=2.8, 2.4 Hz, 1H), 7.54-7.50 (m, 1H), 7.40-7.32 (m, 2H), 5.98 (s, 2H), 3.51 (s, 3H), 3.42-3.35 (m, 1H), 3.34 (s, 2H), 2.55 (s, 2H), 2.20-2.13 (m, 2H), 1.91 (dd, J=8.8, 8.0 Hz, 2H), 1.80-1.76 (m, 2H), 1.64-1.56 (m, 2H).

AIA-255-3 and AIA-255-4

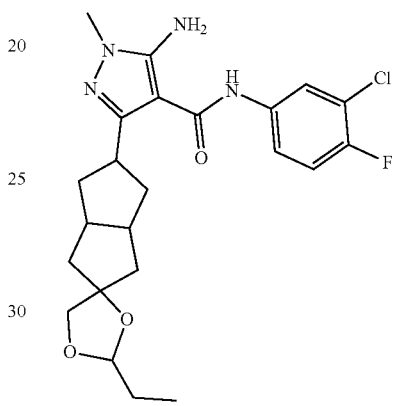

5-Amino-N-(3-chloro-4-fluorophenyl)-3-(2'-ethylhexahydro-1H-spiro[pentalene-2,4'-[1,3]dioxolan]-5-yl)-1-methyl-1H-pyrazole-4-carboxamide. Diastereomer 1 (CP-AIA-255-3), Diastereomer 2 (CP-AIA-255-4). To a solution of 5-amino-N-(3-chloro-4-fluorophenyl)-3-(hexahydro-1'H-spiro[oxirane-2,2'-pentalen]-5'-yl)-1-methyl-1H-pyrazole-4-carboxamide (200 mg, 0.49 mmol) in THF (3 mL) was added cyclopropanol (287 mg, 4.90 mmol). The mixture was cooled to 0° C. and H$_2$SO$_4$ (conc., 1 drop) was added. The resulting mixture was stirred at 0° C. for 1 h, and warmed to RT for 1 h, followed by quenching with Na$_2$CO$_3$ solution and extraction with ethyl acetate (15 mL×3). The organic layer was dried and concentrated, and the residue was purified by prep-TLC then prep-HPLC to afford CP-AIA-255-3 (5 mg, 2.2%) and CP-AIA-255-4 (3 mg, 0.7%) as white solid. CP-AIA-255-3: MS Calcd.: 462.2. $^1$H-NMR (DMSO-d$_6$, 400 MHz): δ 8.94 (s, 1H), 7.91 (dd, J=6.8, 2.4 Hz, 1H), 7.54-7.50 (m, 1H), 7.34 (t, J=9.2 Hz, 1H), 5.97 (s, 2H), 4.79 (t, J=4.8 Hz, 1H), 3.70 (dd, J=34.8, 8.0 Hz, 2H), 3.57-3.51 (m, 1H), 3.48 (s, 3H), 2.62-2.58 (m, 2H), 2.19-2.13 (m, 2H), 2.05-2.00 (m, 1H), 1.93-1.88 (m, 1H), 1.56-1.49 (m, 3H), 1.45-1.38 (m, 3H), 0.84 (t, J=7.2 Hz, 3H); MS Found: 463.2 [M+1]$^+$. CP-AIA-255-4: $^1$H-NMR (DMSO-d$_6$, 400 MHz): δ 8.95 (s, 1H), 7.91 (dd, J=6.8, 2.4 Hz, 1H), 7.53-7.49 (m, 1H), 7.34 (t, J=9.2 Hz, 1H), 5.96 (s, 2H), 4.80 (t, J=4.4 Hz, 1H), 3.65 (dd, J=48.4, 8.0 Hz, 2H), 3.48 (s, 3H), 3.42-3.37 (m, 1H), 2.45-2.41 (m, 2H), 2.15-2.12 (m, 2H), 1.87-1.77 (m, 2H), 1.65-1.48 (m, 6H), 0.84 (t, J=7.2 Hz, 3H) MS Calcd.: 462.2; MS Found: 463.2 [M+1]$^+$.

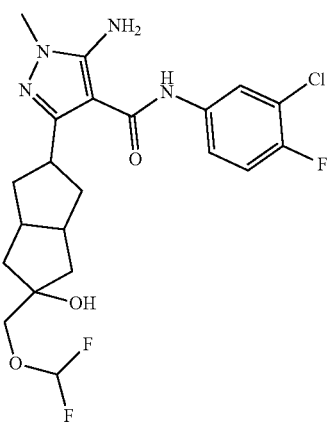

AIAI-253

5-Amino-N-(3-chloro-4-fluorophenyl)-3-(5-((difluoromethoxy)methyl)-5-hydroxyoctahydropentalen-2-yl)-1-methyl-1H-pyrazole-4-carboxamide. To a solution of 5-amino-N-(3-chloro-4-fluorophenyl)-3-(5-hydroxy-5-(hydroxymethyl)octahydropentalen-2-yl)-1-methyl-1H-pyrazole-4-carboxamide. (480 mg, 1.14 mmol) in CHCl$_3$/H$_2$O (20 mL/4 mL) was added KHF$_2$ (450 mg, 5.7 mmol) and (bromodifluoromethyl)trimethylsilane (1.2 g, 5.7 mmol). The mixture was stirred at RT overnight. The solvent was removed, and the product purified by silica gel column chromatography using 1:1 ethyl acetate/petroleum ether to afford 5-amino-N-(3-chloro-4-fluorophenyl)-3-(5-((difluoromethoxy)methyl)-5-hydroxyoctahydropentalen-2-yl)-1-methyl-1H-pyrazole-4-carboxamide (1.4 mg, 0.3%) as white solid. MS Calcd.: 472.15; MS Found: 473.3 [M+H]$^+$. $^1$H-NMR (DMSO, 400 MHz): δ 8.95 (s, 1H), 7.90-7.93 (dd, J=6.8, 2.4 Hz, 1H), 7.54-7.50 (m, 1H), 7.35 (t, J=9.2 Hz, 1H), 6.66 (t, J=76 Hz, 1H), 5.98 (s, 2H), 4.54 (s, 1H), 3.69 (s, 2H), 3.59-3.51 (m, 1H), 3.49 (s, 3H), 2.70-2.64 (m, 2H), 2.18-2.12 (m, 2H), 1.79-1.74 (m, 2H), 1.41-1.34 (m, 4H).

AIA-267-1, AIA-267-2

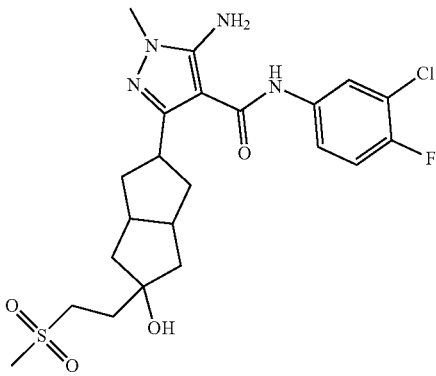

5-Amino-N-(3-chloro-4-fluorophenyl)-3-(5-hydroxy-5-(2-(methylsulfonyl)ethyl)octahydropentalen-2-yl)-1-methyl-1H-pyrazole-4-carboxamide. Diastereomer 1 (AIA-267-1), Diastereomer 2 (AIA-267-2): To a solution of dimethylsulfone (1.5 g, 15.8 mmol) in dry THF (20 mL) was added a solution of n-BuLi in THF (6.3 mL, 15.8 mmol, 2.5 M) slowly at −78° C., and the mixture was stirred at this temperature for 1 hour. A solution of 5-amino-N-(3-chloro-4-fluorophenyl)-3-(hexahydro-1′H-spiro[oxirane-2,2′-pentalene]-5′-yl)-1-methyl-1H-pyrazole-4-carboxamide (800.0 mg, 2.0 mmol) in THF (15 mL) was added slowly and the reaction was allowed to warm to RT and stirred overnight. After quenching with NH$_4$Cl (aq, 30 mL), the suspension was extracted with ethyl acetate (3×25 mL), dried over Na$_2$SO$_4$ and concentrated in vacuo to give the crude product. The crude product was purified by basic prep-HPLC to afford AIA-267-1 (42.0 mg, 4.2%) as a white solid and AIA-267-2 (34.0 mg, 3.4%) as a white solid. MS Calcd.: 499.0; MS Found: 500.2 [M+1]$^+$. AIA-267-1: $^1$H NMR (DMSO-d$_6$, 400 MHz) δ 8.96 (s, 1H), 7.92-7.90 (m, 1H), 7.54-7.50 (m, 1H), 7.35 (t, J=9.2 Hz, 1H), 5.99 (s, 2H), 4.33 (s, 1H), 3.56 (s, 1H), 3.49 (s, 3H), 3.13-3.09 (m, 2H), 2.96 (s, 3H), 2.66-2.64 (m, 2H), 2.16-2.13 (m, 2H), 1.89-1.80 (m, 4H), 1.45-1.40 (m, 2H), 1.30-1.24 (m, 2H). AIA-267-2: $^1$H NMR (DMSO-d$_6$, 400 MHz) δ 8.94 (s, 1H), 7.93-7.91 (m, 1H), 7.53-7.49 (m, 1H), 7.35 (t, J=9.2 Hz, 1H), 5.99 (s, 2H), 4.45 (s, 1H), 3.49 (s, 1H), 3.42-3.37 (m, 3H), 3.13-3.09 (m, 2H), 2.96 (s, 3H), 2.47-2.46 (m, 2H), 2.16-2.11 (m, 2H), 1.81-1.62 (m, 6H), 1.50-1.46 (m, 2H).

Intermediate 116

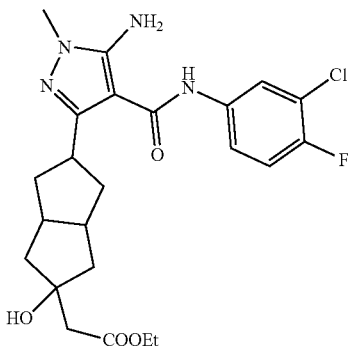

Ethyl 2-(5-(5-amino-4-((3-chloro-4-fluorophenyl)carbamoyl)-1-methyl-1H-pyrazol-3-yl)-2-hydroxyoctahydropentalen-2-yl)acetate. To a solution of EtOAc (338 mg, 3.9 mmol) in THF (15 mL) was added LDA (1.9 mL, 3.9 mmol) at −78° C. and the resulting solution stirred for 10 min. AIA-002 (300 mg, 0.8 mmol) was added and the mixture stirred at −78° C. for 4 h. The mixture was quenched with MeOH and the organic layer was concentrated in vacuo, and the residue was purified by silica gel column chromatography using 1:5 ethyl acetate/petroleum ether to afford ethyl 2-(5-(5-amino-4-((3-chloro-4-fluorophenyl)carbamoyl)-1-methyl-1H-pyrazol-3-yl)-2-hydroxyoctahydropentalen-2-yl)acetate (200 mg, 54%) as a white solid. MS Calcd.: 478.2; MS Found: 479.2 [M+1]$^+$.

AIA-241

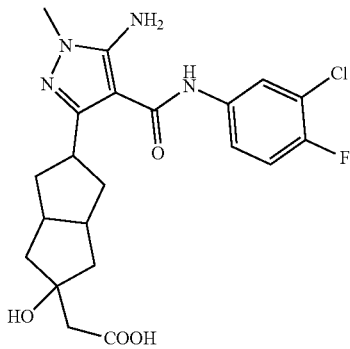

2-(5-(5-Amino-4-((3-chloro-4-fluorophenyl)carbamoyl)-1-methyl-1H-pyrazol-3-yl)-2-hydroxyoctahydropentalen-2-yl)acetic acid. To a solution of ethyl 2-(5-(5-amino-4-((3-chloro-4-fluorophenyl)carbamoyl)-1-methyl-1H-pyrazol-3-yl)-2-hydroxyoctahydropentalen-2-yl)acetate (200 mg, 0.5 mmol) in THF/H₂O (10/10 mL) was added LiOH—H₂O (21 mg, 0.5 mmol) and the mixture was stirred at 40° C. overnight. The mixture was extracted with ethyl acetate and the organic layer was concentrated in vacuo to afford 2-(5-(5-amino-4-((3-chloro-4-fluorophenyl)carbamoyl)-1-methyl-1H-pyrazol-3-yl)-2-hydroxyoctahydropentalen-2-yl)acetic acid. (200 mg) as a white solid. MS Calcd.: 450.1; MS Found: 451.2 [M+1]⁺. ¹H-NMR (DMSO, 400 MHz): δ 8.91 (s, 1H), 7.92 (dd, J=7.2, 2.8 Hz, 1H), 7.53-7.49 (m, 1H), 7.34 (t, J=9.2 Hz, 1H), 5.98 (s, 2H), 3.49 (s, 3H), 3.42-3.35 (m, 1H), 2.39 (s, 2H), 2.12-2.08 (m, 4H), 1.73-1.63 (m, 4H), 1.43-1.39 (m, 2H).

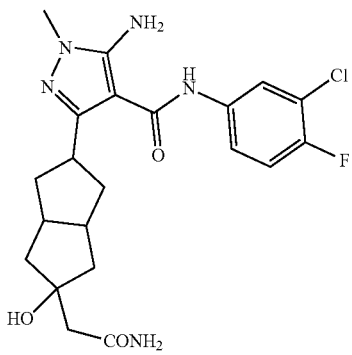

AIA-215

5-Amino-3-(5-(2-amino-2-oxoethyl)-5-hydroxyoctahydropentalen-2-yl)-N-(3-chloro-4-fluorophenyl)-1-methyl-1H-pyrazole-4-carboxamide. To a solution of 2-(5-(5-amino-4-((3-chloro-4-fluorophenyl)carbamoyl)-1-methyl-1H-pyrazol-3-yl)-2-hydroxyoctahydropentalen-2-yl)acetic acid (200 mg 0.4 mmol) in DMF(5 mL) was added HCOONH₄ (60 mg, 0.8 mmol), HATU (370 mg, 0.8 mmol) and Et₃N (88 mg, 0.8 mmol). The mixture was stirred at room temperature overnight. The mixture was extracted with ethyl acetate and washed with saturated NaCl. The organic layer was concentrated in vacuo, and the residue was purified by pre-HPLC to afford AIA-215 (94 mg, 46%) as a white solid. MS Calcd.: 449.2; MS Found: 450.2 [M+1]⁺. ¹H-NMR (DMSO-d₆, 400 MHz): δ 8.94 (s, 1H), 7.90 (dd, J=2.8, 4.4 Hz, 1H), 7.53-7.49 (m, 1H), 7.34 (t, J=8.8 Hz, 2H), 7.00 (s, 1H), 5.96 (s, 2H), 4.98 (s, 1H), 3.49 (s, 3H), 3.46-3.36 (m, 1H), 2.43 (d, J=11.6 Hz, 2H), 2.22 (s, 2H), 2.12 (t, J=5.6 Hz, 2H), 1.79 (dd, J=7.6, 12.0 Hz, 2H), 1.64 (t, J=8.8 Hz, 2H), 1.45 (dd, J=4.0, 12.8 Hz, 2H).

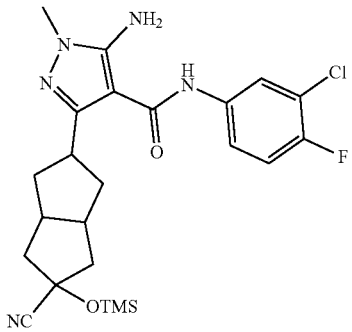

Intermediate 117

5-Amino-N-(3-chloro-4-fluorophenyl)-3-(5-cyano-5-(trimethylsilyloxy)octahydropentalen-2-yl)-1-methyl-1H-pyrazole-4-carboxamide. To a solution of AIA-002 (200 mg, 0.51 mmol) in trimethylsilyl cyanide (3.0 mL) was added ZnCl₂ (0.05 mL, 0.1 mmol, 2 M) and the mixture was stirred at 60° C. for 4 hours. The reaction mixture was diluted with water, extracted with ethyl acetate (3×20 mL), dried over Na₂SO₄, filtered and concentrated under reduced pressure. The residue was purified by column chromatography to afford 5-amino-N-(3-chloro-4-fluorophenyl)-3-(5-cyano-5-(trimethylsilyloxy)octahydropentalen-2-yl)-1-methyl-1H-pyrazole-4-carboxamide (180.0 mg, 72.2%) as yellow oil. MS Calcd.: 489.2, MS Found: 490.2 [M+1]⁺.

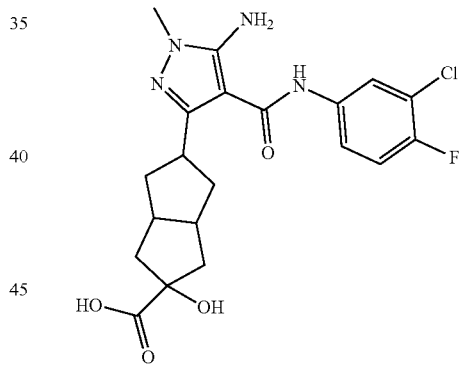

Intermediate 118

5-(5-Amino-4-(3-chloro-4-fluorophenylcarbamoyl)-1-methyl-1H-pyrazol-3-yl)-2-hydroxyoctahydropentalene-2-carboxylic acid. A mixture of 5-amino-N-(3-chloro-4-fluorophenyl)-3-(5-cyano-5-(trimethylsilyloxy)octahydropentalen-2-yl)-1-methyl-1H-pyrazole-4-carboxamide (180.0 mg, 0.37 mmol) and HCl (con.) (5 mL) was stirred at 60° C. for 4 hours. The reaction mixture was diluted with ice-cold water and neutralized with saturated NaHCO₃. The aqueous layer was removed under reduced pressure, and the residue was purified by column chromatography and basic prep-HPLC to afford 5-(5-amino-4-(3-chloro-4-fluorophenylcarbamoyl)-1-methyl-1H-pyrazol-3-yl)-2-hydroxyoctahydropentalene-2-carboxylic acid (90.0 mg, 55.8%) as white solid. MS Calcd.: 436.1, MS Found: 437.1 [M+1]⁺.

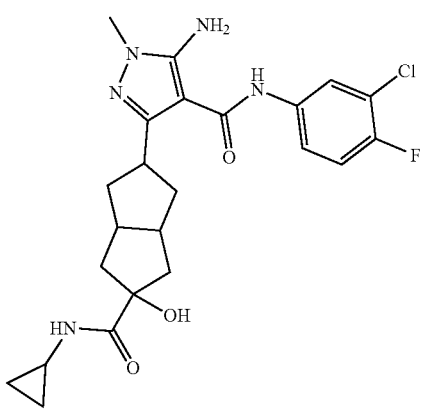

AIA-274-1, AIA-274-2

5-Amino-N-(3-chloro-4-fluorophenyl)-3-(5-(cyclopropylcarbamoyl)-5-hydroxyoctahydropentalen-2-yl)-1-methyl-1H-pyrazole-4-carboxamide. Diastereomer 1 (AIA-274-1), Diastereomer 2(AIA-274-2). To a solution of 5-(5-amino-4-(3-chloro-4-fluorophenylcarbamoyl)-1-methyl-1H-pyrazol-3-yl)-2-hydroxyoctahydropentalene-2-carboxylic acid (90.0 mg, 0.21 mmol) in DMF (3 mL) was added cyclopropylamine (12.9 mg, 0.23 mmol), HATU (119.7 mg, 0.32 mmol) and Et₃N (60.6 mg, 0.6 mmol). The reaction mixture was stirred at RT overnight. Water was added and the mixture extracted with ethyl acetate (15 mL×3), dried over Na₂SO₄, then concentration to give the crude product. The crude product was purified by prep-TLC followed by prep-HPLC to afford AIA-274-1 (10.0 mg, 10.0%) and AIA-274-2 (4.0 mg, 4.0%) as white solid. MS Calcd.: 475.2, MS Found: 476.2 [M+1]⁺. AIA-274-1: ¹H NMR (DMSO-d₆, 400 MHz): δ 8.91 (s, 1H), 7.92 (dd, J=6.8, 2.4 Hz, 1H), 7.60 (d, J=4.8, 1H), 7.53-7.49 (m, 1H), 7.35 (t, J=8.8 Hz, 1H), 5.99 (s, 2H), 5.06 (s, 1H), 3.48 (s, 3H), 3.40-3.36 (m, 1H), 2.67-260 (m, 3H), 2.10-2.05 (m, 4H), 1.82-1.74 (m, 2H), 1.56-1.53 (m, 2H), 0.61-0.56 (m, 2H), 0.49-0.45 (m, 2H).

AIA-274-2: ¹H NMR (DMSO-d₆, 400 MHz): δ 8.96 (s, 1H), 7.91 (dd, J=6.8, 2.4 Hz, 1H), 7.65 (d, J=4.8 Hz, 1H), 7.55-7.51 (m, 1H), 7.35 (t, J=9.2 Hz, 1H), 5.98 (s, 2H), 5.12 (s, 1H), 3.61-3.57 (m, 1H), 3.50 (s, 3H), 2.69-2.65 (m, 3H), 2.18-2.12 (m, 2H), 1.82-1.70 (m, 4H), 1.50-1.42 (m, 2H), 0.61-0.46 (m, 4H).

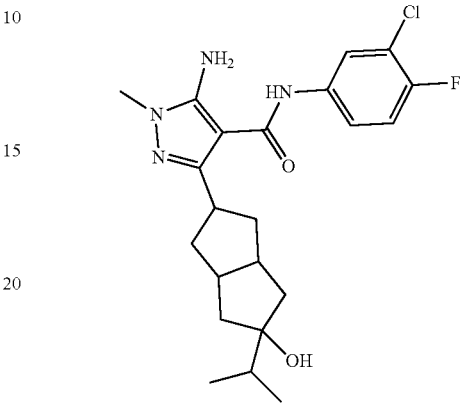

AIA-076

5-Amino-N-(3-chloro-4-fluorophenyl)-3-(5-hydroxy-5-isopropyloctahydropentalen-2-yl)-1-methyl-1H-pyrazole-4-carboxamide. Isopropyl magnesium chloride (1.3 mL, 2.55 mmol) was added slowly to a solution of AIA-002 (200 mg, 0.51 mmol) in anhydrous THF (5 mL) at −10° C. for 30 min. The reaction mixture was warmed to room temperature and was stirred for 2 h. Then this mixture was quenched with NH₄Cl (aq), and the solution extracted with DCM (10 mL×3). The combined organic layer was dried over Na₂SO₄, concentrated and purified by prep-HPLC to afford 5-amino-N-(3-chloro-4-fluorophenyl)-3-(5-hydroxy-5-isopropyloctahydropentalen-2-yl)-1-methyl-1H-pyrazole-4-carboxamide (6.6 mg, 3.1% yield) as a pale white solid. MS Calcd.: 434.1; MS Found: 435.2 [M+1]⁺.

TABLE 12

The compounds in table 12 were synthesized according to the procedure described for 5-amino-N-(3-chloro-4-fluorophenyl)-3-(5-hydroxy-5-isopropyloctahydropentalen-2-yl)-1-methyl-1H-pyrazole-4-carboxamide

| Compound | Structure and Characterization |
|---|---|
| AIA-077 | 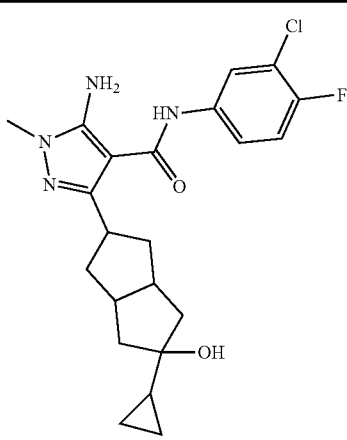 |

TABLE 12-continued

The compounds in table 12 were synthesized according to the procedure described for 5-amino-N-(3-chloro-4-fluorophenyl)-3-(5-hydroxy-5-isopropyloctahydropentalen-2-yl)-1-methyl-1H-pyrazole-4-carboxamide

| Compound | Structure and Characterization |
|---|---|

5-Amino-N-(3-chloro-4-fluorophenyl)-3-(5-cyclopropyl-5-hydroxyoctahydropentalen-2-yl)-1-methyl-1H-pyrazole-4-carboxamide. MS Calcd.: 432.1; MS Found: 433.2 [M + 1]+.

AIA-011

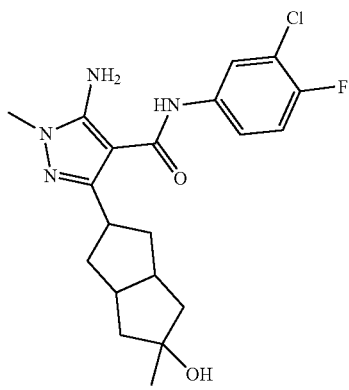 [SMILES: Cn1nc(C2CC3CC(C)(O)CC3C2)c(C(=O)Nc2ccc(F)c(Cl)c2)c1N]

5-Amino-N-(3-chloro-4-fluorophenyl)-3-(5-hydroxy-5-methyloctahydropentalen-2-yl)-1-methyl-1H-pyrazole-4-carboxamide. MS Calcd.: 406.8; MS Found: 407.7 [M + 1]+.

AIA-265

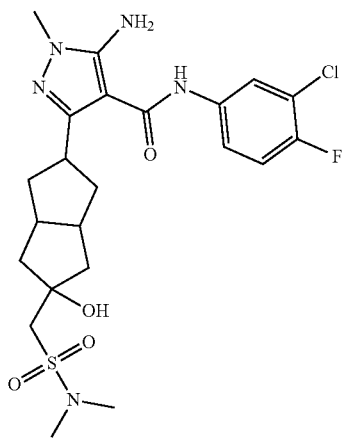 [SMILES: CN(C)S(=O)(=O)CC1(O)CC2CC(c3nn(C)c(N)c3C(=O)Nc3ccc(F)c(Cl)c3)CC2C1]

5-Amino-N-(3-chloro-4-fluorophenyl)-3-(5-((N,N-dimethylsulfamoyl)methyl)-5-hydroxyoctahydropentalen-2-yl)-1-methyl-1H-pyrazole-4-carboxamide. MS Calcd.: 513.2; MS Found: 514.2 [M + 1]+; $^1$H NMR (DMSO-$d_6$, 400 MHz): δ 7.71-7.68 (m, 1H), 7.34-7.27 (m, 2H), 7.11 (t, J = 8.8 Hz, 1H), 5.26 (s, 2H), 3.65 (s, 3H), 3.11 (s, 3H), 2.87 (s, 6H), 2.77-2.73 (m, 2H), 2.38-2.32 (m, 2H), 2.13-1.94 (m, 6H).

TABLE 12-continued

The compounds in table 12 were synthesized according to the procedure described for 5-amino-N-(3-chloro-4-fluorophenyl)-3-(5-hydroxy-5-isopropyloctahydropentalen-2-yl)-1-methyl-1H-pyrazole-4-carboxamide

| Compound | Structure and Characterization |
| --- | --- |

Intermediate 119

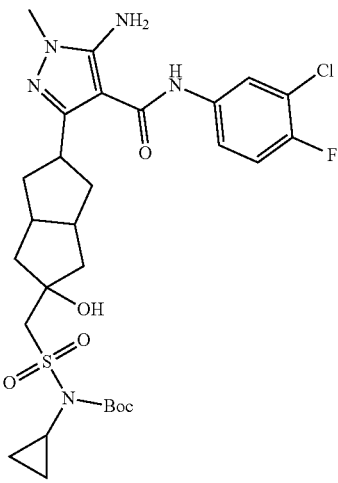 [SMILES: Cn1nc(C2CC3CC(O)(CS(=O)(=O)N(C(=O)OC(C)(C)C)C4CC4)CC3C2)c(C(=O)Nc2ccc(F)c(Cl)c2)c1N]

tert-Butyl (((5-(5-amino-4-((3-chloro-4-fluorophenyl)carbamoyl)-1-methyl-1H-pyrazol-3-yl)-2-hydroxyortahydropentalen-2-yl)methyl)sulfonyl)(cyclopropyl)carbamate. MS Calcd.: 625.2, MS Found: 626.2 [M + ]+.

AIA-273

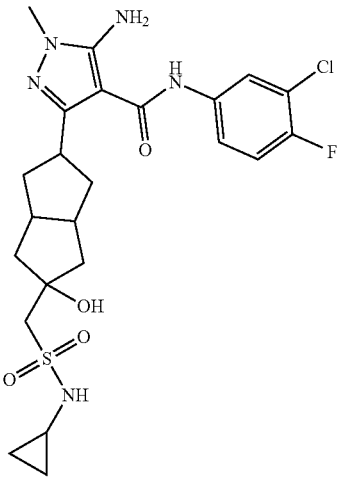 [SMILES: Cn1nc(C2CC3CC(O)(CS(=O)(=O)NC4CC4)CC3C2)c(C(=O)Nc2ccc(F)c(Cl)c2)c1N]

5-Amino-N-(3-chloro-4-fluorophenyl)-3-(5-((N-cyclopropylsulfamoyl)methyl)-5-hydroxyoctahydropentalen-2-yl)-1-methyl- 1H-pyrazole-4-carboxamide. MS Calcd.: 525.2, MS Found: 526.2 [M + ]+. $^1$H NMR (DMSO-$d_6$, 400 MHz): δ 8.94 (s, 1H), 7.92 (dd, J = 6.8, 2.4 Hz, 1H), 7.54-7.50 (m, 1H), 7.35 (t, J = 9.2 Hz, 1H), 7.11 (s, 1H), 5.98 (s, 2H), 4.55 (s, 1H), 3.49 (s, 3H), 3.41-3.35 (m, 1H), 3.25 (s, 2H), 2.15-2.08 (m, 2H), 2.02-1.97 (m, 2H), 1.79-1.71 (m, 2H), 1.66-1.63 (m, 2H), 0.57-0.51 (m ,4H).

TABLE 12-continued

The compounds in table 12 were synthesized according to the procedure
described for 5-amino-N-(3-chloro-4-fluorophenyl)-3-(5-hydroxy-5-
isopropyloctahydropentalen-2-yl)-1-methyl-1H-pyrazole-4-carboxamide

| Compound | Structure and Characterization |
| --- | --- |
| AIA-270 | 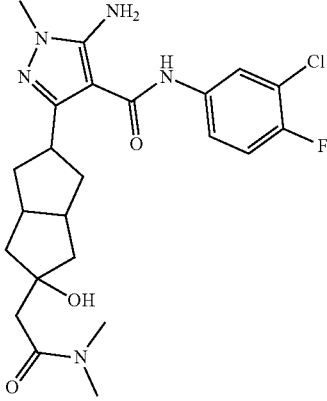 [SMILES: CN(C)C(=O)CC1(O)CC2CC(c3nn(C)c(N)c3C(=O)Nc3ccc(F)c(Cl)c3)CC2C1]<br>5-Amino-N-(3-chloro-4-fluorophenyl)-3-(5-(2-(dimethylamino)-2-oxoethyl)-5-hydroxyoctahydropentalen-2-yl)-1-methyl-1H-pyrazole-4-carboxamide. MS Calcd.:477.19; MS Found: 478.3 [M + H]$^+$; $^1$H NMR (DMSO-d$_6$, 400 MHz): δ 8.94 (s, 1H), 7.91 (dd, J = 6.8, 1.6 Hz, 1H), 7.52-7.50 (m, 1H), 7.35 (t, J = 9.2 Hz, 1H), 5.97 (s, 2H), 4.95 (s, 1H), 3.49 (s, 3H), 3.40-3.36 (m, 1H), 2.98 (s, 3H), 2.82 (s, 3H), 2.51-2.47 (m, 4H), 2.14-2.11 (m, 2H), 1.82-1.79 (m, 2H), 1.70-1.65 (m, 2H), 1.52-1.49 (m, 2H). |
| AIA-271 | 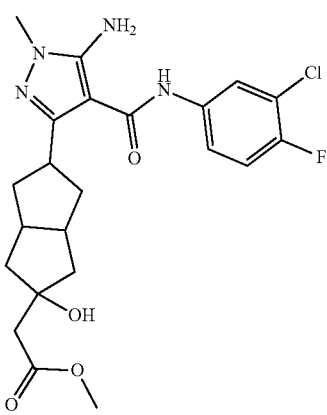 [SMILES: COC(=O)CC1(O)CC2CC(c3nn(C)c(N)c3C(=O)Nc3ccc(F)c(Cl)c3)CC2C1]<br>Methyl 2-(5-(5-amino-4-((3-chloro-4-fluorophenyl)carbamoyl)-1-methyl-1H-pyrazol-3-yl)-2-hydroxyoctahydropentalen-2-yl)acetate. MS Calcd.: 464.2; MS Found: 465.2 [M + 1]$^+$; $^1$H NMR (DMSO-d$_6$, 400 MHz): δ 8.93 (s, 1H), 7.91 (dd, J = 4.0, 2.8 Hz, 1H), 7.53-7.50 (m, 1H), 7.35 (t, J = 9.2 Hz, 1H), 5.97 (s, 2H), 4.49 (s, 1H), 3.56 (s, 3H), 3.48 (s, 3H), 3.40-3.37 (m, 1H), 2.44 (brs, 4H), 2.11-2.08 (m, 2H), 1.88-1.85 (m, 2H), 1.72-1.64 (m, 2H), 1.55-1.51 (m, 2H). |

Intermediate 120

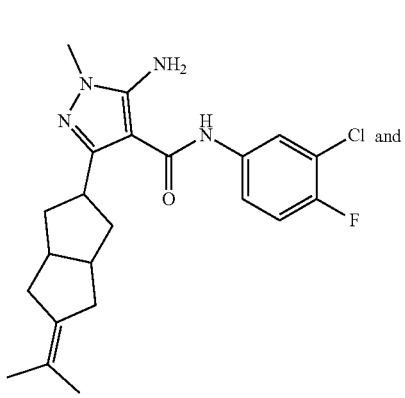

and

Intermediate 121

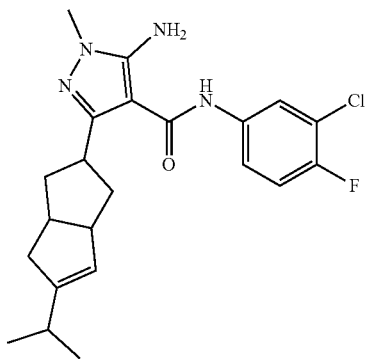

5-Amino-N-(3-chloro-4-fluorophenyl)-1-methyl-3-(5-(propan-2-ylidene)octahydropentalen-2-yl)-1H-pyrazole-4-carboxamide and 5-Amino-N-(3-chloro-4-fluorophenyl)-3-(5-isopropyl-1,2,3,3a,4,6a-hexahydropentalen-2-yl)-1-methyl-1H-pyrazole-4-carboxamide. To a solution of 5-amino-N-(3-chloro-4-fluorophenyl)-3-(5-hydroxy-5-isopropyloctahydropentalen-2-yl)-1-methyl-1H-pyrazole-4-carboxamide (600 mg, 1.38 mmol) in toluene (40 mL) was added p-methylbenzenesulfonic acid (48 mg, 0.28 mmol) at RT, and the mixture was stirred at reflux overnight. The resulting mixture was poured into water and extracted with ethyl acetate (40 mL×3). The organic layer was dried and concentrated, and the residue was purified by silica gel column chromatography to afford the mixture of 5-amino-N-(3-chloro-4-fluorophenyl)-1-methyl-3-(5-(propan-2-ylidene)octahydropentalen-2-yl)-1H-pyrazole-4-carboxamide and 5-amino-N-(3-chloro-4-fluorophenyl)-3-(5-isopropyl-1,2,3,3a,4,6a-hexahydropentalen-2-yl)-1-methyl-1H-pyrazole-4-carboxamide (180 mg). The mixture was separated by prep-chiral-HPLC to give compound to give 5-amino-N-(3-chloro-4-fluorophenyl)-1-methyl-3-(5-(propan-2-ylidene)octahydropentalen-2-yl)-1H-pyrazole-4-carboxamide MS Calcd.: 416.2; MS Found: 417.2 [M+1]$^+$. 5-amino-N-(3-chloro-4-fluorophenyl)-3-(5-isopropyl-1,2,3,3a,4,6a-hexahydropentalen-2-yl)-1-methyl-1H-pyrazole-4-carboxamide MS Calcd.: 416.2; MS Found: 417.2 [M+1]$^+$.

AIA-257

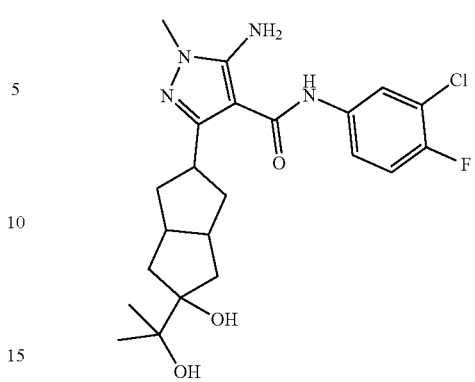

5-Amino-N-(3-chloro-4-fluorophenyl)-3-(5-hydroxy-5-(2-hydroxypropan-2-yl)octahydropentalen-2-yl)-1-methyl-1H-pyrazole-4-carboxamide. A mixture of 5-amino-N-(3-chloro-4-fluorophenyl)-1-methyl-3-(5-(propan-2-ylidene) octahydropentalen-2-yl)-1H-pyrazole-4-carboxamide (35 mg, 0.08 mmol), OsO4 (10 mg, 0.04 mmol), NMO (45 mg, 0.40 mmol) in THF/H$_2$O (5 mL/1 mL) was stirred at room temperature for 4 h. The reaction mixture was concentrated under vacuum and the residue purified by prep-HPLC to afford 5-amino-N-(3-chloro-4-fluorophenyl)-3-(5-hydroxy-5-(2-hydroxypropan-2-yl)octahydropentalen-2-yl)-1-methyl-1H-pyrazole-4-carboxamide (4 mg, 11%) as a white solid. TLC: 10% MeOH/DCM (Rf: 0.3); MS Calcd.: 450.2; MS Found: 451.3 [M+1]$^+$. $^1$H-NMR (DMSO-d$_6$, 400 MHz): δ 8.91 (s, 1H), 7.89 (dd, J=6.8, 2.0 Hz, 1H), 7.52-7.48 (m, 1H), 7.32 (t, J=3.2 Hz, 1H), 5.96 (s, 2H), 4.03 (s, 1H), 3.86 (s, 1H), 3.54-3.39 (m, 4H), 2.57 (t, J=5.6 Hz, 2H), 2.09 (t, J=5.6 Hz, 2H), 1.57 (s, 4H), 1.37 (dd, J=11.6, 19.2 Hz, 2H), 1.03 (s, 6H).

AIA-257-1

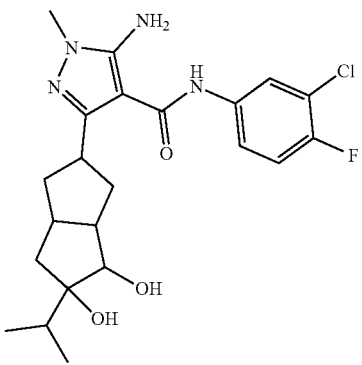

5-Amino-N-(3-chloro-4-fluorophenyl)-3-(4,5-dihydroxy-5-isopropyloctahydropentalen-2-yl)-1-methyl-1H-pyrazole-4-carboxamide. A mixture of 5-amino-N-(3-chloro-4-fluorophenyl)-3-(5-isopropyl-1,2,3,3a,4,6a-hexahydropentalen-2-yl)-1-methyl-1H-pyrazole-4-carboxamide (20 mg, 0.05 mmol), OsO$_4$ (7 mg, 0.03 mmol), NMO (23 mg, 0.20 mmol) in THF/H$_2$O (5 mL/1 mL) was stirred at RT for 4 h. The reaction mixture was concentrated under vacuum and the residue was purified by prep-HPLC to afford 5-amino-N-(3-chloro-4-fluorophenyl)-3-(4,5-dihydroxy-5-isopropyloctahydropentalen-2-yl)-1-methyl-1H-pyrazole-4-carboxamide (2 mg, 9%) as a white solid. MS Calcd.: 450.2; MS Found: 451.3 [M+1]$^+$. $^1$H NMR (DMSO-d$_6$, 400 MHz): δ

8.94 (s, 1H), 7.91 (dd, J=6.8, 2.4 Hz, 1H), 7.54-7.50 (m, 1H), 7.35 (t, J=9.2 Hz, 1H), 5.97 (s, 2H), 4.47 (s, 1H) 3.58-3.45 (m, 6H), 2.86 (s, 2H), 2.67-2.62 (m, 2H), 2.18-2.11 (m, 2H), 1.89-1.84 (m, 2H), 1.44-1.32 (m, 4H).

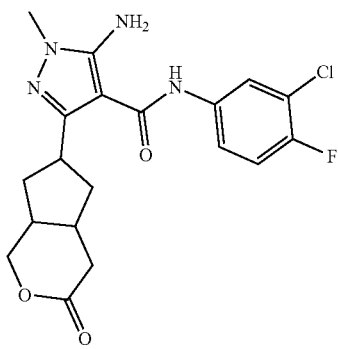

AIA-275

5-Amino-N-(3-chloro-4-fluorophenyl)-1-methyl-3-(3-oxooctahydrocyclopenta[c]pyran-6-yl)-1H-pyrazole-4-carboxamide. To a solution of m-CPBA (528.1 mg, 3.06 mmol) in anhydrous DCM (15 mL) was added TFA (247.4 mg, 2.55 mmol), and the mixture was stirred at RT for 0.5 hour. CP-AIA-002 (199.3 mg, 0.51 mmol) was added, and the mixture was stirred at RT overnight. The mixture was quenched with NaHCO₃(aq), extracted with ethyl acetate. The organic phase was washed with brine, dried over Na₂SO₄, filtered and concentrated to give the crude product which was purified by column chromatography to afford 5-amino-N-(3-chloro-4-fluorophenyl)-1-methyl-3-(3-oxooctahydrocyclopenta[c]pyran-6-yl)-1H-pyrazole-4-carboxamide (30 mg, 14.5%) as a white solid. MS Calcd.: 406.1; MS Found: 407.2 [M+1]⁺. ¹H NMR (DMSO-d₆, 400 MHz): δ 9.02 (s, 1H), 7.91 (dd, J=4.4, 2.4 Hz, 1H), 7.54-7.51 (m, 1H), 7.35 (t, J=9.2 Hz, 1H), 5.99 (s, 2H), 4.29-4.25 (m, 1H), 4.08-4.03 (m, 1H), 3.50 (s, 3H), 3.46-3.41 (m, 1H), 2.67-2.58 (m, 2H), 2.50-2.48 (m, 1H), 2.33 (dd, J=9.6, 4.8 Hz, 1H), 2.22-2.08 (m, 2H), 1.51 (dd, J=4.4, 2.4 Hz, 1H), 1.34-1.26 (m, 1H).

Intermediate 122

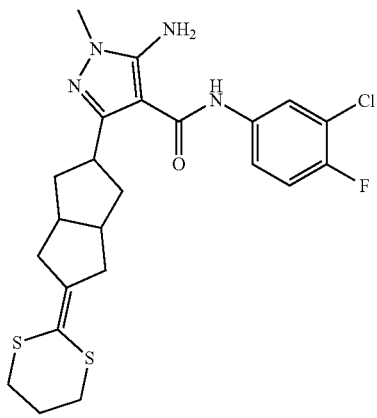

3-(5-(1,3-Dithian-2-ylidene)octahydropentalen-2-yl)-5-amino-N-(3-chloro-4-fluorophenyl)-1-methyl-1H-pyrazole-4-carboxamide. To a mixture solution of (1,3-dithian-2-yl)trimethylsilane (2.1 g, 10.8 mmol) in THF (30 mL) at −78° C. was added n-BuLi (2.5 M, 4.3 mL). After the mixture was attired at −78° C. for 1 hr, a solution of AIA-002 (600 mg, 1.5 mmol) in THF was added slowly and stirring continued for 3 hr. The mixture was quenched with sat. NH₄Cl, the solvent evaporated, and the residue purified by silica gel column (eluted with 1:1 petroleum ether/ethyl acetate) to afford 3-(5-(1,3-dithian-2-ylidene)octahydropentalen-2-yl)-5-amino-N-(3-chloro-4-fluorophenyl)-1-methyl-1H-pyrazole-4-carboxamide (300 mg, 40%) as white solid. MS Calcd.: 492.1; MS Found: 493.1 [M+1]⁺.

Intermediate 123

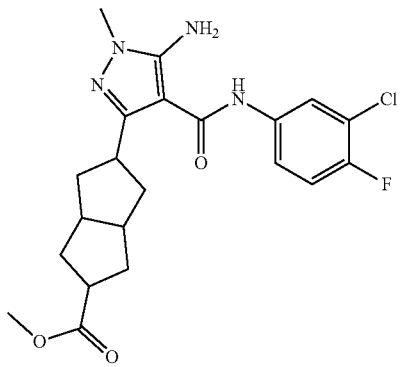

Methyl 5-(5-amino-4-(3-chloro-4-fluorophenylcarbamoyl)-1-methyl-1H-pyrazol-3-yl)octahydropentalene-2-carboxylate. To a solution of 3-(5-(1,3-dithian-2-ylidene)octahydropentalen-2-yl)-5-amino-N-(3-chloro-4-fluorophenyl)-1-methyl-1H-pyrazole-4-carboxamide (200 mg, 0.4 mmol) in MeOH (20 mL) was added successively HCl (6 N, 0.2 mL), HgCl₂ (232 mg, 0.9 mmol) and TFA (118 mg, 1.0 mmol). The mixture was stirred at room temperature for 3 hours then filtered through Celite®. The filter cake was washed with methanol. The filtrate was treated with NaBH₄ at 0° C., the solvent removed, and the residue purified by silica gel column chromatography (eluted with 2:1 petroleum ether/ethyl acetate) to afford methyl 5-(5-amino-4-(3-chloro-4-fluorophenylcarbamoyl)-1-methyl-1H-pyrazol-3-yl) octahydropentalene-2-carboxylate (120 mg, 68%) as a white solid. MS Calcd.: 434.2; MS Found: 435.1 [M+1]⁺.

AIA-014

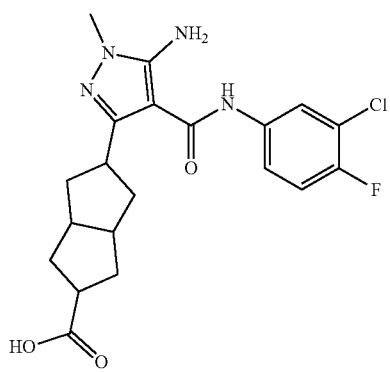

AIA-015

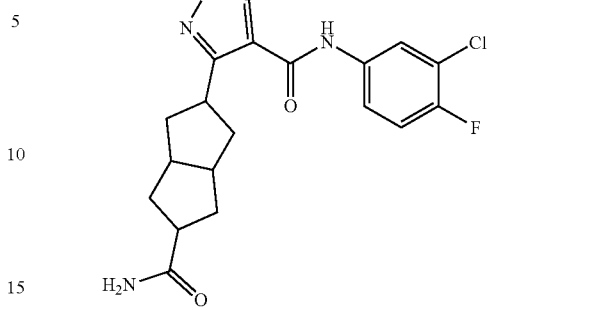

5-(5-Amino-4-(3-chloro-4-fluorophenylcarbamoyl)-1-methyl-1H-pyrazol-3-yl)octahydropentalene-2-carboxylic acid. Methyl 5-(5-amino-4-(3-chloro-4-fluorophenylcarbamoyl)-1-methyl-1H-pyrazol-3-yl)octahydropentalene-2-carboxylate (120 mg, 0.28 mmol) was dissolved in a solution of methanol (20 mL) and water (2 mL), then LiOH—H$_2$O (232 mg, 5.5 mmol) was added in one portion. The mixture solution was stirred at room temperature for 3 hr. The solution was warmed to 40° C. and stirred overnight. 1N HCl was added to adjust the pH to 7. The solvent was evaporated, and the residue purified by silica gel column chromatography (10:1 DCM/MeOH) to afford 5-(5-amino-4-(3-chloro-4-fluorophenylcarbamoyl)-1-methyl-1H-pyrazol-3-yl)octahydropentalene-2-carboxylic acid (100 mg, 86%) as a white solid. MS Calcd.: 420.1; MS Found: 421.2 [M+1]$^+$; 1H NMR (DMSO-d6, 400 MHz): δ 11.98 (s, 1H), 8.96 (s, 1H), 7.92-7.89 (m, 1H), 7.54-7.50 (m, 1H), 7.34 (t, J=9.2, 1H), 5.97 (s, 2H), 3.49 (s, 3H), 3.31-3.27 (m, 1H), 2.69-2.64 (m, 1H), 2.55-2.53 (m, 2H), 2.17-2.02 (m, 2H), 1.73-1.59 (m, 3H), 1.51-1.43 (m, 1H), 1.30-1.25 (m, 2H).

5-Amino-3-(5-carbamoyloctahydropentalen-2-yl)-N-(3-chloro-4-fluorophenyl)-1-methyl-1H-pyrazole-4-carboxamide. 5-(5-Amino-4-(3-chloro-4-fluorophenylcarbamoyl)-1-methyl-1H-pyrazol-3-yl)octahydropentalene-2-carboxylic acid (30 mg, 0.07 mmol), HATU (33 mg, 0.09 mmol), DIEA (14 mg, 0.11 mmol) and HCOONH$_4$ (6 mg, 0.08 mmol) were combined and dissolved in DMF (1 mL). The resulting solution was stirred at room temperature overnight. Prep-HPLC (basic) was employed to purify the final target, and 5-amino-3-(5-carbamoyloctahydropentalen-2-yl)-N-(3-chloro-4-fluorophenyl)-1-methyl-1H-pyrazole-4-carboxamide (19 mg, 64%) was obtained as white solid. MS Calcd.: 419.2; MS Found: 420.3 [M+1]$^+$; 1H NMR (DMSO-d6, 400 MHz): δ 8.96 (s, 0.3H), 8.95 (s, 0.7H), 7.93-7.89 (m, 1H), 7.54-7.50 (m, 1H), 7.35 (t, J=9.2 Hz, 1H), 7.28 (s, 0.7H), 7.16 (s, 0.3H), 6.68 (s, 1H), 5.98 (s, 1.4H), 5.96 (s, 0.6H), 3.53-3.49 (m, 4H), 3.30-3.26 (m, 1H), 2.65-2.60 (m, 1H), 2.46-2.43 (m, 1H), 2.18-2.12 (m, 2H), 1.97-1.94 (m, 2H), 1.68-1.39 (m, 4H), 1.30-1.27 (m, 1H).

TABLE 13

The compounds in table 13 were synthesized according to the procedure described for 5-amino-3-(5-carbamoyloctahydropentalen-2-yl)-N-(3-chloro-4-fluorophenyl)-1-methyl-1H-pyrazole-4-carboxamide.

| Compound | Structure and characterization |
|---|---|
| AIA-016 | 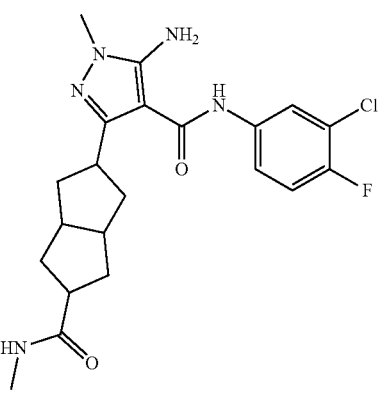 [SMILES: CNC(=O)C1CC2CC(c3nn(C)c(N)c3C(=O)Nc3ccc(F)c(Cl)c3)CC2C1]<br>5-Amino-N-(3-chloro-4-fluorophenyl)-1-methyl-3-(5-(methylcarbamoyl)octahydropentalen-2-yl)-1H-pyrazole-4-carboxamide. MS Calcd.: 433.2; MS Found: 434.3 [M + 1]$^+$; 1H NMR (DMSO-d$_6$, 400 MHz): δ 8.96 (s, 0.3H), 8.94 (s, 0.7H), 7.92-7.89 (m, 1H), 7.76-7.75 (m, 0.7H), 7.64-7.63 (m, 0.3H), 7.53-7.49 (m, 1H), 7.35 (t, J = 9.2 Hz, 1H), 5.98 (s, 1.4H), 5.96 (s, 0.6H), 3.53-3.49 (m, 6H), 3.29- |

TABLE 13-continued

The compounds in table 13 were synthesized according to the procedure described for 5-amino-3-(5-carbamoyloctahydropentalen-2-yl)-N-(3-chloro-4-fluorophenyl)-1-methyl-1H-pyrazole-4-carboxamide.

| Compound | Structure and characterization |
| --- | --- |
| | 3.24 (m, 1H), 2.64-2.59 (m, 1H), 2.55-2.54 (m, 3H), 2.16-2.12 (m, 2H), 1.94-1.91 (m, 1H), 1.69-1.61 (m, 1H), 1.51-1.31 (m, 2H), 1.29-1.23 (m, 1H). |
| AIA-109 | 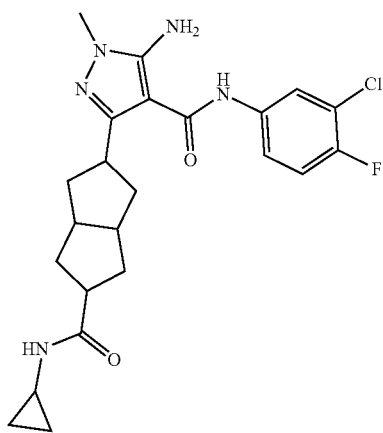 [SMILES: Cn1nc(C2CC3CC(C(=O)NC4CC4)CC3C2)c(C(=O)Nc2ccc(F)c(Cl)c2)c1N]<br>5-Amino-N-(3-chloro-4-fluorophenyl)-3-(5-(cyclopropylcarbamoyl)octahydropentalen-2-yl)-1-methyl-1H-pyrazole-4-carboxamide MS Calcd.: 459.2; MS Found: 460.3 [M + 1]$^+$; 1H NMR (DMSO-d$_6$, 400 MHz): δ 8.95 (s, 1H), 7.92-7.76 (m, 2H), 7.53-7.49 (m, 1H), 7.35 (t, J = 9.2 Hz,1H), 5.99 (s, 2H), 3.50 (s, 3H), 3.48-3.27 (m, 1H), 2.63-2.57 (m, 3H), 2.46-2.43 (m, 1H), 2.17-2.10 (m, 2H), 2.10-1.88 (m, 1H), 1.68-1.39 (m, 4H), 1.28-1.20 (m, 1H), 0.59-0.54 (m, 2H), 0.36-0.32 (m, 2H). |

AIA-017

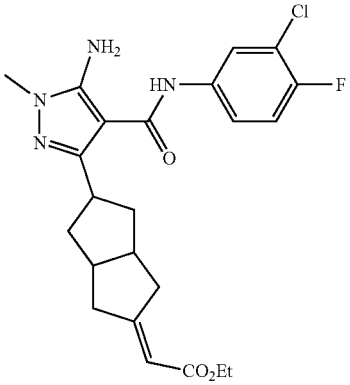

Ethyl 2-(5-(5-amino-4-((3-chloro-4-fluorophenyl)carbamoyl)-1-methyl-1H-pyrazol-3-yl)hexahydropentalen-2(1H)-ylidene)acetate. To a solution of ethyl 2-(diethoxyphosphoryl)acetate (33 mg, 0.2 mmol, 2.0 eq) in THF (5 mL) was added NaH (12 mg, 0.3 mmol, 3 eq) at 0° C. The resulting solution was stirred at 0° C. for 30 mins after which AIA-002 (39 mg, 0.1 mmol, 1 eq) was added. The solution was stirred at 55° C. for 1 h before being quenched with water and extracted with ethyl acetate. The organic phase was concentrated under vacuum and purified by prep-HPLC to give ethyl 2-(5-(5-amino-4-((3-chloro-4-fluorophenyl) carbamoyl)-1-methyl-1H-pyrazol-3-yl)hexahydropentalen-2(1H)-ylidene)acetate (22 mg, 48%) as a white solid. TLC: 30% ethyl acetate/petroleum ether (R$_f$, 0.35); MS Calcd.: 460.2; MS Found: 461.3 [M+1]$^+$. $^1$H-NMR (DMSO-d$_6$, 400 MHz): δ 8.95 (s, 1H), 7.91 (dd, J=7.2, 2.8 Hz, 1H), 7.53-7.50 m, 1H), 7.34 (t, J=8.8 Hz, 1H), 5.96 (s, 2H), 5.74 (s, 1H), 4.05 (q, J=7.2 Hz, 2H), 3.49-3.47 (m, 1H), 3.47 (s, 3H), 2.75-2.73 (m, 2H), 2.66-2.61 (m, 2H), 2.49-2.13 (m, 4H), 1.38-1.33 (m, 2H), 1.18 (t, J=7.2 Hz, 3H).

AIA-018

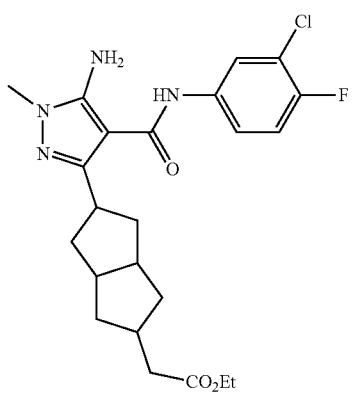

Ethyl 2-(5-(5-amino-4-((3-chloro-4-fluorophenyl)carbamoyl)-1-methyl-1H-pyrazol-3-yl)octahydropentalen-2-yl)acetate. 2-(5-(5-Amino-4-((3-chloro-4-fluorophenyl)carbamoyl)-1-methyl-1H-pyrazol-3-yl)hexahydropentalen-2(1H)-ylidene)acetate (30 mg, 0.06 mmol) was dissolved in THF, Pt/C (10 mg) was added, and the suspension was stirred at 35° C. for 3 h under H$_2$ atmosphere. The mixture was filtered through Celite® and washed with THF. The filtrate was concentrated under vacuum and the residue purified by prep-HPLC to afford ethyl 2-(5-(5-amino-4-((3-chloro-4-fluorophenyl)carbamoyl)-1-methyl-1H-pyrazol-3-yl)octahydropentalen-2-yl)acetate (15 mg, 50%) as a white solid. MS Calcd.: 462.2; MS Found: 463.2 [M+1]$^+$. $^1$H-NMR (DMSO-d$_6$, 400 MHz): δ 8.95 (s, 1H), 7.91 (dd, J=6.8, 2.4 Hz, 1H), 7.53-7.49 (m, 1H), 7.34 (t, J=9.2 Hz, 1H), 5.96 (s, 2H), 4.02 (q, J=7.2 Hz, 2H), 3.56-3.52 (m, 1H), 3.49 (s, 3H), 2.44-2.42 (m, 2H), 2.31-2.29 (m, 2H), 2.21-2.10 (m, 3H), 2.00-1.94 (m, 2H), 1.44-1.36 (m, 2H), 1.16 (t, J=7.2 Hz, 3H), 0.96-0.88 (m, 2H).

afford 5-amino-N-(3-chloro-4-fluorophenyl)-3-(5-(2-hydroxyethyl) octahydropentalen-2-yl)-1-methyl-1H-pyrazole-4-carboxamide (20 mg, 48%) as a white solid. MS Calcd.: 420.2; MS Found: 421.3 [M+1]$^+$. $^1$H-NMR (DMSO-d$_6$, 400 MHz): δ 8.95 (s, 1H), 7.91 (dd, J=6.8, 2.4 Hz, 1H), 7.53-7.49 (m, 1H), 7.34 (t, J=9.2 Hz, 1H), 5.96 (s, 2H), 4.29 (t, J=5.2 Hz, 1H), 3.56-3.51 (m, 1H), 3.49 (s, 3H), 3.38-3.35 (m, 2H), 2.40 (s, 2H), 2.16-2.09 (m, 2H), 1.97-1.94 (m, 3H), 1.48-1.35 (m, 4H), 0.86-0.84 (m, 2H).

Intermediate 124

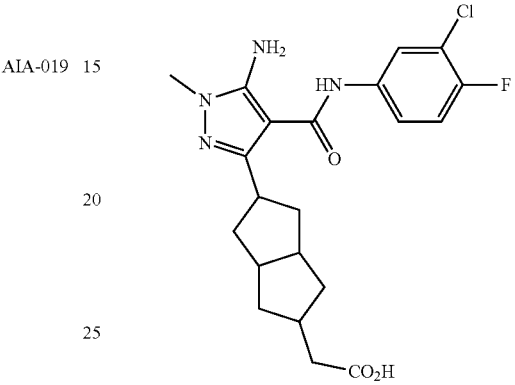

2-(5-(5-Amino-4-(3-chloro-4-fluorophenylcarbamoyl)-1-methyl-1H-pyrazol-3-yl)octahydropentalen-2-yl)acetic acid. To a solution of ethyl 2-(5-(5-amino-4-((3-chloro-4-fluorophenyl)carbamoyl)-1-methyl-1H-pyrazol-3-yl)octahydropentalen-2-yl)acetate (462 mg, 1.0 mmol) in MeOH/H$_2$O (5 mL/1 mL) was added LiOH—H$_2$O (84 mg, 2.0 mmol). The mixture was stirred at 50° C. for 4 h. MeOH was removed under vacuum and the residue neutralized with 3M HCl to pH~5. The resulting solution was lyophilized to give crude 2-(5-(5-amino-4-(3-chloro-4-fluorophenylcarbamoyl)-1-methyl-1H-pyrazol-3-yl)octahydropentalen-2-yl) acetic acid (510 mg, 100%) as a white solid. MS Calcd.: 434.2; MS Found: 435.3 [M+1]$^+$.

AIA-019

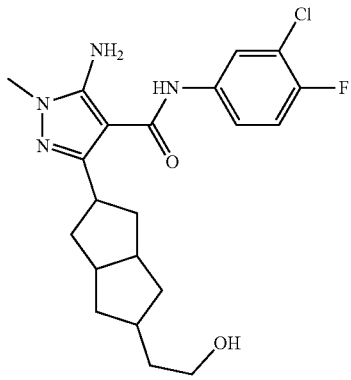

5-Amino-N-(3-chloro-4-fluorophenyl)-3-(5-(2-hydroxyethyl) octahydropentalen-2-yl)-1-methyl-1H-pyrazole-4-carboxamide. To a solution of ethyl 2-(5-(5-amino-4-((3-chloro-4-fluorophenyl)carbamoyl)-1-methyl-1H-pyrazol-3-yl)octahydropentalen-2-yl)acetate (46 mg, 0.1 mmol, 1 eq) in THF (2 mL) was added LiAlH$_4$ (8 mg, 0.2 mmol, 2.0 eq) in portions. The mixture became a yellow solution. The mixture was quenched with water and NaOH (aq.) then filtered and washed with THF. The filtrate was concentrated under vacuum and the residue purified by prep-HPLC to

TABLE 14

The compounds in table 14 were synthesized according to the procedure described for 5-amino-3-(5-carbamoyloctahydropentalen-2-yl)-N-(3-chloro-4-fluorophenyl)-1-methyl-1H-pyrazole-4-carboxamide.

| Compound | Structure and characterization |
|---|---|
| AIA-020 | 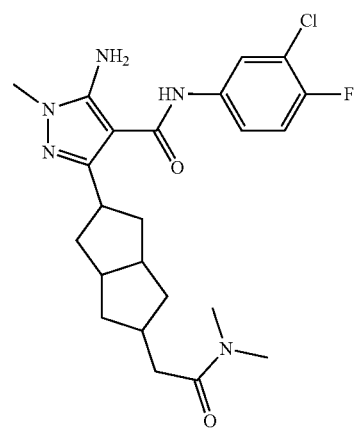 [SMILES: CN(C)C(=O)CC1CC2CC(c3nn(C)c(N)c3C(=O)Nc3ccc(F)c(Cl)c3)CC2C1] <br> 5-Amino-N-(3-chloro-4-fluorophenyl)-3-(5-(2-(dimethylamino)-2-oxoethyl)octahydropentalen-2-yl)-1-methyl-1H-pyrazole-4- |

TABLE 14-continued

The compounds in table 14 were synthesized according to the procedure described for 5-amino-3-(5-carbamoyloctahydropentalen-2-yl)-N-(3-chloro-4-fluorophenyl)-1-methyl-1H-pyrazole-4-carboxamide.

| Compound | Structure and characterization |
|---|---|
|  | carboxamide MS Calcd.: 461.2; MS Found: 462.3 [M + 1]$^+$. $^1$H-NMR (DMSO-d$_6$, 400 MHz): δ 8.95 (s, 1H), 7.91 (d, J = 4.4 Hz, 1H), 7.50 (s, 1H), 7.34 (t, J = 9.2 Hz, 1H), 5.96 (s, 2H), 3.54-3.53 (m, 1H), 3.49 (s, 3H), 2.93 (s, 3H), 2.78 (s, 3H), 2.41 (s, 2H), 2.32-2.31 (m, 2H), 2.22-2.13 (m, 3H), 1.99 (s, 2H), 1.41-1.40 (m, 2H), 0.91-0.89 (m, 2H) |
| AIA-021 | 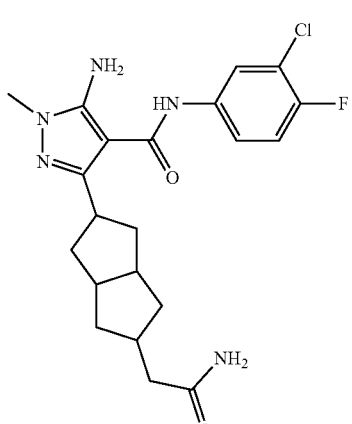<br>5-Amino-3-(5-(2-amino-2-oxoethyl)octahydropentalen-2-yl)-N-(3-chloro-4-fluorophenyl)-1-methyl-1H-pyrazole-4-carboxamide. MS Calcd.: 433.2; MS Found: 434.3 [M + 1]$^+$. $^1$H-NMR (DMSO-d$_6$, 400 MHz): δ 8.94 (s, 1H), 7.91 (dd, J = 6.8, 2.4 Hz, 1H), 7.53-7.49 (m, 1H), 7.34 (t, J = 8.8 Hz, 1H), 7.17 (s, 1H), 6.62 (s, 1H), 5.96 (s, 2H), 3.56-3.51 (m, 1H), 3.49 (s, 3H), 2.41-2.39 (m, 2H), 2.15-2.13 (m, 3H), 2.06-2.04 (m, 2H), 1.96-1.93 (m, 2H), 1.41-1.38 (m, 2H), 0.90-0.88 (m, 2H). |

Intermediate 125

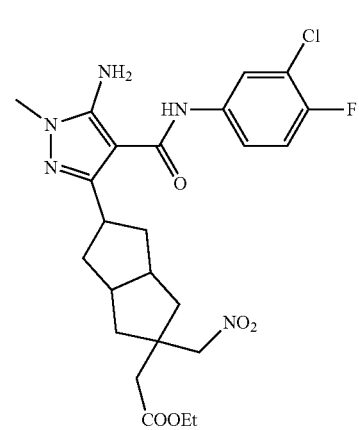

Ethyl 2-(5-(5-amino-4-((3-chloro-4-fluorophenyl)carbamoyl)-1-methyl-1H-pyrazol-3-yl)-2-(nitromethyl)octahydropentalen-2-yl)acetate. To a stirred solution of 2-(5-(5-amino-4-((3-chloro-4-fluorophenyl)carbamoyl)-1-methyl-1H-pyrazol-3-yl)hexahydropentalen-2(1H)-ylidene)acetate (0.8 g, 1.73 mmol) in DMSO (3 mL) at 0° C., was added K$_2$CO$_3$ (0.703 g, 5.09 mmol). To this solution was added MeNO$_2$ (0.265 g, 4.34 mmol) slowly. The resulting reaction mixture was stirred at 70° C. for 16 h. After completion, the reaction mixture was diluted with ice cold water and extracted with ethyl acetate. The combined organic layers were dried over anhydrous sodium sulphate, filtered and concentrated under reduced pressure to afford ethyl 2-(5-(5-amino-4-((3-chloro-4-fluorophenyl)carbamoyl)-1-methyl-1H-pyrazol-3-yl)-2-(nitromethyl)octahydropentalen-2-yl)acetate. (0.7 g, crude) as an off white solid. LCMS Calculated for C$_{24}$H$_{29}$ClFN$_5$O$_5$: 521.18; Observed: 522.20 [M+1]$^+$.

HBV-AIA-039

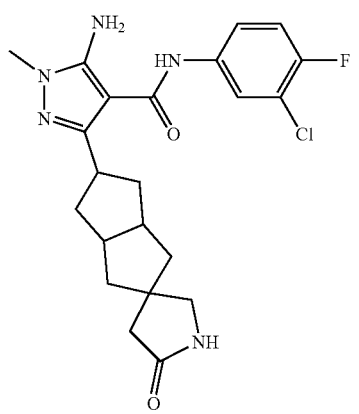

5-Amino-N-(3-chloro-4-fluorophenyl)-1-methyl-3-(5'-oxohexahydro-1H-spiro[pentalene-2,3'-pyrrolidin]-5-yl)-1H-pyrazole-4-carboxamide. To a stirred solution of 2-(5-(5-amino-4-((3-chloro-4-fluorophenyl)carbamoyl)-1-methyl-1H-pyrazol-3-yl)-2-(nitromethyl)octahydropentalen-2-yl)acetate (0.5 g, 0.95 mmol) in AcOH (5 mL), was added iron powder (0.321 g, 4.87 mmol) and the resulting reaction mixture stirred at 80° C. for 16 h. After completion, the reaction mixture was concentrated in vacuo. The residue was neutralized with sat. NaHCO₃ solution and extracted with ethyl acetate. The combined organic layers were washed with water, brine, dried over sodium sulfate, filtered and concentrated in vacuo to afford the crude compound which was purified by prep. HPLC to afford 5-amino-N-(3-chloro-4-fluorophenyl)-1-methyl-3-(5'-oxohexahydro-1H-spiro[pentalene-2,3'-pyrrolidin]-5-yl)-1H-pyrazole-4-carboxamide. H NMR (400 MHz, DMSO-d₆): δ 8.96 (s, 1H), 7.89 (d, J=6.4 Hz, 1H), 7.51-7.49 (m, 1H), 7.45 (s, 1H), 7.34 (t, J=8.8 Hz, 1H), 5.96 (s, 2H), 3.57-3.49 (m, 4H), 3.00 (s, 2H), 2.53-2.45 (m, 2H, merged), 2.17-2.11 (m, 4H), 1.88-1.86 (m, 2H), 1.46-1.32 (m, to 4H).

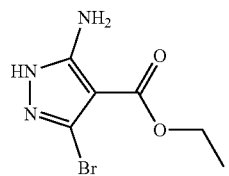

Intermediate 126

Ethyl 5-amino-3-bromo-1H-pyrazole-4-carboxylate. To a solution of ethyl 5-amino-1H-pyrazole-4-carboxylate (20 g, 0.13 mol) in CHCl₃ (200 mL) was added NBS (34.5 g, 0.19 mol) slowly to maintain the temperature between 20-30° C. The solution was stirred at room temperature for 3 h. The reaction was quenched with water (200 ml), extracted with DCM (100 mL×3), dried, filtered and concentrated under reduced pressure. The crude product was purified by column chromatography using 20-30% ethyl acetate/petroleum ether to afford ethyl 5-amino-3-bromo-1H-pyrazole-4-carboxylate. (12.6 g, 42%) as a yellow solid. MS Calcd.: 233.0; MS Found: 234.1 [M+H]⁺.

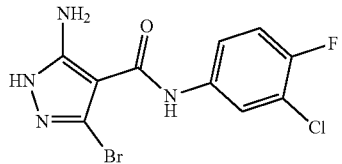

Intermediate 127

5-Amino-3-bromo-N-(3-chloro-4-fluorophenyl)-1H-pyrazole-4-carboxamide. To a solution of 3-chloro-4-fluoroaniline (9.3 g, 64 mmol) in toluene (100 mL) was added trimethylaluminum (2 M in toluene, 129 mL, 258 mmol) at 0° C. The light brown solution was stirred for 30 min. To the solution was added ethyl 5-amino-3-bromo-1H-pyrazole-4-carboxylate. (10 g, 43 mmol) at 0° C. and stirring continued for 30 min. The brown solution was heated to reflux for 48 h. The mixture was cooled to 0° C., quenched with H₂O (200 mL), 5% NaOH (100 mL) and the resulting mixture stirred for 10 min. The solvent was removed under vacuum and the residue purified by column chromatography using 20-30% ethyl acetate/petroleum ether to afford 5-amino-3-bromo-N-(3-chloro-4-fluorophenyl)-1H-pyrazole-4-carboxamide (5 g, 36%) as a white solid. MS Calcd.: 331.9; MS Found: 333.1[M+1]⁺

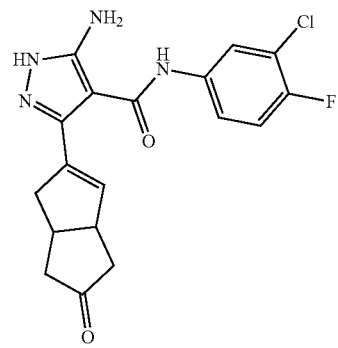

Intermediate 128

5-Amino-N-(3-chloro-4-fluorophenyl)-3-(5-oxo-1,3a,4,5,6,6a-hexahydropentalen-2-yl)-1H-pyrazole-4-carboxamide. A mixture of 5-(4,4,5,5-tetramethyl-1,3,2-dioxaborolan-2-yl)-3,3a,6,6a-tetrahydropentalen-2(1H)-one (5 g, 20 mmol), 5-amino-3-bromo-N-(3-chloro-4-fluorophenyl)-1H-pyrazole-4-carboxamide (5 g, 15 mmol), Pd(dppf)Cl₂ (736 mg, 1.0 mmol) and Na₂CO₃ (2.4 g, 23 mmol) in dioxane/water (80 mL/15 mL) was stirred at 80° C. overnight under N₂. EtOAc (30 mL) was added to the mixture. The mixture was filtered, and the filtrate was washed with H₂O (35 mL×2). The organic layer was separated, dried over Na₂SO₄ and concentrated under vacuum to give a yellow residue. The residue was purified by silica gel column chromatography using 20-30% ethyl acetate petroleum ether to give 5-amino-N-(3-chloro-4-fluorophenyl)-3-(5-oxo-1,3a,4,5,6,6a-hexahydropentalen-2-yl)-1H-pyrazole-4-carboxamide (2.6 g, 46%) as a yellow solid. MS Calcd.: 374.1; MS Found: 375.2 [M+1]⁺.

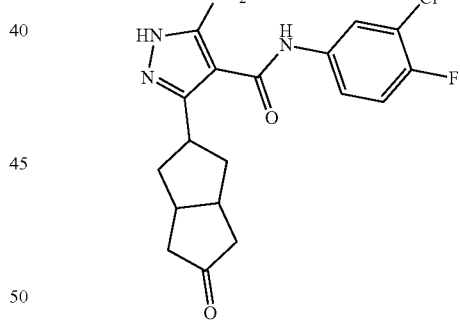

AIA-286

5-Amino-N-(3-chloro-4-fluorophenyl)-3-(5-oxooctahydropentalen-2-yl)-1H-pyrazole-4-carboxamide To a solution of 5-amino-N-(3-chloro-4-fluorophenyl)-3-(5-oxo-1,3a,4,5,6,6a-hexahydropentalen-2-yl)-1H-pyrazole-4-carboxamide (500 mg, 1.3 mmol) in THF (20 mL) was added Pd/C (500 mg) and NH₄OH (12 drops). The flask was evacuated and backfilled with Hz. The solution was stirred at 35° C. for 8 h. DMF (8 mL) was added and the mixture filtered and then concentrated under vacuum. The resulting residue was purified by prep-HPLC to give 5-amino-N-(3-chloro-4-fluorophenyl)-3-(5-oxooctahydropentalen-2-yl)-1H-pyrazole-4-carboxamide (200 mg, 40%) MS Calcd.: 376.1; MS Found: 377.1 [M+1]⁺. (DMSO-d6, 400 MHz): δ 12.05 (s, 0.55H), 11.49 (s, 0.46H), 9.54 (s, 0.46H), 8.96 (s, 0.48H), 7.94 (d, J=4.8 Hz, 1H), 7.55-7.50 (m, 1H), 7.36 (t, J=9.2 Hz, 1H), 5.76 (s, 1H), 4.97 (s, 1H), 3.67-3.60 (m, 1H), 2.72-2.66 (m, 2H), 2.50-2.44 (m, 2H), 2.33-2.25 (m, 2H), 2.08-2.04 (m, 2H), 1.59-1.54 (m, 2H).

Intermediate 129

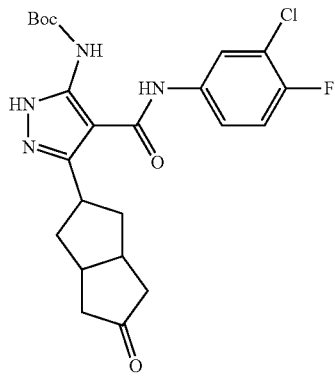

tert-Butyl (4-((3-chloro-4-fluorophenyl)carbamoyl)-3-(5-oxooctahydropentalen-2-yl)-1H-pyrazol-5-yl)carbamate. To a solution of 5-amino-N-(3-chloro-4-fluorophenyl)-3-(5-oxooctahydropentalen-2-yl)-1H-pyrazole-4-carboxamide (200 mg, 0.5 mmol) in THF (10 mL) was added NaH (32 mg, 1.3 mmol) at 0° C., the light brown solution was stirred at 0° C. for 30 min. Boc$_2$O (150 mg, 0.7 mmol) was added and stirring continued at RT for another 30 min. The mixture was cooled to 0° C., quenched with H$_2$O, extracted with ethyl acetate (20 mL×3), dried, filtered and the filtrate concentrated under reduced pressure. The crude product was purified by column chromatography using 10-20% ethyl acetate/petroleum ether to afford tert-butyl (4-((3-chloro-4-fluorophenyl)carbamoyl)-3-(5-oxooctahydropentalen-2-yl)-1H-pyrazol-5-yl)carbamate (200 mg, 80%) as a pale white solid. MS Calcd.: 476.1; MS Found: 421.2 [M−56+1]$^+$.

Intermediate 130

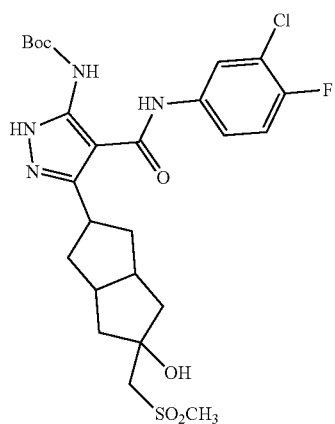

tert-Butyl (4-((3-chloro-4-fluorophenyl)carbamoyl)-3-(5-hydroxy-5-((methylsulfonyl)methyl)octahydropentalen-2-yl)-1H-pyrazol-5-yl)carbamate. To a solution of dimethylsulfone (237 mg, 2.5 mmol) in THF (10 mL) was added n-BuLi (1 mL, 2.5 M, 2.5 mmol) at −45° C. under N$_2$. The mixture was stirred at −45° C. for 30 min. tert-Butyl (4-((3-chloro-4-fluorophenyl)carbamoyl)-3-(5-oxooctahydropentalen-2-yl)-1H-pyrazol-5-yl)carbamate (200 mg, 0.4 mmol) was added to the mixture in one portion. The solution was stirred at room temperature overnight. The reaction mixture was quenched with aq. NH$_4$Cl and extracted with ethyl acetate (10 mL×3). The combined organic layers were dried and concentrated, the residue was purified by silica gel column chromatography using 95:5 DCM/MeOH to afford tert-butyl (4-((3-chloro-4-fluorophenyl)carbamoyl)-3-(5-hydroxy-5-((methylsulfonyl)methyl)octahydropentalen-2-yl)-1H-pyrazol-5-yl)carbamate (140 mg, 60%) as a white solid. MS Calcd.: 570.2; MS Found: 571.2 [M+1]$^+$.

AIA-310

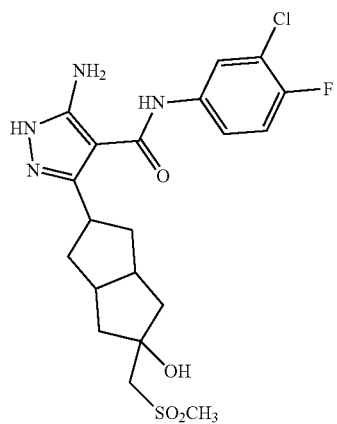

5-Amino-N-(3-chloro-4-fluorophenyl)-3-(5-hydroxy-5-((methylsulfonyl)methyl)octahydropentalen-2-yl)-1H-pyrazole-4-carboxamide. To a solution of tert-butyl (4-((3-chloro-4-fluorophenyl)carbamoyl)-3-(5-hydroxy-5-((methylsulfonyl)methyl)octahydropentalen-2-yl)-1H-pyrazol-5-yl)carbamate (140 mg, 0.25 mmol) in DCM (5 mL) was added trifluoroacetic acid (1 mL). The resulting mixture was stirred at room temperature for 1 h. The reaction mixture was adjusted to pH 8-9 with NaHCO$_3$ and extracted with DCM (10 mL×3). The combined organic layers were dried and concentrated. The residue was purified by silica gel column chromatography using 95:5 DCM/MeOH and prep-HPLC to afford 5-amino-N-(3-chloro-4-fluorophenyl)-3-(5-hydroxy-5-((methylsulfonyl)methyl)octahydropentalen-2-yl)-1H-pyrazole-4-carboxamide (30 mg, 26%) as a white solid. MS Calcd.: 470.1; MS Found: 471.2 [M+1]$^+$.
$^1$H-NMR (DMSO-d$_6$, 400 MHz): δ 11.88 (s, 0.55H), 11.44 (s, 0.45H), 9.49 (s, 0.53H), 8.93 (s, 0.41H), 7.93 (s, 1H), 7.53-7.49 (m, 1H), 7.35 (t, J=8.8 Hz, 1H), 5.73 (s, 1H), 4.92 (t, J=12.0 Hz, 2H), 3.47-3.45 (m, 1H), 3.28-3.26 (m, 2H), 2.98 (s, 3H), 2.51-2.49 (m, 2H), 2.17 (s, 2H), 2.02 (s, 2H), 1.64 (d, J=10.0 Hz, 4H).

Intermediate 131

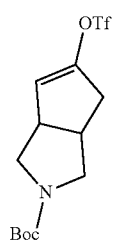

tert-Butyl 5-(trifluoromethylsulfonyloxy)-3,3a,6,6a-tetrahydrocyclopenta[c] pyrrole-2(1H)-carboxylate: LDA (10 mL, 20 mmol) was added slowly to a solution of tert-butyl 5-oxohexahydrocyclopenta[c]pyrrole-2(1H)-carboxylate (3 g, 13.3 mmol) in anhydrous THF (50 mL) at −78° C. for 30 min. 1,1,1-Trifluoro-N-phenyl-N-(trifluoromethylsulfonyl) methanesulfonamide (5.7 g, 16.1 mmol) in THF (20 mL) was added slowly and the solution stirred for 2 h. The reaction mixture was warmed to room temperature and quenched with NH$_4$Cl (aq). The solution was extracted with ethyl acetate (50 mL×3). The combined organic layers were dried over Na$_2$SO$_4$, concentrated and purified by silica gel column chromatography using 5-10% ethyl acetate/petroleum ether to afford tert-butyl 5-(trifluoromethylsulfonyloxy)-3,3a,6,6a-tetrahydrocyclopenta[c] pyrrole-2(1H)-carboxylate (3.7 g, 78%) as a pale-yellow solid.

Intermediate 132

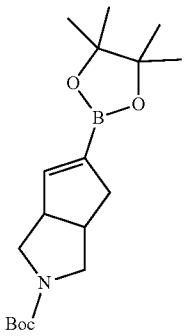

tert-Butyl 5-(4,4,5,5-tetramethyl-1,3,2-dioxaborolan-2-yl)-3,3a,6,6a-tetrahydrocyclopenta[c]pyrrole-2(1H)-carboxylate. A brown mixture of tert-butyl 5-(trifluoromethylsulfonyloxy)-3,3a,6,6a-tetrahydrocyclopenta[c]pyrrole-2 (1H)-carboxylate (2.8 g, 7.8 mmol), 4,4,5,5-tetramethyl-2-(4,4,5,5-tetramethyl-1,3,2-dioxaborolan-2-yl)-1,3,2-dioxaborolane (2.4 g, 9.4 mmol), 1,1'-bis(diphenylphosphino)ferrocene (0.13 g, 0.24 mmol), [1,1'-bis(diphenyl phosphino)ferrocene] dichloropalladium(II) (0.17 g, 0.24 mmol) and potassium acetate (2.3 g, 23.5 mmol) in dioxane (30 mL) was stirred at 80° C. for 16 h under N$_2$. A dark suspension was observed. The reaction was filtered through a pad of Celite®, and the filter cake washed with ethyl acetate (20 mL). The filtrate was concentrated under vacuum and purified by silica gel column chromatography using 5-10% ethyl acetate/petroleum ether to give tert-butyl 5-(4,4,5,5-tetramethyl-1,3,2-dioxaborolan-2-yl)-3,3a,6,6a-tetrahydrocyclopenta[c]pyrrole-2(1H)-carboxylate (2.2 g, 85% yield) as a pale-yellow solid.

Intermediate 133

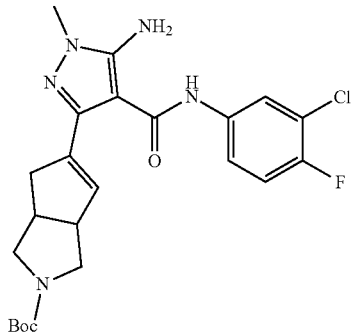

tert-Butyl 5-(5-amino-4-(3-chloro-4-fluorophenylcarbamoyl)-1-methyl-1H-pyrazol-3-yl)-3,3a,6,6a-tetrahydrocyclopenta[c]pyrrole-2(1H)-carboxylate. A mixture of tert-butyl 5-(4,4,5,5-tetramethyl-1,3,2-dioxaborolan-2-yl)-3,3a, 6,6a-tetrahydrocyclopenta[c] pyrrole-2(1H)-carboxylate (1 g, 3.0 mmol), 5-amino-3-bromo-N-(3-chloro-4-fluorophenyl)-1-methyl-1H-pyrazole-4-carboxamide (1 g, 3.0 mmol), Pd(dppf)Cl$_2$ (66 mg, 0.09 mmol) and K$_2$CO$_3$ (0.82 g, 6.0 mmol) in dioxane (20 mL) and H$_2$O (4 mL) was stirred at 80° C. for 16 h under N$_2$. EtOAc (20 mL) was added to the mixture. The mixture was filtered, and the filtrate was washed with H$_2$O (35 mL×2). The organic layer was separated, dried over Na$_2$SO$_4$ and concentrated under vacuum to give a yellow residue. The residue was purified by silica gel column chromatography using 5-10% ethyl acetate/petroleum ether to give tert-butyl 5-(5-amino-4-(3-chloro-4-fluorophenylcarbamoyl)-1-methyl-1H-pyrazol-3-yl)-3,3a,6,6a-tetrahydrocyclopenta[c]pyrrole-2(1H)-carboxylate (0.8 g, 57%) as a yellow solid. MS Calcd.: 475.2; MS Found: 420.3 [M−56+1]$^+$, 476.4 [M+1]$^+$.

AIA-005

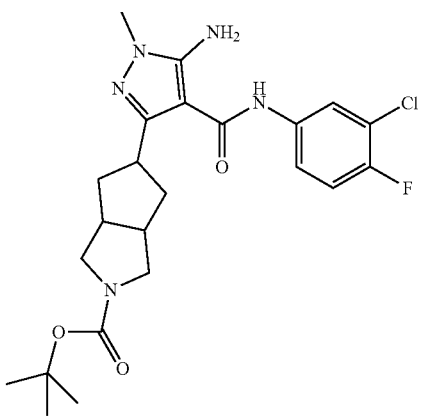

tert-Butyl 5-(5-amino-4-(3-chloro-4-fluorophenylcarbamoyl)-1-methyl-1H-pyrazol-3-yl)hexahydrocyclopenta[c]pyrrole-2(1H)-carboxylate. To a solution of tert-butyl 5-(5-amino-4-(3-chloro-4-fluorophenylcarbamoyl)-1-methyl-1H-pyrazol-3-yl)-3,3a,6,6-tetrahydrocyclopentane[c]pyrrole-2(1H)-carboxylate (800 mg, 1.7 mmol) in THF (20 mL) was added Pt/C (160 mg). The flask was then evacuated and backfilled with H$_2$. The solution was stirred at 30° C. for 16 h. The mixture was filtered and concentrated to give tert-butyl 5-(5-amino-4-(3-chloro-4-fluorophenylcarbamoyl)-1-methyl-1H-pyrazol-3-yl)hexahydrocyclopenta[c]pyrrole-2(1H)-carboxylate (600 mg, 75%) as a white solid. MS Calcd.: 477.2; MS Found: 422.3 [M−56+1]$^+$, 478.4 [M+1]$^+$. $^1$H-NMR (DMSO-d$_6$, 400 MHz): δ 8.98 (s, 1H), 7.91 (dd, J=6.8, 2.4 Hz, 1H), 7.54-7.50 (m, 1H), 7.34 (t, J=9.6 Hz, 1H), 5.98 (s, 2H), 3.59-3.52 (m, 1H), 3.49 (s, 3H), 3.32 (s, 2H), 3.14-3.10 (m, 2H), 2.61-2.57 (m, 2H), 2.21-2.14 (m, 2H), 1.56-1.48 (m, 2H), 1.38 (s, 9H)

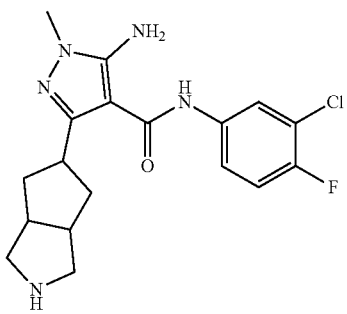

AIA-006

5-Amino-N-(3-chloro-4-fluorophenyl)-1-methyl-3-(octahydrocyclopenta[c] pyrrol-5-yl)-1H-pyrazole-4-carboxamide. To a solution of tert-butyl 5-(5-amino-4-(3-chloro-4-fluorophenylcarbamoyl)-1-methyl-1H-pyrazol-3-yl)hexahydrocyclopenta[c]pyrrole-2(1H)-carboxylate (600 mg, 1.26 mmol) in DCM (10 mL) was added 1M HCl (0.5 mL), the resulting mixture was stirred at room temperature for 1 h. The reaction mixture was adjusted to pH 8-9 with aq. NaHCO$_3$ and the solution extracted with DCM (10 mL×3). The combined organic layers were dried, and the solvent removed in vacuo. The residue was purified by prep-HPLC to afford 5-amino-N-(3-chloro-4-fluorophenyl)-1-methyl-3-(octahydrocyclopenta[c]pyrrol-5-yl)-1H-pyrazole-4-carboxamide (355 mg, 75%) as a white solid. MS Calcd.: 377.1; MS Found: 378.4 [M+1]$^+$. (DMSO-d$_6$, 400 MHz): δ 8.97 (s, 1H), 7.91 (dd, J=6.8, 2.8 Hz, 1H), 7.53-7.51 (m, 1H), 7.34 (t, J=9.2 Hz, 1H), 5.97 (s, 2H), 3.55-3.53 (m, 1H), 3.49 (s, 3H), 3.44-3.41 (m, 3H), 3.22-3.14 (m, 1H), 2.57 (s, 3H), 2.19-2.13 (m, 2H), 1.52-1.50 (m, 1H), 1.34-1.32 (m, 1H).

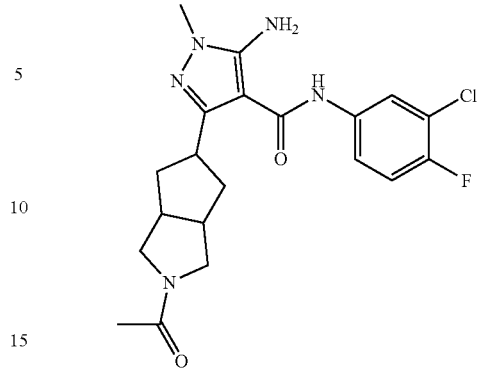

AIA-007

3-(2-Acetyloctahydrocyclopenta[c]pyrrol-5-yl)-5-amino-N-(3-chloro-4-fluorophenyl)-1-methyl-1H-pyrazole-4-carboxamide. To a flask containing a stirred mixture of 5-amino-N-(3-chloro-4-fluorophenyl)-1-methyl-3-(octahydrocyclopenta[c] pyrrol-5-yl)-1H-pyrazole-4-carboxamide (80 mg, 0.21 mmol) and Et$_3$N (43 mg, 0.42 mmol) in DCM (2 mL) was added acetic anhydride (32 mg, 0.32 mmol) at 0° C. The mixture was stirred at RT for 16 h then quenched with water, extracted with ethyl acetate, dried and concentrated. The crude product was purified by prep-HPLC to afford 3-(2-acetyloctahydrocyclopenta[c]pyrrol-5-yl)-5-amino-N-(3-chloro-4- fluorophenyl)-1-methyl-1H-pyrazole-4-carboxamide (30 mg, 34%) as a white solid. MS Calcd.: 419.2; MS Found: 420.2 [M+1]$^+$. $^1$H-NMR (DMSO-d$_6$, 400 MHz): δ 8.96 (s, 1H), 7.89 (dd, J=6.8, 2.8 Hz, 1H), 7.53-7.49 (m, 1H), 7.32 (t, J=9.2 Hz, 1H), 5.95 (s, 2H), 3.59-3.48 (m, 2H), 3.46 (s, 3H), 3.36-3.33 (m, 1H), 3.26-3.18 (m, 2H), 2.68-2.57 (m, 2H), 2.21-2.13 (m, 2H), 1.88 (s, 3H), 1.55-1.48 (m, 2H).

TABLE 15

The compounds in table 15 were synthesized according to the procedure disclosed for 3-(2-acetyloctahydrocyclopenta[c]pyrrol-5-yl)-5-amino-N-(3-chloro-4-fluorophenyl)-1-methyl-1H-pyrazole-4-carboxamide.

| Compound | Structure and characterization |
| --- | --- |
| AIA-022 | 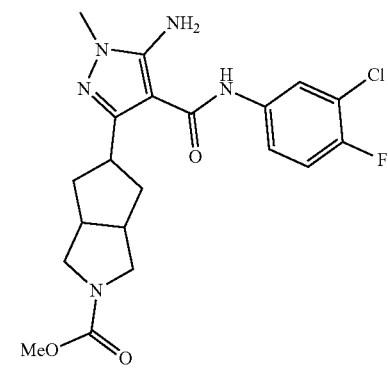 [SMILES: COC(=O)N1CC2CC(c3nn(C)c(N)c3C(=O)Nc3ccc(F)c(Cl)c3)CC2C1]<br>Methyl 5-(5-amino-4-((3-chloro-4-fluorophenyl)carbamoyl)-1-methyl-1H-pyrazol-3-yl)hexahydrocyclopenta[c]pyrrole-2(1H)-carboxylate. MS Calcd.: 435.1; MS Found: 436.2 [M + 1]$^+$. $^1$H-NMR (DMSO-d$_6$, 400 MHz): δ 8.95 (s, 1H), 7.89 (dd, J = 6.8, 2.4 Hz, 1H), 7.52-7.49 (m, 1H), 7.32 (t, J = 9.2 Hz, 1H), 5.96 (s, 2H), 3.55-3.53 (m, 4H), 3.47 (s, 3H), 3.38-3.33 (m, 2H), 3.18-3.15 (m, 2H), 2.61 (s, 2H), 2.19-2.15 (m, 2H), 1.52-1.48 (m, 2H) |

TABLE 15-continued

The compounds in table 15 were synthesized according to the procedure disclosed for 3-(2-acetyloctahydrocyclopenta[c]pyrrol-5-yl)-5-amino-N-(3-chloro-4-fluorophenyl)-1-methyl-1H-pyrazole-4-carboxamide.

| Compound | Structure and characterization |
| --- | --- |
| AIA-023 | 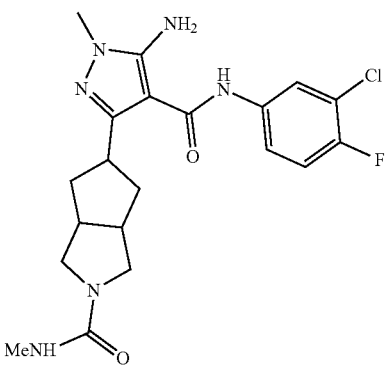 5-(5-Amino-4-(3-chloro-4-fluorophenylcarbamoyl)-1-methyl-1H-pyrazol-3-yl)-N-methylhexahydrocyclopenta[c]pyrrole-2(1H)-carboxamide. MS Calcd.: 434.1; MS Found: 435.3 [M + 1]$^+$. $^1$H-NMR (DMSO-d$_6$, 400 MHz): δ 8.95 (s, 1H), 7.89 (dd, J = 6.8, 2.4 Hz, 1H), 7.53-7.49 (m, 1H), 7.32 (t, J = 9.2 Hz, 1H), 5.99-5.95 (m, 3H), 3.52-3.50 (m, 1H), 3.47 (s, 3H), 3.25-3.20 (m, 2H), 3.13-3.10 (m, 2H), 2.59-2.58 (m, 2H), 2.52 (d, J = 4.0 Hz, 3H), 2.20-2.13 (m, 2H), 1.52-1.45 (m, 2H) |
| AIA-025 | 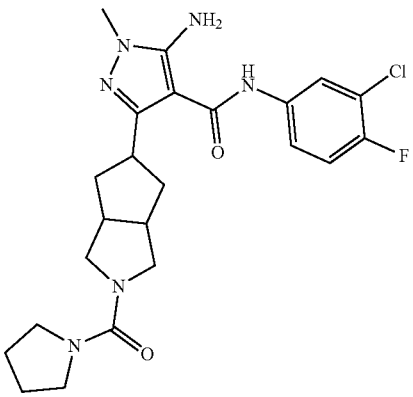 [SMILES: Cn1nc(C2CC3CN(C(=O)N4CCCC4)CC3C2)c(C(=O)Nc2ccc(F)c(Cl)c2)c1N] 5-Amino-N-(3-chloro-4-fluorophenyl)-1-methyl-3-(2-(pyrrolidine-1-carbonyl)octahydrocyclopenta[c]pyrrol-5-yl)-1H-pyrazole-4-carboxamide. MS Calcd.: 474.2; MS Found: 475.3 [M + 1]$^+$. $^1$H-NMR (DMSO-d$_6$, 400 MHz): δ 8.95 (s, 1H), 7.89 (dd, J = 6.8, 2.4 Hz, 1H), 7.52-7.48 (m, 1H), 7.32 (t, J = 8.8 Hz, 1H), 5.95 (s, 2H), 3.53-3.49 (m, 1H), 3.47 (s, 3H), 3.27-3.17 (m, 8H), 2.56-2.55 (m, 2H), 2.18-2.12 (m, 2H), 1.72-1.68 (m, 4H), 1.53-1.46 (m, 2H) |
| AIA-053 | 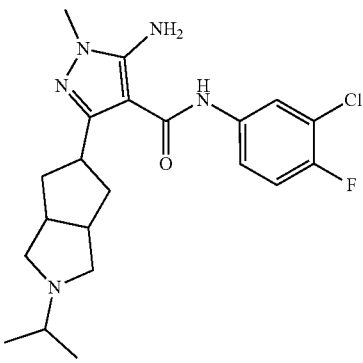 [SMILES: CC(C)N1CC2CC(c3nn(C)c(N)c3C(=O)Nc3ccc(F)c(Cl)c3)CC2C1] |

TABLE 15-continued

The compounds in table 15 were synthesized according to the procedure disclosed for 3-(2-acetyloctahydrocyclopenta[c]pyrrol-5-yl)-5-amino-N-(3-chloro-4-fluorophenyl)-1-methyl-1H-pyrazole-4-carboxamide.

| Compound | Structure and characterization |
| --- | --- |
| | 5-Amino-N-(3-chloro-4-fluorophenyl)-3-(2-isopropyloctahydrocyclopenta[c] pyrrol-5-yl)-1-methyl-1H-pyrazole-4-carboxamide. MS Calcd.: 419.2; MS Found: 420.3 [M + 1]$^+$. $^1$H-NMR (DMSO-d$_6$, 400 MHz): δ 8.94 (s, 1H), 7.91 (dd, J = 6.8, 2.4 Hz, 1H), 7.53-7.49 (m, 1H), 7.34 (t, J = 8.8 Hz, 1H), 5.96 (s, 2H), 3.49 (s, 3H), 3.32-3.26 (m, 1H), 2.59-2.57 (m, 2H), 2.50-2.49 (m, 2H), 2.25-2.19 (m, 1H), 2.15-2.12 (m, 4H), 1.47-1.39 (m, 2H), 0.99 (d, J = 6.4 Hz, 6H) |
| AIA-052 | 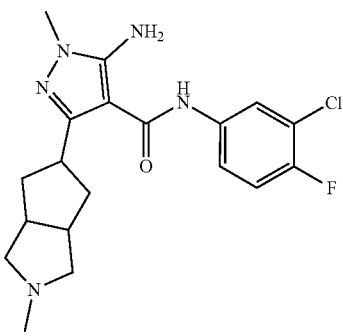 [SMILES: CN1CC2CC(c3nn(C)c(N)c3C(=O)Nc3ccc(F)c(Cl)c3)CC2C1] |
| | 5-Amino-N-(3-chloro-4-fluorophenyl)-1-methyl-3-(2-methyloctahydrocyclopenta [c]pyrrol-5-yl)-1H-pyrazole-4-carboxamide. MS Calcd.: 391.2; MS Found: 392.3 [M + 1]$^+$. $^1$H-NMR (DMSO-d$_6$, 400 MHz): δ 8.93 (s, 1H), 7.91 (dd, J = 6.8, 2.4 Hz, 1H), 7.53-7.49 (m, 1H), 7.34 (t, J = 8.8 Hz, 1H), 5.96 (s, 2H), 3.48 (s, 3H), 3.30-3.29 (m, 1H), 2.49-2.46 (m, 4H), 2.18 (s, 3H), 2.16-2.10 (m, 2H), 2.06-2.03 (m, 2H), 1.47-1.44 (m, 2H) |
| AIA-054 | 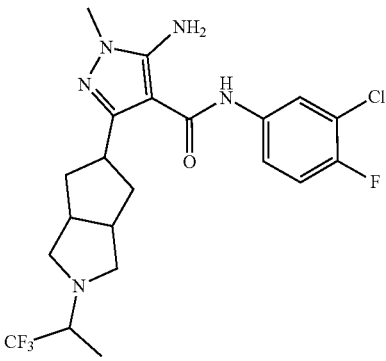 [SMILES: CC(N1CC2CC(c3nn(C)c(N)c3C(=O)Nc3ccc(F)c(Cl)c3)CC2C1)C(F)(F)F] |
| | 5-Amino-N-(3-chloro-4-fluorophenyl)-1-methyl-3-(2-(1,1,1-trifluoropropan-2-yl) octahydrocyclopenta[c]pyrrol-5-yl)-1H-pyrazole-4-carboxamide. MS Calcd.: 473.2; MS Found: 474.3 [M + 1]$^+$. $^1$H-NMR (DMSO-d$_6$, 400 MHz): δ 8.93 (s, 1H), 7.89 (dd, J = 6.8, 2.4 Hz, 1H), 7.51-7.47 (m, 1H), 7.32 (t, J = 8.8 Hz, 1H), 5.94 (s, 2H), 3.47 (s, 3H), 3.41-3.37 (m, 1H), 2.60-2.48 (m, 4H), 2.48-2.47 (m, 3H), 2.16-2.12 (m, 2H), 1.40-1.38 (m, 2H), 1.11 (d, J = 6.4 Hz, 3H) |

TABLE 15-continued

The compounds in table 15 were synthesized according to the procedure disclosed for 3-(2-acetyloctahydrocyclopenta[c]pyrrol-5-yl)-5-amino-N-(3-chloro-4-fluorophenyl)-1-methyl-1H-pyrazole-4-carboxamide.

| Compound | Structure and characterization |
| --- | --- |

AIA-024

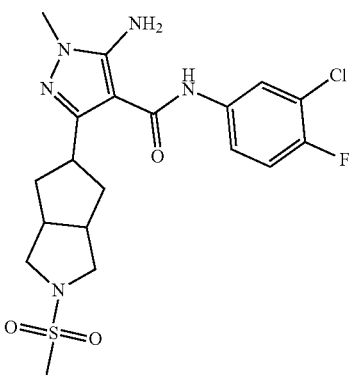 [SMILES: Cn1nc(C2CC3CN(S(C)(=O)=O)CC3C2)c(C(=O)Nc2ccc(F)c(Cl)c2)c1N]

5-Amino-N-(3-chloro-4-fluorophenyl)-1-methyl-3-(2-(methylsulfonyl)octa hydrocyclopenta[c]pyrrol-5-yl)-1H-pyrazole-4-carboxamide. MS Calcd.: 455.1; MS Found: 456.2 [M + 1]$^+$. $^1$H-NMR (DMSO-d$_6$, 400 MHz): δ 8.97 (s, 1H), 7.89 (dd, J = 7.2, 2.8 Hz, 1H), 7.53-7.49 (m, 1H), 7.32 (t, J = 9.2 Hz, 1H), 5.96 (s, 2H), 3.48 (s, 3H), 3.47-3.42 (m, 1H), 3.16-3.12 (m, 2H), 3.01-2.99 (m, 2H), 2.85 (s, 3H), 2.69-2.67 (m, 2H), 2.24-2.21 (m, 2H), 1.53-1.45 (m, 2H)

AIA-085

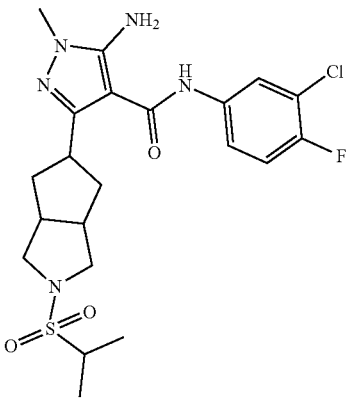 [SMILES: CC(C)S(=O)(=O)N1CC2CC(c3nn(C)c(N)c3C(=O)Nc3ccc(F)c(Cl)c3)CC2C1]

5-Amino-N-(3-chloro-4-fluorophenyl)-3-(2-(isopropylsulfonyl)octahydro cyclopentyl[c]pyrrol-5-yl)-1-methyl-1H-pyrazole-4-carboxamide. MS Calcd.: 483.2; MS Found: 484.2 [M + 1]$^+$. $^1$H-NMR (DMSO-d$_6$, 400 MHz): δ 8.97 (s, 1H), 7.89 (dd, J = 6.8, 2.4 Hz, 1H), 7.52-7.48 (m, 1H), 7.32 (t, J = 8.8 Hz, 1H), 5.96 (s, 2H), 3.47 (s, 3H), 3.44-3.41 (m, 1H), 3.34-3.33 (m, 1H), 3.27-3.23 (m, 2H), 3.13-3.11 (m, 2H), 2.65-2.64 (m, 2H), 2.22-2.17 (m, 2H), 1.51-1.43 (m, 2H), 1.19 (d, J = 6.8, 6H)

Intermediate 134

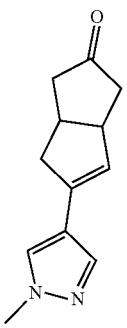

5-(1-Methyl-1H-pyrazol-4-yl)-3,3a,6,6a-tetrahydropentalen-2(1H)-one. A mixture of 4-bromo-1-methyl-1H-pyrazole (2.0 g, 8.1 mmol), 5-(4,4,5,5-tetramethyl-1,3,2-dioxaborolan-2-yl)-3,3a,6,6a-tetrahydropentalen-2(1H)-one (1.4 g, 8.9 mmol), $K_3PO_4$ (3.4 g, 16.1 mmol) and $Pd(dppf)Cl_2$ (589.8 mg, 0.8 mmol) in dioxane (10 mL) and $H_2O$ (2 mL) was stirred at 80° C. overnight under an $N_2$ atmosphere. The solvent was removed under vacuum and the residue purified by silica gel column chromatography using 2:1 petroleum ether/ethyl acetate to afford 5-(1-methyl-1H-pyrazol-4-yl)-3,3a,6,6a-tetrahydropentalen-2(1H)-one (1.0 g, 62.5%) as a yellow solid. MS Calcd.: 202.1, MS Found: 203.4 $[M+1]^+$.

Intermediate 136

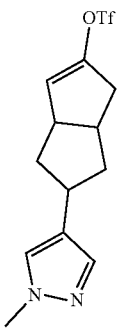

5-(1-Methyl-1H-pyrazol-4-yl)-1,3a,4,5,6,6a-hexahydropentalen-2-yl trifluoromethanesulfonate. To a solution of 5-(1-methyl-1H-pyrazol-4-yl)hexahydropentalen-2(1H)-one (550.0 mg, 2.7 mmol) in THF (20 mL) was added LiHMDS (4.0 mmol, 1 M, 4.0 mL,) at −78° C. The reaction mixture was stirred at −78° C. for 1 hour, then a solution of 1,1,1-trifluoro-N-phenyl-N-((trifluoromethyl)sulfonyl)methanesulfonamide (1.4 g, 4.0 mmol) in THF (5 mL) was added dropwise. The reaction mixture was warmed to 30° C. and stirred overnight. The reaction mixture was quenched by the addition of $NH_4Cl$ (2 mL) at 25° C., then diluted with $H_2O$ (10 mL) and extracted with EtOAc (20 mL×2). The combined organic layers were washed with brine (20 mL), dried over $Na_2SO_4$, filtered and concentrated under reduced pressure, and the residue purified by silica gel column chromatography using 3:1 petroleum ether/ethyl acetate to afford 5-(1-methyl-1H-pyrazol-4-yl)-1,3a,4,5,6,6a-hexahydropentalen-2-yl trifluoromethanesulfonate (800.0 mg, 88.4%) as a yellow oil. MS Calcd.: 336.1, MS Found: 337.3 $[M+1]^+$.

Intermediate 135

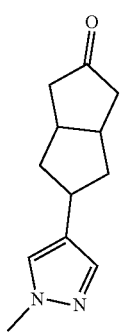

5-(1-Methyl-1H-pyrazol-4-yl)hexahydropentalen-2(1H)-one. A mixture of 5-(1-methyl-1H-pyrazol-4-yl)-3,3a,6,6a-tetrahydropentalen-2(1H)-one (1.0 g, 4.9 mmol) and Pd/C (0.1 g) in ethyl acetate (20 mL) was stirred under $H_2$ at 30° C. overnight. The mixture was filtered over a pad of Celite®. The filtrate was concentrated then purified by silica gel column chromatography using 1:1 petroleum ether/ethyl acetate to afford 5-(1-methyl-1H-pyrazol-4-yl)hexahydropentalen-2(1H)-one (800.0 mg, 80.0%) as a yellow solid MS Calcd.: 204.1, MS Found: 205.4 $[M+1]^+$.

Intermediate 137

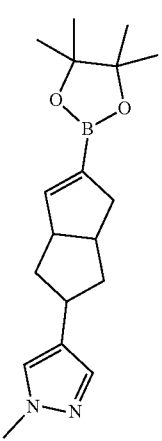

1-Methyl-4-(5-(4,4,5,5-tetramethyl-1,3,2-dioxaborolan-2-yl)-1,2,3,3a,4,6a-hexahydropentalen-2-yl)-1H-pyrazole. A mixture of 5-(1-methyl-1H-pyrazol-4-yl)-1,3a,4,5,6,6a-hexahydropentalen-2-yltrifluoromethanesulfonate (90.0 mg, 0.3 mmol), 4,4,5,5-tetramethyl-2-(4, 4,5,5-tetramethyl-1,3, 2-dioxaborolan-2-yl)-1,3,2-dioxaborolane (81.5 mg, 0.3 mmol), $Pd(dppf)Cl_2$ (19.6 mg, 0.03 mmol) and potassium acetate (52.5 mg, 0.5 mmol) in dioxane (5 mL) was stirred at 80° C. under an $N_2$ atmosphere for 4 hours. The reaction mixture was filtered through a pad of Celite®, and the filter cake washed with EtOAc (10 mL×3). The filtrate was concentrated under vacuum and the residue purified by silica gel column chromatography using 3:1 petroleum ether/ethyl acetate to afford 1-methyl-4-(5-(4,4,5,5-tetramethyl-1,3,2-dioxaborolan-2-yl)-1,2,3,3a,4,6a-hexahydropentalen-2-yl)-1H-pyrazole (50.0 mg, 59.5%) as a yellow oil. MS Calcd.: 314.2, MS Found: 315.4 [M+1]⁺.

Intermediate 138

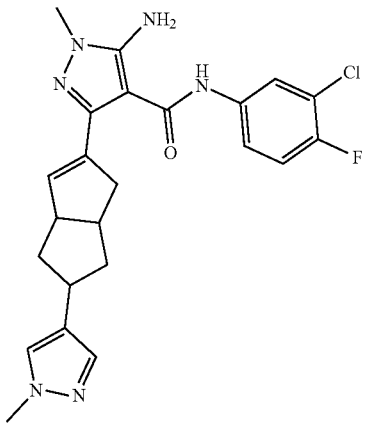

5-Amino-N-(3-chloro-4-fluorophenyl)-1-methyl-3-(5-(1-methyl-1H-pyrazol-4-yl)-1,3a,4,5,6,6a-hexahydropentalen-2-yl)-1H-pyrazole-4-carboxamide. A mixture of 5-amino-3-bromo-N-(3-chloro-4-fluorophenyl)-1-methyl-1H-pyrazole-4-carboxamide (55.3 mg, 0.2 mmol), 1-methyl-4-(5-(4,4,5,5-tetramethyl-1,3,2-dioxaborolan-2-yl)-1,2,3,3a,4,6a-hexahydropentalen-2-yl)-1H-pyrazole (50.0 mg, 0.2 mmol), K₃PO₄ (67.6 mg, 0.3 mmol) and Pd(dppf)Cl₂ (11.6 mg, 0.02 mmol) in dioxane (5 mL) and H₂O (1 mL) were stirred at 100° C. for 4 hours under an N₂ atmosphere. The solvent was removed under vacuum and the residue purified by silica gel column chromatography using 1:1 petroleum ether/ethyl acetate to afford 5-amino-N-(3-chloro-4-fluorophenyl)-1-methyl-3-(5-(1-methyl-1H-pyrazol-4-yl)-1,3a,4,5,6,6a-hexahydropentalen-2-yl)-1H-pyrazole-4-carboxamide (50.0 mg, 69.4%) as a yellow solid. (R_f 0.2); MS Calcd.: 454.2, MS Found: 455.3 [M+1]⁺.

AIA-049

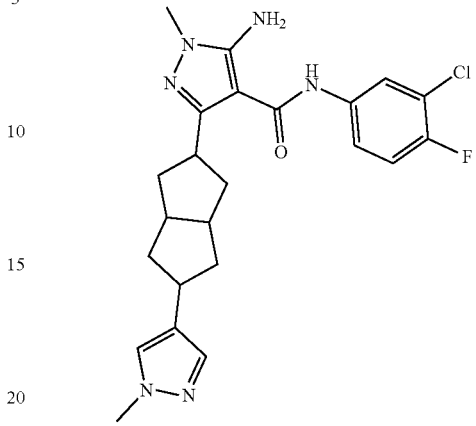

5-Amino-N-(3-chloro-4-fluorophenyl)-1-methyl-3-(5-(1-methyl-1H-pyrazol-4-yl)octahydropentalen-2-yl)-1H-pyrazole-4-carboxamide. A mixture of 5-amino-N-(3-chloro-4-fluorophenyl)-1-methyl-3-(5-(1-methyl-1H-pyrazol-4-yl)-1,3a,4,5,6,6a-hexahydropentalen-2-yl)-1H-pyrazole-4-carboxamide (800.0 mg, 1.8 mmol) and RhCl(PPh₃)₃ (81.3 mg, 0.09 mmol) in MeOH (50 mL) was stirred under 10 atm of H₂ at 70° C. overnight. The solvent was removed under vacuum and the residue purified by silica gel column chromatography using 1: petroleum ether/ethyl acetate to afford 5-amino-N-(3-chloro-4-fluorophenyl)-1-methyl-3-(5-(1-methyl-1H-pyrazol-4-yl)octahydropentalen-2-yl)-1H-pyrazole-4-carboxamide (55 mg, 6.8%) as a white solid. ¹H-NMR (DMSO-d₆, 400 MHz): δ 8.97 (s, 1H), 7.91 (dd, J=6.8, 2.4 Hz, 1H), 7.54-7.50 (m, 1H), 7.44 (s, 1H), 7.35 (t, J=9.2 Hz, 1H), 7.22 (s, 1H), 5.97 (s, 2H), 3.74 (s, 3H), 3.64-3.53 (m, 1H), 3.50 (m, 3H), 2.99-2.90 (m, 1H), 2.51-2.50 (m, 2H), 2.20-2.10 (m, 4H), 1.52-1.44 (m, 2H), 1.27-1.19 (m, 2H); MS Calcd.: 456.2, MS Found: 457.4 [M+1]⁺.

TABLE 16

The compounds in table 16 were synthesized according to the procedure described for 5-amino-N-(3-chloro-4-fluorophenyl)-1-methyl-3-(5-(1-methyl-1H-pyrazol-4-yl)octahydropentalen-2-yl)-1H-pyrazole-4-carboxamide.

| Compound | Structure and characterization |
|---|---|
| AIA-119 | 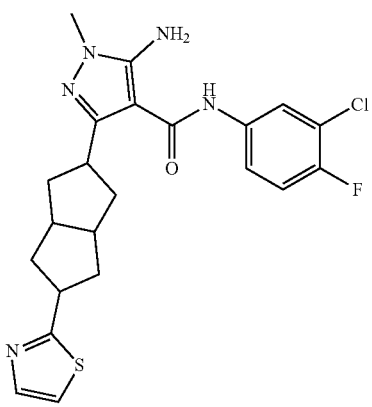 [SMILES: Cn1nc(C2CC3CC(c4nccs4)CC3C2)c(C(=O)Nc2ccc(F)c(Cl)c2)c1N] |

TABLE 16-continued

The compounds in table 16 were synthesized according to the procedure described for 5-amino-N-(3-chloro-4-fluorophenyl)-1-methyl-3-(5-(1-methyl-1H-pyrazol-4-yl)octahydropentalen-2-yl)-1H-pyrazole-4-carboxamide.

| Compound | Structure and characterization |
|---|---|
| | 5-Amino-N-(3-chloro-4-fluorophenyl)-1-methyl-3-(5-(thiazol-2-yl)octahydropentalen-2-yl)-1H-pyrazole-4-carboxamide. MS Calcd.: 459.1; MS Found: 460.2 [M + 1]$^+$; $^1$H NMR (DMSO-d$_6$, 400 MHz): δ 8.97 (brs, 1H), 7.92 (dd, J = 7.2, 2.8 Hz, 1H), 7.66 (d, J = 3.2 Hz, 1H), 7.55-7.51 (m, 2H), 7.35 (t, J = 8.8 Hz, 1H), 5.98 (brs, 2H), 3.66-3.61 (m, 1H), 3.56-3.50 (m, 4H), 2.60-2.59 (m, 2H), 3.36-2.30 (m, 2H), 2.22-2.18 (m, 2H), 1.57-1.49 (m, 4H). |
| AIA-121 | 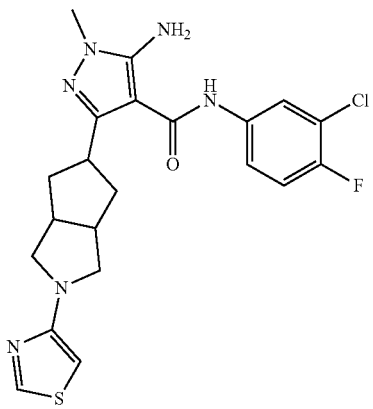 [SMILES: Cn1nc(C2CC3CN(c4cscn4)CC3C2)c(C(=O)Nc2ccc(F)c(Cl)c2)c1N] 5-Amino-N-(3-chloro-4-fluorophenyl)-1-methyl-3-(5-(thiazol-4-yl)octahydropentalen-2-yl)-1H-pyrazole-4-carboxamide MS Calcd.: 459.1, MS Found: 460.2 [M + 1]$^+$. $^1$H-NMR (DMSO-d$_6$, 400 MHz): δ 8.99 (d, J = 2.4 Hz, 2H), 7.92 (dd, J = 6.8, 2.8 Hz, 1H), 7.55-7.51 (m, 1H), 7.35 (t, J = 9.2 Hz, 1H), 7.32 (d, J = 2.4 Hz, 1H), 5.98 (s, 2H), 3.65-3.59 (m, 1H), 3.50 (s, 3H), 3.35-3.30 (m, 1H), 2.58-2.54 (m, 2H), 2.22-2.18 (m, 4H), 1.56-1.45 (m, 4H). |

Intermediate 139

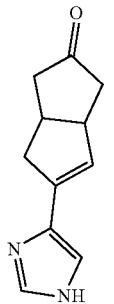

5-(1H-Imidazol-4-yl)-3,3a,6,6a-tetrahydropentalen-2 (1H)-one. A mixture of 5-(4,4,5,5-tetramethyl-1,3,2-dioxaborolan-2-yl)-3,3a,6,6a-tetrahydropentalen-2(1H)-one (1.5 g, 6.0 mmol), 4-bromo-1H-imidazole (0.88 g, 6.0 mmol), Pd(dppf)Cl$_2$ (0.44 g, 0.6 mmol) and K$_3$PO$_4$ (2.6 g, 12 mmol) in dioxane (50 mL) and H$_2$O (8 mL) was stirred at 80° C. for 16 h under N$_2$. The mixture was a brown suspension. EtOAc (40 mL) was added to the mixture. The mixture was filtered, and the filtrate washed with H$_2$O (35 mL×2). The organic layer was dried over Na$_2$SO$_4$ and evaporated under vacuum to give a yellow residue. The residue was purified by purified by silica gel column chromatography using 5-50% ethyl acetate/petroleum ether to give 5-(1H-imidazol-4-yl)-3,3a,6,6a-tetrahydropentalen-2(1H)-one (0.6 g, 55%) as a yellow solid. MS Calcd.: 188.1; MS Found: 189.2 [M+1]$^+$.

Intermediate 140

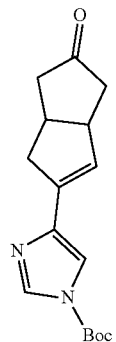

tert-Butyl 4-(5-oxo-1,3a,4,5,6,6a-hexahydropentalen-2-yl)-1H-imidazole-1-carboxylate. To a solution of 5-(1H-imidazol-4-yl)-3,3a,6,6a-tetrahydropentalen-2(1H)-one (600 mg, 3.2 mmol) in DCM (20 mL) was added Boc$_2$O (765 mg, 3.5 mmol) and DMAP (39 mg, 0.32 mmol). The solution was stirred at room temperature for 0.5 h. The solvent was removed in vacuo and the crude product purified by silica gel column chromatography using 5-10% ethyl acetate/petroleum ether to afford tert-butyl 4-(5-oxo-1,3a,4,5,6,6a-hexahydropentalen-2-yl)-1H-imidazole-1-carboxylate (500 mg, 75%) as a pale yellow solid. MS Calcd.: 288.1; MS Found: 232.2 [M−56+1]$^+$, 288.2 [M+1]$^+$.

Intermediate 141

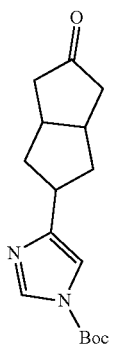

AIA-118

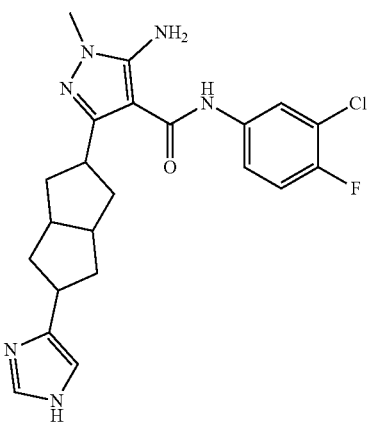

tert-Butyl 4-(5-oxooctahydropentalen-2-yl)-1H-imidazole-1-carboxylate. To a solution of tert-butyl 4-(5-oxo-1,3a,4,5,6,6a-hexahydropentalen-2-yl)-1H-imidazole-1-carboxylate (500 mg, 1.7 mmol) in ethyl acetate (20 mL) was added Pd/C (100 mg). The flask was then evacuated and backfilled with $H_2$. The solution was stirred at 40° C. for 16 h. The mixture was filtered, and the filtrate was concentrated to give tert-butyl 4-(5-oxooctahydropentalen-2-yl)-1H-imidazole-1-carboxylate (480 mg, 95%) as a pale yellow solid. MS Calcd.: 290.2; MS Found: 234.2 $[M-56+1]^+$, 291.2 $[M+1]^+$.

3-(5-(1H-Imidazol-4-yl)octahydropentalen-2-yl)-5-amino-N-(3-chloro-4-fluorophenyl)-1-methyl-1H-pyrazole-4-carboxamide. To a solution of tert-butyl 4-(5-(5-amino-4-((3-chloro-4-fluorophenyl)carbamoyl)-1-methyl-1H-pyrazol-3-yl)octahydropentalen-2-yl)-1H-imidazole-1-carboxylate (70 mg, 0.13 mmol) in DCM (5 mL) was added trifluoroacetic acid (0.5 mL) and the resulting mixture stirred at room temperature for 1 h. The reaction mixture was adjusted to pH 8-9 with $NaHCO_3$, filtered and the filtrate concentrated in vacuo. The crude product was purified by prep-HPLC to afford 3-(5-(1H-imidazol-4-yl)octahydropentalen-2-yl)-5-amino-N-(3-chloro-4-fluorophenyl)-1-methyl-1H-pyrazole-4-carboxamide (30 mg, 53%) as a white solid. MS Calcd.: 442.2; MS Found: 443.3 $[M+1]^+$.

Intermediate 142

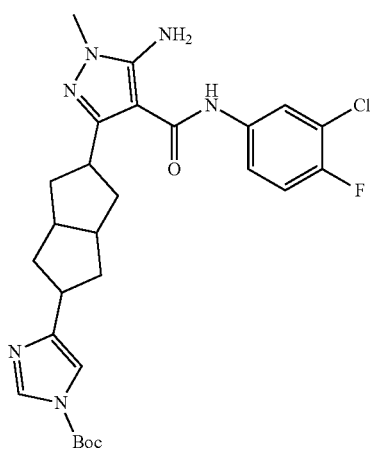

AIA-129

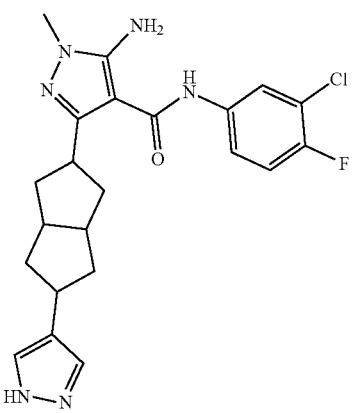

tert-Butyl 4-(5-(5-amino-4-((3-chloro-4-fluorophenyl)carbamoyl)-1-methyl-1H-pyrazol-3-yl)octahydropentalen-2-yl)-1H-imidazole-1-carboxylate. The title compound was synthesized according to the procedure described for 5-amino-N-(3-chloro-4-fluorophenyl)-1-methyl-3-(5-(1-methyl-1H-pyrazol-4-yl)octahydropentalen-2-yl)-1H-pyrazole-4-carboxamide. MS Calcd.: 542.2; MS Found: 487.2 $[M-56+1]^+$, 543.3 $[M+1]^+$.

3-(5-(1H-Pyrazol-4-yl)octahydropentalen-2-yl)-5-amino-N-(3-chloro-4-fluorophenyl)-1-methyl-1H-pyrazole-4-carboxamide. The title compound was synthesized according to the procedure described for 3-(5-(1H-imidazol-4-yl)octahydropentalen-2-yl)-5-amino-N-(3-chloro-4-fluorophenyl)-1-methyl-1H-pyrazole-4-carboxamide. MS Calcd.: 442.2, MS Found: 443.3 $[M+1]^+$; (DMSO-$d_6$, 400 MHz): δ 12.47 (brs, 1H), 8.97 (s, 1H), 7.92 (dd, J=6.8, 2.4 Hz, 1H), 7.55-7.51 (m, 1H), 7.40 (s, 2H), 7.35 (t, J=9.2 Hz, 1H), 5.97 (s, 2H), 3.63-3.57 (m, 1H), 3.50 (s, 3H), 3.01-2.95 (m, 1H), 2.50-2.51 (m, 2H), 2.18-2.17 (m, 4H), 1.52-1.45 (m, 2H), 1.30-1.21 (m, 2H).

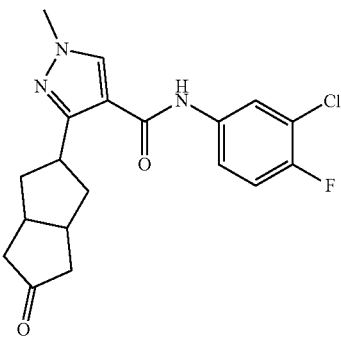

AIA-394

N-(3-Chloro-4-fluorophenyl)-1-methyl-3-(5-oxooctahydropentalen-2-yl)-1H-pyrazole-4-carboxamide. To a solution of AIA-002 (200.0 mg, 0.51 mmol) in anhydrous THF (10 mL) was added t-BuNO$_2$ (210.1 mg, 2.04 mmol) at 0° C., and the mixture stirred at room temperature for 5 hours. The reaction was quenched with saturated aqueous NaHSO$_3$ solution (5.0 mL). The solution was diluted with water (10 mL) and extracted with DCM (10 mL×3). The organic layer was separated, dried over anhydrous Na$_2$SO$_4$ and concentrated to give the crude product, which was purified by column chromatography to afford N-(3-chloro-4-fluorophenyl)-1-methyl-3-(5-oxooctahydropentalen-2-yl)-1H-pyrazole-4-carboxamide (80.0 mg, 41.8%) as a yellow solid. MS Calcd.: 375.1; MS Found: 376.1 [M+1]$^+$. $^1$H-NMR (CDCl$_3$, 400 MHz): δ7.74 (dd, J=2.4 Hz, 6.4 Hz, 1H), 7.68 (s, 1H), 7.36-7.31 (m, 1H), 7.11 (t, J=8.8 Hz, 1H), 3.87 (s, 3H), 3.80-3.70 (m, 1H), 2.86-2.78 (m, 2H), 2.57-2.42 (m, 4H), 2.23-2.16 (m, 2H), 1.78-1.65 (m, 2H).

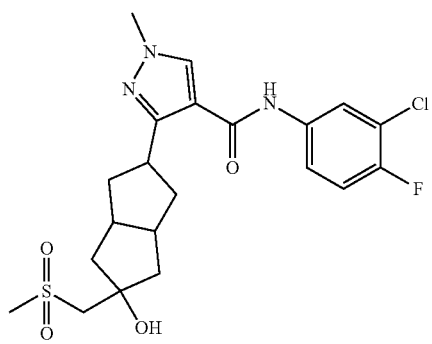

AIA-397

N-(3-Chloro-4-fluorophenyl)-3-(5-hydroxy-5-((methylsulfonyl)methyl)octahydropentalen-2-yl)-1-methyl-1H-pyrazole-4-carboxamide A solution of methylsulfone (160 mg, 1.7 mmol) in anhydrous tetrahydrofuran (10 mL) was cooled to −78° C. and then treated with a solution of n-butyllithium (0.68 mL, 1.7 mmol, 2.5 M). The resulting solution was stirred at −78° C. to −30° C. for 2 hours. Following this, the reaction mixture was cooled to −78° C. and treated with a solution of N-(3-chloro-4-fluorophenyl)-1-methyl-3-(5-oxooctahydropentalen-2-yl)-1H-pyrazole-4-carboxamide (80.0 mg, 0.21 mmol) in anhydrous tetrahydrofuran (2.0 mL). The mixture was stirred at −78° C. for 2 hours. The reaction was then warmed to room temperature and was stirred at room temperature for 3 hours. The reaction mixture was quenched by saturated aqueous ammonium chloride (2.0 mL). This mixture was concentrated in vacuo, diluted with water, and extracted with DCM (10 mL×4), dried over Na$_2$SO$_4$, filtered and concentrated under reduced pressure. The residue was purified by silica gel column chromatography using 1:15 MeOH/DCM followed by prep-HPLC to afford N-(3-chloro-4-fluorophenyl)-3-(5-hydroxy-5-((methylsulfonyl)methyl)octahydropentalen-2-yl)-1-methyl-1H-pyrazole-4-carboxamide (40.0 mg, 40.6%) as a white solid. MS Calcd.: 469.1, MS Found: 470.1 [M+1]$^+$. $^1$H NMR (DMSO-d$_6$, 400 MHz): δ 9.85 (s, 1H), 8.24 (s, 1H), 8.02 (dd, J=2.8 Hz, 7.2 Hz, 1H), 7.60-7.56 (m, 1H), 7.37 (t, J=9.2 Hz, 1H), 4.90 (s, 1H), 3.83 (s, 3H), 3.51-3.48 (m, 1H), 3.27 (s, 2H), 2.99 (s, 3H), 2.51-2.49 (m, 2H), 2.20-2.13 (m, 2H), 2.06-1.99 (m, 2H), 1.80-1.63 (m, 4H).

Intermediate 143

3,3a,4,6a-Tetrahydro-1H-cyclopenta[c]thiophen-5-yl trifluoromethanesulfonate Pyridine (3.3 g, 42 mmol) was added to a solution of tetrahydro-1H-cyclopenta[c]thiophen-5(3H)-one (4.0 g, 28 mmol) in anhydrous DCM (50 mL) at 0° C. Tf$_2$O (12.2 g, 34 mmol) was added slowly and stirred for 4 h. The reaction mixture was warmed to room temperature and quenched with H$_2$O, and the solution was extracted with ethyl acetate (50 mL×3). The combined organic layers were dried over Na$_2$SO$_4$, concentrated and purified by silica gel column chromatography using 5-10% ethyl acetate/petroleum ether to afford 3,3a,4,6a-tetrahydro-1H-cyclopenta[c]thiophen-5-yltrifluoromethanesulfonate (3.2 g, 44% yield) as a pale-yellow solid. MS Calcd.: 274.2; MS Found: 275.7 [M+1]$^+$.

Intermediate 144

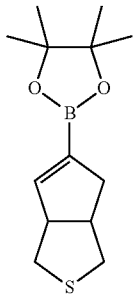

4,4,5,5-Tetramethyl-2-(3,3a,4,6a-tetrahydro-1H-cyclopenta[c]thiophen-5-yl)-1,3,2-dioxaborolane. A brown mixture of compound 3,3a,4,6a-tetrahydro-1H-cyclopenta[c]thiophen-5-yl trifluoromethanesulfonate (3.20 g, 11.34 mmol), pin$_2$B$_2$ (2.80 g, 11.34 mmol), Pd(dppf)Cl$_2$ (0.68 g, 0.56 mmol), dppf (0.68 g, 0.56 mmol) and potassium acetate (3.33 g, 34.02 mmol) in dioxane (30 mL) was stirred at 80° C. for 2 h under N$_2$. A dark suspension was observed. The reaction was filtered through a pad of Celite®, the filter cake was washed with ethyl acetate (20 mL). The filtrate was concentrated under vacuum and the residue purified by silica gel column chromatography using 5-10% ethyl acetate/ petroleum ether to give 4,4,5,5-tetramethyl-2-(3,3a,4,6a-tetrahydro-1H-cyclopenta[c]thiophen-5-yl)-1,3,2-dioxaborolane (1.8 g, 60% yield) as a pale-yellow solid. MS Calcd.:252.1; MS Found: 253.7 [M+1]⁺.

a white solid. MS Calcd.:394.8; MS Found: 395.7 [M+1]⁺. ¹H-NMR (DMSO-d₆, 400 MHz): δ 8.87 (s, 1H), 7.94 (dd, J=7.2, 2.8 Hz, 1H), 7.53-7.52 (m, 1H), 7.36 (t, J=8.8 Hz, 1H), 6.03 (s, 2H), 3.77-3.74 (m, 1H), 3.48 (s, 3H), 2.92-2.87 (m, 2H), 2.82-2.77 (m, 2H), 2.49-2.48 (m, 2H), 2.02-1.95 (m, 2H), 1.73-1.67 (m, 2H).

Intermediate 145

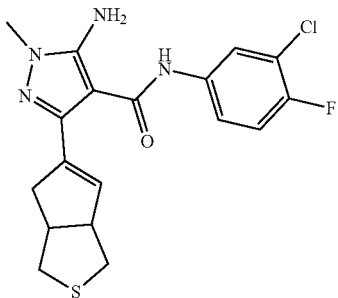

5-Amino-N-(3-chloro-4-fluorophenyl)-1-methyl-3-(3,3a,4,6a-tetrahydro-1H-cyclopenta[c]thiophen-5-yl)-1H-pyrazole-4-carboxamide. A mixture of 4,4,5,5-tetramethyl-2-(3,3a,4,6a-tetrahydro-1H-cyclopenta[c]thiophen-5-yl)-1,3,2-dioxaborolane (1.8 g, 7 mmol), 5-amino-3-bromo-N-(3-chloro-4-fluorophenyl)-1-methyl-1H-pyrazole-4-carboxamide (2.4 g, 7 mmol), Pd(dppf)Cl₂ (0.6 g, 0.35 mmol) and sodium carbonate (14.9 g, 14 mmol) in dioxane/H₂O (36 mL, v/v=5:1) was stirred at 80° C. for 2 h under N₂. A dark suspension was observed. The reaction was filtered through a pad of Celite®, and the filter cake washed with ethyl acetate (20 mL). The filtrate was concentrated under vacuum and the residue purified by silica gel column chromatography using 1-5% ethyl acetate/petroleum ether to give 5-amino-N-(3-chloro-4-fluorophenyl)-1-methyl-3-(3,3a,4,6a-tetrahydro-1H-cyclopenta[c]thiophen-5-yl)-1H-pyrazole-4-carboxamide. (0.3 g, 10% yield) as a pale-yellow solid. MS Calcd.:392.8; MS Found: 393.7 [M+1]⁺.

AIA-055

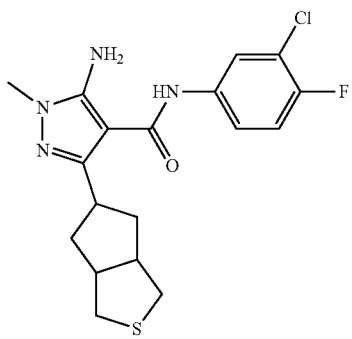

5-Amino-N-(3-chloro-4-fluorophenyl)-3-(hexahydro-1H-cyclopenta[c]thiophen-5-yl)-1-methyl-1H-pyrazole-4-carboxamide. To a solution of compound 5-amino-N-(3-chloro-4-fluorophenyl)-1-methyl-3-(3,3a,4,6a-tetrahydro-1H-cyclopenta[c]thiophen-5-yl)-1H-pyrazole-4-carboxamide (300 mg, 0.7 mmol) in EtOAc (20 mL) was added Pt/C (160 mg). The flask was then evacuated and back-filled with Hz. The solution was stirred at 45° C. for 16 h. The mixture was filtered and concentrated to give 5-amino-N-(3-chloro-4-fluorophenyl)-3-(hexahydro-1H-cyclopenta[c]thiophen-5-yl)-1-methyl-1H-pyrazole-4-carboxamide (280 mg, 93%) as AIA-056-A and AIA-056-B

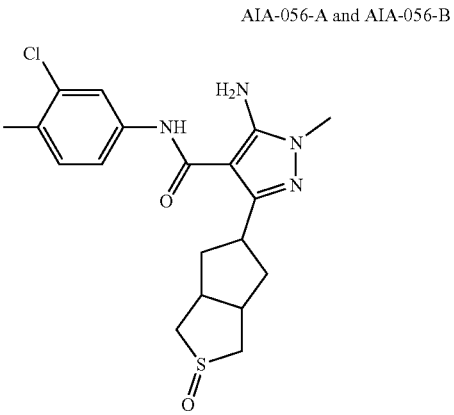

5-Amino-N-(3-chloro-4-fluorophenyl)-1-methyl-3-(2-oxidohexahydro-1H-cyclopenta[c]thiophen-5-yl)-1H-pyrazole-4-carboxamide. Diastereomer 1 (CP-AIA-056-A), Diastereomer 2 (CP-AIA-056-B) To a solution of 5-amino-N-(3-chloro-4-fluorophenyl)-3-(hexahydro-1H-cyclopenta[c]thiophen-5-yl)-1-methyl-1H-pyrazole-4-carboxamide (150 mg, 0.4 mmol) in DCM (5 mL) was added m-CPBA (32 mg, 0.2 mmol), and the resulting mixture was stirred at 25° C. for 1 h. The solvent was removed in vacuo, and the residue purified by chiral-HPLC to afford CP-AIA-056-A and CP-AIA-05-6B. CP-AIA-056-A (9 mg, 5% yield) as a white solid. MS Calcd.: 410.9; MS Found: 411.7 [M+1]⁺; and CP-AIA-056-B (8.5 mg, 5% yield) as a gray solid. MS Calcd.: 410.9; MS Found: 411.7 [M+1]⁺.

Intermediate 146

2-(3-Phenylcyclopentylidene)-1,3-dithiane. To a solution of (1,3-dithian-2-yl)trimethylsilane (10.8 g, 56.3 mmol) in THF was added dropwise n-BuLi (22.5 mL, 2.5 M in THF, 56.3 mmol) at −78° C. The mixture was stirred at −78° C. for 1 h then 3-phenylcyclopentan-1-one (6.0 g, 37.5 mmol) was added. The mixture was stirred at the same temperature for 2 h. The reaction was quenched with aq. NH₄Cl. The solvent was removed under vacuum to residue was purified by column chromatography using petroleum ether/ethyl acetate=10:1 to afford 2-(3-phenylcyclopentylidene)-1,3-dithiane (4.5 g, 46% yield) as a yellowish oil. MS Calcd.: 262.1, MS Found: 262.3 [M+1]⁺.

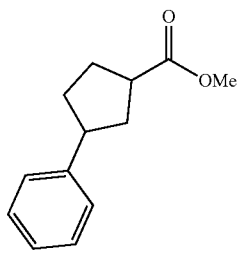

Intermediate 147

Methyl 3-phenylcyclopentanecarboxylate. A mixture of 2-(3-phenylcyclopentylidene)-1,3-dithiane (4.5 g, 17.2 mmol), HgCl$_2$ (9.4 g, 34.4 mmol), 6 N HCl (5.7 mL, 34.4 mmol) and TFA (3.9 g, 34.4 mmol) in MeOH was stirred at room temperature for 4 h. Following filtration, the filtrate was concentrated in vacuum and the residue purified by column chromatography using petroleum ether/ethyl acetate=10:1 to afford methyl 3-phenylcyclopentanecarboxylate (2.9 g, 83% yield) as a colorless oil. MS Calcd.: 204.1, MS Found: 205.3 [M+1]$^+$.

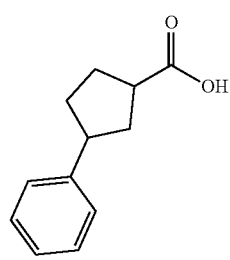

Intermediate 148

3-Phenylcyclopentanecarboxylic acid. A mixture of methyl 3-phenylcyclopentanecarboxylate (2.9 g, 14.2 mmol) and LiOH—H$_2$O (3.0 g, 71.0 mmol) in THF/H$_2$O=1:1 (20 mL) was heated at 60° C. overnight. The reaction was neutralized with 2N HCl. The solvent was removed under vacuum and the residue purified by silica gel column chromatography using petroleum ether/ethyl acetate=1:4 to afford 3-phenylcyclopentanecarboxylic acid (2.4 g, 89% yield) as a white solid. MS Calcd.: 190.1, MS Found: 191.1 [M+1]$^+$.

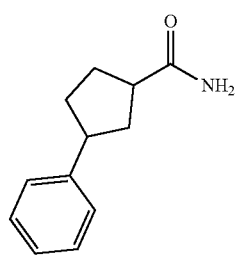

Intermediate 149

3-Phenylcyclopentanecarboxamide. A mixture of 3-phenylcyclopentanecarboxylic acid (2.4 g, 12.6 mmol), HCOONH$_4$ (1.6 g, 25.2 mmol), HATU (7.2 g, 18.9 mmol) and TEA (2.5 g, 25.2 mmol) in DMF (20 mL) was stirred at room temperature overnight. The reaction was quenched with water (100 mL) and extracted with EtOAc (100 mL×3). The combined organic layers were concentrated under reduced pressure. The residue was purified by silica gel column chromatography using petroleum ether/ethyl acetate=1:2 to afford 3-phenylcyclopentanecarboxamide (2.0 g, 83% yield) as a white solid. MS Calcd.: 189.1, MS Found: 190.4 [M+1]$^+$.

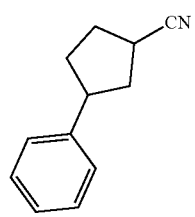

Intermediate 150

3-Phenylcyclopentanecarbonitrile. To a solution of 3-phenylcyclopentanecarboxamide (2.0 g, 10.6 mmol) in pyridine (20 mL) was added POCl$_3$ (4.9 g, 31.8 mmol) at −40° C. and the mixture stirred for 30 min. The reaction was quenched with water (30 mL) extracted with EtOAc (30 mL×3). The combined organic layers were concentrated under vacuum and the residue purified by silica gel column chromatography using petroleum ether/ethyl acetate=10:1 to afford 3-phenylcyclopentanecarbonitrile (1.1 g, 61% yield) as a colorless oil. MS Calcd.: 171.1, MS Found: 172.2 [M+1]$^+$.

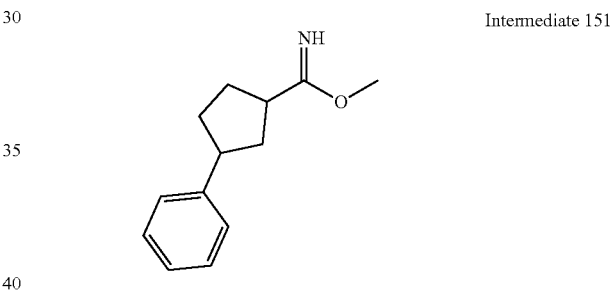

Intermediate 151

Methyl 3-phenylcyclopentanecarbimidate hydrochloride. To a solution of 3-phenylcyclopentanecarbonitrile (1.1 g, 6.4 mmol) in MeOH (10 mL) was bubbled in HCl (gas) and the reaction stirred for 2 h. The solvent was removed under vacuum and the residue used for the next step without further purification. Methyl 3-phenylcyclopentanecarbimidate hydrochloride was obtained (1.3 g crude, 100% yield) as a white solid. MS Calcd.: 203.1, MS Found: 204.3 [M+1]$^+$.

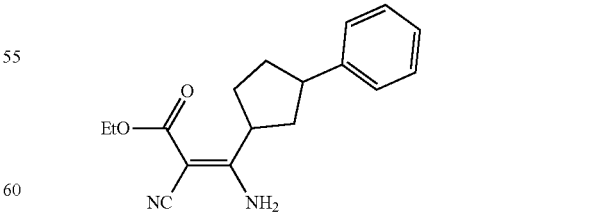

Intermediate 152

Ethyl 3-amino-2-cyano-3-(3-phenylcyclopentyl)acrylate. A mixture of methyl 3-phenylcyclopentanecarbimidate hydrochloride (1.3 g, 6.4 mmol), ethyl 2-cyanoacetate (1.4 g, 12.8 mmol) and TEA (1.3 g, 12.8 mmol) in MeOH was stirred at room temperature overnight. The solvent was removed under vacuum and the residue purified by silica gel column chromatography using petroleum ether/ethyl acetate=2:1 to afford ethyl 3-amino-2-cyano-3-(3-phenylcyclopentyl)acrylate (500 mg, 28% yield) as a white solid. MS Calcd.: 284.2, MS Found: 285.3 [M+1]⁺.

Intermediate 153

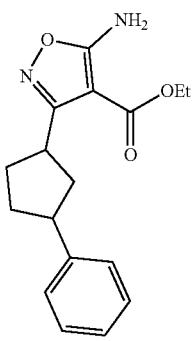

Ethyl 5-amino-3-(3-phenylcyclopentyl)isoxazole-4-carboxylate. A mixture of ethyl 3-amino-2-cyano-3-(3-phenylcyclopentyl)acrylate (500 mg, 1.8 mmol) and hydroxylamine/EtOH (1 mL) in EtOH (2 mL) was heated at reflux for 4 h. The solvent was removed under vacuum and the residue purified by silica gel column chromatography using petroleum ether/ethyl acetate=10:1 to afford ethyl 5-amino-3-(3-phenylcyclopentyl)isoxazole-4-carboxylate (200 mg, 38% yield) as a white solid. MS Calcd.: 300.1, MS Found: 301.3 [M+1]⁺.

Intermediate 154

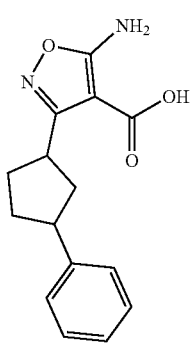

5-Amino-3-(3-phenylcyclopentyl)isoxazole-4-carboxylic acid. A mixture of ethyl 5-amino-3-(3-phenylcyclopentyl)isoxazole-4-carboxylate (100 mg, 0.3 mmol) and LiOH—H₂O (140 mg, 71.03.3 mmol) in THF/H₂O=1:1 (10 mL) was heated at 60° C. overnight. The reaction was neutralized with 2N HCl. The solvent was removed under vacuum and the residue purified by silica gel column chromatography using petroleum ether/ethyl acetate=1:4 to afford 5-amino-3-(3-phenylcyclopentyl)isoxazole-4-carboxylic acid (70 mg, 78% yield) as a white solid. MS Calcd.: 272.1, MS Found: 273.1 [M+1]⁺.

AIA-149

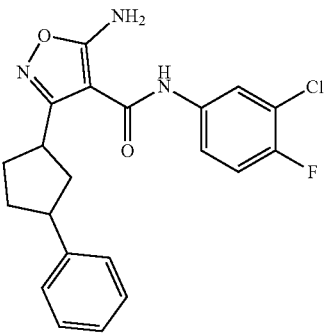

5-Amino-N-(3-chloro-4-fluorophenyl)-3-(3-phenylcyclopentyl) isoxazole-4-carboxamide: A mixture of 5-amino-3-(3-phenylcyclopentyl)isoxazole-4-carboxylic acid (70 mg, 0.3 mmol), 3-chloro-4-fluoroaniline (60 mg, 0.4 mmol), HATU (170 mg, 0.4 mmol) and TEA (60 mg, 0.6 mmol) in DCM (5 mL) was stirred at room temperature for 1 h. The reaction was quenched with water (20 mL) and extracted with EtOAc (20 mL×3). The combined organic layers were concentrated under reduced pressure and the residue purified by silica gel column chromatography using petroleum ether/ethyl acetate=1:1 and Prep-HPLC to afford 5-amino-N-(3-chloro-4-fluorophenyl)-3-(3-phenylcyclopentyl) isoxazole-4-carboxamide (3 mg, 3% yield) as a white solid. MS Calcd.: 399.1, MS Found: 400.0 [M+1]⁺. ¹H-NMR (DMSO-d₆, 400 MHz): δ 9.26-9.21 (m, 1H), 7.89-7.85 (m, 1H), 7.52 (brs, 3H), 7.37-7.15 (m, 6H), 3.85-3.66 (m, 1H), 3.19-3.10 (m, 1H), 2.35-2.32 (m, 1H), 2.19-1.83 (m, 4H), 1.67-1.62 (m, 1H).

VI. Biological Data

Assay Measuring Activity of Test Compounds on Viral Production from HepAD38 Cells HepAD38 cells grown in a T-150 flask (Corning, cat #: 430825) with Growth Medium (DMEM/F12 (1:1) (Hyclone, cat #: SH30023.02), 1× Pen/Strep (Invitrogen, cat #: 15140-122), 10% FBS (Tissue Culture Biologics, cat #: 101), 250 µg/mL G418 (Alfa Aesar, cat #: J62671), 1 µg/mL Tetracycline (Teknova, cat #: T3320)) were detached with 0.25% trypsin-EDTA to (Invitrogen, cat #: 25200-056). Tetracycline-free treatment medium (15 mL DMEM/F12 (1:1) 1× Pen/step, with 2% FBS, Tet-system approved (Clontech, cat #: 631106) were then added to mix, transferred into a 50 ml conical tube (Falcon, cat #: 21008-918,) and spun at 1300 rpm for 5 min. Pelleted cells were then re-suspended/washed with 50 mL of 1×DPBS (Invitrogen, cat #: 14190-136) 2 times and 50 mL treatment medium twice. HepAD38 cells were then re-suspended with 10 mL of treatment medium, syringed and counted. Wells of 96-well clear bottom TC plate (Corning, cat #: 3904,) were seeded at 50,000 cells/well in 180 µL of treatment medium, and 20 µL of either 10% DMSO (Sigma, cat #: D4540) as controls or a 10× solution of test compounds in 10% DMSO in treatment media was added for a final compound concentration starting at 10 µM, and plates were incubated in 5% CO₂ incubator at 37° C. for 5 days.

Subsequently viral load production was assayed by quantitative PCR (qPCR) of the HBV core sequence. PCR reaction mixture containing forward primers HBV-f 5'-CTGTGCCTTGGGTGGCTTT-3' (IDT DNA), Reverse primers HBV-r 5'-AAGGAAAGAAGTCAGAAGGCAAAA-3' (IDT DNA), Fluorescent TaqMan™ Probes HBV-probe 5'-FAM/AGCTCCAAA/ZEN/TTCTTTATAAGGGTCGATGTC/3IABkFQ-3' (IDT DNA), 10 µL/well of PerfeCTa® qPCR ToughMix® (Quanta Biosciences, Cat #: 95114-05K), and 6 µL/well of DEPC water (Alfa Aesar, cat #: J62087) was prepared. Four 4 of supernatant was added to 16 µL of the reaction mixture in a qPCR plate (Applied Biosytems, Cat #: 4309849), sealed with a film (Applied Biosystems, Cat #: 4311971), centrifuged for a few seconds, and subsequently run on an Applied Biosystems VIIA7. The PCR mixture was incubated at 45° C. for 5 min, then 95° C. for 10 min, followed by 40 cycles of 10 seconds at 95° C. and 20 seconds at 60° C. Viral load was quantified against known HBV DNA standards by using ViiA™ 7 Software. Viral load in the supernatant from wells with treated cells were compared against viral load in supernatant from DMSO control wells (>3 per plate). Cell viability assay was performed with CellTiter-Glo Luminescent Cell Viability Assay (Promega, cat #: G7573) with modification. Mixed appropriate amount of CellTiter-Glo (CTG) 1×DPBS in a 1:1 ratio, added 100 uL of the mixture to each well followed completely removal of all supernatant in each well without touching cell surface. Incubated the plate at room temperature for 10 min on an orbital shaker, and then read the plate with a plate reader (TECAN M1000 or Envision). $EC_{50}$ or $CC_{50}$ values were calculated through curve-fitting of the four-parameter non-linear-logistic-regression model (GraphPad Prism or Dotmatics). $CC_{50}$ values were all >10 µM.

Table 17 gives the viral load lowering $EC_{50}$ values for exemplified compounds of the invention grouped in the following ranges: A indicates $EC_{50}$<0.1 µM; B indicates $EC_{50}$ of 0.1-0.5 µM; C indicates $EC_{50}$ of 0.5-10 µM.

TABLE 17

Viral load lowering for exemplified compounds of the invention.

| Compound | Viral Load EC50 Activity range |
|---|---|
| AIA-202A | A |
| AIA-202B | A |
| AIA-202C | C |
| AIA-202D | A |
| AIA-224A | A |
| AIA-224B | B |
| AIA-232 | A |
| AIA-249 | A |
| AIA-249A | A |
| AIA-249B | B |
| AIA-262 | B |
| AIA-268 | A |
| AIA-270 | A |
| AIA-271 | A |
| AIA-272 | A |
| AIA-273 | B |
| AIA-274 | B |
| AIA-275 | A |
| AIA-275A | B |
| AIA-275B | B |
| AIA-275D | A |
| AIA-276 | A |
| AIA-276C | A |
| AIA-276D | A |
| AIA-278 | B |
| AIA-279 | A |
| AIA-280 | B |
| AIA-281 | A |
| AIA-282 | A |
| AIA-283 | A |
| AIA-284 | A |
| AIA-285 | A |
| AIA-286 | B |

TABLE 17-continued

Viral load lowering for exemplified compounds of the invention.

| Compound | Viral Load EC50 Activity range |
|---|---|
| AIA-288 | A |
| AIA-290 | A |
| AIA-292 | C |
| AIA-293 | A |
| AIA-294 | A |
| AIA-296 | A |
| AIA-297 | A |
| AIA-027 | A |
| AIA-032-B | A |
| AIA-011 | A |
| AIA-042 | A |
| AIA-049 | A |
| AIA-050-A | A |
| AIA-048 | A |
| AIA-077 | A |
| AIA-100 | A |
| AIA-021 | A |
| AIA-031 | A |
| AIA-044 | A |
| AIA-020 | A |
| AIA-019 | A |
| AIA-072 | A |
| AIA-075 | A |
| AIA-032-A | A |
| AIA-030 | A |
| AIA-046 | A |
| AIA-015 | A |
| AIA-016 | A |
| AIA-018 | A |
| AIA-074 | A |
| AIA-058 | A |
| AIA-050-B | A |
| AIA-029 | A |
| AIA-028 | A |
| AIA-014 | A |
| AIA-085 | A |
| AIA-043 | A |
| AIA-022 | A |
| AIA-041 | A |
| AIA-047 | A |
| AIA-025 | A |
| AIA-024 | A |
| AIA-101 | A |
| AIA-004-D | A |
| AIA-007 | A |
| AIA-005 | A |
| AIA-003-B | A |
| AIA-004-A | A |
| AIA-023 | A |
| AIA-017 | A |
| AIA-054 | A |
| AIA-003-D | A |
| AIA-003-A | A |
| AIA-033-B | A |
| AIA-086 | A |
| AIA-092 | A |
| AIA-033 | A |
| AIA-055 | A |
| AIA-040 | A |
| AIA-227-1 | A |
| AIA-227-2 | A |
| AIA-004-C | B |
| AIA-073 | B |
| AIA-004-B | B |
| AIA-013 | B |
| AIA-102 | B |
| AIA-003-C | B |
| AIA-033-A | B |
| AIA-103 | B |
| AIA-012 | B |
| AIA-057 | B |
| AIA-052 | C |
| AIA-053 | C |
| AIA-006 | C |
| AIA-056-A | C |
| AIA-056-B | C |

TABLE 17-continued

Viral load lowering for exemplified compounds of the invention.

| Compound | Viral Load EC50 Activity range |
|---|---|
| AIA-009 | A |
| AIA-241 | A |
| AIA-242 | B |
| AIA-244-1 | A |
| AIA-244-2 | A |
| AIA-246 | A |
| AIA-248 | A |
| AIA-249 | C |
| AIA-250-1 | A |
| AIA-250-2 | A |
| AIA-252-1 | A |
| AIA-252-2 | A |
| AIA-253-1 | A |
| AIA-254 | A |
| AIA-255-3 | A |
| AIA-255-4 | A |
| AIA-255-5 | A |
| AIA-257 | A |
| AIA-257-1 | A |
| AIA-258-1 | A |
| AIA-258-2 | A |
| AIA-259-A | A |
| AIA-259-B | A |
| AIA-259-C | A |
| AIA-259-D | A |
| AIA-260-1 | A |
| AIA-260-2 | A |
| AIA-262-1 | A |
| AIA-262-2 | A |
| AIA-263-1 | A |
| AIA-263-2 | A |
| AIA-264 | A |
| AIA-265 | A |
| AIA-266-1 | A |
| AIA-266-2 | A |
| CP-AIA-270 | A |
| AIA-271 | A |
| AIA-273 | A |
| AIA-274-1 | A |
| AIA-274-2 | A |
| AIA-275 | A |
| AIA-283-1 | A |
| AIA-283-2 | A |
| AIA-284-1 | A |
| AIA-284-2 | A |
| AIA-149 | B |
| AIA-310 | A |
| HBV-AIA-039 | A |
| AIA-339-1 | C |
| AIA-339-2 | B |
| AIA-349-b | B |
| AIA-350 | C |
| AIA-351-a | C |
| AIA-352-1 | C |
| AIA-352-2 | A |
| AIA-354 | C |
| AIA-355 | C |
| AIA-363-1 | B |
| AIA-363-2 | B |
| AIA-364-1 | C |
| AIA-364-2 | B |
| AIA-365-1 | B |
| AIA-365-2 | A |
| AIA-366-1 | B |
| AIA-366-2 | A |
| AIA-367-1 | B |
| AIA-367-2 | A |
| AIA-369 | B |
| AIA-371 | C |
| AIA-372 | A |
| AIA-387-1 | B |
| AIA-387-2 | A |
| AIA-388 | B |
| AIA-394 | C |
| AIA-397 | C |

VII. Stereochemistry of Examples

A crystal with size of 0.08×0.10×0.20 mm of compound AIA-227-2 was obtained from EtOH after 20 days of volatilization and was used for X-ray diffraction data collection. The data were collected on a Bruker SMART CCD area-detector diffractometer at room temperature using CuKα radiation by ω/φ scan mode. 10846 reflections were collected, of which 3754 reflections were unique (Rint=0.0507).

The crystal belongs to monoclinic crystal system, with a space group $P2_1/c$. The unit cell parameters were as follows: a=6.6143(3), b=14.0381(8), c=23.6870(14)Å, α=γ=90.0°, β97.702(3)°, V=2179.5(2)Å$^3$, Z=4.

The structure was solved by direct methods and all of the non-H atoms were refined against $F^2$ by full-matrix least-squares methods using the SHELXTL program. All H atoms were placed in geometrically idealized positions and constrained to ride on their parent atoms. Multi-scans absorption correction method was used, and the maximum and minimum transmission parameters were 0.7531 and 0.6017, respectively. The final R, $wR_2$, GOF are 0.0457, 0.1293 and 1.024, respectively.

There is one $C_{21}H_{26}FClN_4O_4S$ molecule in the asymmetric unit and hydrogen bonds can be found between them, which play an important role for the stable packing of the crystal structure.

The ORTEP plot for compound AIA-227-2 is present in FIG. 1. The relative stereochemistry scheme of compound AIA-227-2 is shown in FIG. 2. The depictions of stereochemistry in the chemical structures of related examples are based on this assignment.

INCORPORATION BY REFERENCE

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

EQUIVALENTS

While specific embodiments of the subject disclosure have been discussed, the above specification is illustrative and not restrictive. Many variations of the disclosure will become apparent to those skilled in the art upon review of this specification. The full scope of the disclosure should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present disclosure.

The invention claimed is:
1. A compound of Formula I

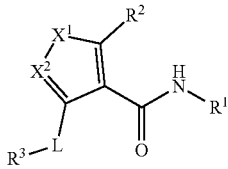

Formula I or a pharmaceutically acceptable salt thereof, wherein:
$X^1$ is $NR^{x1}$;
$X^2$ is N;
$X^3$ is O, $NR^7$, $CR^4R^8$, C(O), S(O)$_t$, C=$CR^4R^0$—, or C=$NR^4$;
$X^4$ and $X^6$ are independently O or S;
$X^5$ is O, S, or $NR^0$;
L is a bond or $C_{1-6}$alkylene;
$L^1$ is a bond, $C_{1-6}$alkylene, O, $NR^c$, C(O), C(O)$NR^c$, S(O)$_t$—, or S(O)$_t NR^c$;
$R^{x1}$ independently is selected from the group consisting of hydrogen, $C_{1-6}$ alkyl, halo$C_{1-6}$ alkyl, and $C_{3-6}$ monocycloalkyl;
$R^a$, $R^b$ and $R^c$ is independently selected for each occurrence from the group consisting of hydrogen, $C_{1-6}$ alkyl, halo$C_{1-6}$ alkyl, and $C_{3-6}$ monocycloalkyl;
$R^d$ is hydrogen, OH, $C_{1-6}$alkyl or $C_{1-6}$ alkoxy;
$R^0$, $R^6$, $R^8$ and $R^{11}$ is independently selected for each occurrence from the group consisting of hydrogen, halogen, OH, CN, NO$_2$, oxo, $R^d$N=, hydrazino, formyl, azido, silyl, siloxy, HOC(O)—, $R^aR^bN$—, $R^aR^bNS(O)_t$—, $C_{1-6}$ alkyl, $C_{2-6}$ alkenyl, $C_{2-6}$ alkynyl, $C_{3-6}$ monocycloalkyl, halo$C_{1-6}$ alkyl, hydroxy$C_{1-6}$ alkyl-, $R^aR^bNC_{1-6}$ alkyl-, HOC(O)$C_{1-6}$ alkyl-, $R^aR^bNC_{1-6}$ alkylNR$^c$—, $C_{1-6}$ alkylNR$^a$C$_{1-6}$ alkylNR$^c$—, $C_{1-6}$ alkoxy, halo$C_{1-6}$ alkoxy, hydroxy$C_{1-6}$ alkoxy-, $R^aR^bNC_{1-6}$ alkoxy-, $C_{1-6}$alkoxy$C_{1-6}$ alkyl-, halo$C_{1-6}$ alkoxy$C_{1-6}$ alkyl-, $R^aR^bNC(O)$—, $C_{1-6}$ alkylC(O)—, $C_{1-6}$ alkoxyC(O)—, $C_{1-6}$ alkylC(O)O—, $C_{1-6}$ alkylS(O)$_q$—, $C_{1-6}$ alkylS(O)$_t$NR$^c$—, $C_{1-6}$ alkylS(O)$_t C_{1-6}$ alkyl-, $C_{1-6}$ alkylS(O)$_t NR^a C_{1-6}$ alkyl-, $C_{3-6}$ cycloalkylS(O)$_t C_{1-6}$ alkyl-, $C_{1-6}$ alkylC(O)$C_{1-6}$ alkyl-, and $C_{1-6}$ alkylC(O)O$C_{1-6}$ alkyl-;
$R^{0a}$ is independently selected for each occurrence from the group consisting of hydrogen, halogen, OH, CN, NO$_2$, $R^aR^bN$—, $C_{1-6}$alkyl, and halo$C_{1-6}$alkyl;
$R^1$ is a phenyl, naphthyl, $C_{3-6}$ monocycloalkyl, $C_{3-6}$ monoheterocycloalkyl, or 5-6 membered monocyclic heteroaryl, wherein: the phenyl, $C_{3-6}$ monocycloalkyl, $C_{3-6}$ monoheterocycloalkyl, or 5-6 membered monocyclic heteroaryl is optionally substituted with one, two, or three independently selected $R^{11}$ groups;
$R^2$ is $R^aR^bN$—;
$R^3$ is selected from the group consisting of:

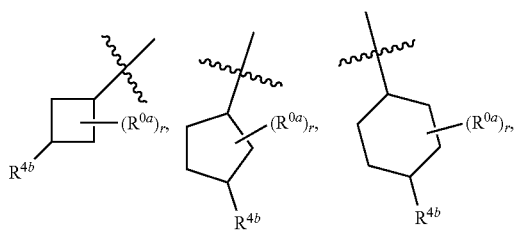

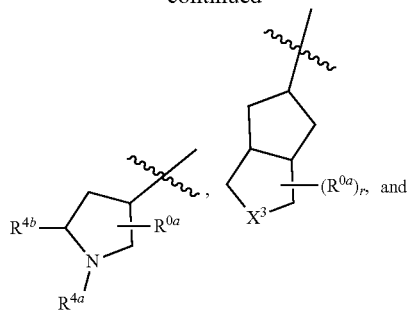

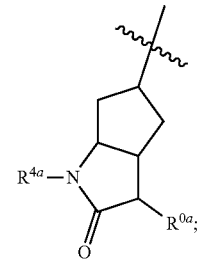

$R^4$ is $R^5$, $R^6$, or $R^5$-$L^1$—;
or $R^4$ and $R^8$ together with the carbon atom to which they are attached form a

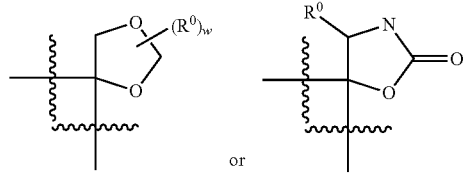

group;
$R^{4a}$ is hydrogen or $C_{1-6}$alkyl;
$R^{4b}$ is $R^5$, $R^{5a}$, $R^6$, or $R^5$-$L^1$—;
$R^5$ is selected from the group consisting of:

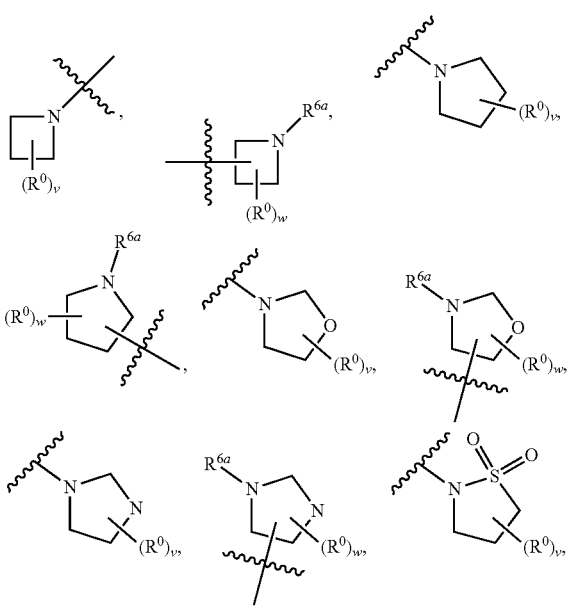

267

-continued

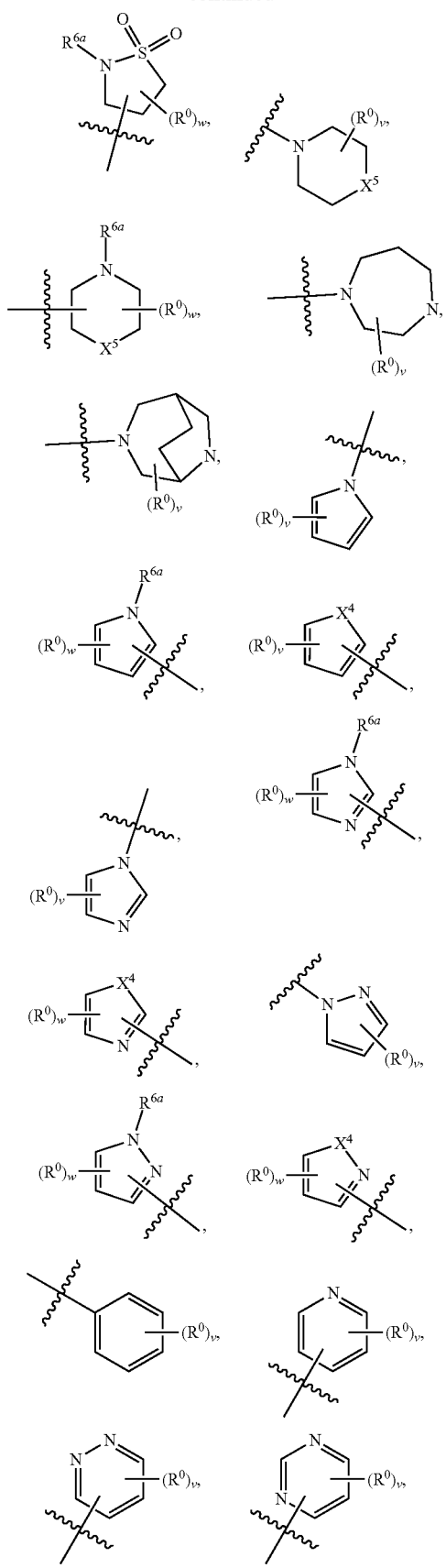

268

-continued

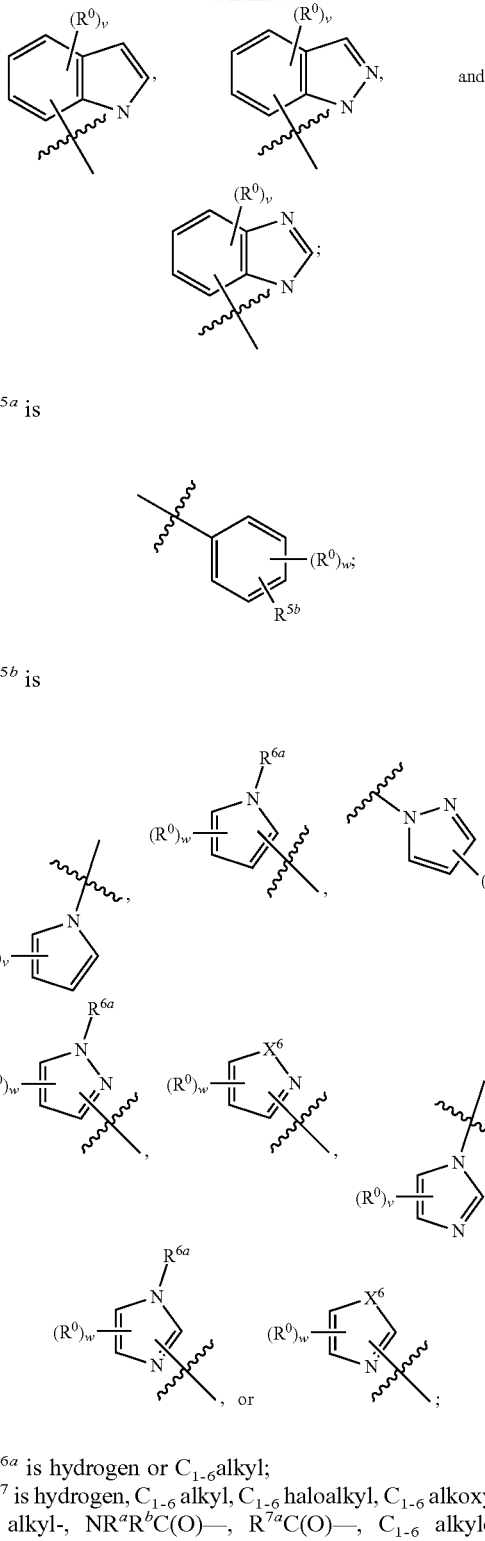

$R^{5a}$ is $R^{5b}$ is $R^{6a}$ is hydrogen or $C_{1-6}$alkyl;
$R^7$ is hydrogen, $C_{1-6}$ alkyl, $C_{1-6}$ haloalkyl, $C_{1-6}$ alkoxy$C_{1-6}$ alkyl-, $NR^aR^bC(O)-$, $R^{7a}C(O)-$, $C_{1-6}$ alkyloxyC(O)—, $C_{1-6}$ alkylS(O)$_q$—, or $C_{1-6}$ haloalkylS(O)$_q$—;
$R^{7a}$ is $C_{1-6}$alkyl or $C_{3-6}$monocycloalkyl;
q, r, t, and w is independently selected for each occurrence from 0, 1, and 2; and
v is independently selected for each occurrence from 0, 1, 2, and 3.

2. The compound of claim 1, or a pharmaceutically acceptable salt thereof, wherein $R^{x1}$ is hydrogen or methyl.

3. The compound of claim 1, or a pharmaceutically acceptable salt thereof, wherein $R^{x1}$ is methyl.

4. The compound according to claim 1, or a pharmaceutically acceptable salt thereof, wherein is L is a bond.

5. The compound according to claim 1, or a pharmaceutically acceptable salt thereof, wherein $L^1$ is a bond.

6. The compound of claim 1, or a pharmaceutically acceptable salt thereof, wherein $R^2$ is $NH_2$.

7. The compound according to claim 1, or a pharmaceutically acceptable salt thereof, wherein:
$R^1$ is

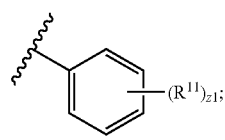

$R^{11}$ is independently selected for each occurrence from the group consisting of halogen, CN, $C_{1-6}$ alkyl, and halo$C_{1-6}$ alkyl; and
z1 is 0, 1, 2, or 3.

8. The compound of claim 7, or a pharmaceutically acceptable salt thereof, wherein for each occurrence $R^{11}$ is independently selected from the group consisting of F, Cl, Br, and I.

9. The compound of claim 8, or a pharmaceutically acceptable salt thereof, wherein $R^1$ is

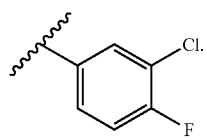 [SMILES: *c1ccc(F)c(Cl)c1]

10. The compound according to claim 1, or a pharmaceutically acceptable salt thereof, wherein $R^3$ is

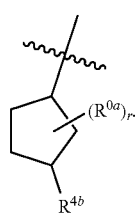

11. The compound of claim 10, or a pharmaceutically acceptable salt thereof, wherein $R^3$ is

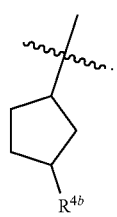

12. The compound of claim 11, or a pharmaceutically acceptable salt thereof, wherein $R^3$ is

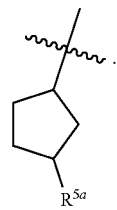

13. The compound according to claim 1, or a pharmaceutically acceptable salt thereof, wherein $R^3$ is

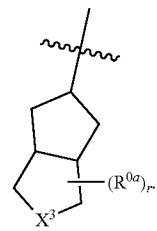

14. The compound of claim 13, or a pharmaceutically acceptable salt thereof, wherein $R^3$ is

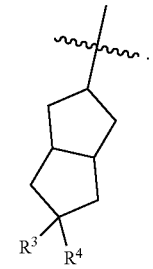

15. The compound of claim 14, or a pharmaceutically acceptable salt thereof, wherein $R^3$ is

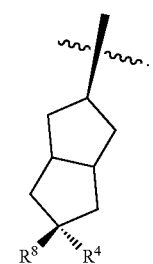

16. The compound of claim 14, or a pharmaceutically acceptable salt thereof, wherein $R^4$ and $R^8$ together with the carbon atom to which they are attached form a

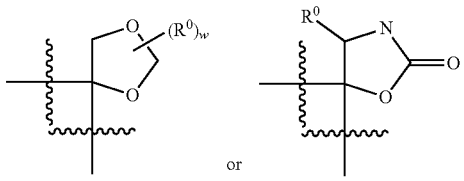

group.

17. The compound of claim 14, or a pharmaceutically acceptable salt thereof, wherein $R^3$ is

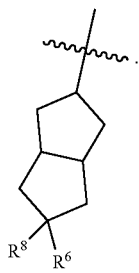

18. The compound of claim 17, or a pharmaceutically acceptable salt thereof, wherein $R^3$ is

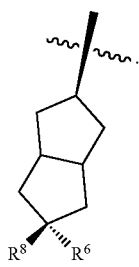

19. The compound of claim 17, or a pharmaceutically acceptable salt thereof, wherein $R^6$ is $C_{1-6}$alkylS(O)$_t$ $C_{1-6}$alkyl- or $C_{1-6}$alkylS(O)$_t$NR$^a$C$_{1-6}$alkyl-.

20. The compound of claim 19, or a pharmaceutically acceptable salt thereof, wherein $R^6$ is $C_{1-6}$alkylS(O)$_t$ $C_{1-6}$alkyl-, and t is 1 or 2.

21. The compound of claim 20, or a pharmaceutically acceptable salt thereof, wherein t is 2.

22. The compound according to claim 17, or a pharmaceutically acceptable salt thereof, wherein $R^8$ is hydrogen, OH, or $C_{1-6}$alkoxy.

23. The compound of claim 22, or a pharmaceutically acceptable salt thereof, wherein $R^8$ is OH.

24. A pharmaceutical composition comprising the compound according to claim 1, or a pharmaceutically acceptable salt thereof, and a pharmaceutically acceptable excipient.

25. A method of treating Hepatitis B (HBV) infection in a subject in need thereof, the method comprising: administering to the subject a therapeutically effective amount of a compound according to claim 1, or a pharmaceutically acceptable salt thereof.

26. A method of treating Hepatitis B (HBV) infection in a subject in need thereof, the method comprising: administering to the subject a therapeutically effective amount of pharmaceutical composition of claim 24.

27. A compound

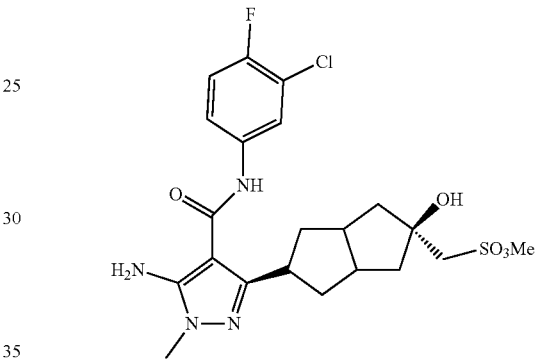

or a pharmaceutically acceptable alt thereof.

28. A pharmaceutical composition comprising the compound according to claim 27, or a pharmaceutically acceptable salt thereof, and a pharmaceutically acceptable excipient.

29. A method of treating Hepatitis B (HBV) infection in a subject in need thereof, the method comprising: administering to the subject a therapeutically effective amount of a compound according to claim 27, or a pharmaceutically acceptable salt thereof.

30. A method of treating Hepatitis B (HBV) infection in a subject in need thereof, the method comprising: administering to the subject a therapeutically effective amount of pharmaceutical composition of claim 28.

* * * * *

UNITED STATES PATENT AND TRADEMARK OFFICE
CERTIFICATE OF CORRECTION

PATENT NO. : 11,560,370 B1
APPLICATION NO. : 17/287681
DATED : January 24, 2023
INVENTOR(S) : Simon Nicolas Haydar et al.

Page 1 of 1

It is certified that error appears in the above-identified patent and that said Letters Patent is hereby corrected as shown below:

In the Claims

In Claim 27, Column 272, Line 37, please delete "alt" and insert --salt--

Signed and Sealed this
Eighteenth Day of April, 2023

Katherine Kelly Vidal
*Director of the United States Patent and Trademark Office*